(12) United States Patent
Nakamura et al.

(10) Patent No.: US 8,053,183 B2
(45) Date of Patent: Nov. 8, 2011

(54) METHOD OF DIAGNOSING ESOPHAGEAL CANCER

(75) Inventors: Yusuke Nakamura, Bunkyo-ku (JP); Yataro Daigo, Bunkyo-ku (JP); Shuichi Nakatsuru, Kawasaki (JP)

(73) Assignee: Oncotherapy Science, Inc., Kawasaki-Shi, Kanagawa (JP)

( * ) Notice: Subject to any disclaimer, the term of this patent is extended or adjusted under 35 U.S.C. 154(b) by 0 days.

(21) Appl. No.: 11/913,170

(22) PCT Filed: Jul. 26, 2006

(86) PCT No.: PCT/JP2006/315342
§ 371 (c)(1),
(2), (4) Date: Dec. 29, 2008

(87) PCT Pub. No.: WO2007/013671
PCT Pub. Date: Feb. 1, 2007

(65) Prior Publication Data
US 2009/0208514 A1    Aug. 20, 2009

Related U.S. Application Data

(60) Provisional application No. 60/703,263, filed on Jul. 27, 2005.

(51) Int. Cl.
*C12Q 1/68* (2006.01)
*C12M 1/34* (2006.01)
*C12M 3/00* (2006.01)
*C12N 5/00* (2006.01)
*C12N 5/02* (2006.01)
*A61K 48/00* (2006.01)
*C07H 21/02* (2006.01)

(52) U.S. Cl. ...... 435/6; 435/287.1; 435/287.2; 435/325; 514/44 R; 536/23.1

(58) Field of Classification Search .................. None
See application file for complete search history.

(56) References Cited

U.S. PATENT DOCUMENTS

| | | | |
|---|---|---|---|
| 6,485,936 B1 | 11/2002 | Yoshima et al. | |
| 2006/0074565 A1* | 4/2006 | Miller et al. | 702/20 |
| 2009/0270267 A1* | 10/2009 | Akiyama et al. | 506/9 |

FOREIGN PATENT DOCUMENTS

| | | |
|---|---|---|
| CN | 1283695 A | 2/2001 |
| WO | WO 01/74405 A1 | 10/2001 |
| WO | WO 02/30963 A1 | 4/2002 |

OTHER PUBLICATIONS

Miyata et al., CDC25B and p53 are independently implicated in radiation sensitivity for human esophageal cancers, 2000, Clinical Cancer Research, vol. 6, pp. 4859-4865.*
Freeman et al., Minichromosome maintenance proteins as biological markers of dysplasia and malignancy, 1999, Clinical Cancer Research, vol. 5, pp. 2121-2132.*
Shimada et al., Cell culture in esophageal squamous cell carcinoma and the association with molecular markers, 2003, Clinical Cancer Research, vol. 9, pp. 243-249.*
Ishibashi et al., Profiling gene expression ratios of paired cancerous and normal tissue predicts relapse of esophageal squamous cell carcinoma, 2003, Cancer Research, vol. 63, pp. 5159-5164.*
Brabender et al., A multigene expression panel for the molecular diagnosis of Barrett's esophagus and Barret's adenocarcinoma of the esophagus, 2004, Oncogene, vol. 23, pp. 4780-4788.*
Tamoto et al., Gene-expression profile changes correlated with tumor progression and lymph node metastasis in esophageal cancer, 2004, Clinical Cancer Research, vol. 10, pp. 3629-3638.*
Zhang et al., Changes in gene expression that accompany the immortalization or transformation of human bronchial epithelial cells, 2004, Proceedings of the American Association for Cancer Research, vol. 45, Abstract No. 1720.*
Tanaka et al., The clinical significance of Aurora-A/STK15/BTAK expression in human esophageal squamous cell carcinoma, 2005, Clinical Cancer Research, vol. 11, pp. 1827-1834.*
Conn et al., Incomplete cytokinesis and induction of apoptosis by overexpression of the mammalian polo-like kinase, Plk3, 2000, Cancer Research, vol. 60, pp. 6826-6831.*
Ikeguchi et al., survivin messenger RNA expression is a good prognostic biomarker for oesophageal carcinoma, 2002, British Journal of Cancer, vol. 87, pp. 883-887.*
Yu et al., Gene expression profiling of the irinotecan pathway in colorectal cancer, 2005, Clinical Cancer Research, vol. 11, pp. 2053-2062.*
Su et al., Gene expression analysis of esophageal squamous cell carcinoma reveals consistent molecular profiles related to a family history of upper gastrointestinal cancer, 2003, Cancer Research, vol. 63, pp. 3872-3876.*
Kim, Ja-Eun et al.; "The Tandem BRCT Domains of Ect2 Are Required for Both Negative and Positive Regulation of Ect2 in Cytokinesis"; 2005, *The Journal of Biological Chemistry*, vol. 280, No. 7, pp. 5733-5739.

(Continued)

*Primary Examiner* — Dana Shin
(74) *Attorney, Agent, or Firm* — Kilpatrick Townsend & Stockton LLP

(57) ABSTRACT

In order to identify the molecules involved in esophageal carcinogenesis and those to be useful for diagnostic markers as well as targets for new drugs and immunotherapy, a cDNA microarray representing 32,256 genes was constructed to analyze the expression profiles of 19 esophageal squamous-cell carcinomas (ESCCS) purified by laser-capture microdissection. a detailed genome-wide database for sets of genes that are significantly up- or down-regulated in esophageal cancer is disclosed herein. these genes find use in the development of therapeutic drugs or immunotherapy as well as tumor markers. additionally, genes associated with lymph-node metastasis and post-surgery recurrence are disclosed herein. among the candidate molecular target genes, ECT2 and CDC45L and DKK1 are further characterized. treatment of ESCC cells with small interfering RNAs (siRNAs) of ECT2 or CDC45L suppressed growth of the cancer cells. Thus, the data herein provide valuable information for identifying diagnostic systems and therapeutic target molecules for esophageal cancer.

5 Claims, 13 Drawing Sheets

OTHER PUBLICATIONS

Saito, Snin'ichi et al.; "Rho Exchange Factor ECT2 is Induced by Growth Fctors and Regulates Cytokinesis Through the N-Terminal Cell Cycle Regulator-Related Domains"; 2003, *Journal of Cellular Biochemistry*, vol. 90, pp. 819-836.

Tatsumoto, Takashi et al.; "Human ECT2 is an Exchange Factor for Rho GTPases, Phosphorylated in G2/M Phases, and Involved in Cytokinesis"; 1999, *The Journal of Cell Biology*, vol. 147, No. 5, pp. 921-927.

Yen, Chuen-Chuan et al.; "Copy number changes of target genes in chromosome 3q25.3-qter of esophageal squamous cell carcinoma: TP63 is amplified in early carcinogenesis but down-regulated as disease progressed"; 2005, *World J. Gastroenterol*, vol. 11, No. 9, pp. 1267-1272.

Kan, T., et al., "Prediction of lymph node metastasis with use of artificial neural networks based on gene expression profiles in esophageal squamous cell carcinoma," *Annals of Surgical Oncology: The Office Journal of the Society of Surgical Oncology*, vol. 11(12), pp. 1070-1078 (Dec. 2004).

Kazemi-Noureini, S., et al., "Differential gene expression between squamous cell carcinoma of esophagus and its normal epithelium," *World Journal of Gastroenterology*, vol. 10(12), pp. 1716-1721 (2004).

Kihara, C., et al., "Prediction of sensitivity of esophageal tumors to adjuvant chemotherapy by cDNA microarray analysis of gene-expression profiles," *Cancer Research*, vol. 61(17), pp. 6474-6479 (Sep. 2001).

Kimchi, E., et al., "Progression of Barrett's metaplasia to adenocarcinoma is associated with the suppression of the transcriptional programs of epidermal differentiation," *Cancer Research*, vol. 65(8), pp. 3146-3154 (Apr. 15, 2005).

Porte, H., et al., "Overexpression of stromelysin-3, BM-40/SPARC, and MET genes in human esophageal carcinoma: implications for prognosis," *Clinical Cancer Research: An Official Journal of the American Association for Cancer Research*, vol. 4(6), pp. 1375-1382 (Jun. 1998).

Yamabuki, T., et al., "Genome-wide expression profile analysis of esophageal squamous cell carcinomas," *International Journal of Oncology*, vol. 28(6), pp. 1375-1384 (Jun. 2006).

Zhou, J., et al., "Gene expression profiles at different stages of human esophageal squamous cell carcinoma," *World Journal of Gastroenterology*, vol. 9(1), pp. 9-15 (Jan. 2003).

Manufacturer: AFFYMETRIX, "Affymetrix GeneChip U133 Array Set HG-U133A," *Gene Expression Omnibus, NCBI*, Published Mar. 11, 2002, Platform GPL96.

U.S. Appl. No. 12/377,024, filed May 12, 2010, 353 pgs.
U.S. Appl. No. 12/673,434, which is a U.S. National Phase application of PCT/JP2008/060837, filed Jun. 13, 2008, 105 pgs.
U.S. Appl. No. 12/673,432, which is a U.S. National Phase application of PCT/JP2008/064437, filed Aug. 12, 2008, 83 pgs.
U.S. Appl. No. 12/674,660, filed May 27, 2010, 85 pgs.
U.S. Appl. No. 12/666,253, filed Jun. 14, 2010, 75 pgs.
U.S. Appl. No. 12/674,659, which is a U.S. National Phase application of PCT/JP2008/065353, filed Aug. 21, 2008, 255 pgs.

* cited by examiner

Continuation of Fig. 2
B
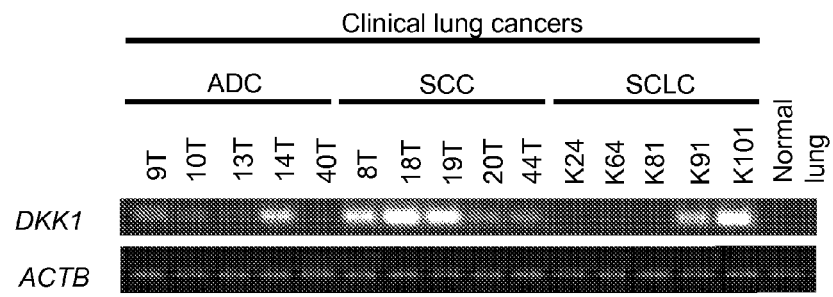
C
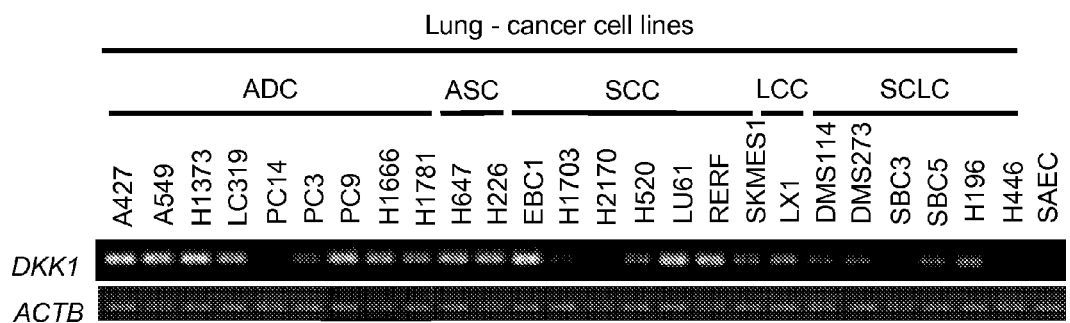
D
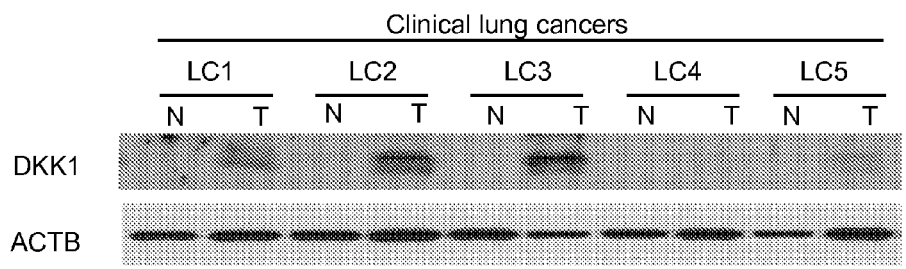

Continuation of Fig. 3
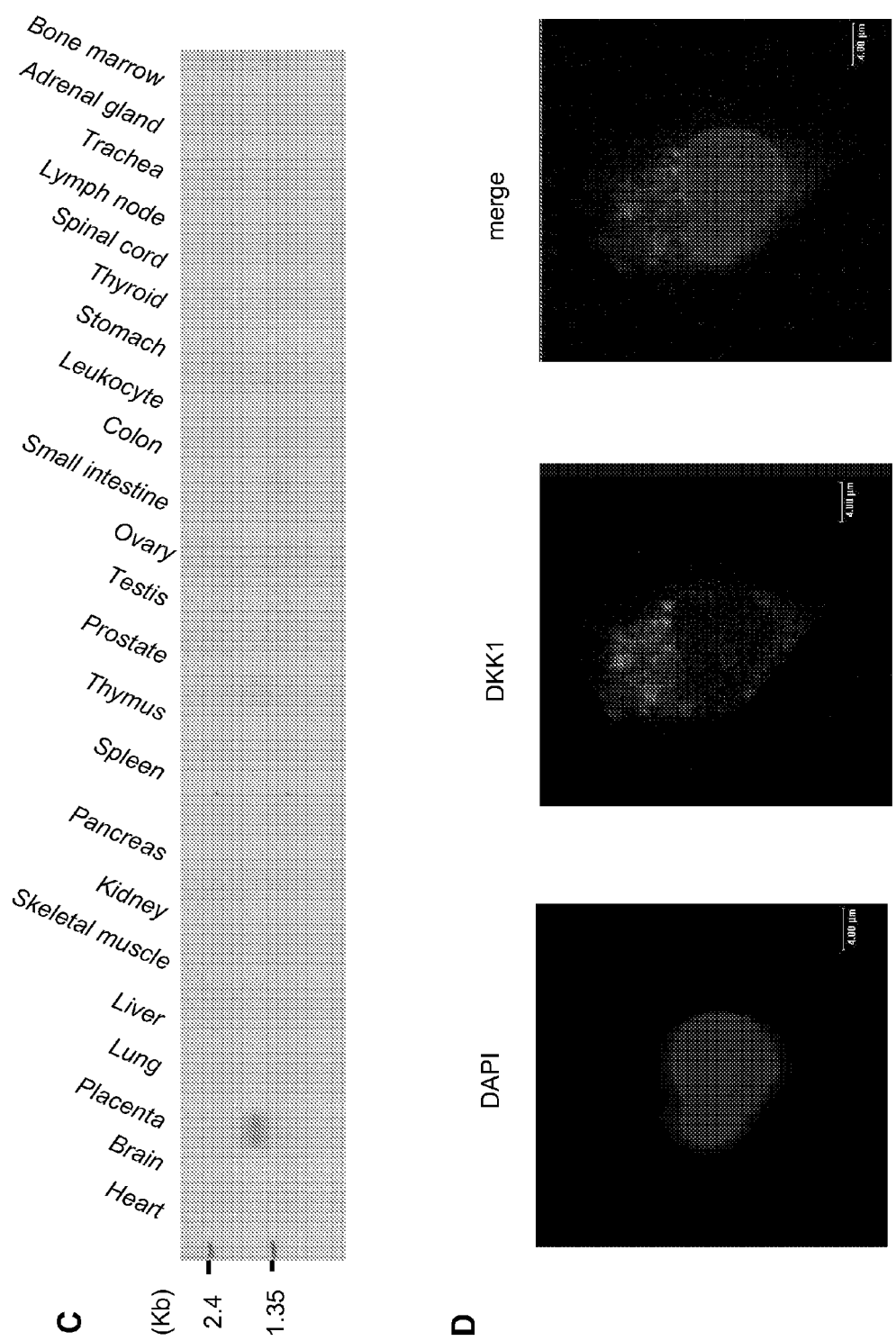

A

B

C

A

B

Continuation of Fig. 8
C
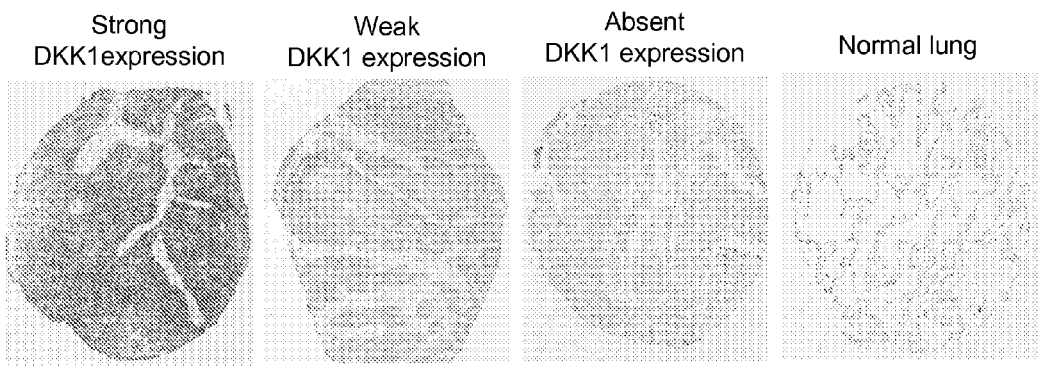
Strong DKK1 expression    Weak DKK1 expression    Absent DKK1 expression    Normal lung
D
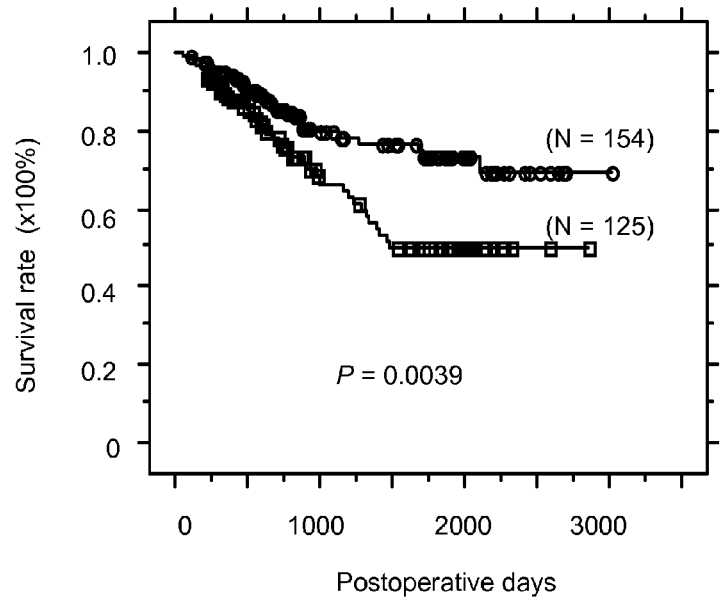
—○— Absent or weak DKK1 expression
—□— Strong DKK1 expression

A

B

C

SEQUENCE LISTING

<160> NUMBER OF SEQ ID NOS: 111

<210> SEQ ID NO 1
<211> LENGTH: 22
<212> TYPE: DNA
<213> ORGANISM: Artificial
<220> FEATURE:
<223> OTHER INFORMATION: An artificially synthesized primer sequence
      for PCR

<400> SEQUENCE: 1
caattttccc atggtcttat cc                                              22

<210> SEQ ID NO 2
<211> LENGTH: 23
<212> TYPE: DNA
<213> ORGANISM: Artificial
<220> FEATURE:
<223> OTHER INFORMATION: An artificially synthesized primer sequence
      for PCR

<400> SEQUENCE: 2
gcgttttcaa gatctagcat gtg                                             23

<210> SEQ ID NO 3
<211> LENGTH: 22
<212> TYPE: DNA
<213> ORGANISM: Artificial
<220> FEATURE:
<223> OTHER INFORMATION: An artificially synthesized primer sequence
      for PCR

<400> SEQUENCE: 3
atgaggagaa cacactctcc gt                                              22

<210> SEQ ID NO 4
<211> LENGTH: 24
<212> TYPE: DNA
<213> ORGANISM: Artificial
<220> FEATURE:
<223> OTHER INFORMATION: An artificially synthesized primer sequence
      for PCR

<400> SEQUENCE: 4
gcttctacat ctcaaatcat gtcc                                            24

<210> SEQ ID NO 5

```
<211> LENGTH: 9
<212> TYPE: DNA
<213> ORGANISM: Artificial
<220> FEATURE:
<223> OTHER INFORMATION: loop sequence for siRNA

<400> SEQUENCE: 5 ttcaagaga                                                                  9

<210> SEQ ID NO 6
<211> LENGTH: 19
<212> TYPE: DNA
<213> ORGANISM: Artificial
<220> FEATURE:
<223> OTHER INFORMATION: target sequence for siRNA

<400> SEQUENCE: 6
gaagcagcac gacttcttc                                                      19

<210> SEQ ID NO 7
<211> LENGTH: 19
<212> TYPE: DNA
<213> ORGANISM: Artificial
<220> FEATURE:
<223> OTHER INFORMATION: target sequence for siRNA

<400> SEQUENCE: 7
gcgcgctttg taggattcg                                                      19

<210> SEQ ID NO 8
<211> LENGTH: 19
<212> TYPE: DNA
<213> ORGANISM: Artificial
<220> FEATURE:
<223> OTHER INFORMATION: target sequence for siRNA

<400> SEQUENCE: 8
gatgcactca ccttgtagt                                                      19

<210> SEQ ID NO 9
<211> LENGTH: 19
<212> TYPE: DNA
<213> ORGANISM: Artificial
<220> FEATURE:
<223> OTHER INFORMATION: target sequence for siRNA

<400> SEQUENCE: 9
ggcaaatact cctgagctc                                                      19

<210> SEQ ID NO 10
<211> LENGTH: 19
<212> TYPE: DNA
<213> ORGANISM: Artificial
<220> FEATURE:
<223> OTHER INFORMATION: target sequence for siRNA

<400> SEQUENCE: 10
gagacatcct ctttgacta                                                      19

<210> SEQ ID NO 11
<211> LENGTH: 19
<212> TYPE: DNA
<213> ORGANISM: Artificial
<220> FEATURE:
<223> OTHER INFORMATION: target sequence for siRNA

<400> SEQUENCE: 11
```

```
cagaccagtg ggtgcaaga                                                  19
```

<210> SEQ ID NO 12
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 12

```
tcccgaagca gcacgacttc ttcttcaaga gagaagaagt cgtgctgctt c              51
```

<210> SEQ ID NO 13
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 13

```
aaaagaagca gcacgacttc ttctctcttg aagaagaagt cgtgctgctt c              51
```

<210> SEQ ID NO 14
<211> LENGTH: 47
<212> TYPE: DNA
<213> ORGANISM: Artificial
<220> FEATURE:
<223> OTHER INFORMATION: siRNA hairpin design

<400> SEQUENCE: 14

```
gaagcagcac gacttcttct tcaagagaga agaagtcgtg ctgcttc                   47
```

<210> SEQ ID NO 15
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 15

```
tcccgcgcgc tttgtaggat tcgttcaaga gacgaatcct acaaagcgcg c              51
```

<210> SEQ ID NO 16
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 16

```
aaaagcgcgc tttgtaggat tcgtctcttg aacgaatcct acaaagcgcg c              51
```

<210> SEQ ID NO 17
<211> LENGTH: 47
<212> TYPE: DNA
<213> ORGANISM: Artificial
<220> FEATURE:
<223> OTHER INFORMATION: siRNA hairpin design

<400> SEQUENCE: 17

```
gcgcgctttg taggattcgt tcaagagacg aatcctacaa agcgcgc                   47
```

<210> SEQ ID NO 18

```
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 18
tcccgatgca ctcaccttgt agtttcaaga gaactacaag gtgagtgcat c          51

<210> SEQ ID NO 19
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 19
aaaagatgca ctcaccttgt agttctcttg aaactacaag gtgagtgcat c          51

<210> SEQ ID NO 20
<211> LENGTH: 47
<212> TYPE: DNA
<213> ORGANISM: Artificial
<220> FEATURE:
<223> OTHER INFORMATION: siRNA hairpin design

<400> SEQUENCE: 20
gatgcactca ccttgtagtt tcaagagaac tacaaggtga gtgcatc               47

<210> SEQ ID NO 21
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 21
tcccggcaaa tactcctgag ctcttcaaga gagagctcag gagtatttgc c          51

<210> SEQ ID NO 22
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 22
aaaaggcaaa tactcctgag ctctctcttg aagagctcag gagtatttgc c          51

<210> SEQ ID NO 23
<211> LENGTH: 47
<212> TYPE: DNA
<213> ORGANISM: Artificial
<220> FEATURE:
<223> OTHER INFORMATION: siRNA hairpin design

<400> SEQUENCE: 23
ggcaaatact cctgagctct tcaagagaga gctcaggagt atttgcc               47

<210> SEQ ID NO 24
<211> LENGTH: 51
<212> TYPE: DNA
<213> ORGANISM: Artificial
<220> FEATURE:
```

```
<223> OTHER INFORMATION: An artificially synthesized oligonucleotide
      sequence for construction of siRNA expression vector

<400> SEQUENCE: 24
tcccgagaca tcctctttga ctattcaaga gatagtcaaa gaggatgtct c              51

<210> SEQ ID NO 25
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 25
aaaagagaca tcctctttga ctatctcttg aatagtcaaa gaggatgtct c              51

<210> SEQ ID NO 26
<211> LENGTH: 47
<212> TYPE: DNA
<213> ORGANISM: Artificial
<220> FEATURE:
<223> OTHER INFORMATION: siRNA hairpin design

<400> SEQUENCE: 26
gagacatcct ctttgactat tcaagagata gtcaaagagg atgtctc                   47

<210> SEQ ID NO 27
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 27
tccccagacc agtgggtgca agattcaaga gatcttgcac ccactggtct g              51

<210> SEQ ID NO 28
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 28
aaaacagacc agtgggtgca agatctcttg aatcttgcac ccactggtct g              51

<210> SEQ ID NO 29
<211> LENGTH: 47
<212> TYPE: DNA
<213> ORGANISM: Artificial
<220> FEATURE:
<223> OTHER INFORMATION: siRNA hairpin design

<400> SEQUENCE: 29
cagaccagtg ggtgcaagat tcaagagatc ttgcacccac tggtctg                   47

<210> SEQ ID NO 30
<211> LENGTH: 4349
<212> TYPE: DNA
<213> ORGANISM: Homo sapiens
<220> FEATURE:
<221> NAME/KEY: CDS
<222> LOCATION: (445)..(3093)

<400> SEQUENCE: 30
```

```
tttttgaatc ggttgtggcg gccgcggcga ggaatggcgg tatttgtgag aggagtcggc      60
gtttgaagag gtggaactcc tagggctttt ttgagagtga cggagtctac ctcttgttac     120
ctagactgga gtgcagtggc acgatctcgg ctcactgcaa cctctgcctc ccgggttcaa     180
gcgattctcc tgcctcagcc tcctgagtag ctgggattac aggtgcctgc caccaagccc     240
agctaatttt tgtatttta gtagagatgg ggtttcattg tgttggccag ctggtctcg      300 aactcctgac ctcgtgatcc gcccgccttg gcctcccaaa gtgctaggat tacaagtgtg     360
agccaccgcg tccggccttt caaatggtat tttgatttt cctcttccag tccttaaagc     420
agctgattta gaagaataca aatc atg gct gaa aat agt gta tta aca tcc       471
                          Met Ala Glu Asn Ser Val Leu Thr Ser
                            1               5 act act ggg agg act agc ttg gca gac tct tcc att ttt gat tct aaa       519
Thr Thr Gly Arg Thr Ser Leu Ala Asp Ser Ser Ile Phe Asp Ser Lys
 10              15                  20                  25 gtt act gag att tcc aag gaa aac tta ctt att gga tct act tca tat       567
Val Thr Glu Ile Ser Lys Glu Asn Leu Leu Ile Gly Ser Thr Ser Tyr
             30                  35                  40 gta gaa gag atg cct cag att gaa aca aga gtg ata ttg gtt caa gaa       615
Val Glu Glu Met Pro Gln Ile Glu Thr Arg Val Ile Leu Val Gln Glu
         45                  50                  55 gct gga aaa caa gaa gaa ctt ata aaa gcc tta aag gac att aaa gtg       663
Ala Gly Lys Gln Glu Glu Leu Ile Lys Ala Leu Lys Asp Ile Lys Val
     60                  65                  70 ggc ttt gta aag atg gag tca gtg gaa gaa ttt gaa ggt ttg gat tct       711
Gly Phe Val Lys Met Glu Ser Val Glu Glu Phe Glu Gly Leu Asp Ser
 75                  80                  85 ccg gaa ttt gaa aat gta ttt gta gtc acg gac ttt cag gat tct gtc       759
Pro Glu Phe Glu Asn Val Phe Val Val Thr Asp Phe Gln Asp Ser Val
 90                  95                 100                 105 ttt aat gac ctc tac aag gct gat tgt aga gtt att gga cca cca gtt       807
Phe Asn Asp Leu Tyr Lys Ala Asp Cys Arg Val Ile Gly Pro Pro Val
             110                 115                 120 gta tta aat tgt tca caa aaa gga gag cct ttg cca ttt tca tgt cgc       855
Val Leu Asn Cys Ser Gln Lys Gly Glu Pro Leu Pro Phe Ser Cys Arg
         125                 130                 135 ccg ttg tat tgt aca agt atg atg aat cta gta cta tgc ttt act gga       903
Pro Leu Tyr Cys Thr Ser Met Met Asn Leu Val Leu Cys Phe Thr Gly
     140                 145                 150 ttt agg aaa aaa gaa gaa cta gtc agg ttg gtg aca ttg gtc cat cac       951
Phe Arg Lys Lys Glu Glu Leu Val Arg Leu Val Thr Leu Val His His
 155                 160                 165 atg ggt gga gtt att cga aaa gac ttt aat tca aaa gtt aca cat ttg       999
Met Gly Gly Val Ile Arg Lys Asp Phe Asn Ser Lys Val Thr His Leu
170                 175                 180                 185 gtg gca aat tgt aca caa gga gaa aaa ttc agg gtt gct gtg agt cta      1047
Val Ala Asn Cys Thr Gln Gly Glu Lys Phe Arg Val Ala Val Ser Leu
             190                 195                 200 ggt act cca att atg aag cca gaa tgg att tat aaa gct tgg gaa agg      1095
Gly Thr Pro Ile Met Lys Pro Glu Trp Ile Tyr Lys Ala Trp Glu Arg
         205                 210                 215 cgg aat gaa cag gat ttc tat gca gca gtt gat gac ttt aga aat gaa      1143
Arg Asn Glu Gln Asp Phe Tyr Ala Ala Val Asp Asp Phe Arg Asn Glu
     220                 225                 230 ttt aaa gtt cct cca ttt caa gat tgt att tta agt ttc ctg gga ttt      1191
Phe Lys Val Pro Pro Phe Gln Asp Cys Ile Leu Ser Phe Leu Gly Phe
 235                 240                 245 tca gat gaa gag aaa acc aat atg gaa gaa atg act gaa atg caa gga      1239
```

```
                                                                  -continued Ser Asp Glu Glu Lys Thr Asn Met Glu Glu Met Thr Glu Met Gln Gly
250             255                 260                 265 ggt aaa tat tta ccg ctt gga gat gaa aga tgc act cac ctt gta gtt      1287
Gly Lys Tyr Leu Pro Leu Gly Asp Glu Arg Cys Thr His Leu Val Val
                270                 275                 280 gaa gag aat ata gta aaa gat ctt ccc ttt gaa cct tca aag aaa ctt      1335
Glu Glu Asn Ile Val Lys Asp Leu Pro Phe Glu Pro Ser Lys Lys Leu
            285                 290                 295 tat gtt gtc aag caa gag tgg ttc tgg gga agc att caa atg gat gcc      1383
Tyr Val Val Lys Gln Glu Trp Phe Trp Gly Ser Ile Gln Met Asp Ala
        300                 305                 310 cga gct gga gaa act atg tat tta tat gaa aag gca aat act cct gag      1431
Arg Ala Gly Glu Thr Met Tyr Leu Tyr Glu Lys Ala Asn Thr Pro Glu
    315                 320                 325 ctc aag aaa tca gtg tca atg ctt tct cta aat acc cct aac agc aat      1479
Leu Lys Lys Ser Val Ser Met Leu Ser Leu Asn Thr Pro Asn Ser Asn
330                 335                 340                 345 cgc aaa cga cgt cgt tta aaa gaa aca ctt gct cag ctt tca aga gag      1527
Arg Lys Arg Arg Arg Leu Lys Glu Thr Leu Ala Gln Leu Ser Arg Glu
                350                 355                 360 aca gac gtg tca cca ttt cca ccc cgt aag cgc cca tca gct gag cat      1575
Thr Asp Val Ser Pro Phe Pro Pro Arg Lys Arg Pro Ser Ala Glu His
                365                 370                 375 tcc ctt tcc ata ggg tca ctc cta gat atc tcc aac aca cca gag tct      1623
Ser Leu Ser Ile Gly Ser Leu Leu Asp Ile Ser Asn Thr Pro Glu Ser
            380                 385                 390 agc att aac tat gga gac acc cca aag tct tgt act aag tct tct aaa      1671
Ser Ile Asn Tyr Gly Asp Thr Pro Lys Ser Cys Thr Lys Ser Ser Lys
        395                 400                 405 agc tcc act cca gtt cct tca aag cag tca gca agg tgg caa gtt gca      1719
Ser Ser Thr Pro Val Pro Ser Lys Gln Ser Ala Arg Trp Gln Val Ala
410                 415                 420                 425 aaa gag ctt tat caa act gaa agt aat tat gtt aat ata ttg gca aca      1767
Lys Glu Leu Tyr Gln Thr Glu Ser Asn Tyr Val Asn Ile Leu Ala Thr
                430                 435                 440 att att cag tta ttt caa gta cca ttg gaa gag gaa gga caa cgt ggt      1815
Ile Ile Gln Leu Phe Gln Val Pro Leu Glu Glu Glu Gly Gln Arg Gly
                445                 450                 455 gga cct atc ctt gca cca gag gag att aag act att ttt ggt agc atc      1863
Gly Pro Ile Leu Ala Pro Glu Glu Ile Lys Thr Ile Phe Gly Ser Ile
            460                 465                 470 cca gat atc ttt gat gta cac act aag ata aag gat gat ctt gaa gac      1911
Pro Asp Ile Phe Asp Val His Thr Lys Ile Lys Asp Asp Leu Glu Asp
475                 480                 485 ctt ata gtt aat tgg gat gag agc aaa agc att ggt gac att ttt ctg      1959
Leu Ile Val Asn Trp Asp Glu Ser Lys Ser Ile Gly Asp Ile Phe Leu
            490                 495                 500                 505 aaa tat tca aaa gat ttg gta aaa acc tac cct ccc ttt gta aac ttc      2007
Lys Tyr Ser Lys Asp Leu Val Lys Thr Tyr Pro Pro Phe Val Asn Phe
                510                 515                 520 ttt gaa atg agc aag gaa aca att att aaa tgt gaa aaa cag aaa cca      2055
Phe Glu Met Ser Lys Glu Thr Ile Ile Lys Cys Glu Lys Gln Lys Pro
                525                 530                 535 aga ttt cat gct ttt ctc aag ata aac caa gca aaa cca gaa tgt gga      2103
Arg Phe His Ala Phe Leu Lys Ile Asn Gln Ala Lys Pro Glu Cys Gly
            540                 545                 550 cgg cag agc ctt gtt gaa ctt ctt atc cga cca gta cag agg tta ccc      2151
Arg Gln Ser Leu Val Glu Leu Leu Ile Arg Pro Val Gln Arg Leu Pro
555                 560                 565 agt gtt gca tta ctt tta aat gat ctt aag aag cat aca gct gat gaa      2199
```

-continued

```
Ser Val Ala Leu Leu Leu Asn Asp Leu Lys Lys His Thr Ala Asp Glu
570             575                 580                 585 aat cca gac aaa agc act tta gaa aaa gct att gga tca ctg aag gaa    2247
Asn Pro Asp Lys Ser Thr Leu Glu Lys Ala Ile Gly Ser Leu Lys Glu
            590                 595                 600 gta atg acg cat att aat gag gat aag aga aaa aca gaa gct caa aag    2295
Val Met Thr His Ile Asn Glu Asp Lys Arg Lys Thr Glu Ala Gln Lys
            605                 610                 615 caa att ttt gat gtt gtt tat gaa gta gat gga tgc cca gct aat ctt    2343
Gln Ile Phe Asp Val Val Tyr Glu Val Asp Gly Cys Pro Ala Asn Leu
            620                 625                 630 tta tct tct cac cga agc tta gta cag cgg gtt gaa aca att tct cta    2391
Leu Ser Ser His Arg Ser Leu Val Gln Arg Val Glu Thr Ile Ser Leu
635                 640                 645 ggt gag cac ccc tgt gac aga gga gaa caa gta act ctc ttc ctc ttc    2439
Gly Glu His Pro Cys Asp Arg Gly Glu Gln Val Thr Leu Phe Leu Phe
650                 655                 660                 665 aat gat tgc cta gag ata gca aga aaa cgg cac aag gtt att ggc act    2487
Asn Asp Cys Leu Glu Ile Ala Arg Lys Arg His Lys Val Ile Gly Thr
            670                 675                 680 ttt agg agt cct cat ggc caa acc cga ccc cca gct tct ctt aag cat    2535
Phe Arg Ser Pro His Gly Gln Thr Arg Pro Pro Ala Ser Leu Lys His
            685                 690                 695 att cac cta atg cct ctt tct cag att aag aag gta ttg gac ata aga    2583
Ile His Leu Met Pro Leu Ser Gln Ile Lys Lys Val Leu Asp Ile Arg
            700                 705                 710 gag aca gaa gat tgc cat aat gct ttt gcc ttg ctt gtg agg cca cca    2631
Glu Thr Glu Asp Cys His Asn Ala Phe Ala Leu Leu Val Arg Pro Pro
715                 720                 725 aca gag cag gca aat gtg cta ctc agt ttc cag atg aca tca gat gaa    2679
Thr Glu Gln Ala Asn Val Leu Leu Ser Phe Gln Met Thr Ser Asp Glu
730                 735                 740                 745 ctt cca aaa gaa aac tgg cta aag atg ctg tgt cga cat gta gct aac    2727
Leu Pro Lys Glu Asn Trp Leu Lys Met Leu Cys Arg His Val Ala Asn
            750                 755                 760 acc att tgt aaa gca gat gct gag aat ctt att tat act gct gat cca    2775
Thr Ile Cys Lys Ala Asp Ala Glu Asn Leu Ile Tyr Thr Ala Asp Pro
            765                 770                 775 gaa tcc ttt gaa gta aat aca aaa gat atg gac agt aca ttg agt aga    2823
Glu Ser Phe Glu Val Asn Thr Lys Asp Met Asp Ser Thr Leu Ser Arg
            780                 785                 790 gca tca aga gca ata aaa aag act tca aaa aag gtt aca aga gca ttc    2871
Ala Ser Arg Ala Ile Lys Lys Thr Ser Lys Lys Val Thr Arg Ala Phe
795                 800                 805 tct ttc tcc aaa act cca aaa aga gct ctt cga agg gct ctt atg aca    2919
Ser Phe Ser Lys Thr Pro Lys Arg Ala Leu Arg Arg Ala Leu Met Thr
810                 815                 820                 825 tcc cac ggc tca gtg gag gga aga agt cct tcc agc aat gat aag cat    2967
Ser His Gly Ser Val Glu Gly Arg Ser Pro Ser Ser Asn Asp Lys His
            830                 835                 840 gta atg agt cgt ctt tct agc aca tca tca tta gca ggt atc cct tct    3015
Val Met Ser Arg Leu Ser Ser Thr Ser Ser Leu Ala Gly Ile Pro Ser
            845                 850                 855 ccc tcc ctt gtc agc ctt cct tcc ttc ttt gaa agg aga agt cat acg    3063
Pro Ser Leu Val Ser Leu Pro Ser Phe Phe Glu Arg Arg Ser His Thr
            860                 865                 870 tta agt aga tct aca act cat ttg ata tga agcgttacca aaatcttaaa      3113
Leu Ser Arg Ser Thr Thr His Leu Ile
            875                 880 ttatagaaat gtatagacac ctcatactca aataagaaac tgacttaaat ggtacttgta   3173
```

-continued

```
attagcacgt tggtgaaagc tggaaggaag ataaataaca ctaaactatg ctatttgatt   3233
tttcttcttg aaagagtaag gtttacctgt tacattttca agttaattca tgtaaaaaat   3293
gatagtgatt ttgatgtaat ttatctcttg tttgaatctg tcattcaaag gccaataatt   3353
taagttgcta tcagctgata ttagtagctt tgcaaccctg atagagtaaa taaattttat   3413
gggtgggtgc caaatactgc tgtgaatcta tttgtatagt atccatgaat gaatttatgg   3473
aaatagatat ttgtgcagct caatttatgc agagattaaa tgacatcata atactggatg   3533
aaaacttgca tagaattctg attaaatagt gggtctgttt cacatgtgca gtttgaagta   3593
tttaaataac cactcctttc acagtttatt ttcttctcaa gcgttttcaa gatctagcat   3653
gtggatttta aaagatttgc cctcattaac aagaataaca tttaaaggag attgtttcaa   3713 aatattttg caaattgaga taaggacaga agattgaga acattgtat attttgcaaa     3773 aacaagatgt ttgtagctgt ttcagagaga gtacggtata tttatggtaa ttttatccac   3833
tagcaaatct tgatttagtt tgatagtcgt cgtcggaatt ttattttgaa ggataagacc   3893
atgggaaaat tgtggtaaag actgtttgta cccttcatga ataattctg aagttgccat    3953 cagttttact aatcttctgt gaatgcata gatatgcgca tgttcaactt tttattgtgg    4013
tcttataatt aaatgtaaaa ttgaaaattc atttgctgtt tcaaagtgtg atatctttca   4073
caatagcctt tttatagtca gtaattcaga ataatcaagt tcatatggat aaatgcatt    4133 ttatttccta tttctttagg gagtgctaca aatgtttgtc acttaaattt caagtttctg   4193
ttttaatagt taactgacta tagattgttt tctatgccat gtatgtgcca cttctgagag   4253
tagtaaatga ctctttgcta cattttaaaa gcaattgtat tagtaagaac tttgtaaata   4313 aataccctaaa acccaagtgt aaaaaaaaaa aaaaaa                            4349
```

<210> SEQ ID NO 31
<211> LENGTH: 882
<212> TYPE: PRT
<213> ORGANISM: Homo sapiens

<400> SEQUENCE: 31

```
Met Ala Glu Asn Ser Val Leu Thr Ser Thr Thr Gly Arg Thr Ser Leu
1               5                   10                  15

Ala Asp Ser Ser Ile Phe Asp Ser Lys Val Thr Glu Ile Ser Lys Glu
            20                  25                  30

Asn Leu Leu Ile Gly Ser Thr Ser Tyr Val Glu Glu Met Pro Gln Ile
        35                  40                  45

Glu Thr Arg Val Ile Leu Val Gln Glu Ala Gly Lys Gln Glu Glu Leu
    50                  55                  60

Ile Lys Ala Leu Lys Asp Ile Lys Val Gly Phe Val Lys Met Glu Ser
65                  70                  75                  80

Val Glu Glu Phe Glu Gly Leu Asp Ser Pro Glu Phe Glu Asn Val Phe
                85                  90                  95

Val Val Thr Asp Phe Gln Asp Ser Val Phe Asn Asp Leu Tyr Lys Ala
            100                 105                 110

Asp Cys Arg Val Ile Gly Pro Pro Val Val Leu Asn Cys Ser Gln Lys
        115                 120                 125

Gly Glu Pro Leu Pro Phe Ser Cys Arg Pro Leu Tyr Cys Thr Ser Met
    130                 135                 140

Met Asn Leu Val Leu Cys Phe Thr Gly Phe Arg Lys Lys Glu Glu Leu
145                 150                 155                 160

Val Arg Leu Val Thr Leu Val His His Met Gly Gly Val Ile Arg Lys
```

```
                        165                 170                 175
Asp Phe Asn Ser Lys Val Thr His Leu Val Ala Asn Cys Thr Gln Gly
                180                 185                 190

Glu Lys Phe Arg Val Ala Val Ser Leu Gly Thr Pro Ile Met Lys Pro
            195                 200                 205

Glu Trp Ile Tyr Lys Ala Trp Glu Arg Arg Asn Glu Gln Asp Phe Tyr
            210                 215                 220

Ala Ala Val Asp Asp Phe Arg Asn Glu Phe Lys Val Pro Pro Phe Gln
225                 230                 235                 240

Asp Cys Ile Leu Ser Phe Leu Gly Phe Ser Asp Glu Glu Lys Thr Asn
                245                 250                 255

Met Glu Glu Met Thr Glu Met Gln Gly Gly Lys Tyr Leu Pro Leu Gly
                260                 265                 270

Asp Glu Arg Cys Thr His Leu Val Val Glu Glu Asn Ile Val Lys Asp
                275                 280                 285

Leu Pro Phe Glu Pro Ser Lys Lys Leu Tyr Val Val Lys Gln Glu Trp
            290                 295                 300

Phe Trp Gly Ser Ile Gln Met Asp Ala Arg Ala Gly Glu Thr Met Tyr
305                 310                 315                 320

Leu Tyr Glu Lys Ala Asn Thr Pro Glu Leu Lys Lys Ser Val Ser Met
                325                 330                 335

Leu Ser Leu Asn Thr Pro Asn Ser Asn Arg Lys Arg Arg Arg Leu Lys
                340                 345                 350

Glu Thr Leu Ala Gln Leu Ser Arg Glu Thr Asp Val Ser Pro Phe Pro
            355                 360                 365

Pro Arg Lys Arg Pro Ser Ala Glu His Ser Leu Ser Ile Gly Ser Leu
370                 375                 380

Leu Asp Ile Ser Asn Thr Pro Glu Ser Ser Ile Asn Tyr Gly Asp Thr
385                 390                 395                 400

Pro Lys Ser Cys Thr Lys Ser Ser Lys Ser Ser Thr Pro Val Pro Ser
                405                 410                 415

Lys Gln Ser Ala Arg Trp Gln Val Ala Lys Glu Leu Tyr Gln Thr Glu
                420                 425                 430

Ser Asn Tyr Val Asn Ile Leu Ala Thr Ile Ile Gln Leu Phe Gln Val
            435                 440                 445

Pro Leu Glu Glu Glu Gly Gln Arg Gly Pro Ile Leu Ala Pro Glu
            450                 455                 460

Glu Ile Lys Thr Ile Phe Gly Ser Ile Pro Asp Ile Phe Asp Val His
465                 470                 475                 480

Thr Lys Ile Lys Asp Asp Leu Glu Asp Leu Ile Val Asn Trp Asp Glu
                485                 490                 495

Ser Lys Ser Ile Gly Asp Ile Phe Leu Lys Tyr Ser Lys Asp Leu Val
            500                 505                 510

Lys Thr Tyr Pro Pro Phe Val Asn Phe Phe Glu Met Ser Lys Glu Thr
            515                 520                 525

Ile Ile Lys Cys Glu Lys Gln Lys Pro Arg Phe His Ala Phe Leu Lys
            530                 535                 540

Ile Asn Gln Ala Lys Pro Glu Cys Gly Arg Gln Ser Leu Val Glu Leu
545                 550                 555                 560

Leu Ile Arg Pro Val Gln Arg Leu Pro Ser Val Ala Leu Leu Leu Asn
                565                 570                 575

Asp Leu Lys Lys His Thr Ala Asp Glu Asn Pro Asp Lys Ser Thr Leu
                580                 585                 590
```

```
Glu Lys Ala Ile Gly Ser Leu Lys Glu Val Met Thr His Ile Asn Glu
        595                 600                 605
Asp Lys Arg Lys Thr Glu Ala Gln Lys Gln Ile Phe Asp Val Val Tyr
610                 615                 620
Glu Val Asp Gly Cys Pro Ala Asn Leu Leu Ser Ser His Arg Ser Leu
625                 630                 635                 640
Val Gln Arg Val Glu Thr Ile Ser Leu Gly Glu His Pro Cys Asp Arg
                645                 650                 655
Gly Glu Gln Val Thr Leu Phe Leu Phe Asn Asp Cys Leu Glu Ile Ala
            660                 665                 670
Arg Lys Arg His Lys Val Ile Gly Thr Phe Arg Ser Pro His Gly Gln
        675                 680                 685
Thr Arg Pro Pro Ala Ser Leu Lys His Ile His Leu Met Pro Leu Ser
690                 695                 700
Gln Ile Lys Lys Val Leu Asp Ile Arg Glu Thr Glu Asp Cys His Asn
705                 710                 715                 720
Ala Phe Ala Leu Leu Val Arg Pro Pro Thr Glu Gln Ala Asn Val Leu
                725                 730                 735
Leu Ser Phe Gln Met Thr Ser Asp Glu Leu Pro Lys Glu Asn Trp Leu
            740                 745                 750
Lys Met Leu Cys Arg His Val Ala Asn Thr Ile Cys Lys Ala Asp Ala
        755                 760                 765
Glu Asn Leu Ile Tyr Thr Ala Asp Pro Glu Ser Phe Glu Val Asn Thr
770                 775                 780
Lys Asp Met Asp Ser Thr Leu Ser Arg Ala Ser Arg Ala Ile Lys Lys
785                 790                 795                 800
Thr Ser Lys Lys Val Thr Arg Ala Phe Ser Phe Ser Lys Thr Pro Lys
                805                 810                 815
Arg Ala Leu Arg Arg Ala Leu Met Thr Ser His Gly Ser Val Glu Gly
            820                 825                 830
Arg Ser Pro Ser Ser Asn Asp Lys His Val Met Ser Arg Leu Ser Ser
        835                 840                 845
Thr Ser Ser Leu Ala Gly Ile Pro Ser Pro Ser Leu Val Ser Leu Pro
850                 855                 860
Ser Phe Phe Glu Arg Arg Ser His Thr Leu Ser Arg Ser Thr Thr His
865                 870                 875                 880
Leu Ile

<210> SEQ ID NO 32
<211> LENGTH: 1871
<212> TYPE: DNA
<213> ORGANISM: Homo sapiens
<220> FEATURE:
<221> NAME/KEY: CDS
<222> LOCATION: (31)..(1731)

<400> SEQUENCE: 32
gcgagcgcca ggcgtccggc cgccgtggct atg ttc gtg tcc gat ttc cgc aaa        54
                                Met Phe Val Ser Asp Phe Arg Lys
                                  1               5 gag ttc tac gag gtg gtc cag agc cag agg gtc ctt ctc ttc gtg gcc       102
Glu Phe Tyr Glu Val Val Gln Ser Gln Arg Val Leu Leu Phe Val Ala
        10                  15                  20 tcg gac gtg gat gct ctg tgt gcg tgc aag atc ctt cag gcc ttg ttc       150
Ser Asp Val Asp Ala Leu Cys Ala Cys Lys Ile Leu Gln Ala Leu Phe
25                  30                  35                  40 cag tgt gac cac gtg caa tat acg ctg gtt cca gtt tct ggg tgg caa       198
```

-continued

| | | | | | | | | | | | | |
|---|---|---|---|---|---|---|---|---|---|---|---|---|
| Gln | Cys | Asp | His | Val | Gln | Tyr | Thr | Leu | Val | Pro | Val | Ser | Gly | Trp | Gln |
| | | | 45 | | | | 50 | | | | 55 | |

```
gaa ctt gaa act gca ttt ctt gag cat aaa gaa cag ttt cat tat ttt      246
Glu Leu Glu Thr Ala Phe Leu Glu His Lys Glu Gln Phe His Tyr Phe
            60              65              70 att ctc ata aac tgt gga gct aat gta gac cta ttg gat att ctt caa      294
Ile Leu Ile Asn Cys Gly Ala Asn Val Asp Leu Leu Asp Ile Leu Gln
    75              80              85 cct gat gaa gac act ata ttc ttt gtg tgt gac acc cat agg cca gtc      342
Pro Asp Glu Asp Thr Ile Phe Phe Val Cys Asp Thr His Arg Pro Val
    90              95              100 aat gtc gtc aat gta tac aac gat acc cag gtc aaa tta ctc att aaa      390
Asn Val Val Asn Val Tyr Asn Asp Thr Gln Val Lys Leu Leu Ile Lys
105         110             115             120 caa gat gat gac ctt gaa gtt ccc gcc tat gaa gac atc ttc agg gat      438
Gln Asp Asp Asp Leu Glu Val Pro Ala Tyr Glu Asp Ile Phe Arg Asp
                125             130             135 gaa gag gag gat gaa gag cat tca gga aat gac agt gat ggg tca gag      486
Glu Glu Glu Asp Glu Glu His Ser Gly Asn Asp Ser Asp Gly Ser Glu
            140             145             150 cct tct gag aag cgc aca cgg tta gaa gag gag ata gtg gag caa acc      534
Pro Ser Glu Lys Arg Thr Arg Leu Glu Glu Glu Ile Val Glu Gln Thr
        155             160             165 atg cgg agg agg cag cgg cga gag tgg gag gcc cgg aga aga gac atc      582
Met Arg Arg Arg Gln Arg Arg Glu Trp Glu Ala Arg Arg Arg Asp Ile
170             175             180 ctc ttt gac tac gag cag tat gaa tat cat ggg aca tcg tca gcc atg      630
Leu Phe Asp Tyr Glu Gln Tyr Glu Tyr His Gly Thr Ser Ser Ala Met
185             190             195             200 gtg atg ttt gag ctg gct tgg atg ctg tcc aag gac ctg aat gac atg      678
Val Met Phe Glu Leu Ala Trp Met Leu Ser Lys Asp Leu Asn Asp Met
            205             210             215 ctg tgg tgg gcc atc gtt gga cta aca gac cag tgg gtg caa gac aag      726
Leu Trp Trp Ala Ile Val Gly Leu Thr Asp Gln Trp Val Gln Asp Lys
        220             225             230 atc act caa atg aaa tac gtg act gat gtt ggt gtc ctg cag cgc cac      774
Ile Thr Gln Met Lys Tyr Val Thr Asp Val Gly Val Leu Gln Arg His
    235             240             245 gtt tcc cgc cac aac cac cgg aac gag gat gag gag aac aca ctc tcc      822
Val Ser Arg His Asn His Arg Asn Glu Asp Glu Glu Asn Thr Leu Ser
250             255             260 gtg gac tgc aca cgg atc tcc ttt gag tat gac ctc cgc ctg gtg ctc      870
Val Asp Cys Thr Arg Ile Ser Phe Glu Tyr Asp Leu Arg Leu Val Leu
265             270             275             280 tac cag cac tgg tcc ctc cat gac agc ctg tgc aac acc agc tat acc      918
Tyr Gln His Trp Ser Leu His Asp Ser Leu Cys Asn Thr Ser Tyr Thr
            285             290             295 gca gcc agg ttc aag ctg tgg tct gtg cat gga cag aag cgg ctc cag      966
Ala Ala Arg Phe Lys Leu Trp Ser Val His Gly Gln Lys Arg Leu Gln
        300             305             310 gag ttc ctt gca gac atg ggt ctt ccc ctg aag cag gtg aag cag aag     1014
Glu Phe Leu Ala Asp Met Gly Leu Pro Leu Lys Gln Val Lys Gln Lys
    315             320             325 ttc cag gcc atg gac atc tcc ttg aag gag aat ttg cgg gaa atg att     1062
Phe Gln Ala Met Asp Ile Ser Leu Lys Glu Asn Leu Arg Glu Met Ile
330             335             340 gaa gaa tct gca aat aaa ttt ggg atg aag gac atg cgc gtg cag act     1110
Glu Glu Ser Ala Asn Lys Phe Gly Met Lys Asp Met Arg Val Gln Thr
345             350             355             360 ttc agc att cat ttt ggg ttc aag cac aag ttt ctg gcc agc gac gtg     1158
```

```
Phe Ser Ile His Phe Gly Phe Lys His Lys Phe Leu Ala Ser Asp Val
            365                 370                 375 gtc ttt gcc acc atg tct ttg atg gag agc ccc gag aag gat ggc tca    1206
Val Phe Ala Thr Met Ser Leu Met Glu Ser Pro Glu Lys Asp Gly Ser
            380                 385                 390 ggg aca gat cac ttc atc cag gct ctg gac agc ctc tcc agg agt aac    1254
Gly Thr Asp His Phe Ile Gln Ala Leu Asp Ser Leu Ser Arg Ser Asn
            395                 400                 405 ctg gac aag ctg tac cat ggc ctg gaa ctc gcc aag aag cag ctg cga    1302
Leu Asp Lys Leu Tyr His Gly Leu Glu Leu Ala Lys Lys Gln Leu Arg
        410                 415                 420 gcc acc cag cag acc att gcc agc tgc ctt tgc acc aac ctc gtc atc    1350
Ala Thr Gln Gln Thr Ile Ala Ser Cys Leu Cys Thr Asn Leu Val Ile
425                 430                 435                 440 tcc cag ggg cct ttc ctg tac tgc tct ctc atg gag ggc act cca gat    1398
Ser Gln Gly Pro Phe Leu Tyr Cys Ser Leu Met Glu Gly Thr Pro Asp
                445                 450                 455 gtc atg ctg ttc tct agg ccg gca tcc cta agc ctg ctc agc aaa cac    1446
Val Met Leu Phe Ser Arg Pro Ala Ser Leu Ser Leu Leu Ser Lys His
            460                 465                 470 ctg ctc aag tcc ttt gtg tgt tcg aca aag aac cgg cgc tgc aaa ctg    1494
Leu Leu Lys Ser Phe Val Cys Ser Thr Lys Asn Arg Arg Cys Lys Leu
            475                 480                 485 ctg ccc ctg gtg atg gct gcc ccc ctg agc atg gag cat ggc aca gtg    1542
Leu Pro Leu Val Met Ala Ala Pro Leu Ser Met Glu His Gly Thr Val
        490                 495                 500 acc gtg gtg ggc atc ccc cca gag acc gac agc tcg gac agg aag aac    1590
Thr Val Val Gly Ile Pro Pro Glu Thr Asp Ser Ser Asp Arg Lys Asn
505                 510                 515                 520 ttt ttt ggg agg gcg ttt gag aag gca gcg gaa agc acc agc tcc cgg    1638
Phe Phe Gly Arg Ala Phe Glu Lys Ala Ala Glu Ser Thr Ser Ser Arg
                525                 530                 535 atg ctg cac aac cat ttt gac ctc tca gta att gag ctg aaa gct gag    1686
Met Leu His Asn His Phe Asp Leu Ser Val Ile Glu Leu Lys Ala Glu
            540                 545                 550 gat cgg agc aag ttt ctg gac gca ctt att tcc ctc ctg tcc tag       1731
Asp Arg Ser Lys Phe Leu Asp Ala Leu Ile Ser Leu Leu Ser
            555                 560                 565 gaatttgatt cttccagaat gaccttctta tttatgtaac tggctttcat ttagattgta  1791
agttatggac atgatttgag atgtagaagc cattttttat taaataaaat gcttatttta  1851
gaaaaaaaaa aaaaaaaaaa                                              1871

<210> SEQ ID NO 33
<211> LENGTH: 566
<212> TYPE: PRT
<213> ORGANISM: Homo sapiens

<400> SEQUENCE: 33

Met Phe Val Ser Asp Phe Arg Lys Glu Phe Tyr Glu Val Val Gln Ser
1               5                   10                  15

Gln Arg Val Leu Leu Phe Val Ala Ser Asp Val Asp Ala Leu Cys Ala
            20                  25                  30

Cys Lys Ile Leu Gln Ala Leu Phe Gln Cys Asp His Val Gln Tyr Thr
        35                  40                  45

Leu Val Pro Val Ser Gly Trp Gln Glu Leu Glu Thr Ala Phe Leu Glu
    50                  55                  60

His Lys Glu Gln Phe His Tyr Phe Ile Leu Ile Asn Cys Gly Ala Asn
65                  70                  75                  80
```

```
Val Asp Leu Leu Asp Ile Leu Gln Pro Asp Glu Asp Thr Ile Phe Phe
            85                  90                  95

Val Cys Asp Thr His Arg Pro Val Asn Val Val Asn Val Tyr Asn Asp
            100                 105                 110

Thr Gln Val Lys Leu Leu Ile Lys Gln Asp Asp Asp Leu Glu Val Pro
            115                 120                 125

Ala Tyr Glu Asp Ile Phe Arg Asp Glu Glu Asp Glu Glu His Ser
    130                 135                 140

Gly Asn Asp Ser Asp Gly Ser Glu Pro Ser Glu Lys Arg Thr Arg Leu
145                 150                 155                 160

Glu Glu Glu Ile Val Glu Gln Thr Met Arg Arg Gln Arg Arg Glu
                165                 170                 175

Trp Glu Ala Arg Arg Arg Asp Ile Leu Phe Asp Tyr Glu Gln Tyr Glu
            180                 185                 190

Tyr His Gly Thr Ser Ser Ala Met Val Met Phe Glu Leu Ala Trp Met
    195                 200                 205

Leu Ser Lys Asp Leu Asn Asp Met Leu Trp Trp Ala Ile Val Gly Leu
    210                 215                 220

Thr Asp Gln Trp Val Gln Asp Lys Ile Thr Gln Met Lys Tyr Val Thr
225                 230                 235                 240

Asp Val Gly Val Leu Gln Arg His Val Ser Arg His Asn His Arg Asn
            245                 250                 255

Glu Asp Glu Glu Asn Thr Leu Ser Val Asp Cys Thr Arg Ile Ser Phe
            260                 265                 270

Glu Tyr Asp Leu Arg Leu Val Leu Tyr Gln His Trp Ser Leu His Asp
            275                 280                 285

Ser Leu Cys Asn Thr Ser Tyr Thr Ala Ala Arg Phe Lys Leu Trp Ser
    290                 295                 300

Val His Gly Gln Lys Arg Leu Gln Glu Phe Leu Ala Asp Met Gly Leu
305                 310                 315                 320

Pro Leu Lys Gln Val Lys Gln Lys Phe Gln Ala Met Asp Ile Ser Leu
            325                 330                 335

Lys Glu Asn Leu Arg Glu Met Ile Glu Glu Ser Ala Asn Lys Phe Gly
            340                 345                 350

Met Lys Asp Met Arg Val Gln Thr Phe Ser Ile His Phe Gly Phe Lys
            355                 360                 365

His Lys Phe Leu Ala Ser Asp Val Val Phe Ala Thr Met Ser Leu Met
    370                 375                 380

Glu Ser Pro Glu Lys Asp Gly Ser Gly Thr Asp His Phe Ile Gln Ala
385                 390                 395                 400

Leu Asp Ser Leu Ser Arg Ser Asn Leu Asp Lys Leu Tyr His Gly Leu
            405                 410                 415

Glu Leu Ala Lys Lys Gln Leu Arg Ala Thr Gln Gln Thr Ile Ala Ser
            420                 425                 430

Cys Leu Cys Thr Asn Leu Val Ile Ser Gln Gly Pro Phe Leu Tyr Cys
            435                 440                 445

Ser Leu Met Glu Gly Thr Pro Asp Val Met Leu Phe Ser Arg Pro Ala
    450                 455                 460

Ser Leu Ser Leu Leu Ser Lys His Leu Leu Lys Ser Phe Val Cys Ser
465                 470                 475                 480

Thr Lys Asn Arg Arg Cys Lys Leu Leu Pro Leu Val Met Ala Ala Pro
            485                 490                 495

Leu Ser Met Glu His Gly Thr Val Thr Val Val Gly Ile Pro Pro Glu
            500                 505                 510
```

```
Thr Asp Ser Ser Asp Arg Lys Asn Phe Phe Gly Arg Ala Phe Glu Lys
        515                 520                 525

Ala Ala Glu Ser Thr Ser Ser Arg Met Leu His Asn His Phe Asp Leu
    530                 535                 540

Ser Val Ile Glu Leu Lys Ala Glu Asp Arg Ser Lys Phe Leu Asp Ala
545                 550                 555                 560

Leu Ile Ser Leu Leu Ser
                565

<210> SEQ ID NO 34
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 34
cacaaccatt ttgacctctc agt                                              23

<210> SEQ ID NO 35
<211> LENGTH: 24
<212> TYPE: DNA
<213> ORGANISM: Artificial
<220> FEATURE:
<223> OTHER INFORMATION: An artificially synthesized primer sequence
      for RT-PCR

<400> SEQUENCE: 35
cctcaggtct tcactctttc ttct                                             24

<210> SEQ ID NO 36
<211> LENGTH: 24
<212> TYPE: DNA
<213> ORGANISM: Artificial
<220> FEATURE:
<223> OTHER INFORMATION: An artificially synthesized primer sequence
      for RT-PCR

<400> SEQUENCE: 36
tgccatgtac aatgtagtaa cagc                                             24

<210> SEQ ID NO 37
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 37
tagagaaccc catgccccdt a                                                21

<210> SEQ ID NO 38
<211> LENGTH: 25
<212> TYPE: DNA
<213> ORGANISM: Artificial
<220> FEATURE:
<223> OTHER INFORMATION: An artificially synthesized primer sequence
      for RT-PCR

<400> SEQUENCE: 38
tcagtaagaa agactggcta atggt                                            25

<210> SEQ ID NO 39
```

```
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 39
agccatttga tggagaagaa tg                                              22

<210> SEQ ID NO 40
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 40
tggatgaagg ggttcccgaa t                                               21

<210> SEQ ID NO 41
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 41
ccagtcttgg ctgaaatgtt tt                                              22

<210> SEQ ID NO 42
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 42
ctctctgaaa tgcaactgtt cgt                                             23

<210> SEQ ID NO 43
<211> LENGTH: 25
<212> TYPE: DNA
<213> ORGANISM: Artificial
<220> FEATURE:
<223> OTHER INFORMATION: An artificially synthesized primer sequence
      for RT-PCR

<400> SEQUENCE: 43
gaggaagaat tgcttttctc ttacc                                           25

<210> SEQ ID NO 44
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 44
ttttaaagtg catctgtgga gg                                              22

<210> SEQ ID NO 45
<211> LENGTH: 21
<212> TYPE: DNA
```

```
<213> ORGANISM: Artificial
<220> FEATURE:
<223> OTHER INFORMATION: An artificially synthesized primer sequence
      for RT-PCR

<400> SEQUENCE: 45
gtggtaacgt tcagcaaaag c                                              21

<210> SEQ ID NO 46
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 46
atggctcctt acctgagaga aac                                            23

<210> SEQ ID NO 47
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 47
gacagcaaag tcttgactcc ttc                                            23

<210> SEQ ID NO 48
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 48
aaagtggctg ggagtaaggt atc                                            23

<210> SEQ ID NO 49
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 49
agacaaagag agaaagagac gca                                            23

<210> SEQ ID NO 50
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 50
agaggatcct attgtcttgg agg                                            23

<210> SEQ ID NO 51
<211> LENGTH: 22
<212> TYPE: DNA
<213> ORGANISM: Artificial
<220> FEATURE:
```

<223> OTHER INFORMATION: An artificially synthesized primer sequence
      for RT-PCR

<400> SEQUENCE: 51
cagaatcgca ggatgaaaga ta                                         22

<210> SEQ ID NO 52
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 52
gtgactcatg ccttgatatg aca                                        23

<210> SEQ ID NO 53
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 53
tatctgtgat tgttgctcac ctg                                        23

<210> SEQ ID NO 54
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 54
gcccatcctt actttcctca tac                                        23

<210> SEQ ID NO 55
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 55
cttgaagaag aacttccaga cga                                        23

<210> SEQ ID NO 56
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 56
aatgttctaa agatgagagg ggg                                        23

<210> SEQ ID NO 57
<211> LENGTH: 23
<212> TYPE: DNA
<213> ORGANISM: Artificial
<220> FEATURE:
<223> OTHER INFORMATION: An artificially synthesized primer sequence
      for RT-PCR

```
<400> SEQUENCE: 57
gccttaaaac tggagagagg aat                                              23

<210> SEQ ID NO 58
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 58
tagcagagcg cacaaacatt ta                                               22

<210> SEQ ID NO 59
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 59
gtgcaccaaa acactgacat tt                                               22

<210> SEQ ID NO 60
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 60
ggctttgcaa ctttgtccat t                                                21

<210> SEQ ID NO 61
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 61
tctgaagcct gattactgtg tga                                              23

<210> SEQ ID NO 62
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 62
atgtgcactg gactgaaaca tct                                              23

<210> SEQ ID NO 63
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 63
```
tgtgtgagca tttgacaaga ct                                                22

<210> SEQ ID NO 64
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 64
aattttaaca gcaagtggtg gg                                                22

<210> SEQ ID NO 65
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 65
actgcaaatg ggagtgctta gta                                               23

<210> SEQ ID NO 66
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 66
ggagagggta tgagtccttt gat                                               23

<210> SEQ ID NO 67
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 67
cagctgtatc ccctaaacaa cc                                                22

<210> SEQ ID NO 68
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 68
ggtgaggtat cctgtcttca gag                                               23

<210> SEQ ID NO 69
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 69
tccagaattg cttgttacgt agg                                               23

```
<210> SEQ ID NO 70
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 70
ggttctcaga gctgttttgc tt                                              22

<210> SEQ ID NO 71
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 71
gtattaccga tgcctctgaa aag                                             23

<210> SEQ ID NO 72
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 72
tgaggtgtat ggcaagttga atc                                             23

<210> SEQ ID NO 73
<211> LENGTH: 24
<212> TYPE: DNA
<213> ORGANISM: Artificial
<220> FEATURE:
<223> OTHER INFORMATION: An artificially synthesized primer sequence
      for RT-PCR

<400> SEQUENCE: 73
tagagtctag aacgcaagga tctc                                            24

<210> SEQ ID NO 74
<211> LENGTH: 24
<212> TYPE: DNA
<213> ORGANISM: Artificial
<220> FEATURE:
<223> OTHER INFORMATION: An artificially synthesized primer sequence
      for RT-PCR

<400> SEQUENCE: 74
caaaaactat cacagcctaa aggg                                            24

<210> SEQ ID NO 75
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 75
attagaattc tggggctgta agg                                             23
```

<210> SEQ ID NO 76
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 76
ctaccctggg gtgttttcta aat                                          23

<210> SEQ ID NO 77
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 77
ggtgcataaa cactaatgca gtc                                          23

<210> SEQ ID NO 78
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 78
gttaaaagga gcacagggac ata                                          23

<210> SEQ ID NO 79
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 79
cacccataac caagagaact cag                                          23

<210> SEQ ID NO 80
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 80
gggatgtctg ttccttttat tcc                                          23

<210> SEQ ID NO 81
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 81
gtggccactg aatgtaaaac aac                                          23

<210> SEQ ID NO 82
<211> LENGTH: 23

```
<212> TYPE: DNA
<213> ORGANISM: Artificial
<220> FEATURE:
<223> OTHER INFORMATION: An artificially synthesized primer sequence
      for RT-PCR

<400> SEQUENCE: 82
agtaactctg tcttcatccg cag                                              23

<210> SEQ ID NO 83
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 83
gttttggccc aattaaccag ta                                               22

<210> SEQ ID NO 84
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 84
gcacttggaa ggggtattgt att                                              23

<210> SEQ ID NO 85
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 85
attcattctg gaccaaagat cc                                               22

<210> SEQ ID NO 86
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 86
tctactgtgg acaagaagcc tgt                                              23

<210> SEQ ID NO 87
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 87
agcagtcagg gacagacata cat                                              23

<210> SEQ ID NO 88
<211> LENGTH: 23
<212> TYPE: DNA
<213> ORGANISM: Artificial
```

```
<220> FEATURE:
<223> OTHER INFORMATION: An artificially synthesized primer sequence
      for RT-PCR

<400> SEQUENCE: 88
aaggtaaact ctaggcatcc gtc                                            23

<210> SEQ ID NO 89
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 89
aaagaggaac acactgggtg taa                                            23

<210> SEQ ID NO 90
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 90
aggagcctag agaagcaatc atc                                            23

<210> SEQ ID NO 91
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 91
tcttcagcat gatgtgttgt gt                                             22

<210> SEQ ID NO 92
<211> LENGTH: 24
<212> TYPE: DNA
<213> ORGANISM: Artificial
<220> FEATURE:
<223> OTHER INFORMATION: An artificially synthesized primer sequence
      for RT-PCR

<400> SEQUENCE: 92
tgagagattc atgaggaagt cttg                                           24

<210> SEQ ID NO 93
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 93
aggtgtactg agtggggaag aat                                            23

<210> SEQ ID NO 94
<211> LENGTH: 23
<212> TYPE: DNA
<213> ORGANISM: Artificial
<220> FEATURE:
<223> OTHER INFORMATION: An artificially synthesized primer sequence
``` for RT-PCR

<400> SEQUENCE: 94
ctggcataac agtggcttaa gtt                                              23

<210> SEQ ID NO 95
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 95
gctccttctc tcatggatta cct                                              23

<210> SEQ ID NO 96
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 96
caagtgggta aaatgctgtc ttc                                              23

<210> SEQ ID NO 97
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 97
acaagtgcga agtctggtaa g                                                21

<210> SEQ ID NO 98
<211> LENGTH: 22
<212> TYPE: DNA
<213> ORGANISM: Artificial
<220> FEATURE:
<223> OTHER INFORMATION: An artificially synthesized primer sequence
      for RT-PCR

<400> SEQUENCE: 98
acagtggtat ttgtggcgta tc                                               22

<210> SEQ ID NO 99
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 99
ccaaaagcta agcagtggtg aac                                              23

<210> SEQ ID NO 100
<211> LENGTH: 22
<212> TYPE: DNA
<213> ORGANISM: Artificial
<220> FEATURE:
<223> OTHER INFORMATION: An artificially synthesized primer sequence
      for RT-PCR

```
<400> SEQUENCE: 100
ctgtgcaaca gttcccaaaa tg                                            22

<210> SEQ ID NO 101
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 101
ttgacaagct gtagaactgg att                                           23

<210> SEQ ID NO 102
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 102
aaagttggaa tgccgatgac a                                             21

<210> SEQ ID NO 103
<211> LENGTH: 20
<212> TYPE: DNA
<213> ORGANISM: Artificial
<220> FEATURE:
<223> OTHER INFORMATION: An artificially synthesized primer sequence
      for RT-PCR

<400> SEQUENCE: 103
cagcctcaat ggatactggc                                               20

<210> SEQ ID NO 104
<211> LENGTH: 24
<212> TYPE: DNA
<213> ORGANISM: Artificial
<220> FEATURE:
<223> OTHER INFORMATION: An artificially synthesized primer sequence
      for RT-PCR

<400> SEQUENCE: 104
gctagaaagc aaactcatgc tctg                                          24

<210> SEQ ID NO 105
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 105
gaggtgatag cattgctttc g                                             21

<210> SEQ ID NO 106
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 106
```

```
caagtcagtg tacaggtaag c                                              21
```

<210> SEQ ID NO 107
<211> LENGTH: 21
<212> TYPE: DNA
<213> ORGANISM: Artificial
<220> FEATURE:
<223> OTHER INFORMATION: An artificially synthesized primer sequence
      for RT-PCR

<400> SEQUENCE: 107

```
tatggtctcc gtgcctacca c                                              21
```

<210> SEQ ID NO 108
<211> LENGTH: 23
<212> TYPE: DNA
<213> ORGANISM: Artificial
<220> FEATURE:
<223> OTHER INFORMATION: An artificially synthesized primer sequence
      for RT-PCR

<400> SEQUENCE: 108

```
atacagacag gaaaagcaga gca                                            23
```

<210> SEQ ID NO 109
<211> LENGTH: 1815
<212> TYPE: DNA
<213> ORGANISM: Homo sapiens
<220> FEATURE:
<221> NAME/KEY: CDS
<222> LOCATION: (155)..(955)

<400> SEQUENCE: 109

```
gcagagctct gtgctccctg cagtcaggac tctgggaccg caggggggctc ccggaccctg    60 actctgcagc cgaaccggca cggtttcgtg gggacccagg cttgcaaagt gacggtcatt   120
ttctctttct ttctccctct tgagtccttc tgag atg atg gct ctg ggc gca gcg   175
                                    Met Met Ala Leu Gly Ala Ala
                                     1               5 gga gct acc cgg gtc ttt gtc gcg atg gta gcg gcg gct ctc ggc ggc     223
Gly Ala Thr Arg Val Phe Val Ala Met Val Ala Ala Ala Leu Gly Gly
         10                  15                  20 cac cct ctg ctg gga gtg agc gcc acc ttg aac tcg gtt ctc aat tcc     271
His Pro Leu Leu Gly Val Ser Ala Thr Leu Asn Ser Val Leu Asn Ser
 25                  30                  35 aac gct atc aag aac ctg ccc cca ccg ctg ggc ggc gct gcg ggg cac     319
Asn Ala Ile Lys Asn Leu Pro Pro Pro Leu Gly Gly Ala Ala Gly His
 40                  45                  50                  55 cca ggc tct gca gtc agc gcc gcg ccg gga atc ctg tac ccg ggc ggg     367
Pro Gly Ser Ala Val Ser Ala Ala Pro Gly Ile Leu Tyr Pro Gly Gly
                 60                  65                  70 aat aag tac cag acc att gac aac tac cag ccg tac ccg tgc gca gag     415
Asn Lys Tyr Gln Thr Ile Asp Asn Tyr Gln Pro Tyr Pro Cys Ala Glu
             75                  80                  85 gac gag gag tgc ggc act gat gag tac tgc gct agt ccc acc cgc gga     463
Asp Glu Glu Cys Gly Thr Asp Glu Tyr Cys Ala Ser Pro Thr Arg Gly
         90                  95                 100 ggg gac gca ggc gtg caa atc tgt ctc gcc tgc agg aag cgc cga aaa     511
Gly Asp Ala Gly Val Gln Ile Cys Leu Ala Cys Arg Lys Arg Arg Lys
105                 110                 115 cgc tgc atg cgt cac gct atg tgc tgc ccc ggg aat tac tgc aaa aat     559
Arg Cys Met Arg His Ala Met Cys Cys Pro Gly Asn Tyr Cys Lys Asn
120                 125                 130                 135 gga ata tgt gtg tct tct gat caa aat cat ttc cga gga gaa att gag     607
```

```
                Gly Ile Cys Val Ser Ser Asp Gln Asn His Phe Arg Gly Glu Ile Glu
                                140                 145                 150 gaa acc atc act gaa agc ttt ggt aat gat cat agc acc ttg gat ggg        655
Glu Thr Ile Thr Glu Ser Phe Gly Asn Asp His Ser Thr Leu Asp Gly
            155                 160                 165 tat tcc aga aga acc acc ttg tct tca aaa atg tat cac acc aaa gga        703
Tyr Ser Arg Arg Thr Thr Leu Ser Ser Lys Met Tyr His Thr Lys Gly
        170                 175                 180 caa gaa ggt tct gtt tgt ctc cgg tca tca gac tgt gcc tca gga ttg        751
Gln Glu Gly Ser Val Cys Leu Arg Ser Ser Asp Cys Ala Ser Gly Leu
    185                 190                 195 tgt tgt gct aga cac ttc tgg tcc aag atc tgt aaa cct gtc ctg aaa        799
Cys Cys Ala Arg His Phe Trp Ser Lys Ile Cys Lys Pro Val Leu Lys
200                 205                 210                 215 gaa ggt caa gtg tgt acc aag cat agg aga aaa ggc tct cat gga cta        847
Glu Gly Gln Val Cys Thr Lys His Arg Arg Lys Gly Ser His Gly Leu
                220                 225                 230 gaa ata ttc cag cgt tgt tac tgt gga gaa ggt ctg tct tgc cgg ata        895
Glu Ile Phe Gln Arg Cys Tyr Cys Gly Glu Gly Leu Ser Cys Arg Ile
            235                 240                 245 cag aaa gat cac cat caa gcc agt aat tct tct agg ctt cac act tgt        943
Gln Lys Asp His His Gln Ala Ser Asn Ser Ser Arg Leu His Thr Cys
        250                 255                 260 cag aga cac taa accagctatc caaatgcagt gaactccttt tatataatag            995
Gln Arg His
    265 atgctatgaa aaccttttat gaccttcatc aactcaatcc taaggatata caagttctgt     1055 ggtttcagtt aagcattcca ataacacctt ccaaaaacct ggagtgtaag agctttgttt     1115 ctttatggaa ctcccctgtg attgcagtaa attactgtat tgtaaattct cagtgtggca     1175 cttacctgta aatgcaatga aacttttaat tattttttcta aaggtgctgc actgcctatt    1235 tttcctcttg ttatgtaaat ttttgtacac attgattgtt atcttgactg acaaatattc     1295 tatattgaac tgaagtaaat catttcagct tatagttctt aaaagcataa ccctttaccc     1355 catttaattc tagagtctag aacgcaagga tctcttggaa tgacaaatga taggtaccta     1415 aaatgtaaca tgaaaatact agcttatttt ctgaaatgta ctatcttaat gcttaaatta     1475 tatttccctt taggctgtga tagttttttga aataaaattt aacatttaat atcatgaaat    1535 gttataagta gacatacatt ttgggattgt gatcttagag gtttgtgtgt gtgtacgtat     1595 gtgtgtgttc tacaagaacg gaagtgtgat atgtttaaag atgatcagag aaaagacagt     1655 gtctaaatat aagacaatat tgatcagctc tagaataact ttaaagaaag acgtgttctg     1715 cattgataaa ctcaaatgat catggcagaa tgagagtgaa tcttacatta ctactttcaa     1775 aaatagtttc caataaatta ataataccta aaaaaaaaa                            1815

<210> SEQ ID NO 110
<211> LENGTH: 266
<212> TYPE: PRT
<213> ORGANISM: Homo sapiens

<400> SEQUENCE: 110

Met Met Ala Leu Gly Ala Ala Gly Ala Thr Arg Val Phe Val Ala Met
1               5                   10                  15

Val Ala Ala Ala Leu Gly Gly His Pro Leu Leu Gly Val Ser Ala Thr
                20                  25                  30

Leu Asn Ser Val Leu Asn Ser Asn Ala Ile Lys Asn Leu Pro Pro Pro
            35                  40                  45
```

-continued

```
Leu Gly Gly Ala Ala Gly His Pro Gly Ser Ala Val Ser Ala Ala Pro
 50                  55                  60
Gly Ile Leu Tyr Pro Gly Asn Lys Tyr Gln Thr Ile Asp Asn Tyr
 65                  70                  75                  80
Gln Pro Tyr Pro Cys Ala Glu Asp Glu Glu Cys Gly Thr Asp Glu Tyr
                 85                  90                  95
Cys Ala Ser Pro Thr Arg Gly Gly Asp Ala Gly Val Gln Ile Cys Leu
                100                 105                 110
Ala Cys Arg Lys Arg Arg Lys Arg Cys Met Arg His Ala Met Cys Cys
            115                 120                 125
Pro Gly Asn Tyr Cys Lys Asn Gly Ile Cys Val Ser Ser Asp Gln Asn
            130                 135                 140
His Phe Arg Gly Glu Ile Glu Glu Thr Ile Thr Glu Ser Phe Gly Asn
145                 150                 155                 160
Asp His Ser Thr Leu Asp Gly Tyr Ser Arg Arg Thr Thr Leu Ser Ser
                165                 170                 175
Lys Met Tyr His Thr Lys Gly Gln Glu Gly Ser Val Cys Leu Arg Ser
            180                 185                 190
Ser Asp Cys Ala Ser Gly Leu Cys Cys Ala Arg His Phe Trp Ser Lys
            195                 200                 205
Ile Cys Lys Pro Val Leu Lys Glu Gly Gln Val Cys Thr Lys His Arg
            210                 215                 220
Arg Lys Gly Ser His Gly Leu Glu Ile Phe Gln Arg Cys Tyr Cys Gly
225                 230                 235                 240
Glu Gly Leu Ser Cys Arg Ile Gln Lys Asp His His Gln Ala Ser Asn
                245                 250                 255
Ser Ser Arg Leu His Thr Cys Gln Arg His
            260                 265

<210> SEQ ID NO 111
<211> LENGTH: 20
<212> TYPE: DNA
<213> ORGANISM: Artificial
<220> FEATURE:
<223> OTHER INFORMATION: An artificially synthesized primer sequence
      for RT-PCR

<400> SEQUENCE: 111
catcagactg tgcctcagga                                                 20
```

METHOD OF DIAGNOSING ESOPHAGEAL CANCER

CROSS-REFERENCES TO RELATED APPLICATIONS

This application is a U.S. National Stage Application of PCT/JP2006/315342, filed Jul. 26, 2006, which claims the benefit of U.S. Provisional Application Ser. No. 60/703,263 filed Jul. 27, 2005, all of which are hereby incorporated by reference in their entirety.

FIELD OF THE INVENTION

The present invention relates to methods for detecting, diagnosing, and providing a prognosis of esophageal cancer, for example esophageal squamous-cell carcinoma (ESCC), and lung cancer, as well as methods of treating and preventing esophageal cancer, esophageal cancer metastasis, esophageal cancer recurrence. Alternatively, the present invention further relates to methods for detecting, diagnosing, and providing a prognosis of cancer, including esophageal cancer, or lung cancer.

BACKGROUND OF THE INVENTION

Lung cancer is the leading cause of cancer-related death in the world. Despite some advances in early detection and recent improvements in its treatment, the prognosis of the patients with lung cancer remains poor (Parkin et al, Lancet Oncol. 2001 September; 2(9):533-43). On the other hand, esophageal squamous-cell carcinoma (ESCC) is one of the most lethal malignant tumors in the gastrointestinal carcinoma family. The majority of esophageal cancers are advanced at the time of presentation and diagnosis, rendering cure unlikely, especially by surgery alone (Shimada et al., Surgery. 2003; 133(5):486-94). In spite of the use of modern surgical techniques combined with multi-treatment modalities, such as radiotherapy and chemotherapy, the over all 5-year survival rate remains 40-60% (Tamoto et al., Clin Cancer Res. 2004; 10(1):3629-38) while that of lung cancer is only 15% (Parkin et al, Lancet Oncol. 2001 September; 2(9): 533-43). In fact, it is reported that recurrent ESCC had developed in almost half of the patients who underwent an apparently curative resection, at a median follow up of 37.3 months (Mariette et al., Cancer. 2003; 97(7):1616-23). Consequently, much research effort has been directed towards studies of adjuvant chemotherapy and chemoradiation, particularly in defining the best regimens from the standpoint of efficacy and minimal toxicity and in an attempt to predict response. However, developments in neoadjuvant and adjuvant therapies have led to mixed conclusions. Collectively, past studies have not shown an optimal neoadjuvant or adjuvant regimen in terms of survival benefit. Therefore, there is an urgent need for novel diagnostic tools for early detection of cancer and molecular-targeted therapies involving small-molecule and antibody-based approaches.

In that vein, several tumor markers are used for diagnosis and follow-up of patients with ESCC, for example, SCC (squamous-cell carcinoma antigen), CEA (carcinoembryonic antigen), and CYFRA 21-1. Recently, serum MK (midkine), CD147, MMP-2 (matrix metalloproteinase-2), MMP-26 and MMP-9 in patients with ESCC was reported to be associated with poor prognosis (Shimada et al., Cancer Sci. 2003; 94(7): 628-32; Kawaguchi et al., Cancer. 2000; 89(7):1413-7; Ishibashi et al., Cancer. 2004; 101(9):1994-2000; Yamamoto et al., Carcinogenesis. 2004; 25(12):2353-60). However, at present, no specific tumor marker is clinically useful for detection of ESCC at an early and potentially curative stage. Therefore, new diagnostic and therapeutic strategies such as development of molecular-targeted agents and antibodies as well as cancer vaccines, are urgently needed. Several tumor markers, such as proGPP, NSE, cytokeratin 19-fragment (CYFRA 21-1), squamous-cell carcinoma antigen (SCC), and carcinoembryonic antigen (CEA) have been increased in the circulation of lung cancer patients (Castaldo G, et al., J Clin Oncol. 1997 November; 15(11):3388-93; Peck et al., Cancer Res. 1998 Jul. 1; 58(13):2761-5; Salerno et al., Chest. 1998 June; 113(6):1526-32), while SCC, CEA, and CYFRA 21-1 for ESCC, are used in clinic for diagnosis as well as in follow-up of the patients (Shimada et al., Surgery. 2003 May; 133(5):486-94, Kawaguchi et al., Cancer. 2000 Oct. 1; 89(7): 1413-7). In NSCLC patients, the sensitivity of CEA was 25% in squamous-cell carcinoma and 50% in adenocarcinoma, whereas, the sensitivity of SCC was 30% in squamous-cell carcinoma (Rastel et al., Eur J. Cancer. 1994; 30A(5):601-6). The sensitivity of CYFRA 21-1 was 57% in squamous-cell carcinoma and 27% in adenocarcinoma (Rastel et al., Eur J. Cancer. 1994; 30A(5):601-6). Reportedly, the positive rate of serum SCC in patients with ESCC was 18% in stage I, 22% in stage II, 34% in stage III, and 37% in stage IV. The incidence of CEA positivity in patients with stage IV ESCC was only 16%. Although CEA was not a prognostic factor, SCC was shown to be an independent prognostic factor to pTNM factors by using multivariate analysis (Shimada et al., Surgery. 2003 May; 133(5):486-94). These facts indicate that no tumor marker has been proven to be useful for detection of lung cancer and ESCC at potentially curative stage, and a limited number of practical prognostic marker is presently available for selection of treatment modalities for individual patients.

Analysis of gene-expression profiles on cDNA microarray enables the comprehensive analysis of gene expression profiles in cancer cells, and some studies describing such transcription profiles have been reported. For example, with regard to ESCC, several studies reported gene expression profiles of human ESCC that are candidates as diagnostic markers or therapeutic targets (Luo et al., Oncogene. 2004; 23(6):1291-9; Kihara et al., Cancer Res. 2001; 61(17):6474-9; Tamoto et al., Clin Cancer Res. 2004; 10(11):3629-38). However, all of the previous studies in human ESCC involved bulk tumor tissues and, since ESCC contains various types of cells, such as mesenchymal cells and inflammatory cells, fail to reflect accurate expressional changes during esophageal carcinogenesis (Nishida et al., Cancer Res. 2005; 65(2):401-9). Accordingly, more accurate studies are needed.

The present invention addresses these needs. Specifically, in an effort to understand the carcinogenic mechanisms associated with cancer and identify targets for developing novel anti-cancer agents, the present inventors performed large scale, genome-wide analyses of gene expression profiles found in purified populations of esophageal cancer cells, including 19 ESCC samples purified by laser microbeam microdissection (LMM), using a cDNA microarray consisting of 32,256 transcribed genes.

To isolate potential molecular targets for diagnosis, treatment, and/or prevention of lung and esophageal carcinomas, the present inventors performed a genome-wide analysis of gene expression profiles of cancer cells from 101 lung cancer and 19 ESCC patients, all of which had been purified by laser microbeam microdissection (LMM) using a cDNA microarray (Kikuchi et al., Oncogene. 2003 Apr. 10; 22(14):2192-205, Int J. Oncol. 2006 April; 28(4):799-805; Kakiuchi et al., Mol Cancer Res. 2003 May; 1(7):485-99, Hum Mol Genet. 2004 Dec. 15; 13(24):3029-43. Epub 2004 Oct. 20; Yamabuki T, et al, Int J Oncol. 2006 June; 28(6):1375-84). To verify the biological and clinicopathological significance of the respective gene products, the present inventors have established a screening system by a combination of the tumor-tissue microarray analysis of clinical lung-cancer materials with RNA interference (RNAi) technique (Suzuki et al., Cancer Res. 2003 Nov. 1; 63(21):7038-41, Cancer Res. 2005 Dec. 15; 65(24):11314-25; Ishikawa et al., Clin Cancer Res. 2004 Dec. 15; 10(24):8363-70, Cancer Res. 2005 Oct. 15; 65(20): 9176-84; Kato et al., Cancer Res. 2005 Jul. 1; 65(13):5638-46; Furukawa et al., Cancer Res. 2005 Aug. 15; 65(16):7102-10). In the process, the present inventors identified Dikkopf-1 (DKK1) as a novel serological and histochemical biomarker and as a therapeutic target for lung and esophageal cancers.

DKK1 is reported to be a secreted protein which plays a crucial role in head formation in vertebrate development, and is known as a negative regulator of Wnt signaling (Niida et al., Oncogene. 2004 Nov. 4; 23(52):8520-6). Dkk1 binds to LRP5/6 and Kremen proteins, thus inducing LRP endocytosis which prevents the formation of Wnt-Frizzled-LRP5/6 receptor complexes (Gonzalez et al., Oncogene. 2005 Feb. 3; 24(6):1098-103). In spite of these biological studies, there has been no report describing the significance of activation of DKK1 in human cancer and its potential as a diagnostic and therapeutic target.

The present inventors report here the identification of DKK1 as a novel diagnostic and prognostic biomarker and a potential target for therapeutic agents/antibodies, and also provide evidence for its possible role in human pulmonary and esophageal carcinogenesis.

SUMMARY OF THE INVENTION

Accordingly, the present invention involves the discovery of unique patterns of gene expression that correlate with esophageal cancer as well as the discovery of targets for the development of signal-suppressing strategies in human esophageal cancer. Genes that are differentially expressed in esophageal cancer (EC), for example, esophageal squamous-cell carcinoma (ESCC), are collectively referred to herein as "EC nucleic acids" or "EC polynucleotides" and the corresponding encoded polypeptides are referred to herein as "EC polypeptides" or "EC proteins".

Thus, it is an objective of the present invention is to provide a method for detecting, diagnosing, providing a prognosis, or determining a predisposition to esophageal cancer in a subject by determining an expression level of an EC-associated gene in a biological sample from a patient, for example, a solid tissue or bodily fluid sample. The term "EC-associated gene" refers to a gene that is characterized by an expression level which differs in an EC cell as compared to a normal cell. A normal cell is one obtained from esophageal tissue from an individual known not to have EC. In the context of the present invention, an EC-associated gene is a gene listed in tables 1-2 and 4-7 (i.e., genes of EC Nos. 1-1716), or a gene having at least 90%, 95%, 96%, 97% 98%, or 99% sequence identity to a gene listed in tables 1-2 and 4-7 and the same function (e.g., homologs, genetic variants and polymorphisms). Algorithms known in the art can be used to determine the sequence identity of two or more nucleic acid sequences (e.g., BLAST, see below). An alteration, e.g., an increase or decrease in the level of expression of a gene as compared to a normal control level of the gene, indicates that the subject suffers from or is at risk of developing EC.

In the context of the present invention, the phrase "control level" refers to a mRNA or protein expression level detected in a control sample and includes both a normal control level and an esophageal cancer control level. A control level can be a single expression pattern from a single reference population or from a plurality of expression patterns. For example, the control level can be a database of expression patterns from previously tested cells. A "normal control level" refers to a level of gene expression detected in a normal, healthy individual or in a population of individuals known not to be suffering from esophageal cancer. A normal individual is one with no clinical symptoms of esophageal cancer. On the other hand, an "EC control level" refers to an expression profile of EC-associated genes found in a population suffering from esophageal cancer.

An increase in the expression level of one or more EC-associated genes listed in tables 2, 5, and 7 (i.e., genes of EC Nos. 728-1543, 1603-1679, and 1689-1716) detected in a test sample as compared to the expression level from a normal control sample indicates that the subject (from which the test sample was obtained) suffers from or is at risk of developing EC. In contrast, a decrease in the expression level of one or more EC-associated genes listed in tables 1, 4, and 6 (i.e., genes of EC Nos. 1-727, 1544-1602, and 1680-1688) detected in a test sample compared to the expression level from a normal control sample indicates that the subject (from which the test sample was obtained) suffers from or is at risk of developing EC.

Alternatively, expression levels of a panel of EC-associated genes in a test sample can be compared to expression levels of an EC control panel of the same genes. A similarity in expression levels between genes in the test sample panel and genes in the EC control panel indicates that the subject (from which the test sample was obtained) suffers from or is at risk of developing EC.

According to the present invention, gene expression level is deemed to "altered" or "differ" when gene expression is increased or decreased 10%, 25%, or 50% as compared to the control level. Alternatively, an expression level is deemed "increased" or "decreased" when gene expression is increased or decreased by at least 0.1, at least 0.2, at least 1, at least 2, at least 5, or at least 10 or more fold as compared to a control level. Expression is determined by detecting hybridization, e.g., on an array, of an EC-associated gene probe to a gene transcript in a tissue sample from a patient.

In the context of the present invention, the tissue sample from a patient is any tissue obtained from a test subject, e.g., a patient known to or suspected of having EC. For example, the tissue can contain epithelial cells. More particularly, the tissue can be epithelial cells from esophageal squamous-cell carcinoma.

The present invention also provides an EC reference expression profile, comprising a gene expression level of two or more of EC-associated genes listed in tables 1-2 and 4-7.

The present invention further provides methods of identifying an agent that inhibits or enhances the expression or activity of an EC-associated gene, e.g. an EC-associated gene listed in tables 1-2 and 4-7, by contacting a test cell expressing an EC-associated gene with a test compound and determining the expression level of the EC-associated gene or the activity of its gene product. The test cell can be an epithelial cell, for example, an epithelial cell obtained from an esophageal squamous-cell carcinoma. A decrease in the expression level of an up-regulated EC-associated gene or the activity of its gene product as compared to a normal control expression level or activity of the gene or gene product indicates that the test agent is an inhibitor of the EC-associated gene and can be used to reduce a symptom of EC, e.g the expression of one or more EC-associated genes listed in tables 2, 5, and 7. Alternatively, an increase in the expression level of a down-regulated EC-associated gene or the activity of its gene product as compared to a normal control expression level or activity of the gene or gene product indicates that the test agent is an enhancer of expression or function of the EC-associated gene and can be used to reduce a symptom of EC, e.g., the underexpression of one or more EC-associated genes listed in tables 1, 4, and 6.

The present invention also provides a kit comprising a detection reagent which binds to one or more EC nucleic acids or EC polypeptides. Also provided is an array of nucleic acids that binds to one or more EC nucleic acids.

Therapeutic methods of the present invention include methods of treating or preventing EC in a subject including the step of administering to the subject a composition comprising one or more antisense oligonucleotides. In the context of the present invention, the antisense composition reduces the expression of one or more specific target genes. For example, the antisense composition can contain one or more nucleotides which are complementary to one or more up-regulated EC-associated gene sequences selected from the group consisting of the EC-associated genes listed in tables 2, 5, and 7. Alternatively, the present methods can include the steps of administering to a subject a composition comprising one or more small interfering RNA (siRNA) oligonucleotides. In the context of the present invention, the siRNA composition reduces the expression of one or more EC nucleic acids selected from the group consisting of the up-regulated EC-associated genes listed in tables 2, 5, and 7. In yet another method, the treatment or prevention of EC in a subject can be carried out by administering to a subject a composition comprising one or more ribozyme oligonucleotides. In the context of the present invention, the nucleic acid-specific ribozyme composition reduces the expression of one or more EC nucleic acids selected from the group consisting of the up-regulated EC-associated genes listed in tables 2, 5, and 7. The inhibition effect of the siRNA for selected EC-associated genes listed in the tables is confirmed herein. Specifically, siRNA a Homo sapiens epithelial cell transforming sequence 2 oncogene (ECT2) (SEQ ID NO; 30, 31) and a cell division cycle 45, S. Cerevisiae, homolog-like (CDC45L) (SEQ ID NO; 32, 33) are demonstrated herein to inhibit proliferation and viability of esophageal cancer cells. Thus, in some embodiments of the present invention, EC-associated genes listed in tables 2, 5, and 7, including ECT2 and CDC45L, are therapeutic targets of esophageal cancer.

Other therapeutic methods include those in which a subject is administered a compound that increases the expression of one or more of the down-regulated EC-associated genes listed in tables 1, 4, and 6 or the activity of a polypeptide encoded by one or more of the EC-associated genes listed in tables 1, 4, and 6.

The present invention also includes vaccines and vaccination methods. For example, methods of treating or preventing EC in a subject can involve administering to the subject a vaccine composition comprising one or more polypeptides encoded by one or more nucleic acids selected from the group consisting of an up-regulated EC-associated genes listed in tables 2, 5, and 7 or immunologically active fragments of such polypeptides. In the context of the present invention, an immunologically active fragment is a polypeptide that is shorter in length than the full-length naturally-occurring protein yet which induces an immune response analogous to that induced by the full-length protein. For example, an immunologically active fragment is least 8 residues in length and capable of stimulating an immune cell including, a T cell or a B cell. Immune cell stimulation can be measured by detecting cell proliferation, elaboration of cytokines (e.g., IL-2), or production of an antibody. See, for example, Harlow and Lane, *Using Antibodies: A Laboratory Manual,* 1998, Cold Spring Harbor Laboratory Press; and Coligan, et al., *Current Protocols in Immunology,* 1991-2006, John Wiley & Sons.

It is a further objective of the present invention to provide novel molecular targets and expression patterns unique to EC. Identified genes serve as candidates in the development of novel therapeutic drugs or immunotherapy. For example, ECT2 and CDC45L are characterized herein as two representative candidates identified by the promising screening system of the present invention. Additionally, the present invention provides target molecules for treating or preventing malignant esophageal cancer, more particularly for treating or preventing metastasis or post-surgery recurrence of esophageal cancer. According to the present invention, genes listed in tables 4-5 (i.e., genes of EC Nos. 1544-1679) were identified as genes having unique altered expression patterns in esophageal cancer cells with lymph-node metastasis and genes listed in tables 6-7 (i.e., genes of EC Nos. 1680-1716) were identified as genes having unique altered expression patterns in esophageal cancers associated with post-surgery recurrence. Thus, metastasis and/or recurrence of esophageal cancer can be treated or prevented via the suppression of the expression or activity of the up-regulated genes of tables 5 and 7 or their gene products. Alternatively, metastasis and/or recurrence of esophageal cancer can be treated or prevented by enhancing the expression or activity in cancerous cells of the down-regulated genes of tables 4 and 6 or their gene products.

The present invention also provides methods for predicting esophageal cancer metastasis. Specifically, the present method comprises the step of measuring the expression level of one or more marker genes selected from the group consisting of genes listed in tables 4 and 5. These marker genes are identified herein as genes having unique altered expression patterns in the esophageal cancer cells isolated from patients with lymph node metastasis. Therefore, metastasis of the esophageal cancer in a subject can be predicted by determining whether the expression level detected in a sample from the subject is closer to the mean expression level of lymph node metastasis positive cases or negative cases in reference samples.

The present invention also provides methods for predicting post-surgery recurrence of esophageal cancer. Specifically, the present method comprises the step of measuring the expression level of one or more marker genes selected from the group consisting of genes listed in tables 6 and 7. These marker genes are identified herein as genes having unique altered expression patterns in the esophageal cancer cells isolated from patients with recurrence after surgery. Therefore, recurrence of the esophageal cancer in a subject can be predicted by determining whether the expression level detected in a sample from the subject is closer to the mean expression level of recurrence positive cases or negative cases in reference samples.

One advantage of the methods described herein is that esophageal cancer is identified prior to detection of overt clinical symptoms. These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention.

BRIEF DESCRIPTION OF THE DRAWINGS

FIG. 2A depicts the results of semi-quantitative RT-PCR of 38 candidate genes. ACTB is an internal control. FIG. 2B depicts expression of DKK1 in a normal lung tissue and 15 clinical lung cancer samples. FIG. 2C depicts 25 lung cancer cell lines, detected by semi-quantitative RT-PCR analysis. FIG. 2D depicts expression of DKK1 protein in 5 representative pairs of NSCLC samples, detected by western-blot analysis.

FIG. 3A depicts the expression of ECT2 in normal organs using multiple tissue northern blot (MTN). A transcript of about 4.3-kb was expressed only in testis. FIG. 3B depicts the expression of CDC45L in normal organs using multiple tissue northern blot (MTN). A transcript of about 2.2-kb was expressed only in testis. FIG. 3C depicts Northern blot analysis of the DKK1 transcript in normal adult human tissues. A strong signal was observed in placenta and a very weak signal in prostate. FIG. 3D depicts subcellular localization of endogenous DKK1 protein in TE8 cells. DKK1 was stained at the cytoplasm of the cell.

FIGS. 8A, C depicts examples are shown of strong, weak, and absent DKK1 expression in cancer and of no expression in normal tissue (original magnification ×100); (A) esophageal cancer, (C) lung cancer. FIGS. 8B, D depicts Kaplan-Meier analysis of survival of ESCC (B) and NSCLC (D) patients according to expressions of DKK1.

FIG. 9A depicts distribution of DKK1 in sera from patients with ESCC, lung ADC, lung SCC, or SCLC. Differences were significant between ESCC patients and healthy individuals (P<0.001, Mann-Whitney U test), ADC patients and healthy individuals (P<0.001, Mann-Whitney U test), between SCC patients and healthy individuals (P<0.001) and between SCLC patients and healthy individuals (P<0.001). FIG. 9B, Receiver-operating characteristic (ROC) curve analysis of DKK1 (black) as serum markers for lung and esophageal cancer (X-axis, 1-specificity; Y-axis, sensitivity).

FIG. 10 FIG. 10A depicts post-translational modification of secreted DKK1 in cancer cells. Alanine-replacement mutant of DKK1 appeared as immunoreactive bands with similar molecular weight to the deglycosylated form of wild type DKK1. Treatment with N-glycosidase F did not cause any shift of a band of the mutant DKK1 in the conditioned medium as well as that in the cell pellet, suggesting that DKK1 is N-glycosylated at only asparagine-256. Promotion of invasiveness of mammalian cells transfected with DKK1-expressing plasmids. FIG. 10B depicts an assay demonstrating the invasive nature of NIH3T3 and COS-7 cells in Matrigel matrix after transfection with expression plasmids for human DKK1. Upper panels, Transient expression of DKK1 in NIH3T3 and COS-7 cells, detected by western-blot analysis. Middle panels and lower panels, Giemsa staining (×200) and the number of cells migrating through the Matrigel-coated filters. Assays were performed three times, and in triplicate wells.

DETAILED DESCRIPTION OF THE PREFERRED EMBODIMENTS

I. Overview

The words "a", "an", and "the" as used herein mean "at least one" unless otherwise specifically indicated.

Generally, esophageal cancer cells exist as a solid mass having a highly inflammatory reaction and containing various cellular components, including non-cancerous cells such as mesenchymal cells and inflammatory cells. Therefore, previously published gene expression data reflect heterogeneous profiles and do not necessarily reflect accurate expressional changes during esophageal carcinogenesis.

Accordingly, to avoid the contamination of these normal cells, the present invention utilized a laser microbeam microdissection (LMM) system to purify the populations of cancerous cells and normal epithelial cells from surgical specimens (Gjerdrum et al., J Mol. Diagn. 2001; 3(3): 105-10; Kitahara et al., Cancer Res. 2001; 61(9):3544-9; Kakiuchi et al., Hum Mol. Genet. 2004; 13(24):3029-43). This is believed to be the first study for gene expression profiles of human ESCC on cDNA microarray combined with an LMM system.

Specifically, herein, a detailed genome-wide database is established for sets of genes that are differentially expressed in ESCCs. The data on all 32,256 genes was linked to their expression in ESCCs and their distribution determined by the cDNA microarray in 34 normal human tissues (30 adult and 4 fetal organs). The data herein not only provide important information about esophageal carcinogenesis, but also facilitates the identification of candidate genes whose products serve as diagnostic markers and/or as molecular targets for treatment of patients with esophageal cancer and providing clinically relevant information.

Figure 2:
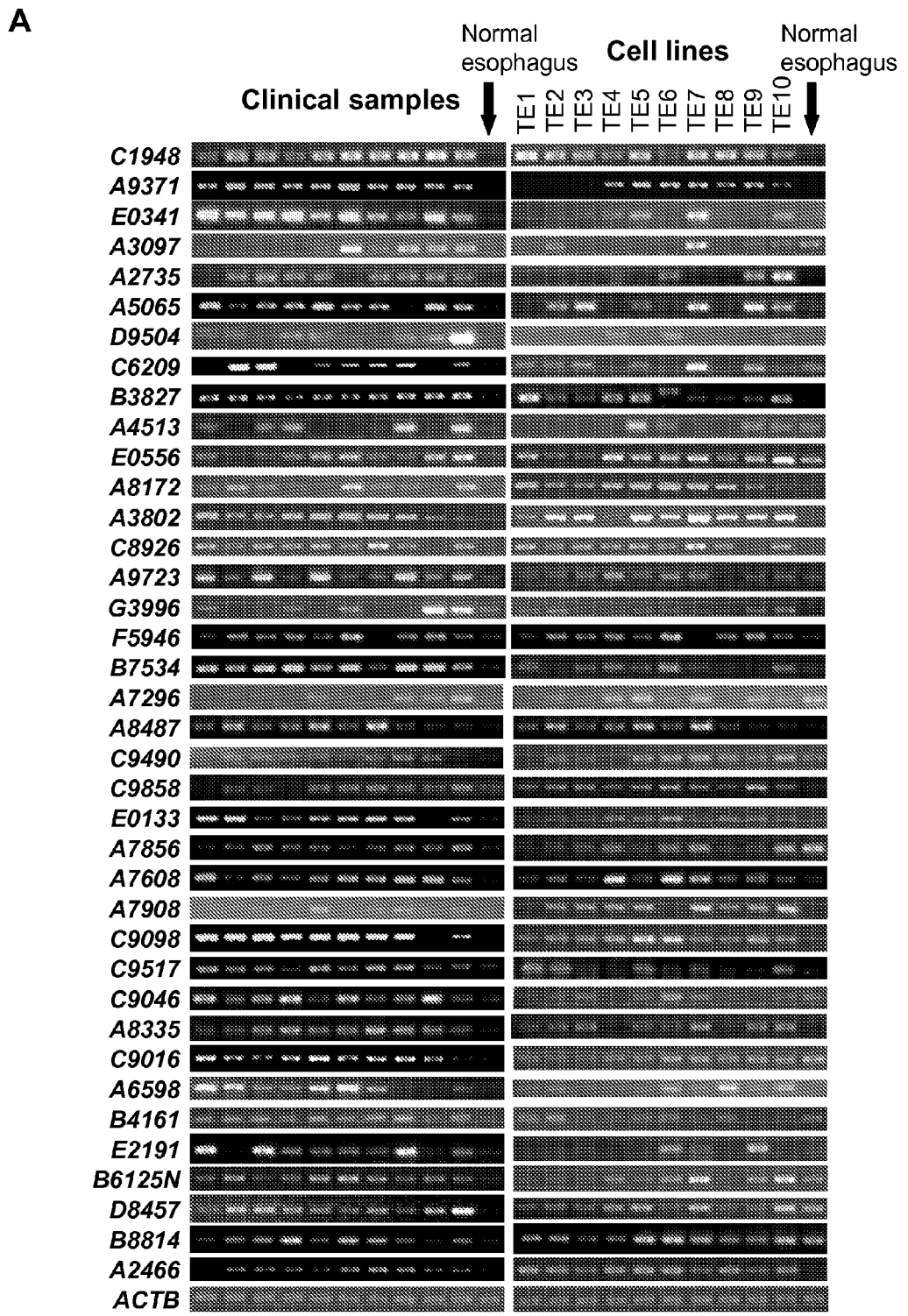
FIG. 2 Expressions of 38 candidate gene in tumors, cell lines, and normal tissues.

To date, 816 candidate genes have been identified as tumor markers or therapeutic targets (see Table 2) specifically up-regulated in cancer. The up-regulated genes represent a variety of functions, including genes encoding cancer-testis or onco-fetal antigens as well as ones important for cell growth, proliferation, survival, motility/invasion and transformation. These targets find utility as diagnostic/prognostic markers as well as therapeutic targets for the development of new molecular-targeted agents or immunotherapy in esophageal-cancer treatment. The up-regulated genes also represent tumor-specific transmembrane/secretory proteins that have significant advantages because they are presented on the cell surface or within the extracellular space, and/or in serum, making them easily accessible as molecular markers and therapeutic targets. Some tumor-specific markers already available, such as CYFRA or Pro-GRP, are transmembrane/ secretory proteins (Pujol J L, et al., Cancer Res. 1993; 53(1): 61-6; Miyake Y, et al., Cancer Res. 1994 Apr. 15; 54(8):2136-40); the example of rituximab (Rituxan), a humanized monoclonal antibody against CD20-positive lymphomas, provides proof that targeting specific cell-surface proteins can result in significant clinical benefits (Hennessy B T, et al., Lancet Oncol. 2004; 5(6):341-53). Among the up-regulated genes, 38 genes were selected for validation by semi-quantitative RT-PCR experiments and confirmed their cancer-specific expression (FIG. 2).

Next, expression profiles of lymph-node-metastasis (node-positive) cases were compared with expression profiles of node-negative cases, because lymph-node metastasis is a key step in tumor progression and a risk factor for poor prognosis. Accordingly, 136 genes were identified that are associated with lymph-node metastasis. Additionally, 37 genes were identified that are associated with recurrence after surgery. The patterns of recurrence during the observation period of 32 months included local recurrence, regional lymph-node, and distant metastasis (lung). Mean (SD) time to recurrence after operation was 21.8±11.1 month (range, 2-32). These genes are key molecules in the process of EC tumor progression. Accordingly, this data enables the identification and selection of patients who can take adjuvant therapy after surgery.

From the cDNA microarray system of the present invention, containing 32,256 genes, ECT2 (GenBank Accession NO. AY376439; SEQ ID NO; 30, 31) was identified as gene up-regulated in esophageal cancer. This molecule, discovered to be a cancer-testis antigen activated in the great majority of ESCCs, is believed to play a pivotal role in cell growth/survival, as demonstrated by northern-blot analysis and siRNA experiments discussed below. The ECT2 gene encodes a protein of 882 amino acids with a pair of BRCT domains, a RhoGEF domain, and a PH domain. It is reported to be a nucleotide exchange factor, and is involved in the regulation of cytokinesis (Tatsumoto et al., J Cell Biol. 1999; 147(5):921-8; Saito et al., J Cell Biochem. 2003; 90(4):819-36, Liu et al., Mol Cell Biol. 2004; 24(15):6665-75).

In addition, CDC45L (GenBank Accession NO. AJ223728; SEQ ID NO; 32, 33) was isolated as an up-regulated gene. This molecule was discovered to be a cancer-testis antigen activated in the most of ESCCs. As demonstrated by northern-blot analysis and siRNA experiments, CDC45L was suggested to be associated with cell growth and survival. The CDC45L gene encodes a protein of 566 amino acids. The protein was identified by its strong similarity with *Saccharomyces cerevisiae* Cdc45, an essential protein required to the initiation of DNA replication (Saha et al., J Biol Chem. 1998; 273(29):18205-9).

Among tumor antigens identified to date, cancer-testis antigens have been recognized as a group of highly attractive targets for cancer vaccine (Li et al., Clin Cancer Res. 2005; 11(5):1809-14). Although other factors, including the in vivo immunogenicity of the protein, are also important (Wang et al., Clin Cancer Res. 2004; 10(19):6544-50), ECT2 and CDC45L both appear to be good targets for immunotherapy as well as for the development of new anti-cancer drugs.

In sum, the cDNA microarray combined with a LMM system described herein revealed characteristic gene expression profiles of ESCC that were associated with carcinogenesis; lymph-node metastasis, and recurrence after surgery. The use of the integrated gene-expression database of human ESCC offers a powerful strategy for rapid identification and further evaluation of target molecules like ECT2 and CDC45L for a personalized therapy of esophageal cancer.

Gene-expression profiles of lung and esophageal carcinomas and subsequent analyses revealed that Dikkopf-1 (DKK1; Accession No. NM_012242; SEQ ID NO: 109, 110) was transactivated in the great majority of various types of lung cancers and esophageal squamous-cell carcinomas (ESCCs). Northern-blot analysis detected expression of DKK1 gene only in placenta and prostate among the normal tissues. Immunohistochemical staining using tumor tissue microarrays consisting of 279 archived non-small cell lung cancers (NSCLCs) and 220 ESCC specimens confirmed that DKK1 protein was frequently over-expressed in these tumors; its positive staining was observed in 227 of 279 (81.4%) NSCLCs and in 135 of 220 (61.4%) ESCCs examined. In addition, a high level of DKK1 expression was associated with poor prognosis of patients with NSCLC as well as ESCC, and multivariate analysis confirmed its independent prognostic value. Serum levels of DKK1 were significantly higher in lung and esophageal cancer patients than in healthy controls. The proportion of the serum DKK1-positive cases defined by our criteria was 101 of 162 (62.3%) NSCLC, 47 of 71 (66.2%) SCLC, and 45 of 67 (67.2%) ESCC patients, while only 11 of 220 (5.0%) healthy volunteers were falsely diagnosed as positive. A combined assay using both DKK1 and CEA increased sensitivity, as 78.6% of the NSCLC patients were then diagnosed as positive while only 8.2% of healthy volunteers were falsely diagnosed as positive. The use of both DKK1 and proGRP increased sensitivity to detect SCLCs up to 84.8%, while false positive rate in healthy donors were only 6.2%. In addition, exogenous expression of DKK1 increased the migratory and invasive activity of mammalian cells, an indication that DKK1 may play a significant role in progression of certain types of cancer. Our data imply that DKK1 should be useful as a novel diagnostic/prognostic marker and probably as a therapeutic target for lung and esophageal cancer.

II. Diagnosing Esophageal Cancer

The differentially expressed genes identified herein find diagnostic and prognostic utility as markers of EC and as EC gene targets, the expression of which can be altered to treat or alleviate a symptom of EC. The genes whose expression level is modulated (i.e., increased or decreased) in EC patients are summarized in tables 1, 2, and 4-7 and are collectively referred to herein as "EC-associated genes," "EC nucleic acids" or "EC polynucleotides" and the corresponding encoded polypeptides are referred to as "EC polypeptides" or "EC proteins." Unless indicated otherwise, "EC" refers to any of the sequences disclosed herein (e.g., EC-associated genes listed in tables 1, 2, and 4-7) and sequences sharing the same function and having at least 90%, 95%, 96%, 97%, 98%, 99% sequence identity (i.e., homologs, variants and polymorphisms). Genes that have been previously described are presented along with a database accession number.

By measuring expression of the various genes in a sample of cells, EC can be diagnosed. Similarly, measuring the expression of these genes in response to various agents can identify agents for treating EC.

The present invention involves determining (e.g., measuring) the expression of at least one, and up to all the EC-associated genes listed in tables 1, 2, and 4-7. Using sequence information provided by the GenBank™ database entries for known sequences, the EC-associated genes can be detected and measured using techniques well known to one of ordinary skill in the art. For example, sequences within the sequence database entries corresponding to EC-associated genes, can be used to construct probes for detecting RNA sequences corresponding to EC-associated genes in, e.g., Northern blot hybridization analyses. Probes typically include at least 10, at least 20, at least 50, at least 100, or at least 200 nucleotides of a reference sequence. As another example, the sequences can be used to construct primers for specifically amplifying the EC nucleic acid in, e.g., amplification-based detection methods, for example, reverse-transcription based polymerase chain reaction.

Expression level of one or more of EC-associated genes in a test cell population, e.g., a tissue sample from a patient, is then compared to the expression level(s) of the same gene(s) in a reference cell population. The reference cell population includes one or more cells for which the compared parameter is known, i.e., esophageal squamous-cell carcinoma cells (e.g., EC cells) or normal esophageal epithelial cells (e.g., non-EC cells).

Whether or not a pattern of gene expression in a test cell population as compared to a reference cell population indicates EC or a predisposition thereto depends upon the composition of the reference cell population. For example, if the reference cell population is composed of non-EC cells, a similarity in gene expression pattern between the test cell population and the reference cell population indicates the test cell population is non-EC. Conversely, if the reference cell population is made up of EC cells, a similarity in gene expression profile between the test cell population and the reference cell population indicates that the test cell population includes EC cells.

A level of expression of an EC marker gene in a test cell population is considered "altered" or "to differ" if it varies from the expression level of the corresponding EC marker gene in a reference cell population by more than 1.1, more than 1.5, more than 2.0, more than 5.0, more than 10.0 or more fold.

Differential gene expression between a test cell population and a reference cell population can be normalized to a control nucleic acid, e.g. a housekeeping gene. For example, a control nucleic acid is one which is known not to differ depending on the cancerous or non-cancerous state of the cell. The expression level of a control nucleic acid can be used to normalize signal levels in the test and reference cell populations. Exemplary control genes include, but are not limited to, e.g., β-actin, glyceraldehyde 3-phosphate dehydrogenase and ribosomal protein P1.

The test cell population can be compared to multiple reference cell populations. Each of the multiple reference cell populations can differ in the known parameter. Thus, a test cell population can be compared to a first reference cell population known to contain, e.g., EC cells, as well as a second reference cell population known to contain, e.g., non-EC cells (normal cells). The test cell population can be included in a tissue or cell sample from a subject known to contain, or suspected of containing, EC cells.

The test cell population can be obtained from a bodily tissue or a bodily fluid, e.g., biological fluid (for example, blood, sputum, saliva). For example, the test cell population can be purified from esophageal tissue. Preferably, the test cell population comprises an epithelial cell. The epithelial cell is preferably from a tissue known to be or suspected to be an esophageal squamous-cell carcinoma.

Cells in the reference cell population are from a tissue type similar to that of the test cell population. Optionally, the reference cell population is a cell line, e.g. an EC cell line (i.e., a positive control) or a normal non-EC cell line (i.e., a negative control). Alternatively, the control cell population can be from a database of molecular information from cells for which the assayed parameter or condition is known.

The subject is preferably a mammal. Exemplary mammals include, but are not limited to, e.g., a human, non-human primate, mouse, rat, dog, cat, horse, or cow.

Expression of the genes disclosed herein can be determined at the protein or nucleic acid level, using methods known in the art. For example, Northern hybridization analysis, using probes which specifically recognize one or more of these nucleic acid sequences can be used to determine gene expression. Alternatively, gene expression can be measured using reverse-transcription-based PCR assays, e.g., using primers specific for the differentially expressed gene sequences. Expression can also be determined at the protein level, i.e., by measuring the level of a polypeptides encoded by a gene described herein, or the biological activity thereof. Such methods are well known in the art and include, but are not limited to, e.g., immunoassays that utilize antibodies to proteins encoded by the genes. The biological activities of the proteins encoded by the genes are generally well known. See, Sambrook and Russell, *Molecular Cloning: A Laboratory Manual*, 3$^{rd}$ Edition, 2001, Cold Spring Harbor Laboratory Press; Ausubel, *Current Protocols in Molecular Biology*, 1987-2006, John Wiley and Sons; and Harlow and Lane, *Using Antibodies: A Laboratory Manual*, 1998, Cold Spring Harbor Laboratory Press.

In the context of the present invention, EC is diagnosed by measuring the expression level of one or more EC nucleic acids from a test population of cells, (i.e., a biological sample from a patient). Preferably, the test cell population contains an epithelial cell, e.g., a cell obtained from esophageal tissue. Gene expression can also be measured from blood or other bodily fluids, for example, saliva or sputum. Other biological samples can be used for measuring protein levels. For example, the protein level in blood or serum from a subject to be diagnosed can be measured by immunoassay or other conventional biological assay.

Expression of one or more EC-associated genes, e.g., genes listed in tables 1, 2, and 4-7, is determined in the test cell population or biological sample and compared to the normal control expression level associated with the one or more EC-associated gene(s) assayed. A normal control level is an expression profile of an EC-associated gene typically found in a cell population from a subject known not to be suffering from EC. An alteration or difference (e.g., an increase or decrease) in the level of expression of one or more EC-associated genes in a tissue sample from a patient in comparison to expression from a normal control sample indicates that the subject is suffering from or is at risk of developing EC. For example, an increase in the expression of one or more up-regulated EC-associated genes listed in tables 2, 5, and 7 in the test cell population as compared to the expression in a normal control cell population indicates that the subject is suffering from or is at risk of developing EC. Conversely, a decrease in expression of one or more down-regulated EC-associated genes listed in tables 1, 4, and 6 in the test cell population as compared to the expression in a normal control cell population indicates that the subject is suffering from or is at risk of developing EC.

Alteration in expression levels of one or more of the EC-associated genes in the test cell population as compared to normal control expression levels indicates that the subject suffers from or is at risk of developing EC. For example, alteration in expression levels of at least 1%, at least 5%, at least 25%, at least 50%, at least 60%, at least 70%, at least 80%, at least 90% or more of the panel of EC-associated genes (genes listed in tables 1, 2, and 4-7) indicates that the subject suffers from or is at risk of developing EC.

III. Screening Assays

Identifying Agents that Inhibit or Enhance EC-Associated Gene Expression

An agent that inhibits the expression of an EC-associated gene or the activity of its gene product can be identified by contacting a test cell population expressing an EC-associated up-regulated gene with a test agent and then determining the expression level of the EC-associated gene or the activity of its gene product. A decrease in the level of expression of the EC-associated gene or in the level of activity of its gene product in the presence of the agent as compared to the expression or activity level in the absence of the test agent indicates that the agent is an inhibitor of an EC-associated up-regulated gene and useful in inhibiting EC.

Alternatively, an agent that enhances the expression of an EC-associated down-regulated gene or the activity of its gene product can be identified by contacting a test cell population expressing an EC-associated gene with a test agent and then determining the expression level or activity of the EC-associated down-regulated gene. An increase in the level of expression of the EC-associated gene or in the level of activity of its gene product in the presence of the test agent as compared to the expression or activity level in the absence of the test agent indicates that the test agent augments expression of the EC-associated down-regulated gene or the activity of its gene product.

The test cell population can be any cells expressing the EC-associated genes. For example, the test cell population can contain epithelial cells, for example, cells from esophageal tissue. Furthermore, the test cell population can be an immortalized cell line from an esophageal squamous-cell carcinoma cell. Alternatively, the test cell population can be comprised of cells which have been transfected with an EC-associated gene or which have been transfected with a regulatory sequence (e.g. promoter sequence) from an EC-associated gene operably linked to a reporter gene.

The agent can be, for example, an inhibitory oligonucleotide (e.g., an antisense oligonucleotide, an siRNA, a ribozyme), an antibody, a polypeptide, a small organic molecule. Screening for agents can be carried out using high throughput methods, by simultaneously screening a plurality of agents using multiwell plates (e.g., 96-well, 192-well, 384-well, 768-well, 1536-well). Automated systems for high throughput screening are commercially available from, for example, Caliper Life Sciences, Hopkinton, Mass. Small organic molecule libraries available for screening can be purchased, for example, from Reaction Biology Corp., Malvern, Pa.; TimTec, Newark, Del.

Identifying Therapeutic Agents

The differentially expressed EC-associated genes disclosed herein can also be used to identify candidate therapeutic agents for treating EC. The methods of the present invention involve screening a candidate therapeutic agent to determine if the test agent can convert an expression profile of one or more EC-associated genes listed in tables 1, 2, and 4-7 characteristic of an EC state to a gene expression pattern characteristic of a non-EC state.

In the instant method, a test cell population is exposed to a test agent or a plurality of test agents (sequentially or in combination) and the expression of one or more of the EC-associated genes listed in tables 1, 2, and 4-7 in the cells is measured. The expression profile of the EC-associated gene(s) assayed in the test cell population is compared to the expression level of the same EC-associated gene(s) in a reference cell population that is not exposed to the test agent.

An agent capable of stimulating the expression of an underexpressed gene or suppressing the expression of an overexpressed gene has clinical benefit. Such agents can be further tested for the ability to prevent esophageal carcinomal growth in animals or test subjects.

In a further embodiment, the present invention provides methods for screening candidate agents which act on the targets in the treatment of EC. As discussed in detail above, by controlling the expression levels of marker genes or the activities of their gene products, one can control the onset and progression of EC. Thus, candidate agents, which act on the targets in the treatment of EC, can be identified through screening methods that use such expression levels and activities as indices of the cancerous or non-cancerous state. In the context of the present invention, such screening can comprise, for example, the following steps:

(a) contacting a test compound with a polypeptide encoded by a polynucleotide selected from the group consisting of the genes listed in table 1, 2, 4, 5, 6 or 7

(b) detecting the binding activity between the polypeptide and the test compound; and (c) selecting the test compound that binds to the polypeptide.

Alternatively, the screening methods of the present invention can comprise the following steps:

(a) contacting a candidate compound with a cell expressing one or more marker genes, wherein the one or more marker genes are selected from the group consisting of the genes listed in table 1, 2, 4, 5, 6 or 7; and (b) selecting the candidate compound that reduces the expression level of one or more marker genes selected from the group consisting of the genes listed in table 2, 5, and 7, or elevates the expression level of one or more marker genes selected from the group consisting of the genes listed in table 1, 4, and 6, as compared to the expression level detected in the absence of the candidate compound.

Cells expressing a marker gene include, for example, cell lines established from EC; such cells can be used for the above screening of the present invention.

Alternatively, the screening methods of the present invention can comprise the following steps:

(a) contacting a test compound with a polypeptide encoded by a polynucleotide selected from the group consisting of the genes listed in table 1, 2, 4, 5, 6 or 7;

(b) detecting the biological activity of the polypeptide of step (a); and (c) selecting a compound that suppresses the biological activity of the polypeptide encoded by the polynucleotide selected from the group consisting of the genes listed in table 2, 5 and 7, or enhances the biological activity of the polypeptide encoded by the polynucleotide selected from the group consisting of the genes listed in table 1, 4, and 6, as compared to the biological activity detected in the absence of the test compound.

A protein for use in the screening methods of the present invention can be obtained as a recombinant protein using the nucleotide sequence of the marker gene. Based on the information regarding the marker gene and its encoded protein, one skilled in the art can select any biological activity of the protein as an index for screening and any suitable measurement method to assay for the selected biological activity.

Alternatively, the screening methods of the present invention can comprise the following steps:

(a) contacting a candidate compound with a cell into which a vector, comprising the transcriptional regulatory region of one or more marker genes and a reporter gene that is expressed under the control of the transcriptional regulatory region, has been introduced, wherein the one or more marker genes are selected from the group consisting of the genes listed in table 1, 2, 4, 5, 6 or 7;

(b) measuring the expression or activity of said reporter gene; and (c) selecting the candidate compound that reduces the expression or activity level of said reporter gene when said marker gene is an up-regulated marker gene selected from the group consisting of the genes listed in table 2, 5 and 7, or that enhances the expression or activity level of said reporter gene when said marker gene is a down-regulated marker gene selected from the group consisting of the genes listed in table 1, 4 and 6, as compared to the expression or activity level detected in the absence of the candidate compound.

Suitable reporter genes and host cells are well known in the art. A reporter construct suitable for the screening methods of the present invention can be prepared by using the transcriptional regulatory region of a marker gene. When the transcriptional regulatory region of the marker gene is known to those skilled in the art, a reporter construct can be prepared by using the previous sequence information. When the transcriptional regulatory region of the marker gene remains unidentified, a nucleotide segment containing the transcriptional regulatory region can be isolated from a genome library based on the nucleotide sequence information of the marker gene.

Selecting a Therapeutic Agent for Treating EC

Differences in the genetic makeup of individuals can result in differences in their relative abilities to metabolize various drugs. An agent that is metabolized in a subject to act as an anti-EC agent can manifest itself by inducing a change in a gene expression pattern in the subject's cells from that characteristic of a cancerous state to a gene expression pattern characteristic of a non-cancerous state. Accordingly, the differentially expressed EC-associated genes disclosed herein allow for a putative therapeutic or prophylactic inhibitor of EC to be tested in a test cell population from a selected subject in order to determine if the agent is a suitable inhibitor of EC in the subject.

To identify an inhibitor of EC that is appropriate for a specific subject, a test cell population from the subject is exposed to a therapeutic agent, and the expression of one or more of EC-associated genes listed in table 1, 2, and 4-7 is determined.

In the context of the methods of the present invention, the test cell population contains EC cells expressing one or more EC-associated genes. Preferably, the test cell population comprises epithelial cells. For example, a test cell population can be incubated in the presence of a candidate agent and the pattern of gene expression of the test cell population can be measured and compared to one or more reference expression profiles, e.g., an EC reference expression profile or a non-EC reference expression profile.

A decrease in expression of one or more of the EC-associated genes listed in tables 2, 5, and 7 or an increase in expression of one or more of the EC-associated genes listed in tables 1, 4, and 6 in a test cell population relative to a reference cell population containing EC indicates that the agent has therapeutic use.

In the context of the present invention, the test agent can be any compound or composition. Exemplary test agents include, but are not limited to, immunomodulatory agents (e.g., antibodies), inhibitory oligonucleotides (e.g., antisense oligonucleotides, short-inhibitory oligonucleotides and ribozymes) and small organic compounds.

Identifying Therapeutic Agents for Metastatic Esophageal Cancer

The present invention provides target molecules for treating or preventing metastasis esophageal cancer. Screening assays for EC metastasis of the present invention can be performed according to the method for EC described above, using marker genes associated with EC metastasis.

In the present invention, marker genes selected from the group consisting of genes listed in tables 4 and 5 are useful for the screening. An agent that suppresses the expression of one or more of up-regulated genes or the activity of their gene products obtained by the present invention are useful for treating or preventing EC with lymph-node metastasis. Alternatively, an agent that enhances the expression of one or more down-regulated genes or the activity of their gene products obtained by the present invention is also useful for treating or preventing EC with lymph-node metastasis.

In the present invention, the agent regulating an expression level of genes listed in tables 4 and 5 can be identified by the same manner for identifying agents that inhibit or enhance EC-associated gene expression. Alternatively, the agent regulating the activity of their gene products can be also identified by the same manner for identifying agents that inhibit or enhance EC-associated gene product.

Identifying Therapeutic Agents for Recurrent Esophageal Cancer

The present invention provides target molecules for treating or preventing recurrent esophageal cancer. Screening assays for EC metastasis of the present invention can be performed according to the method for EC described above, using marker genes associated with EC metastasis.

In the present invention, marker genes selected from the group consisting of genes listed in tables 6 and 7 are useful for the screening. An agent that suppresses the expression of one or more of up-regulated genes or the activity of their gene products obtained by the present invention are useful for treating or preventing EC with post-surgery recurrence. Alternatively, an agent that enhances the expression of one or more down-regulated genes or the activity of their gene products obtained by the present invention is also useful for treating or preventing EC with post-surgery recurrence.

In the present invention, the agent regulating an expression level of genes listed in tables 6 and 7 can be identified by the same manner for identifying agents that inhibit or enhance EC-associated gene expression. Alternatively, the agent regulating the activity of their gene products can be also identified by the same manner for identifying agents that inhibit or enhance EC-associated gene product.

Kits

The present invention also includes an EC-detection reagent, e.g., a nucleic acid that specifically binds to or identifies one or more EC nucleic acids, including oligonucleotide sequences which are complementary to a portion of an EC nucleic acid, or an antibody that bind to one or more proteins encoded by an EC nucleic acid. The detection reagents can be packaged together in the form of a kit. For example, the detection reagents can be packaged in separate containers, e.g., a nucleic acid or antibody (either bound to a solid matrix or packaged separately with reagents for binding them to the matrix), a control reagent (positive and/or negative), and/or a detectable label. Instructions (e.g., written, tape, VCR, CD-ROM, etc.) for carrying out the assay can also be included in the kit. The assay format of the kit can be a Northern hybridization or a sandwich ELISA, both of which are known in the art. See, for example, Sambrook and Russell, *Molecular Cloning: A Laboratory Manual*, $3^{rd}$ Edition, 2001, Cold Spring Harbor Laboratory Press; and *Using Antibodies, supra*.

For example, an EC detection reagent can be immobilized on a solid matrix, for example a porous strip, to form at least one EC detection site. The measurement or detection region of the porous strip can include a plurality of sites, each containing a nucleic acid. A test strip can also contain sites for negative and/or positive controls. Alternatively, control sites can be located on a separate strip from the test strip. Optionally, the different detection sites can contain different amounts of immobilized nucleic acids, i.e., a higher amount in the first detection site and lesser amounts in subsequent sites. Upon the addition of test sample, the number of sites displaying a detectable signal provides a quantitative indication of the amount of EC present in the sample. The detection sites can be configured in any suitably detectable shape and are typically in the shape of a bar or dot spanning the width of a test strip.

Alternatively, the kit can contain a nucleic acid substrate array comprising one or more nucleic acids. The nucleic acids on the array specifically identify one or more nucleic acid sequences represented by the EC-associated genes listed in tables 1, 2, and 4-7. The expression of 2, 3, 4, 5, 6, 7, 8, 9, 10, 15, 20, 25, 40 or 50 or more of the nucleic acids represented by the EC-associated genes listed in tables 1, 2, and 4-7 can be identified by virtue of the level of binding to an array test strip or chip. The substrate array can be on, e.g., a solid substrate, for example a "chip" described in U.S. Pat. No. 5,744,305, the contents of which are incorporated by reference herein in its entirety. Array substrates of use in the present methods are commercially available, for example, from Affymetrix, Santa Clara, Calif.

Arrays and Pluralities

The present invention also includes a nucleic acid substrate array comprising one or more nucleic acids. The nucleic acids on the array specifically correspond to one or more nucleic acid sequences represented by the EC-associated genes listed in tables 1, 2, and 4-7. The level of expression of 2, 3, 4, 5, 6, 7, 8, 9, 10, 15, 20, 25, 40 or 50 or more of the nucleic acids represented by the EC-associated genes listed in tables 1, 2, and 4-7 can be identified by detecting nucleic acid binding to the array.

The present invention also includes an isolated plurality (i.e., a mixture of two or more nucleic acids) of nucleic acids. The nucleic acids can be in a liquid phase or a solid phase, e.g., immobilized on a solid support, for example, a nitrocellulose membrane. The plurality includes one or more of the nucleic acids represented by the EC-associated genes listed in tables 1, 2, and 4-7. In various embodiments, the plurality includes 2, 3, 4, 5, 6, 7, 8, 9, 10, 15, 20, 25, 40 or 50 or more of the nucleic acids represented by the EC-associated genes listed in tables 1, 2, and 4-7.

Candidate Compounds

A compound isolated by the screening serves as a candidate for the development of drugs that inhibit the expression of the marker gene or the activity of the protein encoded by the marker gene and can be applied to the treatment or prevention of esophageal cancer.

Moreover, compounds in which a part of the structure of the compound inhibiting the activity of proteins encoded by marker genes is converted by addition, deletion and/or replacement are also included as the compounds obtainable by the screening methods of the present invention.

When administrating a compound isolated by the methods of the present invention as a pharmaceutical for humans and other mammals, including without limitation, mice, rats, hamsters, guinea-pigs, rabbits, cats, dogs, sheep, pigs, cattle, monkeys, baboons, and chimpanzees, the isolated compound can be directly administered or can be formulated into a dosage form using known pharmaceutical preparation methods. For example, according to the needs of the patient, the drugs can be taken orally, as sugar-coated tablets, capsules, elixirs and microcapsules, or non-orally, in the form of injections of sterile solutions or suspensions with water or any other pharmaceutically acceptable liquid. For example, the compounds can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredient contained in such a preparation makes a suitable dosage within the indicated range acquirable.

Examples of additives that can be admixed into tablets and capsules include, but are not limited to, binders, including gelatin, corn starch, tragacanth gum and arabic gum; excipients, including crystalline cellulose; swelling agents, including corn starch, gelatin and alginic acid; lubricants, including magnesium stearate; sweeteners, including sucrose, lactose or saccharin; and flavoring agents, including peppermint, spearmint, Gaultheria adenothrix oil and cherry. When the unit-dose form is a capsule, a liquid carrier, including an oil, can be further included in the above ingredients. Sterile composites for injection can be formulated following normal drug implementations using vehicles, for example, distilled water or saline solution, suitable for injection.

Physiological saline, glucose, and other isotonic liquids, including adjuvants, such as D-sorbitol, D-mannose, D-mannitol, and sodium chloride, can be used as aqueous solutions for injection. These can be used in conjunction with suitable solubilizers, for example, alcohols including ethanol; polyalcohols, including propylene glycol and polyethylene glycol; and non-ionic surfactants, including Polysorbate 80™ and HCO-50.

Sesame oil or soy-bean oil can be used as an oleaginous liquid, can be used in conjunction with benzyl benzoate or benzyl alcohol as a solubilizer, and can be formulated with a buffer, including phosphate buffer and sodium acetate buffer; a pain-killer, including procaine hydrochloride; a stabilizer, including benzyl alcohol and phenol; and/or an anti-oxidant. A prepared injection can be filled into a suitable ampoule.

Methods well known to those skilled in the art can be used to administer the pharmaceutical composition of the present invention to patients, for example as an intra-arterial, intravenous, or percutaneous injection or as an intranasal, trans-bronchial, intramuscular or oral administration. The dosage and method of administration vary according to the body-weight and age of a patient and the administration method; however, one skilled in the art can routinely select a suitable method of administration. If said compound is encodable by a DNA, the DNA can be inserted into a vector for gene therapy and the vector administered to a patient to perform the therapy. The dosage and method of administration vary according to the body-weight, age, and symptoms of the patient; however, one skilled in the art can suitably select them.

For example, although the dose of a compound that binds to a protein of the present invention and regulates its activity depends on the symptoms, the dose is generally about 0.1 mg to about 100 mg per day, preferably about 1.0 mg to about 50 mg per day and more preferably about 1.0 mg to about 20 mg per day, when administered orally to a normal adult human (weighing about 60 kg).

When administering the compound parenterally, in the form of an injection to a normal adult human (weighing about 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. In the case of other animals, the appropriate dosage amount can be routinely calculated by converting to 60 kg of body-weight.

IV. Monitoring and Prognosing Esophageal Cancer

Assessing the Efficacy of Treatment

The differentially expressed EC-associated genes identified herein also allow for the course of treatment of EC to be monitored. In this method, a test cell population is provided from a subject undergoing treatment for EC. If desired, test cell populations are obtained from the subject at various time points, before, during, and/or after treatment. Expression of one or more of the EC-associated genes in the test cell population is then determined and compared to expression of the same genes in a reference cell population which includes cells whose EC state is known. In the context of the present invention, the reference cells have not been exposed to the treatment of interest.

If the reference cell population contains no EC cells, a similarity in the expression of an EC-associated gene in the test cell population and the reference cell population indicates that the treatment of interest is efficacious. However, a difference in the expression of an EC-associated gene in the test cell population and a normal control reference cell population indicates a less favorable clinical outcome or prognosis. Similarly, if the reference cell population contains EC cells, a difference between the expression of an EC-associated gene in the test cell population and the reference cell population indicates that the treatment of interest is efficacious, while a similarity in the expression of an EC-associated gene in the test population and a EC control reference cell population indicates a less favorable clinical outcome or prognosis.

Additionally, the expression level of one or more EC-associated genes determined in a biological sample from a subject obtained after treatment (i.e., post-treatment levels) can be compared to the expression level of the one or more EC-associated genes determined in a biological sample from a subject obtained prior to treatment onset (i.e., pre-treatment levels). If the EC-associated gene is an up-regulated gene, a decrease in the expression level in a post-treatment sample indicates that the treatment of interest is efficacious while an increase or maintenance in the expression level in the post-treatment sample indicates a less favorable clinical outcome or prognosis. Conversely, if the EC-associated gene is a down-regulated gene, an increase in the expression level in a post-treatment sample can indicate that the treatment of interest is efficacious while a decrease or maintenance in the expression level in the post-treatment sample indicates a less favorable clinical outcome or prognosis.

As used herein, the term "efficacious" indicates that the treatment leads to a reduction in the expression of a pathologically up-regulated gene, an increase in the expression of a pathologically down-regulated gene or a decrease in size, prevalence, or metastatic potential of esophageal ductal carcinoma in a subject. When a treatment of interest is applied prophylactically, the term "efficacious" means that the treatment retards or prevents an esophageal tumor from forming or retards, prevents, or alleviates a symptom of clinical EC. Assessment of esophageal tumors can be made using standard clinical protocols.

In addition, efficaciousness can be determined in association with any known method for diagnosing or treating EC. EC can be diagnosed, for example, by identifying symptomatic anomalies, e.g., weight loss, abdominal pain, back pain, anorexia, nausea, vomiting and generalized malaise, weakness, and jaundice.

Assessing the Prognosis of a Subject with Esophageal Cancer

The present invention also provides methods of assessing the prognosis of a subject with EC including the step of comparing the expression of one or more EC-associated genes in a test cell population to the expression of the same EC-associated genes in a reference cell population from patients over a spectrum of disease stages. By comparing the gene expression of one or more EC-associated genes in the test cell population and the reference cell population(s), or by comparing the pattern of gene expression over time in test cell populations from the subject, the prognosis of the subject can be assessed.

For example, an increase in the expression of one or more of up-regulated EC-associated genes, including those listed in table 2, 5 or 7, in a test sample as compared to a normal control sample, or a decrease in the expression of one or more of down-regulated EC-associated genes, including those listed in tables 1, 4, or 6, in a test sample as compared to a normal control sample, indicates a less favorable prognosis. Conversely, a similarity in the expression of one or more of EC-associated genes listed in tables 1, 2, and 4-7, in a test sample as compared to normal control sample, indicates a more favorable prognosis for the subject. Preferably, the prognosis of a subject can be assessed by comparing the expression profile of the genes selected from the group consisting of genes listed in tables 1, 2, and 4-7.

Furthermore, the present invention also provides a method for predicting metastasis of esophageal cancer in a subject, the method comprising the steps of:
  (a) detecting an expression level of one or more marker genes in a specimen collected from said subject, wherein the one or more marker genes are selected from the group consisting of the genes of EC Nos. 1544-1679 (tables 4-5);
  (b) comparing the expression level of the one or more marker genes in said specimen to that of a metastasis positive case and metastasis negative case; and
  (c) wherein a specimen expression level similar to that of a metastasis positive case indicates a high risk of metastasis of esophageal cancer, and wherein specimen expression level similar to that of a metastasis negative case indicates a low risk of metastasis of esophageal cancer.

Alternatively, the present invention provides a method for predicting recurrence of esophageal cancer in a subject, the method comprising the steps of:

(a) detecting an expression level of one or more marker genes in a specimen collected from said subject, wherein the one or more marker genes are selected from the group consisting of the genes of EC Nos. 1680-1716 (tables 6-7);
(b) comparing the expression level of the one or more marker genes in said specimen to that of a recurrence positive case and recurrence negative case; and
(c) wherein a specimen expression level similar to that of a recurrence positive case indicates a high risk of recurrence of esophageal cancer, and wherein specimen expression level similar to that of a recurrence negative case indicates a low risk of recurrence of esophageal cancer.

The differentially expressed EC Nos. 1544-1679 (tables 4-5) or EC Nos. 1680-1716 (tables 6-7) identified herein can also allow for predicting metastasis and recurrence of esophageal cancer in a subject respectively. In this method, a test biological sample is provided from a subject undergoing treatment for esophageal cancer. If desired, multiple test biological samples are obtained from the subject at various time points before, during or after the treatment e.g. surgery. The expression of one or more genes selected from EC Nos. 1544-1679 (tables 4-5) or EC Nos. 1680-1716 (tables 6-7) in the sample is then determined and compared expression of the same genes in a reference sample with and/or without a metastasis and recurrence of esophageal cancer.

In the present invention, esophageal cancer cells obtained from metastasis negative patients can be used as the reference sample of metastasis negative case. For example, generally, when no lymph-node metastasis was observed in surgically-resected tumors by pathological diagnosis, the patient is metastasis negative. Accordingly, in some preferred embodiments, metastasis of esophageal cancer can be predicted by the method comprising the steps of:
(i) detecting an expression level of one or more marker genes selected from the group consisting of EC Nos. 1544-1679 (tables 4-5) in a specimen collected from a subject whose metastasis of esophageal cancer is to be predicted,
(ii) comparing the expression level of the one or more marker genes in said specimen to the expression level of the same one or more marker genes from a metastasis negative specimen; and
(iii) wherein a decrease in the expression level of one or more genes selected from the group consisting of EC Nos. 1544-1602 (table 4) in step (i), or an increase in the expression level of one or more genes selected from the group consisting of EC Nos. 1603-1679 (table 5) in step (i) as compared to the expression levels of the same genes from the metastasis negative specimen indicates that said subject suffers from or is at risk of metastasis of esophageal cancer.

Similarly, in the present invention, esophageal cancer cells obtained from recurrence negative patients can be used as the reference sample of recurrence negative case. For example, generally, when no recurrence was observed within 32 months after the surgery, the patient is recurrence negative. Accordingly, in some preferred embodiments, recurrence of esophageal cancer can be predicted by the method comprising the steps of:
(i) detecting an expression level of one or more marker genes selected from the group consisting of EC Nos. 1680-1716 (tables 6-7) in a specimen collected from a subject whose recurrence of esophageal cancer is to be predicted,
(ii) comparing the expression level of the one or more marker genes in said specimen to the expression levels of the same one or more marker genes from a recurrence negative specimen; and
(iii) wherein a decrease in the expression level of one or more genes selected from the group consisting of EC Nos. 1680-1688 (table 6) step (i), or an increase in the expression level of one or more genes selected from the group consisting of EC Nos. 1689-1716 (table 7) step (i) as compared to expression levels of the same genes in recurrence negative specimen indicates that said subject suffers from or is at risk of recurrence of esophageal cancer.

In the present methods, the expression level of EC Nos. 1544-1679 (tables 4-5) or EC Nos. 1680-1716 (tables 6-7) can be detected by any one of the following methods:
(a) detecting the mRNA of EC Nos. 1544-1679 (tables 4-5) or EC Nos. 1680-1716 (tables 6-7),
(b) detecting the protein of EC Nos. 1544-1679 (tables 4-5) or EC Nos. 1680-1716 (tables 6-7), and
(c) detecting the biological activity of the protein of EC Nos. 1544-1679 (tables 4-5) or EC Nos. 1680-1716 (tables 6-7).

The present invention also provides kits for predicting a metastasis or recurrence, wherein the kit comprising any one component select from the group consisting of:
(a) reagent for detecting the mRNA of EC Nos. 1544-1679 (tables 4-5) or EC Nos. 1680-1716 (tables 6-7),
(b) reagent for detecting the protein of EC Nos. 1544-1679 (tables 4-5) or EC Nos. 1680-1716 (tables 6-7), and
(c) reagent for detecting the biological activity of the protein of EC Nos. 1544-1679 (tables 4-5) or EC Nos. 1680-1716 (tables 6-7).

V. Treating and Preventing Esophageal Cancer

Methods of Inhibiting Esophageal Cancer

The present invention further provides a method for preventing, treating or alleviating one or more symptoms of EC in a subject by decreasing the expression of one or more of the EC-associated genes listed in tables 2, 5, and 7 (or the activity of its gene product) or increasing the expression of one or more of the EC-associated genes listed in tables 1, 4, and 6 (or the activity of its gene product). Suitable therapeutic compounds can be administered prophylactically or therapeutically to a subject suffering from or at risk of (or susceptible to) developing EC. Such subjects can be identified using standard clinical methods or by detecting an aberrant level of expression of one or more of the EC-associated genes listed in tables 1, 2, and 4-7 or aberrant activity of its gene product. In the context of the present invention, suitable therapeutic agents include, for example, inhibitors of cell cycle regulation, cell proliferation, and protein kinase activity.

The therapeutic methods of the present invention can include the step of increasing the expression, function, or both of one or more gene products of genes whose expression is decreased ("down-regulated" or "under-expressed" genes) in an EC cell relative to normal cells of the same tissue type from which the EC cells are retrieved. In these methods, the subject is treated with an effective amount of a compound that increases the amount of one or more of the under-expressed (down-regulated) genes in the subject. Administration can be systemic or local. Suitable therapeutic compounds include a polypeptide product of an under-expressed gene, a biologically active fragment thereof, and a nucleic acid encoding an under-expressed gene and having expression control elements permitting expression in the EC cells; for example, an agent that increases the level of expression of such a gene endogenous to the EC cells (i.e., which up-regulates the expression of the under-expressed gene or genes). Administration of such compounds counters the effects of aberrantly under-expressed gene or genes in the subject's esophageal cells and improves the clinical condition of the subject.

Alternatively, the therapeutic methods of the present invention can include the step of decreasing the expression, function, or both, of one or more gene products of genes whose expression is aberrantly increased ("up-regulated" or "over-expressed" gene) in esophageal cells. Expression can be inhibited in any of several ways known in the art. For example, expression can be inhibited by administering to the subject a compound, e.g., a nucleic acid that inhibits, or antagonizes the expression of the over-expressed gene or genes, e.g., an antisense oligonucleotide or small interfering RNA which disrupts expression of the over-expressed gene or genes.

Inhibitory Nucleic Acids

As noted above, inhibitory nucleic acids (e.g., antisense oligonucleotides, siRNA, ribozymes) complementary to the nucleotide sequence of the EC-associated genes listed in tables 2, 5, and 7 can be used to reduce the expression level of the genes. For example, inhibitory nucleic acids complementary to the EC-associated genes listed in tables 2, 5, and 7 that are up-regulated in esophageal cancer are useful for the treatment of esophageal cancer. Specifically, the inhibitory nucleic acids of the present invention can act by binding to the EC-associated genes listed in tables 2, 5, and 7, or mRNAs corresponding thereto, thereby inhibiting the transcription or translation of the genes, promoting the degradation of the mRNAs, and/or inhibiting the expression of proteins encoded by the EC-associated genes listed in tables 2, 5, and 7, thereby, inhibiting the function of the proteins.

The term "inhibitory nucleic acids" as used herein encompasses both nucleotides that are entirely complementary to the target sequence and those having a mismatch of one or more nucleotides, so long as the inhibitory nucleic acids can specifically hybridize to the target sequences. The inhibitory nucleic acids of the present invention include polynucleotides that have a sequence identity of at least 70%, 75%, 80%, 85%, 90%, 95%, 96%, 97%, 98%, 99% or higher over a span of at least 15 continuous nucleotides. Algorithms known in the art can be used to determine the sequence identity.

One useful algorithm is BLAST 2.0, originally described in Altschul et al., (1990) *J. Mol. Biol.* 215: 403-10. Software for performing BLAST analyses is publicly available through the National Center for Biotechnology Information (available on the World Wide Web at ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) *Proc. Natl. Acad. Sci. USA* 89: 10915-9).

An additional example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, (1987) *J. Mol. Evol.* 35: 351-60. The method used is similar to the method described by Higgins & Sharp, (1989) CABIOS 5:151-3. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison. For example, in order to determine conserved amino acids in a monomer domain family or to compare the sequences of monomer domains in a family, the sequence of the invention, or coding nucleic acids, are aligned to provide structure-function information.

The antisense nucleic acids of the present invention act on cells producing the proteins encoded by EC-associated marker genes by binding to the DNAs or mRNAs encoding the proteins, inhibiting their transcription or translation, promoting the degradation of the mRNAs, and inhibiting the expression of the proteins, thereby resulting in the inhibition of the protein function.

An antisense nucleic acid of the present invention can be made into an external preparation, for example, a liniment or a poultice, by admixing it with a suitable base material which is inactive against the nucleic acid.

Also, as needed, the antisense nucleic acids of the present invention can be formulated into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following known methods.

The antisense nucleic acids of the present invention can be given to the patient by direct application onto the ailing site or by injection into a blood vessel so that it will reach the site of ailment. An antisense-mounting medium can also be used to increase durability and membrane-permeability. Examples include, but are not limited to, liposomes, poly-L-lysine, lipids, cholesterol, lipofectin or derivatives of these.

The dosage of the inhibitory nucleic acids of the present invention can be adjusted suitably according to the patient's condition and used in desired amounts. For example, a dose range of 0.1 to 100 mg/kg, preferably 0.1 to 50 mg/kg can be administered.

The antisense nucleic acids of the present invention inhibit the expression of a protein of the present invention and are thereby useful for suppressing the biological activity of the protein of the invention. In addition, expression-inhibitors, comprising antisense nucleic acids of the present invention, are useful in that they can inhibit the biological activity of a protein of the present invention.

The methods of the present invention can be used to alter the expression in a cell of an up-regulated EC-associated gene, e.g., up-regulation resulting from the malignant transformation of the cells. Binding of the siRNA to a transcript complementary to one of the EC-associated genes listed in tables 2, 5, and 7 in the target cell results in a reduction in the protein production by the cell. The length of the oligonucleotide is at least 10 nucleotides and can be as long as the naturally-occurring transcript. Preferably, the oligonucleotide is less than 75, 50, 25 nucleotides in length. Most preferably, the oligonucleotide is 19-25 nucleotides in length.

The antisense nucleic acids of present invention include modified oligonucleotides. For example, thiolated oligonucleotides can be used to confer nuclease resistance to an oligonucleotide.

Also, an siRNA against a marker gene can be used to reduce the expression level of the marker gene. Herein, term "siRNA" refers to a double stranded RNA molecule which prevents translation of a target mRNA. Standard techniques for introducing siRNA into the cell can be used, including those in which DNA is a template from which RNA is transcribed. In the context of the present invention, the siRNA comprises a sense nucleic acid sequence and an anti-sense nucleic acid sequence against an up-regulated marker gene, such as an EC-associated gene listed in tables 2, 5, and 7. The siRNA is constructed such that a single transcript has both the sense and complementary antisense sequences from the target gene, e.g., a hairpin.

An siRNA of an EC-associated gene, including those listed in tables 2, 5, and 7, hybridizes to target mRNA and thereby decreases or inhibits production of the polypeptides encoded by EC-associated gene listed in tables 2, 5, and 7 by associating with the normally single-stranded mRNA transcript, thereby interfering with translation and thus, expression of the protein. In the context of the present invention, an siRNA is preferably less than 500, 200, 100, 50, or 25 nucleotides in length. More preferably an siRNA is 19-25 nucleotides in length. Exemplary nucleic acid sequence for the production of ECT2 siRNA includes the sequences of nucleotides of SEQ ID NOs: 8 and 9 as the target sequence. Exemplary nucleic acid sequence for the production of CDC45L siRNA includes the sequences of nucleotides of SEQ ID NOs: 10 and 11 as the target sequence. In order to enhance the inhibition activity of the siRNA, one or more uridine ("u") nucleotides can be added to 3' end of the antisense strand of the target sequence. The number of "u's" to be added is at least 2, generally 2 to 10, preferably 2 to 5. The added "u's" form a single strand at the 3' end of the antisense strand of the siRNA.

An siRNA of an EC-associated gene, including those listed in tables 2, 5, and 7, can be directly introduced into the cells in a form that is capable of binding to the mRNA transcripts. Alternatively, a DNA encoding the siRNA can be carried in a vector.

Vectors can be produced, for example, by cloning an EC-associated gene target sequence into an expression vector having operatively-linked regulatory sequences flanking the sequence in a manner that allows for expression (by transcription of the DNA molecule) of both strands (Lee, N. S., et al., (2002) Nature Biotechnology 20: 500-5). An RNA molecule that is antisense to mRNA of an EC-associated gene is transcribed by a first promoter (e.g., a promoter sequence 3' of the cloned DNA) and an RNA molecule that is the sense strand for the mRNA of an EC-associated gene is transcribed by a second promoter (e.g., a promoter sequence 5' of the cloned DNA). The sense and antisense strands hybridize in vivo to generate siRNA constructs for silencing of the EC-associated gene. Alternatively, the two constructs can be utilized to create the sense and anti-sense strands of a siRNA construct. Cloned EC-associated genes can encode a construct having secondary structure, e.g., hairpins, wherein a single transcript has both the sense and complementary antisense sequences from the target gene.

A loop sequence consisting of an arbitrary nucleotide sequence can be located between the sense and antisense sequence in order to form the hairpin loop structure. Thus, the present invention also provides siRNA having the general formula 5'-[A]-[B]-[A']-3', wherein [A] is a ribonucleotide sequence corresponding to a sequence of a gene selected from table 2, 5 or 7,

[B] is a ribonucleotide sequence consisting of 3 to 23 nucleotides, and

[A'] is a ribonucleotide sequence consisting of the complementary sequence of [A].

The region [A] hybridizes to [A'], and then a loop consisting of region [B] is formed. The loop sequence can be 3 to 23 nucleotides in length. The loop sequence, for example, can be selected from the following sequences (found on the worldwide web at ambion.com/techlib/tb/tb_506.html). Furthermore, a loop sequence consisting of 23 nucleotides also provides active siRNA (Jacque, J. M., et al., (2002) Nature 418: 435-8).

CCC, CCACC or CCACACC: Jacque, J. M, et al., (2002) Nature, Vol. 418: 435-8. UUCG: Lee, N. S., et al., (2002) Nature Biotechnology 20: 500-5; Fruscoloni, P., et al., (2003) Proc. Natl. Acad. Sci. USA 100(4): 1639-44.

UUCAAGAGA: Dykxhoorn, D. M., et al., (2003) Nature Reviews Molecular Cell Biology 4: 457-67.

Accordingly, in some embodiments, the loop sequence can be selected from group consisting of, CCC, UUCG, CCACC, CCACACC, and UUCAAGAGA. A preferable loop sequence is UUCAAGAGA ("ttcaagaga" in DNA). Exemplary hairpin siRNA suitable for use in the context of the present invention include:

for ECT2-siRNA gaugcacucaccuuguagu-[b]-acuacaaggugagugcauc (for target sequence of SEQ ID NO: 8)

ggcaaauacuccugagcuc-[b]-gagcucaggaguauuugcc (for target sequence of SEQ ID NO: 9)

for CDC45L-siRNA gagacauccucuuugacua-[b]-uagucaaagaggaugucuc (for target sequence of SEQ ID NO: 10)

cagaccagugggugcaaga-[b]-ucuugcacccacuggucug (for target sequence of SEQ ID NO: 11)

The nucleotide sequence of suitable siRNAs can be designed using an siRNA design computer program available from the Ambion website on the worldwide web at ambion-.com/techlib/misc/siRNA_finder.html. The computer program selects nucleotide sequences for siRNA synthesis based on the following protocol.

Selection of siRNA Target Sites:

1. Beginning with the AUG start codon of the object transcript, scan downstream for AA dinucleotide sequences. Record the occurrence of each AA and the 3' adjacent 19 nucleotides as siRNA target sites. Tuschl, et al. Genes Dev 13(24):3191-7 (1999) don't recommend against designing siRNA to the 5' and 3' untranslated regions (UTRs) and regions near the start codon (within 75 bases) as these may be richer in regulatory protein binding sites. UTR-binding proteins and/or translation initiation complexes can interfere with binding of the siRNA endonuclease complex.

2. Compare the target sites to the human genome database and eliminate from consideration any target sequences with significant sequence identity to other coding sequences. The sequence identity search can be performed using BLAST 2.0 (Altschul S F, et al., Nucleic Acids Res. 1997; 25(17):3389-402; Altschul S F, J Mol Biol. 1990; 215(3):403-10), which can be found on the NCBI server at ncbi.nlm.nih.gov/BLAST/.

3. Select qualifying target sequences for synthesis. Using the Ambion algorithm, preferably several target sequences can be selected along the length of the gene to evaluate.

The regulatory sequences flanking the EC-associated gene sequences can be identical or different, such that their expression can be modulated independently, or in a temporal or spatial manner. siRNAs are transcribed intracellularly by cloning the EC-associated gene templates, respectively, into a vector containing, e.g., a RNA polymerase III transcription unit from the small nuclear RNA (snRNA) U6 or the human H1 RNA promoter. For introducing the vector into the cell, transfection-enhancing agent can be used. FuGENE (Roche diagnostics), Lipofectamine 2000 (Invitrogen), Oligofectamine (Invitrogen), and Nucleofector (Wako pure Chemical) are useful as the transfection-enhancing agent.

The antisense oligonucleotide or siRNA of the present invention inhibits the expression of a polypeptide of the present invention and is thereby useful for suppressing the biological activity of a polypeptide of the invention. Also, expression-inhibitors, comprising the antisense oligonucleotide or siRNA of the invention, are useful in the point that they can inhibit the biological activity of the polypeptide of the invention. Therefore, a composition comprising one or more antisense oligonucleotides or siRNAs of the present invention is useful for treating an esophageal cancer.

Antibodies

Alternatively, the function of one or more gene products of the genes over-expressed in EC can be inhibited by administering a compound that binds to or otherwise inhibits the function of the gene products. For example, the compound can be an antibody which binds to the over-expressed gene product or gene products.

The present invention refers to the use of antibodies, particularly antibodies against a protein encoded by an up-regulated marker gene, or a fragment of such an antibody. As used herein, the term "antibody" refers to an immunoglobulin molecule having a specific structure, that interacts (i.e., binds) only with the antigen that was used for synthesizing the antibody (i.e., the gene product of an up-regulated marker) or with an antigen closely related thereto. Furthermore, an antibody can be a fragment of an antibody or a modified antibody, so long as it binds to one or more of the proteins encoded by the marker genes. For instance, the antibody fragment can be Fab, F(ab')$_2$, Fv, or single chain Fv (scFv), in which Fv fragments from H and L chains are ligated by an appropriate linker (Huston J. S. et al. Proc. Natl. Acad. Sci. U.S.A. 85:5879-83 (1988)). More specifically, an antibody fragment can be generated by treating an antibody with an enzyme, including papain or pepsin. Alternatively, a gene encoding the antibody fragment can be constructed, inserted into an expression vector, and expressed in an appropriate host cell (see, for example, Co M. S. et al. J. Immunol. 152:2968-76 (1994); Better M. and Horwitz A. H. Methods Enzymol. 178:476-96 (1989); Pluckthun A. and Skerra A. Methods Enzymol. 178:497-515 (1989); Lamoyi E. Methods Enzymol. 121:652-63 (1986); Rousseaux J. et al. Methods Enzymol. 121:663-9 (1986); Bird R. E. and Walker B. W. Trends Biotechnol. 9:132-7 (1991)).

An antibody can be modified by conjugation with a variety of molecules, including polyethylene glycol (PEG). The present invention provides such modified antibodies. The modified antibody can be obtained by chemically modifying an antibody. Such modification methods are conventional in the field.

Alternatively, an antibody can comprise a chimeric antibody having a variable region from a nonhuman antibody and a constant region from a human antibody, or a humanized antibody, comprising a complementarity determining region (CDR) from a nonhuman antibody, a frame work region (FR) and a constant region from a human antibody. Such antibodies can be prepared by using known technologies.

Cancer therapies directed at specific molecular alterations that occur in cancer cells have been validated through clinical development and regulatory approval of anti-cancer drugs including trastuzumab (Herceptin) for the treatment of advanced breast cancer, imatinib methylate (Gleevec) for chronic myeloid leukemia, gefitinib (Iressa) for non-small cell lung cancer (NSCLC), and rituximab (anti-CD20 mAb) for B-cell lymphoma and mantle cell lymphoma (Ciardiello F and Tortora G. Clin Cancer Res. 2001; 7(10):2958-70. Review; Slamon D J, et al., N Engl J. Med. 2001; 344(11): 783-92; Rehwald U, et al., Blood. 2003; 101(2):420-4; Fang G, et al., (2000). Blood, 96, 2246-53). These drugs are clinically effective and better tolerated than traditional anti-cancer agents because they target only transformed cells. Hence, such drugs not only improve survival and quality of life for cancer patients, but also validate the concept of molecularly targeted cancer therapy. Furthermore, targeted drugs can enhance the efficacy of standard chemotherapy when used in combination with it (Gianni L. (2002). Oncology, 63 Suppl 1, 47-56; Klejman A, et al., (2002). Oncogene, 21, 5868-76). Therefore, future cancer treatments will involve combining conventional drugs with target-specific agents aimed at different characteristics of tumor cells, for example, angiogenesis and invasiveness.

These modulatory methods can be performed ex vivo or in vitro (e.g., by culturing the cell with the agent) or, alternatively, in vivo (e.g., by administering the agent to a subject). The methods involve administering a protein or combination of proteins or a nucleic acid molecule or combination of nucleic acid molecules as therapy to counteract aberrant expression of the differentially expressed genes or aberrant activity of their gene products.

Diseases and disorders that are characterized by increased (relative to a subject not suffering from the disease or disorder) expression levels or biological activities of genes and gene products, respectively, can be treated with therapeutics that antagonize (i.e., reduce or inhibit) activity of the over-expressed gene or genes. Therapeutics that antagonize activity can be administered therapeutically or prophylactically.

Accordingly, therapeutics that can be utilized in the context of the present invention include, e.g., (i) a polypeptide of the over-expressed or under-expressed gene or genes, or analogs, derivatives, fragments or homologs thereof; (ii) antibodies to the over-expressed gene or gene products; (iii) nucleic acids encoding the over-expressed or under-expressed gene or genes; (iv) antisense nucleic acids or nucleic acids that are "dysfunctional" (i.e., due to a heterologous insertion within the nucleic acids of one or more over-expressed gene or genes); (v) small interfering RNA (siRNA); or (vi) modulators (i.e., inhibitors, agonists and antagonists that alter the interaction between an over-expressed or under-expressed polypeptide and its binding partner). The dysfunctional antisense molecules are utilized to "knockout" endogenous function of a polypeptide by homologous recombination (see, e.g., Capecchi, Science 244: 1288-92 1989).

Diseases and disorders that are characterized by decreased (relative to a subject not suffering from the disease or disorder) biological activity can be treated with therapeutics that increase (i.e., are agonists to) activity. Therapeutics that up-regulate activity can be administered in a therapeutic or prophylactic manner. Therapeutics that can be utilized include, but are not limited to, a polypeptide (or analogs, derivatives, fragments or homologs thereof) or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a gene whose expression is altered). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic administration occurs prior to the manifestation of overt clinical symptoms of disease or disorder, such that a disease or disorder is prevented or, alternatively, delayed in its progression.

Therapeutic methods of the present invention can include the step of contacting a cell with an agent that modulates one or more of the activities of the gene products of the differentially expressed genes. Examples of agents that modulates protein activity include, but are not limited to, nucleic acids, proteins, naturally-occurring cognate ligands of such proteins, peptides, peptidomimetics, and other small molecule. For example, a suitable agent can stimulate one or more protein activities of one or more differentially under-expressed genes.

Vaccinating Against Esophageal Cancer

The present invention also relates to methods of treating or preventing esophageal cancer in a subject comprising the step of administering to said subject a vaccine comprising one or more polypeptides encoded by one or more nucleic acid selected from the group consisting of the EC-associated genes listed in tables 2, 5, and 7 (i.e., up-regulated genes), an immunologically active fragment of said polypeptide (i.e., an epitope), or a polynucleotide encoding such a polypeptide or fragment thereof. Administration of the polypeptide induces an anti-tumor immunity in a subject. To induce anti-tumor immunity, one or more polypeptides encoded by one or more nucleic acids selected from the group consisting of the EC-associated genes listed in tables 2, 5, and 7, an immunologically active fragment(s) of said polypeptides, or polynucleotide(s) encoding such polypeptide(s) or fragment(s) thereof is administered to subject in need thereof. Furthermore, the one or more polypeptides encoded by the one or more nucleic acids selected from the group consisting of the EC-associated genes listed in tables 5 and 7 can induce anti-tumor immunity against metastatic and recurrent esophageal cancer, respectively. The polypeptide or the immunologically active fragments thereof are useful as vaccines against EC. In some cases, the proteins or fragments thereof can be administered in a form bound to the T cell receptor (TCR) or presented by an antigen presenting cell (APC), including macrophages, dendritic cells (DC), or B-cells. Due to the strong antigen presenting ability of DC, the use of DC is most preferable among the APCs.

Identification of immunologically active fragments (i.e., epitopes) is well known in the art. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding (i.e., conformationally determined) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., *Epitope Mapping Protocols in Methods in Molecular Biology*, Vol. 66, Glenn E. Morris, Ed. (1996). Antibodies that recognize the same epitope can be identified in a simple immunoassay showing the ability of one antibody to block the binding of another antibody to a target antigen (e.g., a competitive ELISA or solid phase radioimmunoassay (SPRIA)). T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., *J. Inf. Dis.* 170, 1110-19 (1994)), by antigen-dependent killing (cytotoxic T lymphocyte assay, Tigges et al., *J. Immunol.* (1996) 156:3901-10) or by cytokine secretion. Methods for determining immunogenic epitopes are described, for example, in Reineke, et al., *Curr Top Microbiol Immunol* (1999) 243:23-36; Mahler, et al., *Clin Immunol* (2003) 107:65-79; Anthony and Lehmann, *Methods* (2003) 29:260-9; Parker and Tomer, *Methods Mol Biol* (2000) 146: 185-201; DeLisser, *Methods Mol Biol* (1999) 96:11-20; Van de Water, et al., *Clin Immunol Immunopathol* (1997) 85:229-35; Carter, *Methods Mol Biol* (1994) 36:207-23; and Pettersson, *Mol Biol Rep* (1992) 16:149-53.

In the present invention, a vaccine against EC refers to a substance that has the ability to induce anti-tumor immunity upon inoculation into animals. According to the present invention, polypeptides encoded by the EC-associated genes listed in tables 2, 5, and 7, or fragments thereof, are HLA-A24 or HLA-A*0201 restricted epitopes peptides that induce potent and specific immune response against EC cells expressing the EC-associated genes listed in tables 2, 5, and 7. Thus, the present invention also encompasses methods of inducing anti-tumor immunity using the polypeptides. In general, anti-tumor immunity includes immune responses including as follows:

induction of cytotoxic lymphocytes against tumors,
induction of antibodies that recognize tumors, and
induction of anti-tumor cytokine production.

Therefore, when a certain protein induces any one of these immune responses upon inoculation into an animal, the protein is determined to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. Specifically, a foreign substance that enters the living body is presented to T cells and B cells by the action of antigen presenting cells (APCs). T cells that respond to the antigen presented by the APCs in an antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to a T cell via an APC, and detecting the induction of CTLs. Furthermore, APCs have the effect of activating CD4+ T cells, CD8+ T cells, macrophages, eosinophils, and NK cells. Since CD4+ T cells and CD8+ T cells are also important in anti-tumor immunity, the anti-tumor immunity-inducing action of the peptide can be evaluated using the activation effect of these cells as indicators. See, Coligan, *Current Protocols in Immunology*, supra.

A method for evaluating the inducing action of CTLs using dendritic cells (DCs) as the APC is well known in the art. DCs are a representative APCs having the strongest CTL-inducing action among APCs. In this method, the test polypeptide is initially contacted with DCs, and then the DCs are contacted with T cells. Detection of T cells having cytotoxic effects against the cells of interest after the contact with DC shows that the test polypeptide has an activity of inducing the cytotoxic T cells. Activity of CTLs against tumors can be detected, for example, using the lysis of $^{51}$Cr-labeled tumor cells as the indicator. Alternatively, methods of evaluating the degree of tumor cell damage using $^3$H-thymidine uptake activity or LDH (lactose dehydrogenase)-release as the indicator is also well known.

Apart from DCs, peripheral blood mononuclear cells (PBMCs) can also be used as the APC. The induction of CTLs has been reported to be enhanced by culturing PBMCs in the presence of GM-CSF and IL-4. Similarly, CTLs have been shown to be induced by culturing PBMCs in the presence of keyhole limpet hemocyanin (KLH) and IL-7.

Test polypeptides confirmed to possess CTL-inducing activity by these methods are deemed to be polypeptides having DC activation effect and subsequent CTL-inducing activity. Therefore, polypeptides that induce CTLs against tumor cells are useful as vaccines against tumors. Furthermore, APCs that have acquired the ability to induce CTLs against tumors through contact with the polypeptides are also useful as vaccines against tumors. Furthermore, CTLs that have acquired cytotoxicity due to presentation of the polypeptide antigens by APCs can be also be used as vaccines against tumors. Such therapeutic methods for tumors, using anti-tumor immunity due to APCs and CTLs, are referred to as cellular immunotherapy.

Generally, when using a polypeptide for cellular immunotherapy, efficiency of the CTL-induction is known to be increased by combining a plurality of polypeptides having different structures and contacting them with DCs. Therefore, when stimulating DCs with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth of tumor cells is suppressed by those antibodies, the polypeptide is deemed to have the ability to induce anti-tumor immunity.

Anti-tumor immunity is induced by administering the vaccine of this invention, and the induction of anti-tumor immunity enables treatment and prevention of EC. Therapy against cancer or prevention of the onset of cancer includes any of the following steps, including inhibition of the growth of cancerous cells, involution of cancer, and suppression of the occurrence of cancer. A decrease in mortality and morbidity of individuals having cancer, decrease in the levels of tumor markers in the blood, alleviation of detectable symptoms accompanying cancer, and such are also included in the therapy or prevention of cancer. Such therapeutic and preventive effects are preferably statistically significant. For example, in observation, at a significance level of 5% or less, wherein the therapeutic or preventive effect of a vaccine against cell proliferative diseases is compared to a control without vaccine administration. For example, Student's t-test, the Mann-Whitney U-test, or ANOVA can be used for statistical analysis.

The above-mentioned protein having immunological activity or a vector encoding the protein can be combined with an adjuvant. An adjuvant refers to a compound that enhances the immune response against the protein when administered together (or successively) with the protein having immunological activity. Exemplary adjuvants include, but are not limited to, cholera toxin, *salmonella* toxin, alum, and such, but are not limited thereto. Furthermore, the vaccine of this invention can be combined appropriately with a pharmaceutically acceptable carrier. Examples of such carriers include sterilized water, physiological saline, phosphate buffer, culture fluid, and such. Furthermore, the vaccine can contain as necessary, stabilizers, suspensions, preservatives, surfactants, and such. The vaccine can be administered systemically or locally, for example, through intradermal, intramuscular, subcutaneous, transdermal, buccal, or intranasal routes. Vaccine administration can be performed by single administration, or boosted by multiple administrations. Doses are as set forth below.

When using an APC or CTL as the vaccine of this invention, tumors can be treated or prevented, for example, by the ex vivo method. More specifically, PBMCs of the subject receiving treatment or prevention are collected, the cells are contacted with the polypeptide ex vivo, and following the induction of APCs or CTLs, the cells can be administered to the subject. APCs can be also induced by introducing a vector encoding the polypeptide into PBMCs ex vivo. APCs or CTLs induced in vitro can be cloned prior to administration. By cloning and growing cells having high activity of damaging target cells, cellular immunotherapy can be performed more effectively. Furthermore, APCs and CTLs isolated in this manner can be used for cellular immunotherapy not only against individuals from whom the cells are retrieved, but also against similar types of tumors from other individuals.

General methods for developing vaccines are described, for example, in *Vaccine Protocols*, Robinson and Cranage, Eds., 2003, Humana Press; Marshall, *Vaccine Handbook: A Practical Guide for Clinicians*, 2003, Lippincott Williams & Wilkins; and *Vaccine Delivery Strategies*, Dietrich, et al., Eds., 2003, Springer Verlag.

Pharmaceutical Compositions

Furthermore, a pharmaceutical composition for treating or preventing a cell proliferative disease, for example cancer, comprising a pharmaceutically effective amount of the polypeptide of the present invention is provided. The pharmaceutical composition can be used for raising anti-tumor immunity.

In the context of the present invention, suitable pharmaceutical formulations include those suitable for oral, rectal, nasal, topical (including buccal and sub-lingual), vaginal or parenteral (including intramuscular, subcutaneous and intravenous) administration, or for administration by inhalation or insufflation. Preferably, administration is intravenous. The formulations are optionally packaged in discrete dosage units.

Pharmaceutical formulations suitable for oral administration include capsules, cachets or tablets, each containing a predetermined amount of active ingredient. Suitable formulations also include powders, granules, solutions, suspensions and emulsions. The active ingredient is optionally administered as a bolus electuary or paste. Tablets and capsules for oral administration can contain conventional excipients, including binding agents, fillers, lubricants, disintegrant and/or wetting agents. A tablet can be made by compression or molding, optionally with one or more formulational ingredients. Compressed tablets can be prepared by compressing in a suitable machine the active ingredients in a free-flowing form, for example, a powder or granules, optionally mixed with a binder, lubricant, inert diluent, lubricating, surface active and/or dispersing agent. Molded tablets can be made by molding in a suitable machine a mixture of the powdered compound moistened with an inert liquid diluent. The tablets can be coated according to methods well known in the art. Oral fluid preparations can be in the form of, for example, aqueous or oily suspensions, solutions, emulsions, syrups or elixirs, or can be presented as a dry product for constitution with water or other suitable vehicle before use. Such liquid preparations can contain conventional additives, for example, suspending agents, emulsifying agents, non-aqueous vehicles (which can include edible oils), and/or preservatives. The tablets can optionally be formulated so as to provide slow or controlled release of the active ingredient therein. A package of tablets can contain one tablet to be taken on each of the month.

Formulations suitable for parenteral administration include aqueous and non-aqueous sterile injection solutions, optionally contain anti-oxidants, buffers, bacteriostats and solutes which render the formulation isotonic with the blood of the intended recipient; as well as aqueous and non-aqueous sterile suspensions including suspending agents and/or thickening agents. The formulations can be presented in unit dose or multi-dose containers, for example as sealed ampoules and vials, and can be stored in a freeze-dried (lyophilized) condition, requiring only the addition of the sterile liquid carrier, for example, saline, water-for-injection, immediately prior to use. Alternatively, the formulations can be presented for continuous infusion. Extemporaneous injection solutions and suspensions can be prepared from sterile powders, granules and tablets of the kind previously described.

Formulations suitable for rectal administration include suppositories with standard carriers for example, cocoa butter or polyethylene glycol. Formulations suitable for topical administration in the mouth, for example, buccally or sublingually, include lozenges, containing the active ingredient in a flavored base, for example, sucrose and acacia or tragacanth, and pastilles, comprising the active ingredient in a base, for example, gelatin and glycerin or sucrose and acacia. For intra-nasal administration, the compounds of the invention can be used as a liquid spray, a dispersible powder, or in the form of drops. Drops can be formulated with an aqueous or non-aqueous base also comprising one or more dispersing agents, solubilizing agents and/or suspending agents.

For administration by inhalation the compounds can be conveniently delivered from an insufflator, nebulizer, pressurized packs or other convenient means of delivering an aerosol spray. Pressurized packs can comprise a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount.

Alternatively, for administration by inhalation or insufflation, the compounds can take the form of a dry powder composition, for example a powder mix of the compound and a suitable powder base, for example, lactose or starch. The powder composition can be presented in unit dosage form, for example, as capsules, cartridges, gelatin or blister packs, from which the powder can be administered with the aid of an inhalator or insufflators.

Other formulations include implantable devices and adhesive patches which release a therapeutic agent.

When desired, the above described formulations, adapted to give sustained release of the active ingredient, can be employed. The pharmaceutical compositions can also contain other active ingredients, including antimicrobial agents, immunosuppressants and/or preservatives.

It should be understood that in addition to the ingredients particularly mentioned above, the formulations of this invention can include other agents conventional in the art with regard to the type of formulation in question. For example, formulations suitable for oral administration can include flavoring agents.

Preferred unit dosage formulations contain an effective dose, as recited below, or an appropriate fraction thereof, of the active ingredient.

For each of the aforementioned conditions, the compositions, e.g., polypeptides and organic compounds, can be administered orally or via injection at a dose ranging from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units can conveniently contain an amount which is effective at such dosage or as a multiple of the same, for instance, units containing about 5 mg to about 500 mg, usually from about 100 mg to about 500 mg.

The dose employed will depend upon a number of factors, including the age and sex of the subject, the precise disorder being treated, and its severity. Also the route of administration can vary depending upon the condition and its severity. In any event, appropriate and optimum dosages can be routinely calculated by those skilled in the art, taking into consideration the above-mentioned factors.

VI. Serodiagnosing Cancer

By measuring the level of DKK1 in a subject-derived biological sample, the occurrence of cancer or a predisposition to develop cancer in a subject can be determined. Preferably, cancer is either of esophageal and lung cancer, or both. Accordingly, the present invention involves determining (e.g., measuring) the level of DKK1 in a biological sample.

Any biological materials may be used as the biological sample for determining the level of DKK1 so long as either the DKK1 gene or the DKK1 protein can be detected in the sample. Preferably, the biological sample comprises blood, serum or other bodily fluids such as sputum. The preferred biological sample is blood or blood derived sample. The blood derived sample includes serum, plasma, or whole blood.

The subject diagnosed for cancer according to the method is preferably a mammal and includes human, non-human primate, mouse, rat, dog, cat, horse and cow.

In one embodiment of the present invention, a gene transcript of the DKK1 gene (e.g., the DKK1 protein) is detected to determine the DKK1 level. The DKK1 gene can be detected and measured using techniques well known to one of ordinary skill in the art. The gene transcripts detected by the method include both the transcription and translation products, such as mRNA and proteins. For example, sequences corresponding to DKK1 gene can be used to construct probes for detecting DKK1 mRNAs by, e.g., Northern blot hybridization analysis. The hybridization of the probe to a gene transcript in a subject biological sample can be also carried out on a DNA array. As another example, the DKK1 sequence can be used to construct primers for specifically amplifying the DKK1 polynucleotide in, e.g., amplification-based detection methods such as reverse-transcription based polymerase chain reaction (RT-PCR).

In an alternate embodiment, the level of DKK1 is determined by measuring the quantity DKK1 protein in a biological sample. A method for determining the quantity of the DKK1 protein in a biological sample includes immunoassay methods. In a preferred embodiment, the immunoassay comprises an ELISA.

The DKK1 level in the biological sample is then compared with an DKK1 level associated with a reference sample, such as a normal control sample. The phrase "normal control level" refers to the level of DKK1 typically found in a biological sample of a population not suffering from cancer. The reference sample is preferably of a similar nature to that of the test sample. For example, if the test sample comprise serum collected from a patient to be diagnosed or prognosed, the reference sample should also be serum. The DKK1 level in the biological samples from control and test subjects may be determined at the same time or, alternatively, the normal control level may be determined by a statistical method based on the results obtained by analyzing the level of DKK1 in samples previously collected from a control group.

The DKK1 level may also be used to monitor the course of treatment of cancer. In this method, a test biological sample is provided from a subject undergoing treatment for cancer. Preferably, cancer is esophageal and lung cancer. Preferably, multiple test biological samples are obtained from the subject at various time points before, during or after the treatment. The level of DKK1 in the post-treatment sample may then be compared with the level of DKK1 in the pre-treatment sample or, alternatively, with a reference sample (e.g., a normal control level). For example, if the post-treatment DKK1 level is lower than the pre-treatment DKK1 level, one can conclude that the treatment was efficacious. Likewise, if the post-treatment DKK1 level is similar to the normal control DKK1 level, one can also conclude that the treatment was efficacious.

An "efficacious" treatment is one that leads to a reduction in the level of DKK1 or a decrease in size, prevalence or metastatic potential of cancer in a subject. When a treatment is applied prophylactically, "efficacious" means that the treatment retards or prevents occurrence of cancer or alleviates a clinical symptom of cancer. The assessment of cancer can be made using standard clinical protocols. Furthermore, the efficaciousness of a treatment can be determined in association with any known method for diagnosing or treating cancer. For example, cancer is routinely diagnosed histopathologically or by identifying symptomatic anomalies such as chronic cough, hoarseness, coughing up blood, weight loss, loss of appetite, shortness of breath, wheezing, repeated bouts of bronchitis or pneumonia and chest pain.

Moreover, the present method for diagnosing cancer may also be applied for assessing the prognosis of a patient with the cancer by comparing the level of DKK1 in a patient-derived biological sample with that of a reference sample. Preferably, cancer is esophageal and lung cancer. Alternatively, the level of DKK1 in the biological sample may be measured over a spectrum of disease stages to assess the prognosis of the patient. An increase in the level of DKK1 as compared to a normal control level indicates less favorable prognosis. A similarity in the level of DKK1 as compared to a normal control level indicates a more favorable prognosis of the patient.

VII. Method for Assessing the Prognosis of Cancer

According to the present invention, it was newly discovered that DKK1 expression is significantly associated with poorer prognosis of patients (see FIG. 2). Thus, the present invention provides a method for determining or assessing the prognosis of a patient with cancer, in particular, esophageal and lung cancer, by detecting the expression level of the DKK1 gene in a biological sample of the patient; comparing the detected expression level to a control level; and determining a increased expression level to the control level as indicative of poor prognosis (poor survival).

Herein, the term "prognosis" refers to a forecast as to the probable outcome of the disease as well as the prospect of recovery from the disease as indicated by the nature and symptoms of the case. Accordingly, a less favorable, negative, poor prognosis is defined by a lower post-treatment survival term or survival rate. Conversely, a positive, favorable, or good prognosis is defined by an elevated post-treatment survival term or survival rate.

The terms "assessing the prognosis" refer to the ability of predicting, forecasting or correlating a given detection or measurement with a future outcome of cancer of the patient (e.g., malignancy, likelihood of curing cancer, survival, and the like). For example, a determination of the expression level of DKK1 over time enables a predicting of an outcome for the patient (e.g., increase or decrease in malignancy, increase or decrease in grade of a cancer, likelihood of curing cancer, survival, and the like).

In the context of the present invention, the phrase "assessing (or determining) the prognosis" is intended to encompass predictions and likelihood analysis of cancer, progression, particularly cancer recurrence, metastatic spread and disease relapse. The present method for assessing prognosis is intended to be used clinically in making decisions concerning treatment modalities, including therapeutic intervention, diagnostic criteria such as disease staging, and disease monitoring and surveillance for metastasis or recurrence of neoplastic disease.

The patient-derived biological sample used for the method may be any sample derived from the subject to be assessed so long as the DKK1 gene can be detected in the sample. Preferably, the biological sample comprises an esophageal and lung cell (a cell obtained from the esophagus and lung). Furthermore, the biological sample includes bodily fluids such as sputum, blood, serum, or plasma. Moreover, the sample may be cells purified from a tissue. The biological samples may be obtained from a patient at various time points, including before, during, and/or after a treatment.

According to the present invention, it was shown that the higher the expression level of the DKK1 gene measured in the patient-derived biological sample, the poorer the prognosis for post-treatment remission, recovery, and/or survival and the higher the likelihood of poor clinical outcome. Thus, according to the present method, the "control level" used for comparison may be, for example, the expression level of the DKK1 gene detected before any kind of treatment in an individual or a population of individuals who showed good or positive prognosis of cancer, after the treatment, which herein will be referred to as "good prognosis control level". Alternatively, the "control level" may be the expression level of the DKK1 gene detected before any kind of treatment in an individual or a population of individuals who showed poor or negative prognosis of cancer, after the treatment, which herein will be referred to as "poor prognosis control level". The "control level" is a single expression pattern derived from a single reference population or from a plurality of expression patterns. Thus, the control level may be determined based on the expression level of the DKK1 gene detected before any kind of treatment in a patient of cancer, or a population of the patients whose disease state (good or poor prognosis) is known. Preferably, cancer is esophageal and lung cancer. It is preferred, to use the standard value of the expression levels of the DKK1 gene in a patient group with a known disease state. The standard value may be obtained by any method known in the art. For example, a range of mean±2 S.D. or mean±3 S.D. may be used as standard value.

The control level may be determined at the same time with the test biological sample by using a sample(s) previously collected and stored before any kind of treatment from cancer patient(s) (control or control group) whose disease state (good prognosis or poor prognosis) are known.

Alternatively, the control level may be determined by a statistical method based on the results obtained by analyzing the expression level of the DKK1 gene in samples previously collected and stored from a control group. Furthermore, the control level can be a database of expression patterns from previously tested cells. Moreover, according to an aspect of the present invention, the expression level of the DKK1 gene in a biological sample may be compared to multiple control levels, which control levels are determined from multiple reference samples. It is preferred to use a control level determined from a reference sample derived from a tissue type similar to that of the patient-derived biological sample.

According to the present invention, a similarity in the expression level of the DKK1 gene to the good prognosis control level indicates a more favorable prognosis of the patient and an increase in the expression level to the good prognosis control level indicates less favorable, poorer prognosis for post-treatment remission, recovery, survival, and/or clinical outcome. On the other hand, a decrease in the expression level of the DKK1 gene to the poor prognosis control level indicates a more favorable prognosis of the patient and a similarity in the expression level to the poor prognosis control level indicates less favorable, poorer prognosis for post-treatment remission, recovery, survival, and/or clinical outcome.

An expression level of the DKK1 gene in a biological sample can be considered altered when the expression level differs from the control level by more than 1.0, 1.5, 2.0, 5.0, 10.0, or more fold. Alternatively, an expression level of the DKK1 gene in a biological sample can be considered altered, when the expression level is increased or decreased to the control level at least 10%, 20%, 30%, 40%, 50%, 60%, 80%, 90%, or more.

The difference in the expression level between the test biological sample and the control level can be normalized to a control, e.g., housekeeping gene. For example, polynucleotides whose expression levels are known not to differ between the cancerous and non-cancerous cells, including those coding for β-actin, glyceraldehyde 3-phosphate dehydrogenase, and ribosomal protein P1, may be used to normalize the expression levels of the DKK1 gene.

The expression level may be determined by detecting the gene transcript in the patient-derived biological sample using techniques well known in the art. The gene transcripts detected by the present method include both the transcription and translation products, such as mRNA and protein.

For instance, the transcription product of the DKK1 gene can be detected by hybridization, e.g., Northern blot hybridization analyses, that use a DKK1 gene probe to the gene transcript. The detection may be carried out on a chip or an array. The use of an array is preferable for detecting the expression level of a plurality of genes including the DKK1 gene. As another example, amplification-based detection methods, such as reverse-transcription based polymerase chain reaction (RT-PCR) which use primers specific to the DKK1 gene may be employed for the detection (see Example). The DKK1 gene-specific probe or primers may be designed and prepared using conventional techniques by referring to the whole sequence of the DKK1 gene (SEQ ID NO: 109). For example, the primers (SEQ ID NOs: 74 and 111, 73 and 74) used in the Example may be employed for the detection by RT-PCR, but the present invention is not restricted thereto.

Specifically, a probe or primer used for the present method hybridizes under stringent, moderately stringent, or low stringent conditions to the mRNA of the DKK1 gene. As used herein, the phrase "stringent (hybridization) conditions" refers to conditions under which a probe or primer will hybridize to its target sequence, but to no other sequences. Stringent conditions are sequence-dependent and will be different under different circumstances. Specific hybridization of longer sequences is observed at higher temperatures than shorter sequences. Generally, the temperature of a stringent condition is selected to be about 5° C. lower than the thermal melting point (Tm) for a specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes or primers (e.g., 10 to 50 nucleotides) and at least about 60° C. for longer probes or primers. Stringent conditions may also be achieved with the addition of destabilizing agents, such as formamide.

Alternatively, the translation product may be detected for the assessment of the present invention. For example, the quantity of the DKK1 protein may be determined. A method for determining the quantity of the protein as the translation product includes immunoassay methods that use an antibody specifically recognizing the DKK1 protein. The antibody may be monoclonal or polyclonal. Furthermore, any fragment or modification (e.g., chimeric antibody, scFv, Fab, F(ab')2, Fv, etc.) of the antibody may be used for the detection, so long as the fragment retains the binding ability to the DKK1 protein. Methods to prepare these kinds of antibodies for the detection of proteins are well known in the art, and any method may be employed in the present invention to prepare such antibodies and equivalents thereof.

As another method to detect the expression level of the DKK1 gene based on its translation product, the intensity of staining may be observed via immunohistochemical analysis using an antibody against DKK1 protein. Namely, the observation of strong staining indicates increased presence of the DKK1 protein and at the same time high expression level of the DKK1 gene.

Furthermore, the DKK1 protein is known to have a cell proliferating activity. Therefore, the expression level of the DKK1 gene can be determined using such cell proliferating activity as an index. For example, cells which express DKK1 are prepared and cultured in the presence of a biological sample, and then by detecting the speed of proliferation, or by measuring the cell cycle or the colony forming ability the cell proliferating activity of the biological sample can be determined.

Moreover, in addition to the expression level of the DKK1 gene, the expression level of other esophageal and lung cell-associated genes, for example, genes known to be differentially expressed in esophageal and lung cancer, may also be determined to improve the accuracy of the assessment. Such other lung cell-associated genes include those described in WO 2004/031413 and WO 2005/090603.

The patient to be assessed for the prognosis of cancer according to the method is preferably a mammal and includes human, non-human primate, mouse, rat, dog, cat, horse, and cow.

VIII. A Kit for Assessing the Prognosis of Cancer

The present invention provides a kit for assessing the prognosis of cancer. Preferably, cancer is esophageal and lung cancer. Specifically, the kit comprises at least one reagent for detecting the expression of the DKK1 gene in a patient-derived biological sample, which reagent may be selected from the group of:

(a) a reagent for detecting mRNA of the DKK1 gene;
(b) a reagent for detecting the DKK1 protein; and
(c) a reagent for detecting the biological activity of the DKK1 protein.

Suitable reagents for detecting mRNA of the DKK1 gene include nucleic acids that specifically bind to or identify the DKK1 mRNA, such as oligonucleotides which have a complementary sequence to a part of the DKK1 mRNA. These kinds of oligonucleotides are exemplified by primers and probes that are specific to the DKK1 mRNA. These kinds of oligonucleotides may be prepared based on methods well known in the art. If needed, the reagent for detecting the DKK1 mRNA may be immobilized on a solid matrix. Moreover, more than one reagent for detecting the DKK1 mRNA may be included in the kit.

On the other hand, suitable reagents for detecting the DKK1 protein include antibodies to the DKK1 protein. The antibody may be monoclonal or polyclonal. Furthermore, any fragment or modification (e.g., chimeric antibody, scFv, Fab, F(ab')2, Fv, etc.) of the antibody may be used as the reagent, so long as the fragment retains the binding ability to the DKK1 protein. Methods to prepare these kinds of antibodies for the detection of proteins are well known in the art, and any method may be employed in the present invention to prepare such antibodies and equivalents thereof. Furthermore, the antibody may be labeled with signal generating molecules via direct linkage or an indirect labeling technique. Labels and methods for labeling antibodies and detecting the binding of antibodies to their targets are well known in the art and any labels and methods may be employed for the present invention. Moreover, more than one reagent for detecting the DKK1 protein may be included in the kit.

Furthermore, when a cell expressing LRP5/6 and Kremen is used as the reagent, the biological activity can be determined by, for example, measuring the cell proliferating activity due to the expressed DKK1 protein in the biological. For example, the cell is cultured in the presence of a patient-derived biological sample, and then by detecting the speed of proliferation, or by measuring the cell cycle or the colony forming ability the cell proliferating activity of the biological sample can be determined. If needed, the reagent for detecting the DKK1 mRNA may be immobilized on a solid matrix. Moreover, more than one reagent for detecting the biological activity of the DKK1 protein may be included in the kit.

The kit may comprise more than one of the aforementioned reagents. Furthermore, the kit may comprise a solid matrix and reagent for binding a probe against the DKK1 gene or antibody against the DKK1 protein, a medium and container for culturing cells, positive and negative control reagents, and a secondary antibody for detecting an antibody against the DKK1 protein. For example, tissue samples obtained from patient with good prognosis or poor prognosis may serve as useful control reagents. A kit of the present invention may further include other materials desirable from a commercial and user standpoint, including buffers, diluents, filters, needles, syringes, and package inserts (e.g., written, tape, CD-ROM, etc.) with instructions for use. These reagents and such may be comprised in a container with a label. Suitable containers include bottles, vials, and test tubes. The containers may be formed from a variety of materials, such as glass or plastic.

As an embodiment of the present invention, when the reagent is a probe against the DKK1 mRNA, the reagent may be immobilized on a solid matrix, such as a porous strip, to form at least one detection site. The measurement or detection region of the porous strip may include a plurality of sites, each containing a nucleic acid (probe). A test strip may also contain sites for negative and/or positive controls. Alternatively, control sites may be located on a strip separated from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of DKK1 mRNA present in the sample. The detection sites may be configured in any suitably detectable shape and are typically in the shape of a bar or dot spanning the width of a test strip.

The kit of the present invention may further comprise a positive control sample or DKK1 standard sample. The positive control sample of the present invention may be prepared by collecting DKK1 positive blood samples and then those DKK1 level are assayed. Alternatively, purified DKK1 protein or polynucleotide may be added to DKK1 free serum to form the positive sample or the DKK1 standard. In the present invention, purified DKK1 may be recombinant protein. The DKK1 level of the positive control sample is, for example more than cut off value.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

Example 1

Materials and Methods

Cell Lines:

The 10 human ESCC cell lines and a pharyngeal carcinoma cell line used herein included 10 squamous-cell carcinomas (SCCs; TE1, TE2, TE3, TE4, TE5, TE6, TE8, TE9, TE10, and FaDu), and one adenocarcinoma (ADC; TE7). The 25 human lung-cancer cell lines used in this study included nine adenocarcinomas (ADCs), A427, A549, LC319, PC-3, PC-9, PC-14, NCI-H1373, NCI-H1666, and NCI-H1781, two adenosquamous carcinomas (ASCs), NCI-H226, NCI-H647, seven squamous-cell carcinomas (SCCs), EBC-1, LU61, NCI-H520, NCI-H1703, NCI-H2170, RERF-LC-AI, and SK-MES-1, one large-cell carcinoma (LCC), LX1, and six small-cell lung cancers (SCLCs), DMS114, DMS273, SBC-3, SBC-5, NCI-H196, and NCI-H446. All cells were grown in monolayers in appropriate media supplemented with 10% fetal calf serum (FCS) and were maintained at 37° C. in an atmosphere of humidified air with 5% $CO_2$.

Tissue Samples and Microdissection:

Tissue samples from ESCC (n=19) and from normal esophagus (n=5) were obtained from surgical specimens with informed consent. This study and the use of all clinical materials mentioned were approved by individual institutional Ethical Committees. All cancer tissues had been confirmed histologically as squamous-cell carcinoma of the esophagus by the pathologists. Clinical information was obtained from medical records (five female and 14 male patients; median age 66.6 with range 51-76 years). Clinical stage was judged according to the UICC TNM classification. Normal esophageal tissues were observed as a normal epithelium pathologically, and they were not dysplasia. All specimens were harvested immediately after surgical resection and were embedded in TissueTek OCT medium (Sakura, Tokyo, Japan) before storage at −80° C. These frozen tissues were cut into 8 µm sections using a cryostat (Sakura, Tokyo, Japan) and then stained with hematoxylin and eosin for histological examination. ESCC cells and normal esophageal epithelial cells were collected selectively using the EZ cut system with a pulsed ultraviolet narrow beam-focus laser (SL Microtest GmbH, Germany) according to the manufacturer's protocols.

Figure 1:
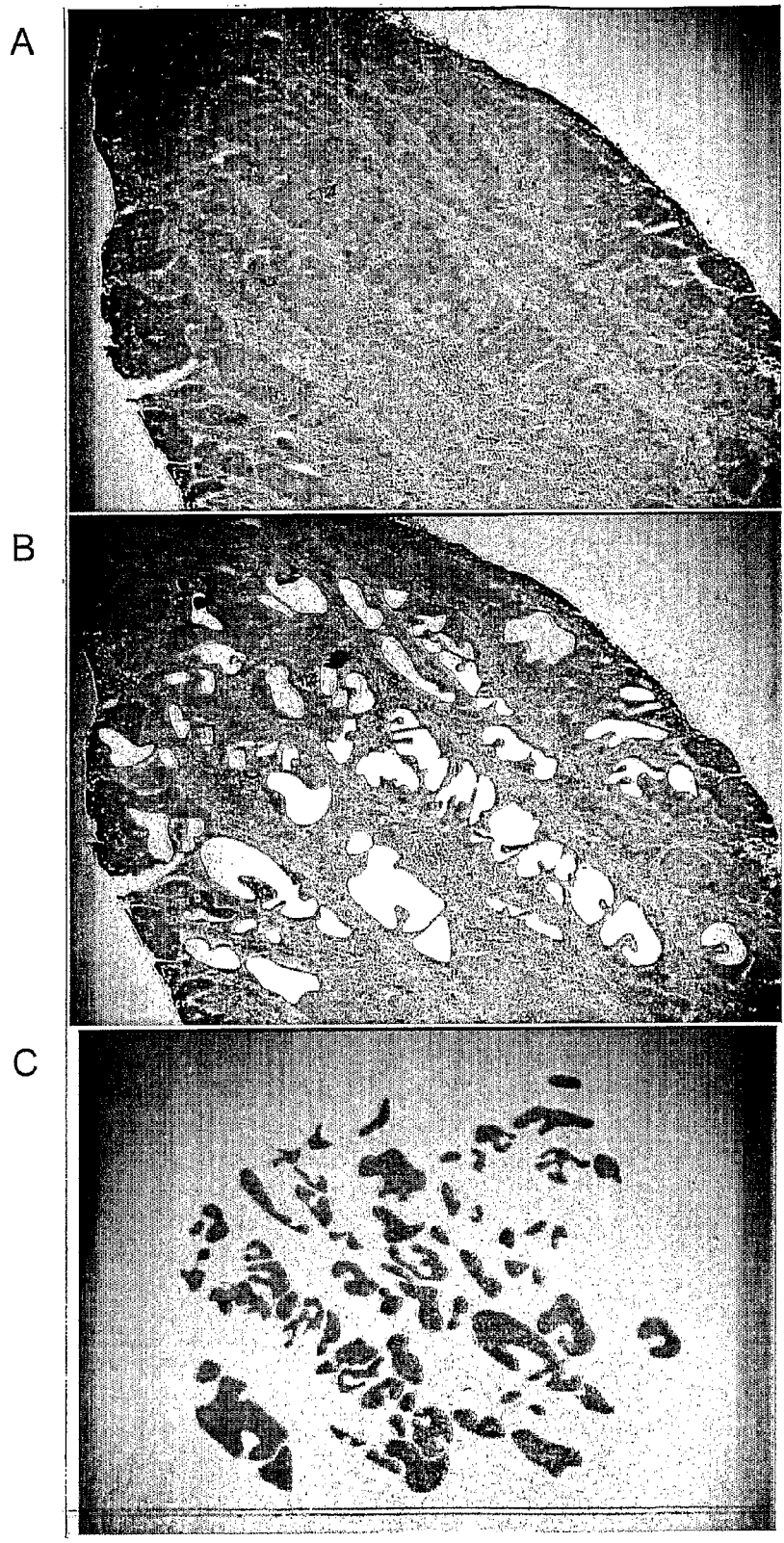
FIG. 1 illustrates laser-microbeam microdissection (LMM) of a representative ES CC. The upper row (A) shows the samples before dissection; the lower row (B), the same sections after microdissection (H.E. stain ×100). The microdissected cancer cells captured on the collecting cap were also shown (C).

To obtain precise expression profiles of ESCC cells, LMM was employed to avoid contamination of the samples by non-cancerous cells. After microdissection, the five normal esophageal epithelial cells were mixed to make a 'universal control' for microarray hybridization. FIG. 1 shows the microscopic images of representative cancers (A) before and after microdissection (B) and dissected cancer cells (C).

Human small airway epithelial cells (SAEC) used as a normal control were grown in optimized medium (SAGM) purchased from Cambrex Bio Science Inc. 15 primary lung-cancer samples, of which 5 were classified as ADCs, 5 as SCCs, and 5 as SCLCs, as well as 10 primary ESCC tissue samples had been obtained earlier with informed consent (Kikuchi et al., Oncogene. 2003 Apr. 10; 22(14):2192-205, Yamabuki et al., Int J. Oncol. 2006 June; 28(6):1375-84). Clinical stage was judged according to the UICC TNM classification (Sobin et al., TNM Classification of Malignant Tumours, 6th edition. New York: Wiley-Liss, Inc., 2002). Formalin-fixed primary lung tumors and adjacent normal lung tissue samples used for immunostaining on tissue microarrays had been obtained from 279 patients (161 ADCs, 96 SCCs, 18 LCCs, 4 ASCs; 96 female and 183 male patients; median age 63.3 with range 26-84 years) undergoing surgery at Saitama Cancer Center (Saitama, Japan), and Hokkaido University and its affiliated hospitals (Sapporo, Japan). A total of 220 formalin-fixed primary ESCCs (18 female and 202 male patients; median age 61.4 with range 42-81 years) and adjacent normal esophageal tissue samples had also been obtained from patients undergoing surgery. This study and the use of all clinical materials mentioned were approved by individual institutional Ethical Committees.

Serum Samples:

Serum samples were obtained with written informed consent from 220 healthy control individuals (179 males and 41 females; median age, 50.2±6.8 SD; range, 31-61 years) who showed no abnormalities in complete blood cell counts, C-reactive proteins, erythrocyte sedimentation rates, liver function tests, renal function tests, urinalyses, fecal examinations, chest X-rays, or electrocardiograms. Serum samples were also obtained with informed consent from 94 lung cancer patients (72 males and 22 females; median age, 65.5±12.3 SD; range, 30-86 years) admitted to Hiroshima University Hospital and its affiliated hospitals, 139 patients with lung cancer enrolled as a part of the Japanese Project for Personalized Medicine (BioBank Japan; 100 males and 39 females; median age, 64.5±8.8 SD; range, 41-89 years). These 233 lung cancer cases included 106 ADCs, 56 SCCs, and 71 SCLCs. Serum samples were also obtained with informed consent from 67 ESCC patients who were registered in the same project of BioBank Japan (55 males and 12 females; median age, 63.8±6.3 SD; range, 46-74 years). These serum samples from 300 cancer patients in total were selected for the study on the basis of the following criteria: (a) patients were newly diagnosed and previously untreated and (b) their tumors were pathologically diagnosed as lung or esophageal cancers (stages I-IV). Serum was obtained at the time of diagnosis and stored at −80° C. Clinicopathological records were fully documented.

cDNA Microarray:

A genome-wide cDNA microarray was fabricated with 32,256 cDNAs selected from the UniGene database (build #131) of the National Center for Biotechnology Information (NCBI). This microarray system was constructed essentially as described previously (Ono et al., Cancer Res. 2000; 60(18):5007-11). Briefly, the cDNAs were amplified by RT-PCR using poly (A)+ RNAs isolated from various human organs as templates; the lengths of the amplicons ranged from 200 to 1100 bp, without any repetitive or poly (A) sequences.

RNA Extraction, T7-Based RNA Amplification, and Hybridization:

Total RNAs were extracted from each sample of laser-microdissected cells into 350 µl of RLT lysis buffer (QIAGEN, Hilden, Germany). The extracted RNAs were treated for 30 min at room temperature with 30 U of DNase I (Roche, Basel, Switzerland) in the presence of 1 U of RNase inhibitor (TOYOBO, Osaka, Japan) to remove any contaminating genomic DNA. After inactivation at 70° C. for 10 min, the RNAs were purified with an RNeasy Mini Kit (QIAGEN) according to the manufacturer's recommendations. All of the DNase I-treated RNAs were subjected to T7-based RNA amplification; two rounds of amplification yielded 50-100 µg of aRNA from each sample. Then 2.5 µg aliquots of aRNA from cancer cells or normal esophageal epithelial cells were labeled by reverse transcription with Cy5-dCTP or Cy3-dCTP (GE Healthcare/Amersham Biosciences Corp.), respectively, as described elsewhere (Ono et al., Cancer Res. 2000; 60(18):5007-11). Hybridization, washing, and scanning were also carried out according to methods described previously (Ono et al., Cancer Res. 2000; 60(18):5007-11).

Data Analysis:

Signal intensities of Cy3 and Cy5 from the 32,256 spots were quantified and analyzed by substituting backgrounds, using ArrayVision software (Imaging Research, Inc., St Catharines, Ontario, Canada). Subsequently, the fluorescent intensities of Cy5 (tumor) and Cy3 (control) for each target spot were adjusted so that the mean Cy3/Cy5 ratio of 52 housekeeping genes on the array was equal to one. Because data derived from low signal intensities are less reliable, a cutoff value was determined on each slide as described previously (Ono et al., Cancer Res. 2000; 60(18):5007-11) and genes were excluded from further analysis when both Cy3 and Cy5 dyes yielded signal intensities lower than the cutoff (Saito-Hisaminato et al., DNA Res. 2002; 9(2):35-45). For other genes, the Cy5/Cy3 ratio was calculated using the raw data of each sample.

Semi-Quantitative RT-PCR:

Highly up-regulated genes were selected and examined their expression levels by means of semi-quantitative RT-PCR experiments. A total of 3 µg aliquot of aRNA from each sample was reverse transcribed to single-stranded cDNAs using random primer (Roche) and Superscript II (Invitrogen). Each cDNA mixture was diluted for subsequent PCR amplification with the same primer sets that were prepared for the target DNA- or beta-actin (ACTB)-specific reactions. (Primer sequence shown in Table. 3). Expression of ACTB served as an internal control. PCR reactions were optimized for the number of cycles to ensure product intensity within the linear phase of amplification.

Northern-Blot Analysis:

For Northern analysis, Human Multiple Tissue Northern blots (BD Bioscience, Palo Alto, Calif.) were hybridized with an [$\alpha$-$^{32}$P]-dCTP-labeled, 269-bp PCR product of ECT2 (C9098) that was prepared as a probe by reverse transcription-PCR (RT-PCR) using primers 5'-CAATTTTCCCATG-GTCTTATCC-3' (SEQ ID NO; 1) and 5'-GCGTTTTCAA-GATCTAGCATGTG-3' (SEQ ID NO; 2). 1019-bp PCR product of CDC45L (A2466) was prepared as a probe by reverse transcription-PCR (RT-PCR) using primers 5'-AT-GAGGAGAACACACTCTCCGT-3' (SEQ ID NO; 3) and 5'-GCTTCTACATCTCAAATCATGTCC-3' (SEQ ID NO; 4). 776-bp PCR product of DKK1 that was prepared as a probe using primers 5'-CATCAGACTGTGCCTCAGGA-3' (SEQ ID NO: 111) and 5'-CAAAAACTATCACAGC-CTAAAGGG-3' (SEQ ID NO: 74).

Pre-hybridization, hybridization, and washing were performed following manufacturer's specifications. The blots were autoradiographed with intensifying screens at $-80°$ C. for 7 days.

RNA Interference Assay:

To evaluate the biological functions of ECT2 and CDC45L in cancer cells, a psiH1BX3.0 vector was used for expression of short-hairpin RNA against the target gene, as described previously (Shimokawa T, et al., Cancer Res. 2003; 63(19): 6116-20). The H1 promoter was cloned into upstream of the gene-specific sequence (19-nucleotide sequence from the target transcript, separated from the reverse complement of the same sequence by a short spacer, TTCAAGAGA (SEQ ID NO; 5)), with five thymidines as a termination signal and a neo-cassette for selection by Geneticin (Sigma). The target sequences of the synthetic oligonucleotides for RNAi were as follows: control 1 (EGFP: enhanced green fluorescent protein (GFP) gene, a mutant of Aequorea victoria GFP), 5'-GAAG-CAGCACGACTTCTTC-3' (SEQ ID NO; 6); control 2 (Scramble (SCR): chloroplast Euglena gracilis gene coding for 5S and 16S rRNAs), 5'-GCGCGCTTTGTAGGATTCG-3' (SEQ ID NO; 7);
si-ECT2-1,5'-GATGCACTCACCTTGTAGT-3' (SEQ ID NO; 8);
si-ECT2-2,5'-GGCAAATACTCCTGAGCTC-3'; (SEQ ID NO; 9)
si-CDC45L-1,5'-GAGACATCCTCTTTGACTA-3'; (SEQ ID NO; 10)
si-CDC45L-2,5'-CAGACCAGTGGGTGCAAGA-3' (SEQ ID NO; 11). FaDu and TE9 cells were plated onto 10-cm dishes (1.5×10$^6$ cells per dish), and transfected with psiH1BX vectors that included the target sequences for EGFP, SCR, ECT2, and CDC45L, using Lipofectamine 2000 (Invitrogen), according to the manufacturers' instructions. Cells were selected in medium containing 1 mg/ml of Geneticin (Invitrogen) for 7 days and harvested after 4 days for RT-PCR analysis of knockdown effects on individual genes. Primers for these RT-PCR experiments were the same as those described above. After 7 days of incubation, these cells were stained by Giemsa solution to assess colony formation, and cell numbers were assessed by 3-(4,5-dimethylthiazol-2-yl)-2,5-diphenyltetrazolium bromide (MTT) assay.

Western-Blotting:

Tumor tissues or cells were lysed in lysis buffer; 50 mM Tris-HCl (pH 8.0), 150 mM NaCl, 0.5% NP40, 0.5% sodium deoxycholate, and Protease Inhibitor Cocktail Set III (Calbiochem). The protein content of each lysate was determined by a Bio-Rad protein assay (Bio-Rad, Hercules, Calif.) with bovine serum albumin (BSA) as a standard. Ten micrograms of each lysate were resolved on a 10% to 12% denaturing polyacrylamide gel (with 3% polyacrylamide stacking gel) and transferred electrophoretically to a nitrocellulose membrane (GE Healthcare Bio-sciences). After blocking with 5% non-fat dry milk in TBST, the membrane was incubated with primary antibodies for 1 hour at room temperature. Immunoreactive proteins were incubated with horseradish peroxidase-conjugated secondary antibodies (GE Healthcare Bio-sciences) for 1 hour at room temperature. After washing with TBST, the reactants were developed using the enhanced chemiluminescence kit (GE Healthcare Bio-sciences). A commercially available rabbit polyclonal antibody to human DKK1 (Catalog No. sc-25516, Santa Cruz, Calif.) was proved to be specific to human DKK1, by western-blot analysis using lysates of NSCLC and ESCC tissues and cell lines as well as normal tissues (see FIG. 2).

Immunocytochemical Analysis:

Cells were plated on glass coverslips (Becton Dickinson Labware, Franklin Lakes, N.J.), fixed with 4% paraformaldehyde, and permeabilized with 0.1% Triton X-100 in PBS for 3 minutes at room temperature. Nonspecific binding was blocked by CASBLOCK (ZYMED) for 10 minutes at room temperature. Cells were then incubated for 60 minutes at room temperature with primary antibodies diluted in PBS containing 3% BSA. After being washed with PBS, the cells were stained by FITC-conjugated secondary antibody (Santa Cruz) for 60 minutes at room temperature. After another wash with PBS, each specimen was mounted with Vectashield (Vector Laboratories, Inc, Burlingame, Calif.) containing 4',6'-diamidine-2'-phenylindolendihydrochrolide (DAPI) and visualized with Spectral Confocal Scanning Systems (TSC SP2 AOBS: Leica Microsystems, Wetzlar, Germany).

Immunohistochemistry and Tissue Microarray:

To investigate the presence of DKK1 protein in clinical samples that had been embedded in paraffin blocks, the present inventors stained the sections in the following manner. Briefly, 3.3 µg/ml of a rabbit polyclonal anti-human DKK1 antibody (Santa Cruz) was added to each slide after blocking of endogenous peroxidase and proteins, and the sections were incubated with horseradish peroxidase-labeled anti-rabbit IgG (Histofine Simple Stain MAX PO (G), Nichirei, Tokyo, Japan) as the secondary antibody. Substrate-chromogen was added, and the specimens were counter-stained with hematoxylin. Tumor tissue microarrays were constructed with formalin-fixed 279 primary lung cancers and 220 primary esophageal cancers, as described elsewhere (Chin et al., Mol. Pathol. 2003 October; 56(5):275-9; Callagy et al., Diagn Mol. Pathol. 2003 March; 12(1):27-34, J. Pathol. 2005 February; 205(3):388-96). The tissue area for sampling was selected based on visual alignment with the corresponding H&E-stained section on a slide. Three, four, or five tissue cores (diameter, 0.6 mm; depth, 3-4 mm) taken from a donor tumor block were placed into a recipient paraffin block with a tissue microarrayer (Beecher Instruments, Sun Prairie, Wis.). A core of normal tissue was punched from each case, and 5-μm sections of the resulting microarray block were used for immunohistochemical analysis. Three independent investigators semi-quantitatively assessed DKK1 positivity without prior knowledge of clinicopathological data, as reported previously (Suzuki et al., Cancer Res. 2005 Dec. 15; 65(24): 11314-25; Ishikawa et al., Clin Cancer Res. 2004 Dec. 15; 10(24):8363-70, Cancer Res. 2005 Oct. 15; 65(20):9176-84; Kato et al., Cancer Res. 2005 Jul. 1; 65(13):5638-46; Furukawa et al., Cancer Res. 2005 Aug. 15; 65(16):7102-10). The intensity of DKK1 staining was evaluated using following criteria: strong positive (scored as 2+), dark brown staining in more than 50% of tumor cells completely obscuring cytoplasm; weak positive (1+), any lesser degree of brown staining appreciable in tumor cell cytoplasm; absent (scored as 0), no appreciable staining in tumor cells. Cases were accepted as strongly positive only if reviewers independently defined them as such.

Statistical Analysis:

Statistical analyses were performed using the StatView statistical program (SaS, Cary, N.C.). Tumor-specific survival curves were calculated from the date of surgery to the time of death related to NSCLC or ESCC, or to the last follow-up observation. Kaplan-Meier curves were calculated for each relevant variable and for DKK1 expression; differences in survival times among patient subgroups were analyzed using the log-rank test. Univariate and multivariate analyses were performed with the Cox proportional-hazard regression model to determine associations between clinicopathological variables and cancer-related mortality. First, the present inventors analyzed associations between death and possible prognostic factors including age, gender, histology, pT-classification, and pN-classification taking into consideration one factor at a time. Second, multivariate Cox analysis was applied on backward (stepwise) procedures that always forced strong DKK1 expression into the model, along with any and all variables that satisfied an entry level of a P-value less than 0.05. As the model continued to add factors, independent factors did not exceed an exit level of P<0.05.

ELISA:

Serum levels of DKK1 were measured by ELISA system which had been originally constructed. First of all, a rabbit polyclonal antibody specific for DKK1 (Santa Cruz) was added to a 96-well microplate (Apogent, Denmark) as a capture antibody and incubated for 2 hours at room temperature. After washing away any unbound antibody, 5% BSA was added to the wells and incubated for 16 hours at 4° C. for blocking. After a wash, 3-fold diluted sera were added to the wells and incubated for 2 hours at room temperature. After washing away any unbound substances, a biotinylated polyclonal antibody specific for DKK1 using Biotin Labeling Kit-NH2 (Dojindo Molecular Technologies, Inc.) was added to the wells as a detection antibody and incubated for 2 hours at room temperature. After a wash to remove any unbound antibody-enzyme reagent, HRP-streptavisin was added to the wells and incubated for 20 minutes. After a wash, a substrate solution (R&D Systems, Inc.) was added to the wells and allowed to react for 30 minutes. The reaction was stopped by adding 100 μl of 2 N sulfuric acid. Color intensity was determined by a photometer at a wavelength of 450 nm, with a reference wavelength of 570 nm. Levels of CEA in serum were measured by ELISA with a commercially available enzyme test kit (HOPE Laboratories, Belmont, Calif.), according to the supplier's recommendations. Levels of Pro-GRP in serum were measured by ELISA with a commercially available enzyme test kit (TFB, Tokyo, Japan), according to the manufacturer's protocol. Differences in the levels of DKK1, CEA, and proGRP between tumor groups and a healthy control group were analyzed by Mann-Whitney U tests. The levels of DKK1, CEA, and ProGRP were additionally evaluated by receiver-operating characteristic (ROC) curve analysis to determine cutoff levels with optimal diagnostic accuracy and likelihood ratios. The correlation coefficients between DKK1 and CEA/proGRP were calculated with Spearman rank correlation. Significance was defined as P<0.05.

DKK1 Expression Plasmids:

Constructs of a wild-type and point mutant form of C-terminal FLAG-tagged DKK1 with asparagine 256 to alanine were generated as reported elsewhere (Suzuki et al., Cancer Res. 2005 Dec. 15; 65(24):11314-25). COS-7 cells transfected either with p3XFLAG-tagged plasmids expressing DKK1 (wild-type or point mutant) or with mock plasmids were used for western-blot analyses.

Matrigel Invasion Assay:

NIH3T3 and COS-7 cells transfected either with p3XFLAG-tagged (C-terminal) plasmids expressing DKK1 or with mock plasmids were grown to near confluence in DMEM containing 10% FCS. The cells were harvested by trypsinization, washed in DMEM without addition of serum or proteinase inhibitor, and suspended in DMEM at $1\times10^5$ cells/ml. Before preparing the cell suspension, the dried layer of Matrigel matrix (Becton Dickinson Labware) was rehydrated with DMEM for 2 hours at room temperature. DMEM (0.75 ml) containing 10% FCS was added to each lower chamber in 24-well Matrigel invasion chambers, and 0.5 ml ($5\times10^4$ cells) of cell suspension was added to each insert of the upper chamber. The plates of inserts were incubated for 24 hours at 37° C. After incubation the chambers were processed; cells invading through the Matrigel were fixed and stained by Giemsa as directed by the supplier (Becton Dickinson Labware).

Example 2

Genes Commonly Down/Up-Regulated in ESCC

Genes commonly up- and down-regulated in ESCCs were identified according to the following criteria: (1) genes for which expression data was available in more than 50% (at least 10 of the 19 cases) of the cancers examined; and (2) genes whose expression ratio was more than 3.0 in ESCC cells (defined as up-regulated genes) in more than 40% of informative cases or genes whose expression ratio was less than 0.33 (defined as down-regulated genes) in more than 50% of informative cases. A total of 727 genes commonly down-regulated in ESCC are listed in Table 1, while 816 genes commonly up-regulated are in Table 2.

To validate the expression data obtained by microarray analysis, semi-quantitative RT-PCR experiments were performed for the genes which were highly over-expressed in almost all informative cases. Among the candidates above, 38 genes were selected (C1948, A9371, E0341, A3097, A2735, A5065, D9504, C6209, B3827, A4513, E0556, A8172, A3802, C8926, A9723, G3996, F5946, B7534, A7296, A8487, C9490, C9858, E0133, A7856, A7608, A7908, C9098, C9517, C9046, A8335, C9016, A6598, B4161, E2191, B6125N, D8457, B8814, and A2466) and their gene expression pattern was confirmed in tumor and normal tissues using semi-quantitative RT-PCR (FIG. 2). The results of RT-PCR experiments were exclusively concordant with microarray data in the tested cases.

Example 3

Genes Associated with Lymph-node Metastasis or Post-surgery Recurrence

To detect relations between gene expression profiles and clinico-pathological features, the present inventors searched for genes that were possibly associated with lymph-node metastasis, an important factor in determining a patient's prognosis.

Genes associated with clinico-pathological features, such as lymph-node metastasis positive (node-positive) (r) and node-negative (n), recurrence positive (r) and recurrence negative (n), were chosen according to following two criteria: (i) signal intensities are higher than the cutoff value in at least 80% of the cases; and (ii) |Medr-Medn|≧0.5, where Med indicates the median derived from log-transformed relative expression ratios in two groups. Genes were selected as candidates when they met the criteria with a permutation P-value of smaller than 0.05 in each clinico-pathological status.

To begin with, expression profiles and lymph-node metastasis status were examined using 13 lymph-node-positive and six node-negative cases. A random permutation test was applied to identify genes that were expressed differently in the two groups. The mean ($\mu$) and standard deviation ($\sigma$) were calculated from the log-transformed relative expression ratios of each gene in node-positive (r) and node-negative (n) cases, recurrence-positive (r) and recurrence-negative (n) cases, respectively. A discrimination score (DS) for each gene was defined as follows:

$$DS=(\mu_r-\mu_n)/(\sigma_r+\sigma_n)$$

Permutation tests were carried out to estimate the ability of individual genes to distinguish between two groups; samples were randomly permutated between the two classes 10 000 times. Since the DS data set of each gene showed a normal distribution, the present inventors calculated a P-value for the user-defined grouping (Golub et al., Science. 1999; 286(5439):531-7).

Figure 6:
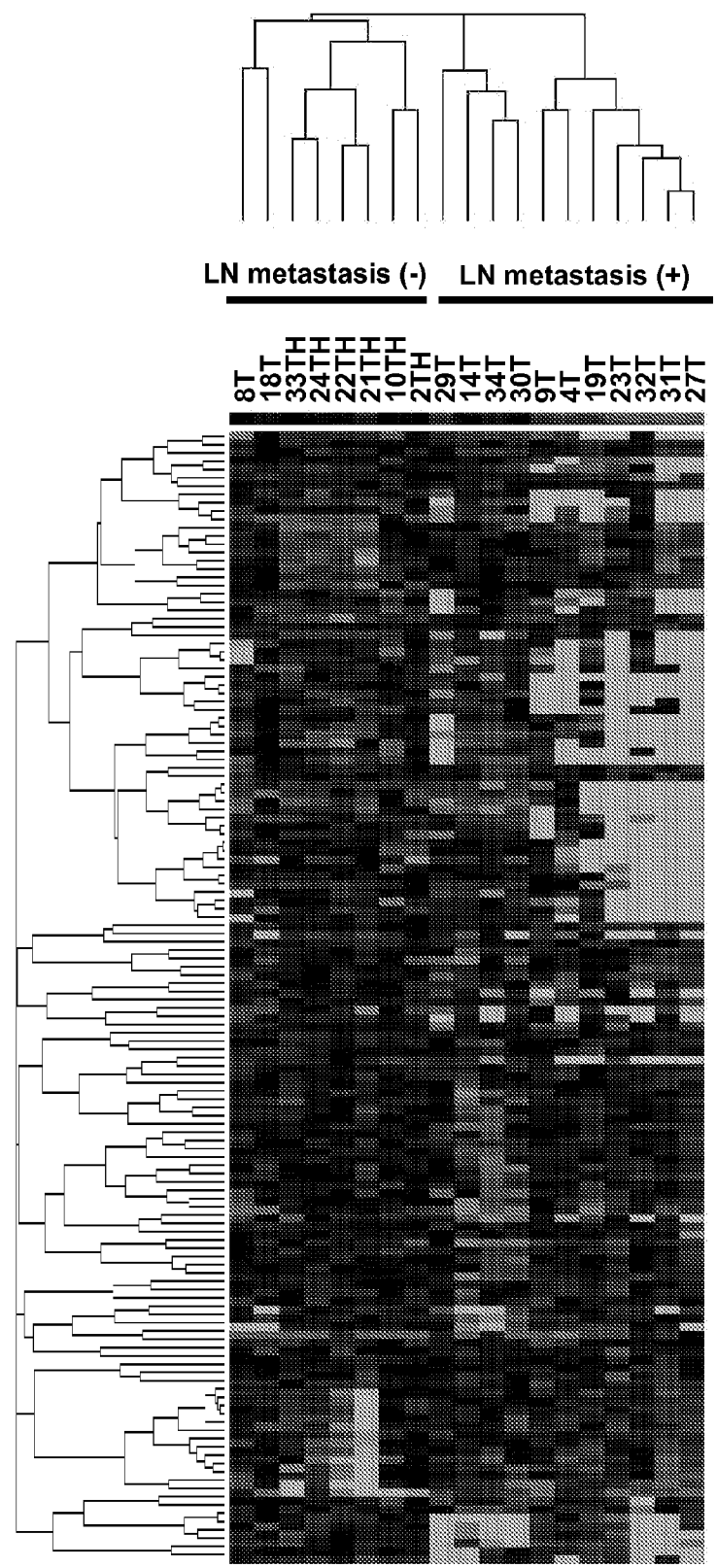
FIG. 6 depicts the results of a supervised two-dimensional hierarchical clustering analysis using 136 genes associated with lymph-node metastasis that were selected by random permutation test.
Figure 7:
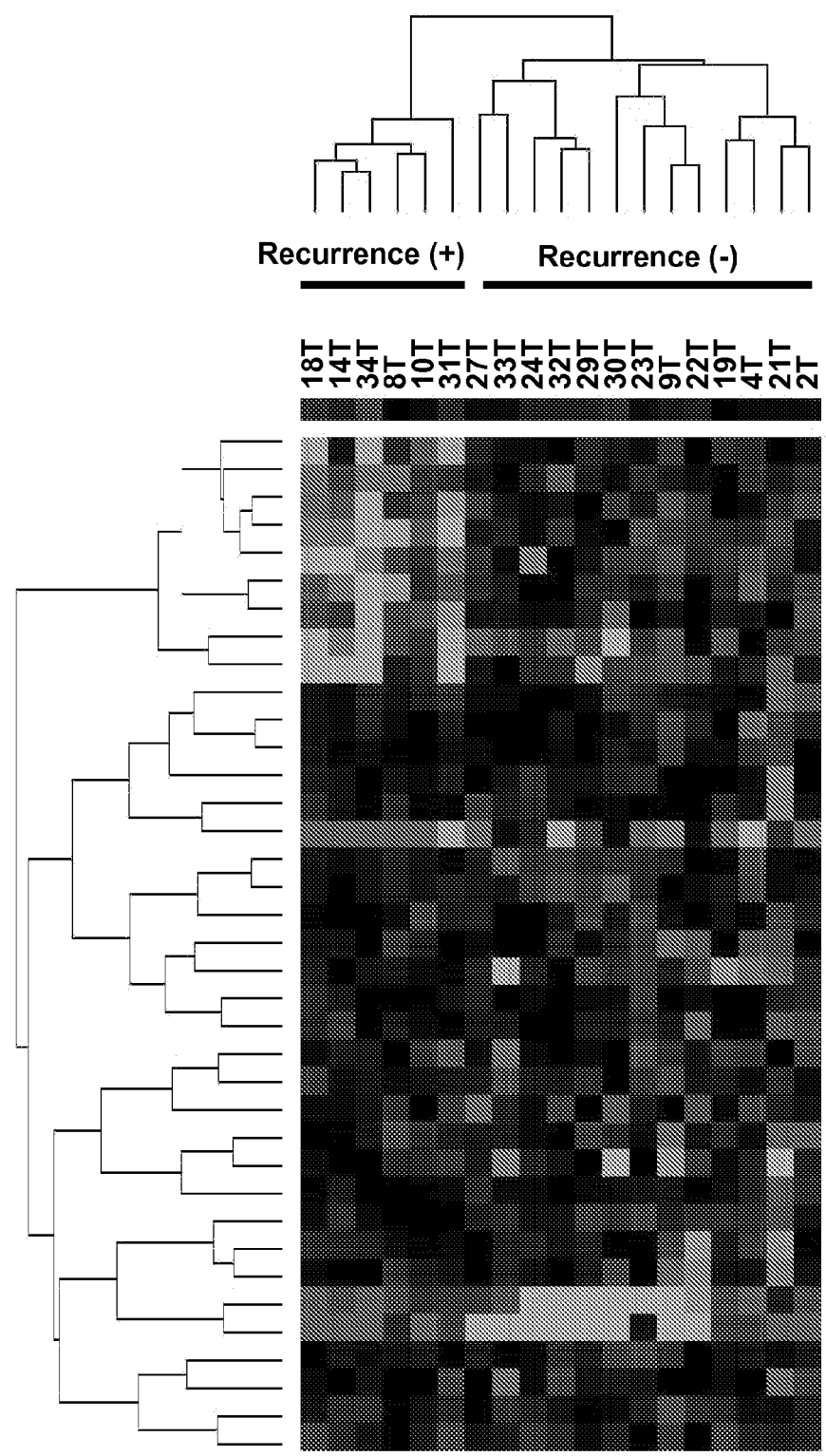
FIG. 7 depicts the results of a supervised two-dimensional hierarchical clustering analysis using 37 genes associated with recurrence after surgery that were selected by random permutation test.

Herein, the expression data of 19 cases consisting of 13 lymph-node-positive and 6 lymph-node-negative cases, and those of 19 cases consisting of six recurrent-positive cases and 13 recurrent-negative cases was utilized. Analysis resulted in the identification of 136 genes that were associated with lymph-node status by a random permutation (P-value<0.05). Of these, 59 genes were down-regulated (Table 4), and 77 genes were relatively up-regulated (Table 5) in node-positive tumors (FIG. 6). In addition, the expression profiles of six cases with recurrence were compared with those of 13 cases without recurrence after surgery during observation periods of 32 months. The sites of recurrence included local, lung, and regional lymph-nodes. 37 genes were identified that showed altered expression patterns uniquely in cases that had recurrence: 28 of them (Table 7) were relatively up-regulated and 9 of them (Table 6) were relatively down-regulated in tumors (FIG. 7). Supervised hierarchical clustering analysis using these identified gene sets was also able to clearly classify the groups with regard to lymph-node status or those with recurrence (FIGS. 6 and 7).

Example 4

ECT2

Figure 3:
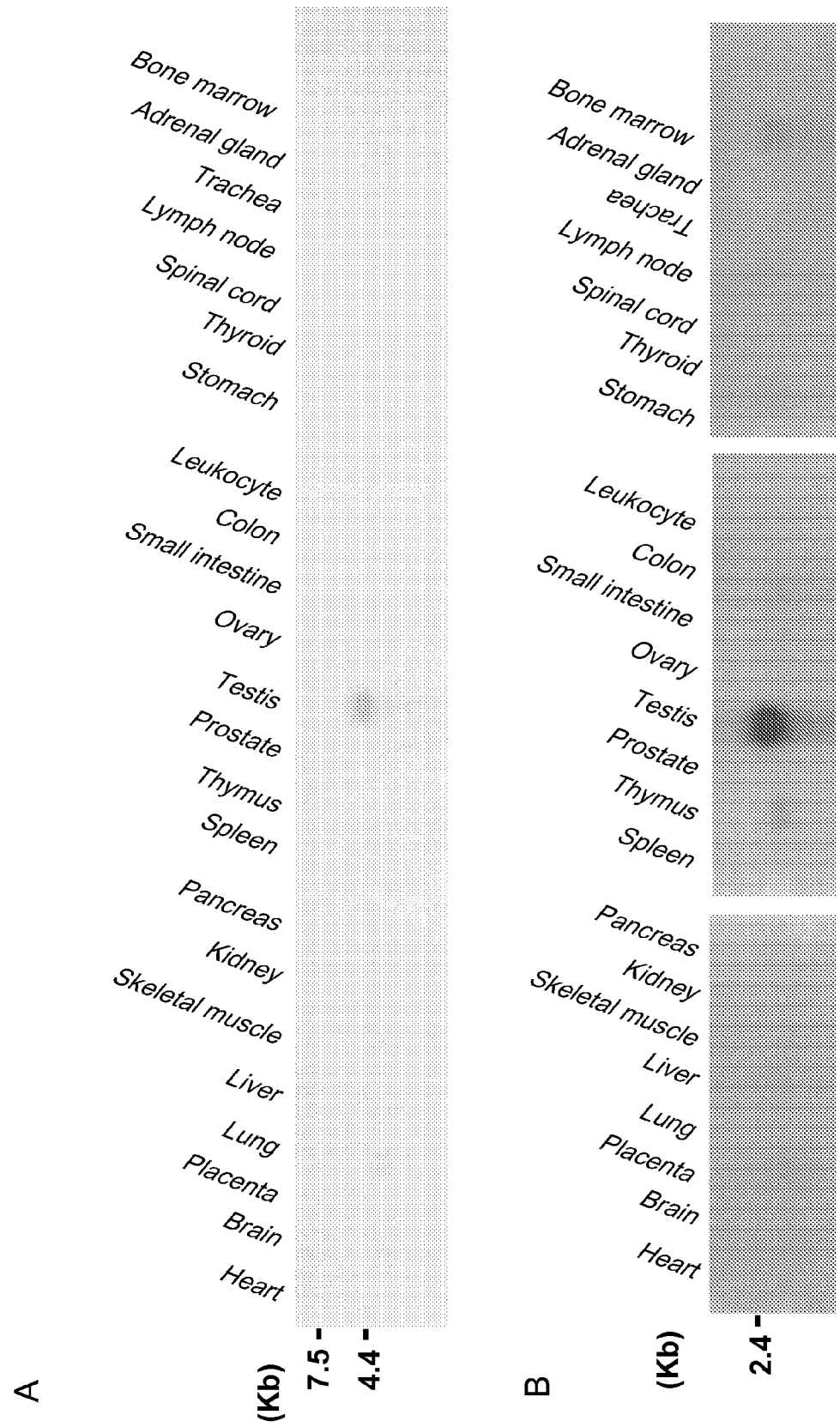
FIG. 3 depicts the results of a northern blot analysis.

Northern blot analysis using an ECT2 cDNA fragment as a probe identified a 4.3-kb transcript that was expressed only in testis; no expression was observed in any other organs examined. ECT2 was thought to encode a cancer-testis antigen (CTA) (FIG. 3A).

Figure 4:
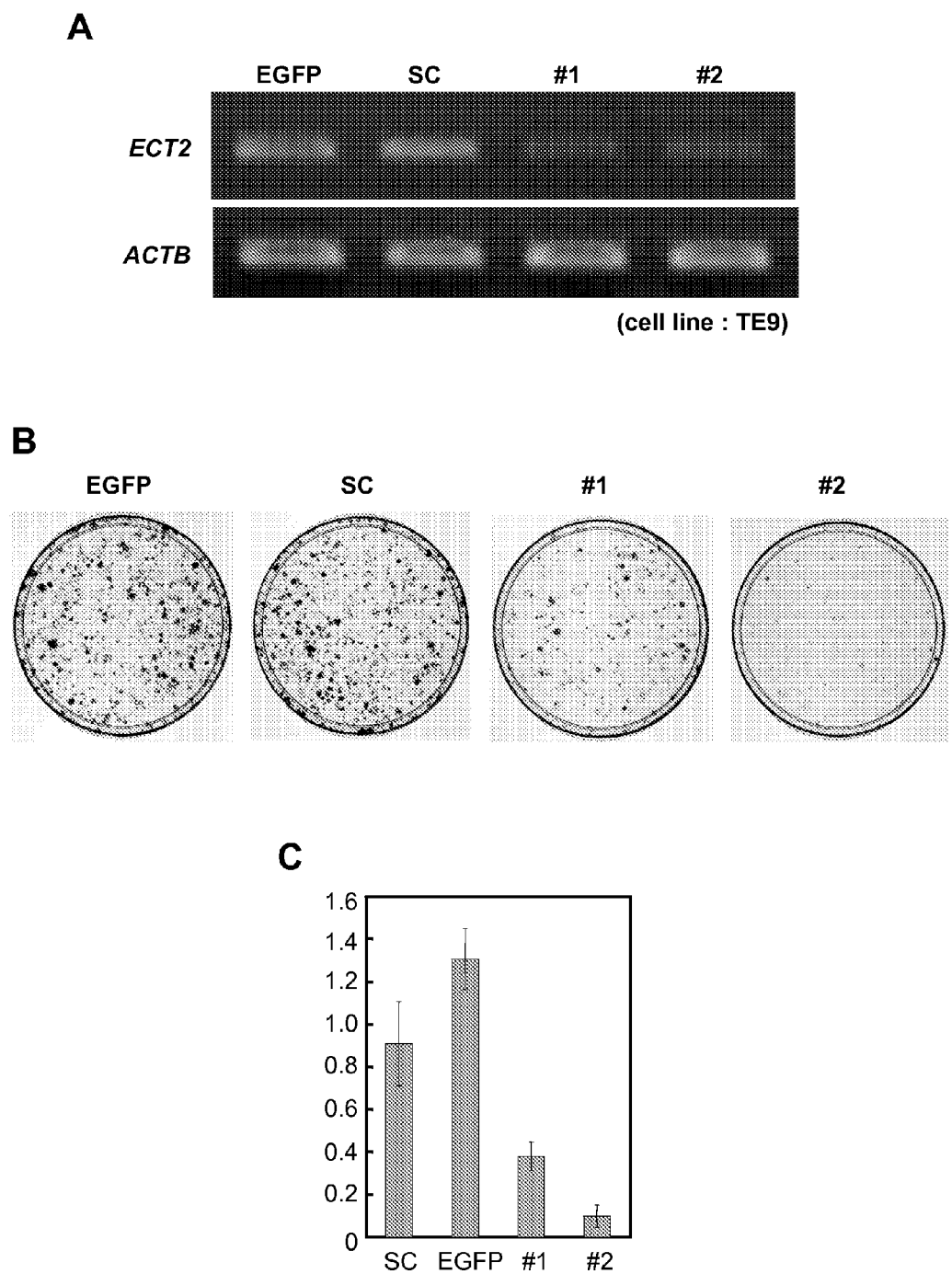
FIG. 4 depicts the results of a small interfering RNA (siRNA) experiment against ECT2. In part (A), the knockdown effect of si-ECT2-1 and si-ECT2-2 was confirmed by RT-PCR. MTT assay (C) and colony formation assay (B) revealed inhibition of cell growth in cells transfected with si-ECT2-1 and si-ECT2-2.

To assess whether ECT2 plays a role in growth or survival of cancer cells, plasmids were designed and constructed to express siRNA against ECT2 (si-ECT2-1 (#1) and -2 (#2)), along with two different control plasmids (siRNAs for EGFP and SCR), and transfected them into TE9 cells that endogenously express high levels of ECT2 to suppress expression of endogenous ECT2. The amount of ECT2 mRNA in the cells transfected with si-ECT2-1 and si-ECT2-2 was significantly decreased in comparison with cells transfected with any of the two control siRNAs (FIG. 4A). In accord with its suppressive effect on levels of ECT2, transfected si-ECT2-1 and si-ECT2-2 caused significant decreases in colony numbers and cell viability measured by colony-formation and MTT assays (FIGS. 4B and 4C). Similar effects were observed in the FaDu cell line (data not shown).

Example 5

CDC45L

Northern blot analysis using a CDC45L cDNA fragment as a probe identified a 2.2-kb transcript that was expressed only in testis; no expression was observed in any other organs examined. CDC45L was thought to encode a cancer-testis antigen (CTA) (FIG. 3B).

Figure 5:
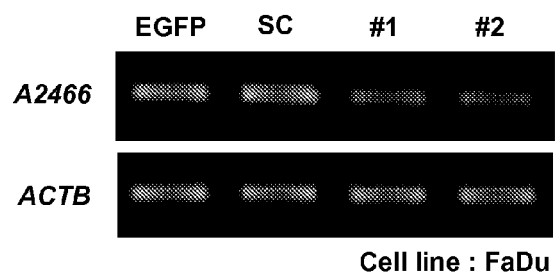
FIG. 5 depicts the results of a small interfering RNA (siRNA) experiment against CDC45L. In part (A), the knockdown effect of si-CDC45L-1 and si-CDC45L-2 was confirmed by RT-PCR. MTT assay (C) and colony formation assay (B) revealed inhibition of cell growth in cells transfected with si-CDC45L-1 and si-CDC45L-2.
Figure 5:
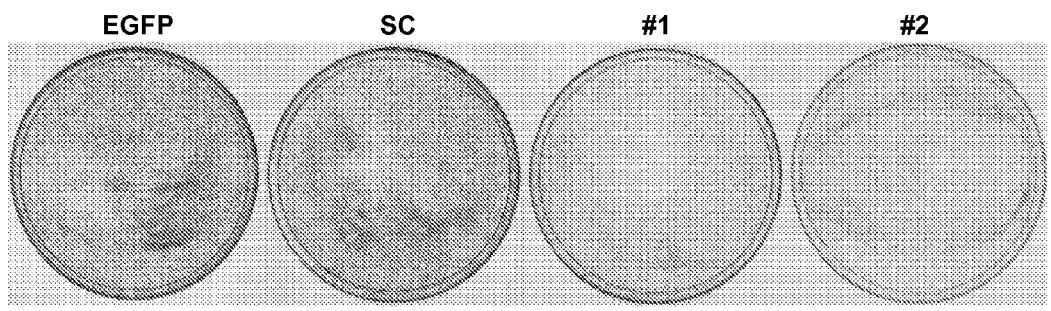
Figure 5:
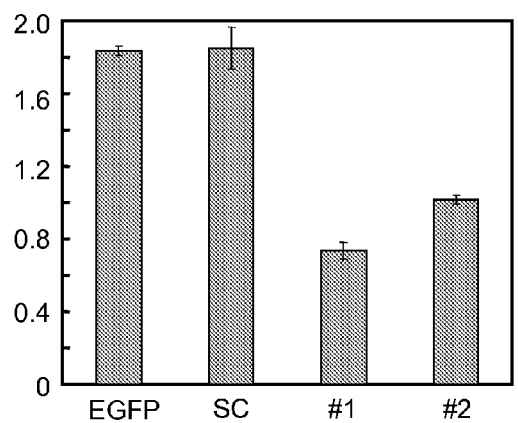

To assess whether CDC45L plays a role in growth or survival of cancer cells, plasmids were designed and constructed to express siRNA against CDC45L (si-CDC45L-1 (#1) and -2 (#2)), along with two different control plasmids (siRNAs for EGFP and SCR), and transfected them into FaDu cells that endogenously express high levels of CDC45L to suppress expression of endogenous CDC45L. The amount of CDC45L mRNA in the cells transfected with si-CDC45L-1 and si-CDC45L-2 was significantly decreased in comparison with cells transfected with any of the two control siRNAs (FIG. 5A). In accord with its suppressive effect on levels of CDC45L, transfected si-CDC45L-1 and si-CDC45L-2 caused significant decreases in colony numbers and cell viability measured by colony-formation and MTT assays (FIGS. 5B and 5C). Similar effects were observed in the TE9 cell line (data not shown).

Example 6

DKK1

DKK1 Expression in Lung and Esophageal Cancers and Normal Tissues:

To identify novel molecules that can detect cancer cells at an early stage and be applied for the individualized treatments based on the biological characteristics of cancer cells, the present inventors performed a genome-wide analysis of gene expression profiles of lung carcinoma and ESCC cells purified by laser microdissection using a cDNA microarray (Kikuchi T et al., Oncogene. 2003 Apr. 10; 22(14):2192-205, Int J. Oncol. 2006 April; 28(4):799-805, Kakiuchi S et al., Mol Cancer Res. 2003 May; 1(7):485-99, Hum Mol Genet. 2004 Dec. 15; 13(24):3029-43. Epub 2004 Oct. 20, Yamabuki et al., Int J Oncol. 2006 June; 28(6):1375-84). Among 27,648 genes screened, the present inventors identified DKK1 transcript, indicating 3-fold or higher mean fold expression in cancer cells than in normal epithelial cells (control) in the great majority of the lung and esophageal cancer samples examined. The present inventors confirmed its over-expression by means of semi-quantitative RT-PCR experiments in 10 of 15 lung cancer tissues, in 21 of 25 lung-cancer cell lines, in 10 of 10 ESCC tissues, and in 10 of 10 ESCC cell lines (FIGS. 2A-C).

The present inventors subsequently confirmed by western-blot analysis using anti-DKK1 antibody an expression of 35-kDa DKK1 protein in tumor tissues in representative pairs of NSCLC samples analyzed (FIG. 2D).

Northern blot analysis using a DKK1 cDNA fragment as a probe identified a transcript of about 1.8 kb that was highly expressed in placenta and at a very low level in prostate; no expression was observed in any other normal tissues (FIG. 3C). The present inventors performed immunofluorescence analysis to examine the subcellular localization of endogenous DKK1 in ESCC cell line TE8 and NSCLC cell line LC319. DKK1 was detected at cytoplasm of tumor cells with granular appearance (representative data of TE8 cells was shown in FIG. 3D).

Association of DKK1 Expression with Poor Prognosis.

Figure 8:
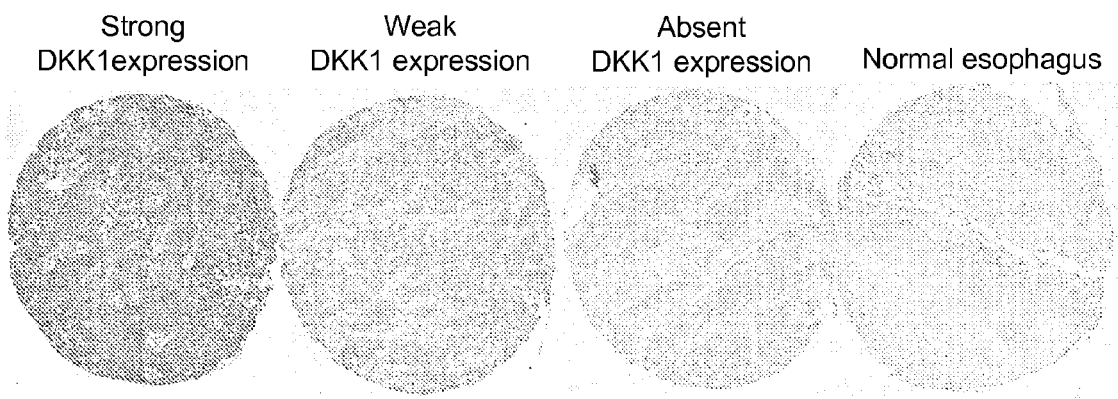
FIG. 8 Association of DKK1 over-expression with poor prognosis of NSCLC and ESCC patients.
Figure 8:
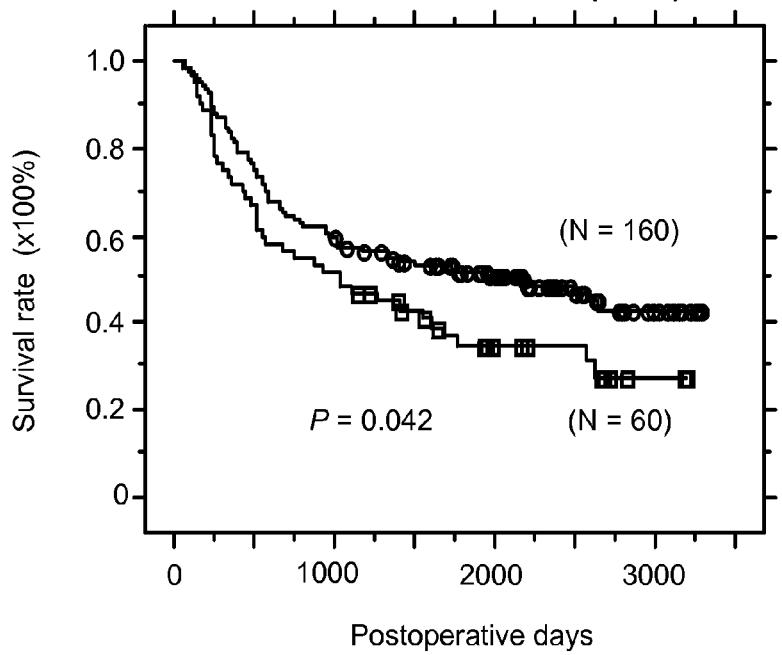

To verify the biological and clinicopathological significance of DKK1, the present inventors carried out immunohistochemical staining on tissue microarray containing tissue sections from 279 NSCLC and 220 ESCC cases that underwent curative surgical resection. DKK1 staining with polyclonal antibody specific for DKK1 was mainly observed at cytoplasm of tumor cells, but not detected in normal cells (FIGS. 8A, C). The present inventors classified a pattern of DKK1 expression on the tissue array ranging from absent (scored as 0) to weak/strong positive (scored as 1+~2+). Of the 279 NSCLCs, DKK1 was strongly stained in 125 (44.8%; score 2+), weakly stained in 102 (36.6%; score 1+), and not stained in 52 cases (18.6%: score 0) (details are shown in Table 10A). The median survival time of NSCLC patients was significantly shorter in accordance with the higher expression levels of DKK1 (P=0.0039 by log-rank test; FIG. 8D). The present inventors also applied univariate analysis to evaluate associations between patient prognosis and several factors including age, gender, histology (ADC versus non-ADC), pT stage (tumor size; T1+T2 versus T3+T4), pN stage (N0 versus N1+N2), and DKK1 status (score 2+ vs 0, 1+). All those parameters were significantly associated with poor prognosis. Multivariate analysis using a Cox proportional-hazard model determined that DKK1 (P=0.0163) was an independent prognostic factor for surgically treated NSCLC patients (Table 10B). On the other hand, of the 220 ESCC cases examined, DKK1 was strongly stained in 60 (27.3%; score 2+), weakly stained in 75 (34.1%; score 1+) and not stained in 85 cases (38.6%; score 0) (details are shown in Table 9A). The median survival time of ESCC patients was significantly shorter in accordance with the higher expression levels of DKK1 (P=0.042 by log-rank test; FIG. 8B). The present inventors also applied univariate analysis to evaluate associations between ESCC patient prognosis and several factors including age, gender, pT stage (tumor depth; T1+T2 versus T3+T4), pN stage (N0 versus N1), and DKK1 status (score 2+ vs 0, 1+). All those parameters were significantly associated with poor prognosis. Multivariate analysis using a Cox proportional-hazard model determined that DKK1 was not an independent prognostic factor for surgically treated ESCC patients (Table 9B).

N-glycosylation of DKK1 in Cancer Cells.

Figure 10:
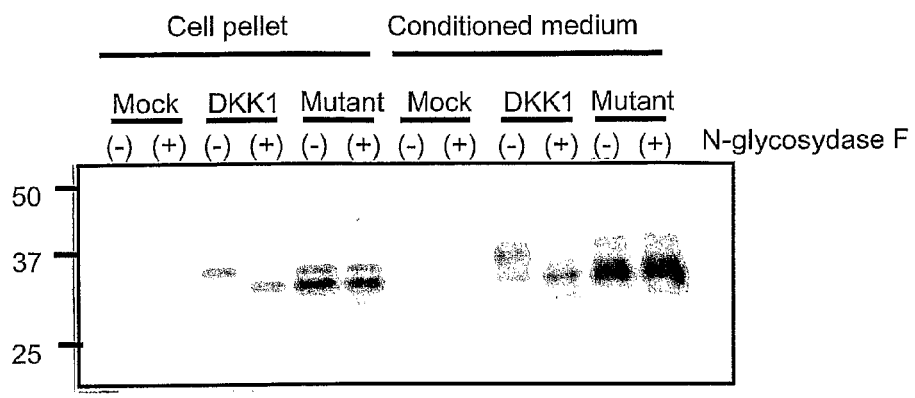
Figure 10:
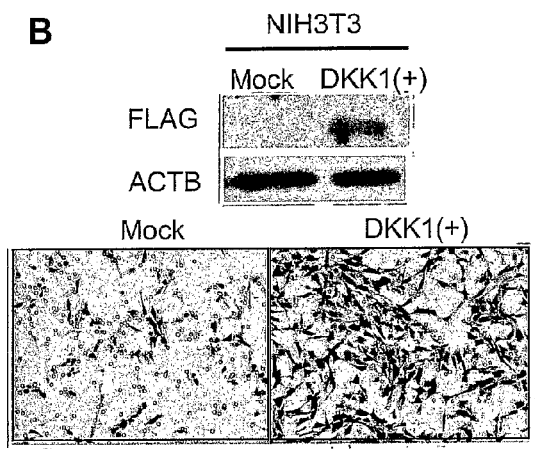
Figure 10:
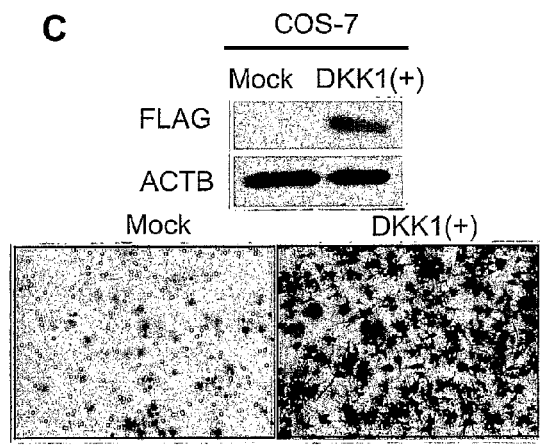
Figure 10:
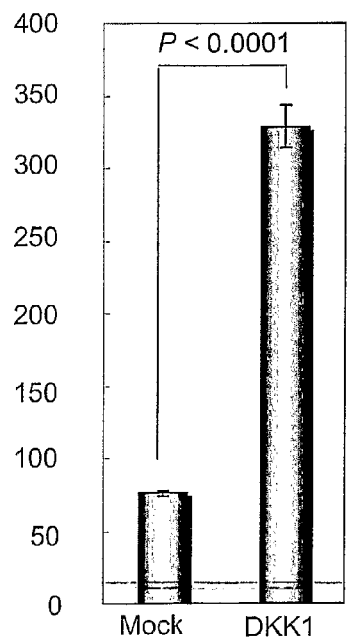
Figure 10:
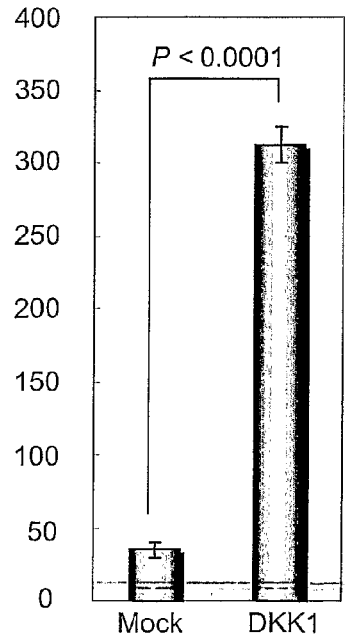

DKK1 protein was reported to be expressed as approximately 35-kDa protein in cells transfected with DKK1 expressing vector, and secreted in the culture medium as forms of 35-40 kDa protein (Fedi et al., J Biol Chem. 1999 Jul. 2; 274(27):19465-72, Niida et al., Oncogene. 2004 Nov. 4; 23(52):8520-6). As shown in FIG. 10A, exogenous DKK1 protein was recognized by western-blot analysis as band around 35-40-kDa in the conditioned medium of transfected COS-7 cells. Secreted DKK1 protein was detected as double bands by western-blotting. Therefore, the present inventors first incubated cell extracts and proteins collected from the conditioned medium from the transfected COS-7 cells in the presence or absence of N-glycosydase F and analyzed the molecular weight of DKK1 protein by western-blot analysis. Expectedly, the measured weight of the majority of DKK1 protein in the cell extracts and conditioned medium treated with N-glycosydase F was smaller than that in the untreated cells (FIG. 10A). Because DKK1 possesses one potential N-glycosylation site located close to the C-terminus of the protein (asparagine-256), the present inventors replaced the potential N-glycosylation site (asparagine-256) in DKK1 to alanine. Mutated DKK1 was detected by western-blot analysis as immunoreactive bands of similar molecular weight to the deglycosylated form of wild type DKK1 in the conditioned medium and in cell pellet (FIG. 10A). Treatment with N-glycosidase F did not cause any shift of a mutant band of DKK1 in the cell pellet and conditioned medium (FIG. 10A). These results suggested that asparagine-256 was a cognate N-glycosylation site of DKK1, but did not affect the secretion of DKK1.

Serum Levels of DKK1 in Patients with Lung Cancer or ESCC.

Since the in vitro findings had suggested a possibility to develop a novel tumor maker using the secreted forms of DKK1, the present inventors investigated whether the DKK1 protein is secreted into sera of patients with lung or esophageal cancer. ELISA experiments detected DKK1 protein in serological samples from these patients. The mean ($\pm 1$ SD) of serum DKK1 in lung cancer patients was $27.2\pm21.0$ U/ml and those in ESCC patients were $33.5\pm25.3$ U/ml. In contrast, the mean ($\pm 1$ SD) serum levels of DKK1 in healthy individuals were $6.3\pm5.0$ U/ml. The difference was significant with P-value of <0.001 (Mann-Whitney U test). When classified according to histologic type in lung cancer, the serum levels of DKK1 were $25.5\pm18.4$ U/ml in ADC patients, $24.7\pm17.7$ U/ml in SCC patients, and $31.8\pm25.8$ U/ml in SCLC patients (FIG. 9A); the differences among the three histologic types were not significant.

Figure 9:
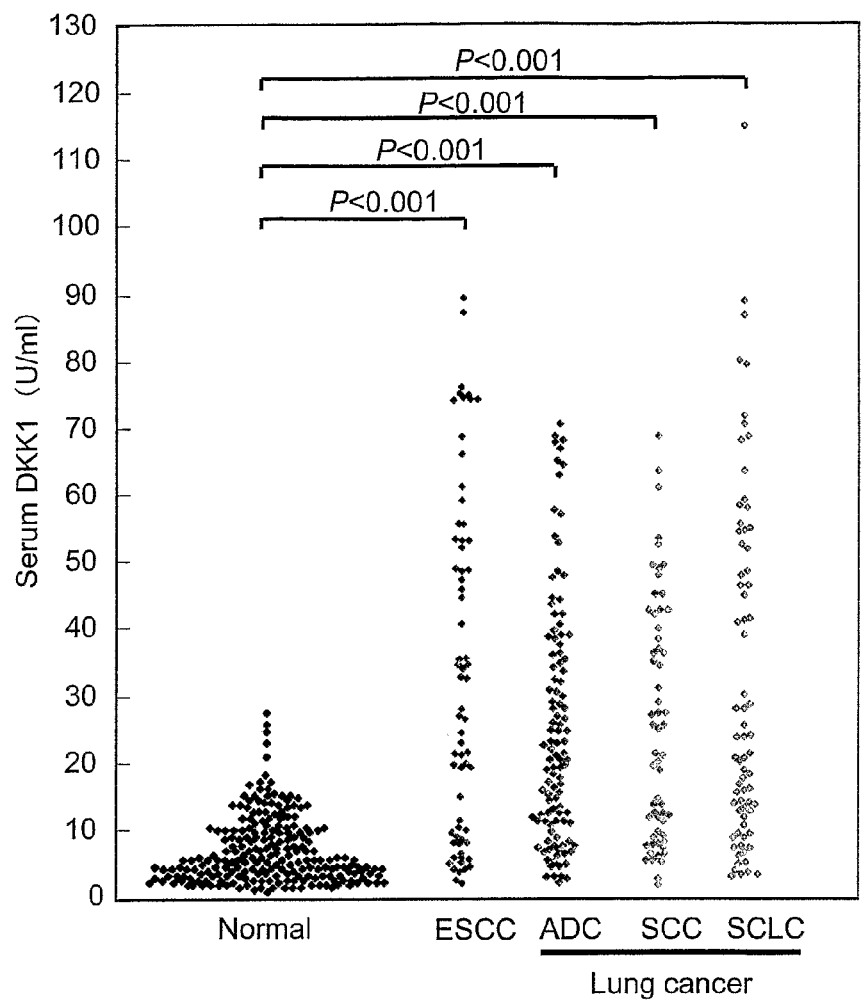
FIG. 9 Serologic concentration of DKK1 determined by ELISA in patients with ESCC, lung cancers and in healthy controls.
Figure 9:
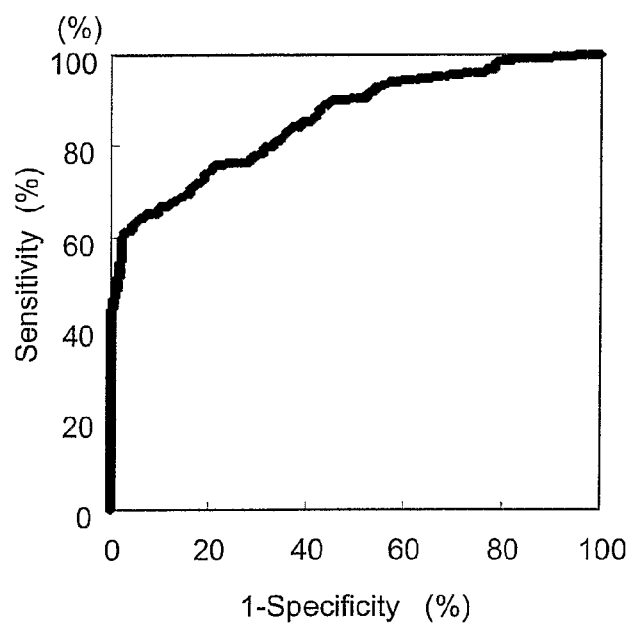

The levels of DKK1 were additionally analyzed in serum samples from both lung cancer and ESCC patients as well as healthy individuals by drawing receiver-operating characteristic (ROC) curves to determine their cutoff levels (FIG. 9B). Cutoff level in this assay was set to result in optimal diagnostic accuracy and likelihood ratios for DKK1, i.e., 14.7 U/ml (with a sensitivity of 63.7% (191/300) and a specificity of 95.9% (211/220). The mean ($\pm 2$SD) of serum DKK1 levels in healthy individuals were 16.3 U/ml, suggesting that this cutoff point is appropriate.

To evaluate the feasibility of using serum DKK1 level as a tumor detection biomarker, the present inventors also measured by ELISA serum levels of CEA for NSCLC and pro-GRP for SCLC patients, two conventional tumor markers for these histological types of lung cancer, in the same patients and controls. The cut off value of CEA was determined to be 2.5 ng/ml (with a sensitivity of 40.3% (64/159) and a specificity of 97.1% (204/210)) in patients with NSCLC. The correlation coefficient between serum DKK1 and CEA values was not significant (Spearman rank correlation coefficient: $\rho=-0.034$, P=0.668), indicating that measuring both markers in serum can improve overall sensitivity for detection of NSCLC to 78.6% (125 of 159) (for diagnosing NSCLC, the sensitivity of CEA alone is 40.3% (64 of 159) and that of DKK1 is 61.6% (98 of 159)). False-positive rates for either of the two tumor markers among normal volunteers (control group) amounted to 8.2% (17 of 208), whereas the false-positive rates for CEA and DKK1 in the same control group were 2.9% (6 of 208) and 5.3% (11 of 208) individually. On the other hand, ROC analyses for proGRP in the patients with SCLC determined the cutoff value of ProGRP as 46.0 pg/ml (with a sensitivity of 60.6% (40 of 66) and a specificity of 99.3% (145 of 146). The correlation coefficient between serum DKK1 and ProGRP values was not significant (Spearman rank correlation coefficient: ρ=0.113, P=0.362), indicating that measuring both markers in serum can improve overall sensitivity for detection of SCLC to 84.8% (56 of 66) (for diagnosing SCLC, the sensitivity of ProGRP alone is 60.6% (40 of 66) and that of DKK1 is 63.6% (42 of 66)). False-positive results for either of the two tumor markers among 146 normal volunteers (control group) amounted to 6.2% (9 of 146), whereas the false-positive rates for proGRP and DKK1 in the same control group were 0.7% (1 of 146) and 5.5% (8 of 146) individually.

Activation of Cellular Invasive Activity by DKK1.

As the immunohistochemical analysis on tissue microarray had indicated that lung and esophageal cancer patients with DKK1 positive tumors showed shorter cancer-specific survival period than patients whose tumors were negative for DKK1, the present inventors examined a possible role of DKK1 in cellular motility and invasion in Matrigel assays, using NIH3T3 and COS-7 cells. As shown in FIGS. 10B, C, transfection of DKK1 cDNA into either cell line significantly enhanced its invasive activity through Matrigel, compared to cells transfected with mock vector.

Discussion

In spite of improvement of modern surgical techniques and adjuvant chemoradiotherapy, lung cancer and ESCC are known to reveal the worst prognosis among malignant tumors. Therefore it is now urgently required to develop novel diagnostic biomarkers for early detection of cancer and for the better choice of adjuvant treatment modalities to appropriate patients. The present inventors performed a genome-wide analysis of gene expression profiles of 101 lung cancers and 19 ESCC cells purified by laser microbeam microdissection (LMM) using a cDNA microarray containing 27,648 genes (Yamabuki et al. Int J Oncol. 2006 June; 28(6):1375-84; Kikuchi et al., Oncogene. 2003 Apr. 10; 22(14):2192-205, Int J Oncol. 2006 April; 28(4):799-805; Kakiuchi et al., Mol Cancer Res. 2003 May; 1(7):485-99, Hum Mol Genet. 2004 Dec. 15; 13(24):3029-43. Epub 2004 Oct. 20). In the process, the present inventors identified a number of genes that were potentially good candidates for development of novel diagnostic markers, therapeutic drugs, and/or immunotherapy (Suzuki et al., Cancer Res. 2003 Nov. 1; 63(21):7038-41, Cancer Res. 2005 Dec. 15; 65(24):11314-25; Ishikawa et al., Clin Cancer Res. 2004 Dec. 15; 10(24):8363-70, Cancer Res. 2005 Oct. 15; 65(20):9176-84; Kato et al., Cancer Res. 2005 Jul. 1; 65(13):5638-46; Furukawa et al., Cancer Res. 2005 Aug. 15; 65(16):7102-10). Among them, the genes encoding putative tumor-specific transmembrane or secretory proteins are considered to have significant advantages, because they are present on the cell surface or within the extracellular space, and/or in serum, making them easily accessible as molecular markers and therapeutic targets. In this study, the present inventors selected an up-regulated gene (DKK1) encoding secretory protein, and examined the protein expression status by means of tissue microarray analysis and ELISA to identify novel diagnostic and prognostic biomarker(s) for lung cancer and/or ESCC.

DKK1 is a 266-amino acid protein that contains a signal peptide sequence and two cysteine-rich domains (Fedi et al., J Biol Chem. 1999 Jul. 2; 274(27):19465-72), and is known to be a secreted protein that functions as a negative regulator of Wnt signaling and plays a crucial role in head formation in vertebrate development (Glinka et al., Nature. 1998 Jan. 22; 391(6665):357-62; Fedi et al., J Biol Chem. 1999 Jul. 2; 274(27):19465-72; Mao et al., Nature. 2002 Jun. 6; 417(6889):664-7. Epub 2002 May 26, Nature. 2001 May 17; 411(6835):321-5; Mukhopadhyay et al., Dev Cell. 2001 September; 1(3):423-34). In addition, DKK1 is reported to be a downstream target of β-catenin/TCF and participate in a negative feedback loop in Wnt signaling (Gonzalez et al., Oncogene. 2005 Feb. 3; 24(6):1098-103; Niida et al., Oncogene. 2004 Nov. 4; 23(52):8520-6).

A family of human DKK (hDKK)-related genes were composed of DKK1, DKK2, DKK3, and DKK4, together with a unique DKK3 related protein termed Soggy (Sgy). hDKKs 1-4 contain two distinct cysteine-rich domains in which the positions of 10 cystein residues are highly conserved between family members. hDKK1 and hDKK4, but not hDKK2, hDKK3 or Sgy, suppress Wnt-induced secondary axis induction in *Xenopus* embryos (Krupnik et al., Gene. 1999 Oct. 1; 238(2):301-13). DKK4 was found to show high specificity for gastric cancer by serial analysis of gene expression (SAGE) and quantitative reverse transcription (RT)-PCR (Aung et al., Oncogene. 2006 Apr. 20; 25(17):2546-57). Other studies have demonstrated over-expression of DKK1 in Wilms' tumor, hepatoblastoma, and hepatocelluar carcinoma (HCC) (Wirths et al., Lab Invest. 2003 March; 83(3):429-34; Patil et al., Oncogene. 2005 May 26; 24(23):3737-47), but clinical utility of DKK1 protein as a serological/histochemical marker in human cancer was not indicated previously. Like a DKK1 protein, Wnt inhibitory factor-1 (WIF-1) and Frizzeled related protein (FRP) were known to be secreted molecules, which have been indicated to bind to Wnt proteins and inhibit their activity (Hsieh et al., Nature. 1999 Apr. 1; 398(6726):431-6; Wodarz et al., Annu Rev Cell Dev Biol. 1998; 14:59-88; Moon et al., Dev Suppl. 1993; 85-94). These two proteins were reported to be associated with human cancer including colorectal carcinoma (Cebrat et al., Cancer Lett. 2004 Mar. 31; 206(1): 107-13). FRP-4 protein showed markedly increased expression levels in colorectal cancers compared to normal mucosa, but no significant associations with pathological features or with patient outcome (Horvath et al., Clin Cancer Res. 2004 Jan. 15; 10(2):615-25). Since various DKK-family proteins had been described as being over-expressed in human cancers (Aung et al., Oncogene. 2006 Apr. 20; 25(17):2546-57; Horvath et al., Clin Cancer Res. 2004 Jan. 15; 10(2):615-25), DKK1 seemed likely to have a potential role in tumor development or progression.

In the present invention, the present inventors demonstrated that induction of exogenous expression of DKK1 enhanced the cellular migration/invasive activity of normal mammalian cells. Concordantly, the strong DKK1-staining in primary NSCLC tissues detected by tissue-microarray analyses correlated with poorer prognosis. Although the precise function of DKK1 in lung and esophageal carcinogenesis is unknown, and the processes of cancer-cell invasion to adjacent tissues and distant metastasis consist of a complex series of sequential step, these results indicate that DKK1 expression could promote dissemination of tumors by stimulating cell migration. DKK1 has been described as a secreted protein which plays a crucial role in head formation in vertebrate development, and is known as a negative regulator of Wnt signaling (Niida et al., Oncogene. 2004 Nov. 4; 23(52):8520-6). DKK1 binds to LRP5/6 and Kremen proteins, thus inducing LRP endocytosis, which prevents the formation of Wnt-Frizzled-LRP5/6 receptor complexes (Gonzalez et al., Oncogene. 2005 Feb. 3; 24(6): 1098-103). However, when the present inventors analyzed mRNA expression of DKK1 and LRP5/6 in lung and esophageal cancer cell lines and cancer tissues by semi-quantitative RT-PCR, the expression pattern of LRP5/6 was not concordant with that of DKK1 (data not shown). Additional studies to identify unknown binding-partners and receptors of DKK1 in human cancers may contribute not only to identification of novel tumor markers and therapeutic targets, but also should yield new understanding of the signaling pathway mediated by DKK1 expression.

The present inventors confirmed the C-terminus potential site, asparagines-256 was an N-glycosylation site in DKK1 by using enzymatic treatment and alanine-replacement mutant, but it did not affect the secretion of DKK1. Recently, various cancer-specific antigen including carbohydrate antigens were reported as a serum tumor marker. Specific glycosylation has been used for diagnostic purposes; i.e. alpha-fetoprotein (AFP) for hepatocarcinoma (Poon et al., Clin Chem. 2002 July; 48(7):1021-7), human pancreatic ribonuclease, which has different oligosaccharide chains when produced by pancreatic tumor cells (Peracaula et al., Glycobiology. 2003 April; 13(4):227-44. Epub 2002 Nov. 26), or prostate-specific antigen (PSA), the tumor marker currently used for prostate cancer screening (Tabarés et al., Glycobiology. 2006 February; 16(2):132-45. Epub 2005 Sep. 21). Changes in N-linked glycosylation were reported to occur during the development of cancer. Increased branching of oligosaccharides has been associated with metastasis and correlated with tumor progression in human cancers of the breast, colon and melanomas (Comunale et al., J Proteome Res. 2006 February; 5(2):308-15). Although further evaluation will be necessary, glycosylation of DKK1 could be a novel diagnostic and therapeutic target for lung and esophageal cancer treatment.

To examine the feasibility of applying DKK1 as the diagnostic tool, the present inventors compared serum levels of DKK1 with those of CEA or ProGRP, a conventional diagnostic markers for NSCLCs and SCLCs, in terms of sensitivity and specificity for diagnosis. The proportions of positive cases among the same serum samples were more than 60% for DKK1, while the false-positive rate for DKK1 was around 5.0%, indicating equivalent or better diagnostic power of DKK1 to that of CEA. Furthermore, an assay combining both markers (DKK1+CEA or DKK1+ProGRP) increased the sensitivity such that about 80% of the patients with lung cancer were diagnosed as positive while 6.2-8.2% of healthy volunteers were falsely diagnosed as positive. Although further validation using a larger set of serum samples covering various clinical stages will be necessary, the data presented here sufficiently demonstrate a potential clinical application of DKK1 itself as a serological/histochemical marker for lung and esophageal cancers.

In conclusion, the present inventors have identified DKK1 as a potential biomarker for diagnosis of lung and esophageal cancers as well as prediction of the poor prognosis of the patients with these diseases. DKK1 was specifically overexpressed in most lung and esophageal cancer tissues the present inventors examined, and was elevated in the sera of a large proportion of patients with these tumors. DKK1, combined with other tumor markers, could significantly improve the sensitivity of cancer diagnosis. Moreover, this molecule is also a likely candidate for development of therapeutic approaches such as antibody therapy.

INDUSTRIAL APPLICABILITY

The gene expression analysis of esophageal cancer described herein, obtained through a combination of laser-capture dissection and genome-wide cDNA microarray, has identified specific genes as targets for cancer prevention and therapy. Based on the expression of a subset of these differentially expressed genes, the present invention provides molecular diagnostic markers for identifying and detecting esophageal cancer.

The methods described herein are also useful in the identification of additional molecular targets for prevention, diagnosis and treatment of esophageal cancer. The data reported herein add to a comprehensive understanding of esophageal cancer, facilitate development of novel diagnostic strategies, and provide clues for identification of molecular targets for therapeutic drugs and preventative agents. Such information contributes to a more profound understanding of esophageal tumorigenesis, and provides indicators for developing novel strategies for diagnosis, treatment, and ultimately prevention of esophageal cancer.

Furthermore, the methods described herein are also useful in diagnosis of cancer including lung and esophageal cancers as well as prediction of the poor prognosis of the patients with these diseases. Moreover, the data reported here is also provide a likely candidate for development of therapeutic approaches for cancer including lung and esophageal cancers.

Unless otherwise defined, all technical and scientific terms used herein have the same meaning as commonly understood by one of ordinary skill in the art to which this invention belongs. In case of conflict, the present specification, including definitions, will control.

All publications, patent applications, patents and other references mentioned herein are incorporated by reference in their entirety.

While the invention has been described in detail and with reference to specific embodiments thereof, it will be apparent to one skilled in the art that various changes and modifications can be made therein without departing from the spirit and scope of the invention.

TABLE 1

| | | down-regulated genes | | |
|---|---|---|---|---|
| Assignment NO | LMMID | ACCESSION | SYMBOL | GENE NAME |
| 1 | A0906 | NM_002939 | RNH | Ribonuclease/angiogenin inhibitor |
| 2 | A1350 | NM_013314 | BLNK | B-cell linker |
| 3 | A1475 | BC017048 | GJB2 | Gap junction protein, beta 2, 26 kDa (connexin 26) |
| 4 | A2014 | L23959 | TFDP1 | Transcription factor Dp-1 |

TABLE 1-continued down-regulated genes

| Assignment NO | LMMID | ACCESSION | SYMBOL | GENE NAME |
|---|---|---|---|---|
| 5 | A2460 | AF000959 | CLDN5 | Claudin 5 (transmembrane protein deleted in velocardiofacial syndrome) |
| 6 | A3340 | M93284 | PNLIPRP2 | Pancreatic lipase-related protein 2 |
| 7 | A3821 | NM_004925 | AQP3 | Aquaporin 3 |
| 8 | A4472 | AF042081 | SH3BGRL | SH3 domain binding glutamic acid-rich protein like |
| 9 | A4587 | AF070609 | SLC1A3 | DKFZP547J0410 protein |
| 10 | A0283 | NM_021120 | DLG3 | Discs, large homolog 3 (neuroendocrine-dlg, *Drosophila*) |
| 11 | A1365 | D10653 | TM4SF2 | Transmembrane 4 superfamily member 2 |
| 12 | A3322 | M80899 | AHNAK | AHNAK nucleoprotein (desmoyokin) |
| 13 | A5658 | AJ243937 | GPSM3 | G-protein signalling modulator 3 (AGS3-like, *C. elegans*) |
| 14 | A0765 | BC004102 | ALDH3A1 | Aldehyde dehydrogenase 3 family, memberA1 |
| 15 | A1215 | NM_002275 | KRT15 | Keratin 15 |
| 16 | A1879 | U45955 | GPM6B | Glycoprotein M6B |
| 17 | A1758 | U60553 | CES2 | Carboxylesterase 2 (intestine, liver) |
| 18 | A2363 | NM_000060 | BTD | Biotinidase |
| 19 | A6156 | BU616881 | ARHE | Ras homolog gene family, member E |
| 20 | A2487 | D10923 | GPR109B | G protein-coupled receptor 109B |
| 21 | A2747 | NM_004347 | CASP5 | Caspase 5, apoptosis-related cysteine protease |
| 22 | A3095 | U26726 | HSD11B2 | Hydroxysteroid (11-beta) dehydrogenase 2 |
| 23 | A3605 | NM_007366 | PLA2R1 | Phospholipase A2 receptor 1, 180 kDa |
| 24 | A3701 | BC028412 | ELL2 | Elongation factor, RNA polymerase II, 2 |
| 25 | A4481 | AF053470 | BLCAP | Bladder cancer associated protein |
| 26 | A4832 | D78011 | DPYS | Dihydropyrimidinase |
| 27 | A4744 | AF020202 | UNC13B | Unc-13 homolog B (*C. elegans*) |
| 28 | A5888 | U56417 | AGPAT1 | 1-acylglycerol-3-phosphate O-acyltransferase 1 (lysophosphatidic acid acyltransferase, alpha) |
| 29 | A1063 | BU600928 | SPRR1B | Small proline-rich protein 1B (cornifin) |
| 30 | A2029 | BC034227 | D4S234E | DNA segment on chromosome 4 (unique) 234 expressed sequence |
| 31 | A2126 | U04241 | AES | Amino-terminal enhancer of split |
| 32 | A3237 | L10386 | TGM3 | Transglutaminase 3 (E polypeptide, protein-glutamine-gamma-glutamyltransferase) |
| 33 | A4875 | NM_000336 | SCNN1B | Sodium channel, nonvoltage-gated 1, beta (Liddle syndrome) |
| 34 | A5816 | AF014398 | IMPA2 | Inositol(myo)-1(or 4)-monophosphatase 2 |
| 35 | A6077 | XM_499570 | PLXNA2 | Plexin A2 |
| 36 | A0365 | U17077 | BENE | BENE protein |
| 37 | A0946 | U62961 | OXCT1 | 3-oxoacid CoA transferase 1 |
| 38 | A1479 | NM_000275 | OCA2 | Oculocutaneous albinism II (pink-eye dilution homolog, mouse) |
| 39 | A2565 | BG676358 | S100A8 | S100 calcium binding protein A8 (calgranulin A) |
| 40 | A2372 | AF458589 | PPP1R12A | Protein phosphatase 1, regulatory (inhibitor) subunit 12A |
| 41 | A2840 | BM480033 | CRABP2 | Cellular retinoic acid binding protein 2 |
| 42 | A4474 | AF047433 | ITGB4BP | Integrin beta 4 binding protein |

TABLE 1-continued down-regulated genes

| Assignment NO | LMMID | ACCESSION | SYMBOL | GENE NAME |
|---|---|---|---|---|
| 43 | A5088 | U24266 | ALDH4A1 | Aldehyde dehydrogenase 4 family, member A1 |
| 44 | A5127 | AF004709 | MAPK13 | Mitogen-activated protein kinase 13 |
| 45 | A0102 | BC053866 | EDN3 | Endothelin 3 |
| 46 | A1064 | NM_024164 | TPSB2 | Tryptase, alpha |
| 47 | A0685 | L05779 | EPHX2 | Epoxide hydrolase 2, cytoplasmic |
| 48 | A1591 | NM_002534 | OAS1 | 2',5'-oligoadenylate synthetase 1, 40/46 kDa |
| 49 | A1199 | NM_005018 | PDCD1 | Programmed cell death 1 |
| 50 | A2031 | NM_003040 | SLC4A2 | Solute carrier family 4, anion exchanger, member 2 (erythrocyte membrane protein band 3-like 1) |
| 51 | A3454 | M59979 | PTGS1 | Prostaglandin-endoperoxide synthase 1 (prostaglandin G/H synthase and cyclooxygenase) |
| 52 | A4242 | BM909803 | LGALS7 | Lectin, galactoside-binding, soluble, 7 (galectin 7) |
| 53 | A4723 | NM_001543 | NDST1 | N-deacetylase/N-sulfotransferase (heparan glucosaminyl) 1 |
| 54 | A1073 | CA312671 | CD58 | CD58 antigen, (lymphocyte function-associated antigen 3) |
| 55 | A2142 | AF055008 | GRN | Granulin |
| 56 | A2566 | BQ927179 | S100A9 | S100 calcium binding protein A9 (calgranulin B) |
| 57 | A2366 | NM_000700 | ANXA1 | Annexin A1 |
| 58 | A4109 | AK075003 | NEFL | Neurofilament, light polypeptide 68 kDa |
| 59 | A5695 | NM_001839 | CNN3 | Calponin 3, acidic |
| 60 | A0961 | NM_001482 | GATM | Glycine amidinotransferase (L-arginine:glycine amidinotransferase) |
| 61 | A1592 | NM_000177 | GSN | Gelsolin (amyloidosis, Finnish type) |
| 62 | A1873 | M58297 | | |
| 63 | A2129 | M29877 | FUCA1 | Fucosidase, alpha-L-1, tissue |
| 64 | A3246 | BC011409 | UGT1A6 | UDP glycosyltransferase 1 family, polypeptide A9 |
| 65 | A3853 | AF007170 | C1orf34 | Chromosome 1 open reading frame 34 |
| 66 | A5399 | R44471 | NEBL | Nebulette |
| 67 | A1074 | D90228 | ACAT1 | Acetyl-Coenzyme A acetyltransferase 1 (acetoacetyl Coenzyme A thiolase) |
| 68 | A1610 | NM_002084 | GPX3 | Glutathione peroxidase 3 (plasma) |
| 69 | A1754 | AB119995 | CES1 | Carboxylesterase 1 (monocyte/macrophage serine esterase 1) |
| 70 | A2336 | BC032528 | LTA4H | Leukotriene A4 hydrolase |
| 71 | A3061 | U07643 | LTF | Lactotransferrin |
| 72 | A2742 | NM_002272 | KRT4 | Keratin 4 |
| 73 | A4614 | NM_007283 | MGLL | Monoglyceride lipase |
| 74 | A0830 | NM_002746 | MAPK3 | Mitogen-activated protein kinase 3 |
| 75 | A1501 | NM_006225 | PLCD1 | Phospholipase C, delta 1 |
| 76 | A2886 | M20643 | MYL1 | Myosin, light polypeptide 1, alkali; skeletal, fast |
| 77 | A5400 | AK122818 | BTBD11 | BTB (POZ) domain containing 11 |
| 78 | A6073 | AI290541 | | CDNA FLJ11723 fis, clone HEMBA1005314 |
| 79 | A0090 | BC040499 | TGFBR2 | Transforming growth factor, beta receptor II (70/80 kDa) |
| 80 | A1046 | AF266280 | LGALS3 | Lectin, galactoside-binding, soluble, 3 (galectin 3) |
| 81 | A0662 | BC034699 | TGM1 | Transglutaminase 1 (K polypeptide epidermal type I, protein-glutamine-gamma-glutamyltransferase) |
| 82 | A2608 | NM_002230 | JUP | Junction plakoglobin |

TABLE 1-continued down-regulated genes

| Assignment NO | LMMID | ACCESSION | SYMBOL | GENE NAME |
|---|---|---|---|---|
| 83 | A3338 | M93056 | SERPINB1 | Serine (or cysteine) proteinase inhibitor, clade B (ovalbumin), member 1 |
| 84 | A3345 | BC004452 | GTF2H1 | General transcription factor IIH, polypeptide 1, 62 kDa |
| 85 | A4076 | BC008837 | AKR1B10 | Aldo-keto reductase family 1, member B10 (aldose reductase) |
| 86 | A3738 | NM_002332 | LRP1 | Low density lipoprotein-related protein 1 (alpha-2-macroglobulin receptor) |
| 87 | A4586 | D86977 | DHX38 | DEAH (Asp-Glu-Ala-His) box polypeptide 38 |
| 88 | A6282 | BC001338 | RHOD | Ras homolog gene family, member D |
| 89 | A5002 | NM_006137 | CD7 | CD7 antigen (p41) |
| 90 | A0249 | U09578 | MAPKAPK3 | Mitogen-activated protein kinase-activated protein kinase 3 |
| 91 | A0922 | NM_004394 | DAP | Death-associated protein |
| 92 | A0654 | BC000458 | MAL | Mal, T-cell differentiation protein |
| 93 | A2733 | NM_005013 | NUCB2 | Nucleobindin 2 |
| 94 | A3114 | M95585 | HLF | Hepatic leukemia factor |
| 95 | A5230 | BC021927 | TBC1D10 | TBC1 domain family, member 10 |
| 96 | A2188 | J02770 | IF | I factor (complement) |
| 97 | A3037 | BC030975 | IL1RL1 | Interleukin 1 receptor-like 1 |
| 98 | A3283 | BQ446473 | FABP5 | Fatty acid binding protein 5 (psoriasis-associated) |
| 99 | A4162 | BM471531 | AP2S1 | Adaptor-related protein complex 2, sigma 1 subunit |
| 100 | A4677 | S80562 | CNN3 | Calponin 3, acidic |
| 101 | A5951 | CR610474 | MPDU1 | Mannose-P-dolichol utilization defect 1 |
| 102 | A4015 | D29767 | TEC | Tec protein tyrosine kinase |
| 103 | A4054 | NM_144505 | KLK8 | Kallikrein 8 (neuropsin/ovasin) |
| 104 | A4146 | BQ941085 | PI3 | Protease inhibitor 3, skin-derived (SKALP) |
| 105 | A4699 | NM_002461 | MVD | Mevalonate (diphospho) decarboxylase |
| 106 | A5159 | BC080193 | ERBB2 | V-erb-b2 erythroblastic leukemia viral oncogene homolog 2, neuro/glioblastoma derived oncogene homolog (avian) |
| 107 | A1010 | D28475 | CLCN6 | Chloride channel 6 |
| 108 | A1414 | NM_001855 | COL15A1 | Collagen, type XV, alpha 1 |
| 109 | A1951 | AL833268 | MEF2C | MADS box transcription enhancer factor 2, polypeptide C (myocyte enhancer factor 2C) |
| 110 | A2158 | NM_005410 | SEPP1 | Selenoprotein P, plasma, 1 |
| 111 | A2189 | NM_000112 | SLC26A2 | Solute carrier family 26 (sulfate transporter), member 2 |
| 112 | A4163 | NM_006001 | TUBA2 | Tubulin, alpha 2 |
| 113 | A4388 | NM_001988 | EVPL | Envoplakin |
| 114 | A2291 | AF003341 | ALDH1A1 | Aldehyde dehydrogenase 1 family, member A1 |
| 115 | A2444 | AY366508 | LOH11CR2A | Loss of heterozygosity, 11, chromosomal region 2, gene A |
| 116 | A2796 | NM_006681 | NMU | Neuromedin U |
| 117 | A2802 | CR592117 | CASP1 | Caspase 1, apoptosis-related cysteine protease (interleukin 1, beta, convertase) |
| 118 | A3412 | NM_000552 | VWF | Von Willebrand factor |
| 119 | A0593 | NM_002290 | LAMA4 | Laminin, alpha 4 |
| 120 | A1415 | L25798 | HMGCS1 | 3-hydroxy-3-methylglutaryl-Coenzyme A synthase 1 (soluble) |
| 121 | A2159 | L10340 | EEF1A2 | Eukaryotic translation elongation factor 1 alpha 2 |
| 122 | A2306 | U70063 | ASAH1 | N-acylsphingosine amidohydrolase (acid ceramidase) 1 |
| 123 | A4810 | AF077599 | RNF41 | Ring finger protein 41 |
| 124 | A5155 | NM_000418 | IL4R | Interleukin 4 receptor |
| 125 | A0304 | U80456 | SIM2 | Single-minded homolog 2 (*Drosophila*) |

TABLE 1-continued down-regulated genes

| Assignment NO | LMMID | ACCESSION | SYMBOL | GENE NAME |
|---|---|---|---|---|
| 126 | A0856 | M32402 | P11 | 26 serine protease |
| 127 | A0574 | NM_033018 | PCTK1 | PCTAIRE protein kinase 1 |
| 128 | A1564 | U70370 | PITX1 | Paired-like homeodomain transcription factor 1 |
| 129 | A1832 | M74297 | HOXA4 | Homeo box A4 |
| 130 | A2664 | BC033820 | FGL2 | Fibrinogen-like 2 |
| 131 | A3291 | BM805032 | PRSS2 | Protease, serine, 2 (trypsin 2) |
| 132 | A4179 | NM_002769 | PRSS1 | Protease, serine, 1 (trypsin 1) |
| 133 | A4297 | NM_012205 | HAAO | 3-hydroxyanthranilate 3,4-dioxygenase |
| 134 | A4695 | NM_001003395 | TPD52L1 | Tumor protein D52-like 1 |
| 135 | A5849 | NM_024095 | ASB8 | Ankyrin repeat and SOCS box-containing 8 |
| 136 | A0971 | AY034086 | DSCR1L1 | Down syndrome critical region gene 1-like 1 |
| 137 | A2307 | NM_004563 | PCK2 | Phosphoenolpyruvate carboxykinase 2 (mitochondrial) |
| 138 | A4517 | L08488 | INPP1 | Inositol polyphosphate-1-phosphatase |
| 139 | A5442 | AF105036 | KLF4 | Kruppel-like factor 4 (gut) |
| 140 | A0461 | NM_001068 | TOP2B | Topoisomerase (DNA) II beta 180 kDa |
| 141 | A6143 | BX648675 | ATP8A1 | ATPase, aminophospholipid transporter (APLT), Class I, type 8A, member 1 |
| 142 | A4298 | Z34821 | CACNA1C | Calcium channel, voltage-dependent, L type, alpha 1C subunit |
| 143 | A5048 | BC014941 | ID4 | Inhibitor of DNA binding 4, dominant negative helix-loop-helix protein |
| 144 | A1553 | BC023505 | ECM1 | Extracellular matrix protein 1 |
| 145 | A2192 | BC011890 | ETFDH | Electron-transferring-flavoprotein dehydrogenase |
| 146 | A3009 | BC009799 | AREG | Amphiregulin (schwannoma-derived growth factor) |
| 147 | A4144 | BC004376 | ANXA8 | Annexin A8 |
| 148 | A5966 | BX647538 | FRMD4A | FERM domain containing 4A |
| 149 | A0578 | NM_004417 | DUSP1 | Dual specificity phosphatase 1 |
| 150 | A1938 | Y08200 | RABGGTA | Rab geranylgeranyltransferase, alpha subunit |
| 151 | A2440 | U96628 | PDCD4 | Programmed cell death 4 (neoplastic transformation inhibitor) |
| 152 | A3027 | M28827 | CD1C | CD1C antigen, c polypeptide |
| 153 | A2836 | BQ926240 | TNNI2 | Troponin I, skeletal, fast |
| 154 | A3269 | NM_002825 | PTN | Pleiotrophin (heparin binding growth factor 8, neurite growth-promoting factor 1) |
| 155 | A3299 | BM696587 | CRYAB | Crystallin, alpha B |
| 156 | A3816 | NM_005938 | MLLT7 | Myeloid/lymphoid or mixed-lineage leukemia (trithorax homolog, Drosophila); translocated to, 7 |
| 157 | A5752 | AL832919 | AGPAT3 | 1-acylglycerol-3-phosphate O-acyltransferase 3 |
| 158 | A0451 | V00497 | HBB | Hemoglobin, beta |
| 159 | A0597 | X72760 | LAMB2 | Laminin, beta 2 (laminin S) |
| 160 | A1240 | AB001895 | ARID1A | AT rich interactive domain 1A (SWI-like) |
| 161 | A1411 | BC035812 | PCDH1 | Protocadherin 1 (cadherin-like 1) |
| 162 | A1932 | J03037 | CA2 | Carbonic anhydrase II |
| 163 | A2822 | BQ015859 | CSTA | Cystatin A (stefin A) |
| 164 | A2935 | BM552331 | MGST2 | Microsomal glutathione S-transferase 2 |
| 165 | A3502 | U43899 | STAM | Signal transducing adaptor molecule (SH3 domain and ITAM motif) 1 |
| 166 | A3534 | NM_005554 | KRT6A | Keratin 6A |
| 167 | A3127 | D29642 | ARHGAP25 | Rho GTPase activating protein 25 |
| 168 | A3923 | AF038440 | PLD2 | Phospholipase D2 |
| 169 | A4145 | AA586894 | S100A7 | S100 calcium binding protein A7 (psoriasin 1) |

TABLE 1-continued down-regulated genes

| Assignment NO | LMMID | ACCESSION | SYMBOL | GENE NAME |
|---|---|---|---|---|
| 170 | A4265 | BM907670 | PPIC | Peptidylprolyl isomerase C (cyclophilin C) |
| 171 | A5739 | AA102482 | C14orf114 | Chromosome 14 open reading frame 114 |
| 172 | A1163 | M94345 | CAPG | Capping protein (actin filament), gelsolin-like |
| 173 | A2450 | NM_001740 | CALB2 | Calbindin 2, 29 kDa (calretinin) |
| 174 | A3380 | L20977 | ATP2B2 | ATPase, Ca++ transporting, plasma membrane 2 |
| 175 | A3187 | NM_000240 | MAOA | Monoamine oxidase A |
| 176 | A3300 | NM_005046 | KLK7 | Kallikrein 7 (chymotryptic, stratum corneum) |
| 177 | A4794 | AF064493 | LDB2 | LIM domain binding 2 |
| 178 | A4830 | NM_004557 | NOTCH4 | Notch homolog 4 (Drosophila) |
| 179 | A5436 | BQ009281 | ELL2 | Elongation factor, RNA polymerase II, 2 |
| 180 | A5200 | U10248 | RPL29 | Ribosomal protein L29 |
| 181 | A8063 | AL832598 | EPB41L3 | Erythrocyte membrane protein band 4.1-like 3 |
| 182 | A7978 | BC025176 | CYP3A5 | Cytochrome P450, family 3, subfamily A, polypeptide 5 |
| 183 | A9285 | AI027810 | KIAA1102 | KIAA1102 protein |
| 184 | A8996 | AK092607 | BSPRY | B-box and SPRY domain containing |
| 185 | B4069 | M77830 | DSP | Desmoplakin |
| 186 | B6764 | M14338 | PROS1 | Protein S (alpha) |
| 187 | C3614 | D31883 | ABLIM1 | Actin binding LIM protein 1 |
| 188 | A8863 | BM678420 | | Transcribed locus |
| 189 | C4904 | AY359010 | KLK5 | Kallikrein 5 |
| 190 | A7103 | NM_004949 | DSC2 | Desmocollin 2 |
| 191 | A7156 | X78706 | CRAT | Carnitine acetyltransferase |
| 192 | B0149 | AF052090 | NNT | Nicotinamide nucleotide transhydrogenase |
| 193 | B0259 | AA234962 | PKP3 | Plakophilin 3 |
| 194 | B4864 | NM_002145 | HOXB2 | Homeo box B2 |
| 195 | A6512 | AA167624 | HSPC159 | HSPC159 protein |
| 196 | A8688 | CR597998 | NPDC1 | Neural proliferation, differentiation and control, 1 |
| 197 | A9175 | NM_015270 | ADCY6 | Adenylate cyclase 6 |
| 198 | C4884 | AA036952 | Gup1 | GRINL1A complex upstream protein |
| 199 | B2793 | AA603460 | FBXL17 | F-box and leucine-rich repeat protein 17 |
| 200 | A7307 | AB032981 | KIAA1155 | KIAA1155 protein |
| 201 | A9545 | AA563634 | | Transcribed locus, moderately similar to XP_126365.1 RIKEN cDNA 9830002I17 gene [*Mus musculus*] |
| 202 | B0878 | NM_005797 | EVA1 | Epithelial V-like antigen 1 |
| 203 | B4406 | AF279865 | KIF13B | Kinesin family member 13B |
| 204 | A8203 | AK026966 | AK3 | Adenylate kinase 3 |
| 205 | A7795 | BC044582 | UBL3 | Ubiquitin-like 3 |
| 206 | A8115 | CA310913 | GLTP | Glycolipid transfer protein |
| 207 | A9458 | AA028101 | KIAA0303 | KIAA0303 protein |
| 208 | A9467 | BC045658 | LOC57228 | Hypothetical protein from clone 643 |
| 209 | A7145 | X52005 | | |
| 210 | A8433 | NM_005843 | STAM2 | Signal transducing adaptor molecule (SH3 domain and ITAM motif) 2 |
| 211 | B4086 | NM_006206 | PDGFRA | Platelet-derived growth factor receptor, alpha polypeptide |
| 212 | B4409 | XM_371116 | MYO5B | Myosin VB |
| 213 | B6820 | XM_497078 | NUP188 | Nucleoporin 188 kDa |
| 214 | A7798 | BC015033 | PLD2 | Phospholipase D2 |
| 215 | A8832 | BX648017 | C2orf18 | Chromosome 2 open reading frame 18 |
| 216 | A9468 | BX110596 | | *Homo sapiens*, clone IMAGE: 4799216, mRNA |
| 217 | B2482 | AI125528 | KIAA0476 | KIAA0476 |
| 218 | A6944 | AI310102 | | Transcribed locus |
| 219 | B0278 | AB037832 | KIAA1411 | KIAA1411 |
| 220 | B2135 | X03212 | KRT7 | Keratin7 |
| 221 | B3676 | NM_013334 | GMPPB | GDP-mannose pyrophosphorylase B |

TABLE 1-continued down-regulated genes

| Assignment NO | LMMID | ACCESSION | SYMBOL | GENE NAME |
|---|---|---|---|---|
| 222 | B4060 | NM_001953 | ECGF1 | Endothelial cell growth factor 1 (platelet-derived) |
| 223 | B2801 | AK130734 | FLJ13710 | Hypothetical protein FLJ13710 |
| 224 | A6388 | AK056894 | FLJ32332 | Likely ortholog of mouse protein phosphatase 2C eta |
| 225 | A6673 | AL137430 | LOC283070 | Hypothetical protein LOC283070 |
| 226 | A8525 | W67837 | EMP2 | Epithelial membrane protein 2 |
| 227 | A9178 | XM_168530 | PCLO | Piccolo (presynaptic cytomatrix protein) |
| 228 | B1734 | AA633746 | | Full-length cDNA clone CS0DF018YA02 of Fetal brain of Homo sapiens (human) |
| 229 | A6522 | BC045177 | FLJ30046 | Hypothetical protein FLJ30046 |
| 230 | A9011 | BQ772268 | PCBP2 | Poly(rC) binding protein 2 |
| 231 | A9307 | BC053677 | FLJ37562 | Hypothetical protein FLJ37562 |
| 232 | B5826 | AK027572 | KCTD6 | Potassium channel tetramerisation domain containing 6 |
| 233 | B4068 | AB011140 | PPL | Periplakin |
| 234 | C2083 | NM_002277 | KRTHA1 | Keratin, hair, acidic, 1 |
| 235 | A6317 | AI205684 | HSPA2 | Heat shock 70 kDa protein 2 |
| 236 | A6581 | AK093231 | TBC1D10 | TBC1 domain family, member 10 |
| 237 | A9099 | N70592 | PIGN | Phosphatidylinositol glycan, class N |
| 238 | A8964 | AI091459 | FLJ20489 | Hypothetical protein FLJ20489 |
| 239 | B0629 | AK126877 | FLJ10521 | Hypothetical protein FLJ10521 |
| 240 | B1354 | XM_496241 | | Similar to solute carrier family 16, member 6; monocarboxylate transporter 6 |
| 241 | B1614 | AY555274 | PF6 | Projection protein PF6 |
| 242 | B4141 | D79994 | ANKRD15 | Ankyrin repeat domain 15 |
| 243 | A7204 | CA430351 | TXN | Thioredoxin |
| 244 | A7244 | BQ706286 | MXD4 | MAX dimerization protein 4 |
| 245 | B1495 | AK000049 | Shax3 | Snf7 homologue associated with Alix 3 |
| 246 | A6712 | NM_182643 | DLC1 | Deleted in liver cancer 1 |
| 247 | A7393 | AK123452 | RAB6A | RAB6A, member RAS oncogene family |
| 248 | A7425 | NM_003250 | THRA | Thyroid hormone receptor, alpha (erythroblastic leukemia viral (v-erb-a) oncogene homolog, avian) |
| 249 | A8162 | AL832955 | TNFAIP9 | Tumor necrosis factor, alpha-induced protein 9 |
| 250 | A7679 | M97675 | ROR1 | Receptor tyrosine kinase-like orphan receptor 1 |
| 251 | B2073 | NM_001002857 | ANXA2 | Annexin A2 |
| 252 | B2084 | S45018 | CHAT | Choline acetyltransferase |
| 253 | A6486 | W67936 | RAI | RelA-associated inhibitor |
| 254 | A7454 | AF007162 | CRYAB | Crystallin, alpha B |
| 255 | B2657 | BM696564 | | CAMP-binding guanine nucleotide exchange factor IV (cAMP-GEFIV) mRNA, clone W15, partial sequence |
| 256 | B0364 | BC002714 | MGC4171 | Hypothetical protein MGC4171 |
| 257 | B0968 | BM271861 | SPATA11 | Spermatogenesis associated 11 |
| 258 | A7235 | M92449 | ASAHL | N-acylsphingosine amidohydrolase (acid ceramidase)-like |
| 259 | A7689 | X00457 | HLA-DPA1 | Major histocompatibility complex, class II, DP alpha 1 |
| 260 | A9203 | CR608541 | PHF17 | PHD finger protein 17 |
| 261 | A9368 | NM_022833 | C9orf88 | Chromosome 9 open reading frame 88 |
| 262 | B4602 | NM_005556 | KRT7 | Keratin 7 |
| 263 | A6719 | AI302184 | SQRDL | Sulfide quinone reductase-like (yeast) |
| 264 | A7464 | AF081287 | CTDP1 | CTD (carboxy-terminal domain, RNA polymerase II, polypeptide A) phosphatase, subunit 1 |

TABLE 1-continued down-regulated genes

| Assignment NO | LMMID | ACCESSION | SYMBOL | GENE NAME |
|---|---|---|---|---|
| 265 | A7773 | NM_002504 | NFX1 | Nuclear transcription factor, X-box binding 1 |
| 266 | A8378 | NM_032859 | C13orf6 | Chromosome 13 open reading frame 6 |
| 267 | B0550 | AA843150 | | Full-length cDNA clone CS0DF014YA22 of Fetal brain of Homo sapiens (human) |
| 268 | B4213 | NM_001001937 | ATP5A1 | ATP synthase, H+ transporting, mitochondrial F1 complex, alpha subunit, isoform 1, cardiac muscle |
| 269 | B4816 | NM_003438 | ZNF137 | Zinc finger protein 137 (clone pHZ-30) |
| 270 | B7573 | BC040481 | ZHX1 | Zinc fingers and homeoboxes 1 |
| 271 | A8790 | H70803 | SASH1 | SAM and SH3 domain containing 1 |
| 272 | B2399 | AY358351 | UNC5B | Unc-5 homolog B (C. elegans) |
| 273 | C4330 | BC006000 | CAPNS2 | Calpain, small subunit 2 |
| 274 | A6336 | AK097223 | NAGK | N-acetylglucosamine kinase |
| 275 | A9115 | BC001080 | MGC2749 | Hypothetical protein MGC2749 |
| 276 | B2659 | AI025259 | | Transcribed locus |
| 277 | B5443 | NM_014992 | DAAM1 | Dishevelled associated activator of morphogenesis 1 |
| 278 | C4095 | NM_002122 | HLA-DQA1 | Major histocompatibility complex, class II, DQ alpha 1 |
| 279 | A6322 | BU623850 | BZRP | Benzodiazapine receptor (peripheral) |
| 280 | A6358 | AK056079 | JAM2 | Junctional adhesion molecule 2 |
| 281 | A7432 | M32313 | SRD5A1 | Steroid-5-alpha-reductase, alpha polypeptide 1 (3-oxo-5 alpha-steroid delta 4-dehydrogenase alpha 1) |
| 282 | A9103 | AK091635 | FLJ11200 | Hypothetical protein FLJ11200 |
| 283 | B0646 | AA644351 | EMP1 | Epithelial membrane protein 1 |
| 284 | B0773 | AA761873 | SNX16 | Sorting nexin 16 |
| 285 | B4674 | AA149429 | ATP10D | ATPase, Class V, type 10D |
| 286 | B6559 | AB002296 | KIAA0298 | KIAA0298 gene product |
| 287 | A6599 | BC035309 | TM4-B | Tetraspanin TM4-B |
| 288 | A7467 | BC034989 | P2RY14 | Purinergic receptor P2Y, G-protein coupled, 14 |
| 289 | B2658 | N62647 | TM4SF9 | Transmembrane 4 superfamily member 9 |
| 290 | B0243 | AK000140 | PLAC8 | Placenta-specific 8 |
| 291 | B1676 | BC025985 | IGHG4 | Immunoglobulin heavy constant gamma 4 (G4m marker) |
| 292 | B2253 | BX494965 | | Transcribed locus |
| 293 | C4665 | AK022877 | | Clone TUA8 Cri-du-chat region mRNA |
| 294 | A6617 | AF182316 | FER1L3 | Fer-1-like 3, myoferlin (C. elegans) |
| 295 | A7917 | AF169797 | APPL | Adaptor protein containing pH domain, PTB domain and leucine zipper motif 1 |
| 296 | A9104 | AF135168 | NSF | N-ethylmaleimide-sensitive factor |
| 297 | A9110 | BC006282 | MGC10540 | Hypothetical protein MGC10540 |
| 298 | B0340 | AK097973 | MGC9850 | Polymerase (RNA) I polypeptide D, 16 kDa |
| 299 | B0774 | AL832398 | MGC26717 | Hypothetical protein MGC26717 |
| 300 | B5066 | AF318353 | MAN1C1 | Mannosidase, alpha, class 1C, member 1 |
| 301 | B6561 | AB014544 | KIAA0644 | KIAA0644 gene product |
| 302 | A6751 | NM_002258 | KLRB1 | Killer cell lectin-like receptor subfamily B, member 1 |
| 303 | A7091 | N31935 | ANGPTL1 | Angiopoietin-like 1 |
| 304 | A8186 | BM551020 | SCAMP2 | Secretory carrier membrane protein 2 |
| 305 | A8823 | N26005 | PPP1R3C | Protein phosphatase 1, regulatory (inhibitor) subunit 3C |
| 306 | A9125 | BG745799 | CRYL1 | Crystallin, lambda 1 |
| 307 | B1647 | BC047536 | SCEL | Sciellin |

TABLE 1-continued down-regulated genes

| Assignment NO | LMMID | ACCESSION | SYMBOL | GENE NAME |
|---|---|---|---|---|
| 308 | B4810 | BM701072 | KIAA0103 | KIAA0103 |
| 309 | B5424 | NM_020039 | ACCN2 | Amiloride-sensitive cation channel 2, neuronal |
| 310 | B2978 | AA442090 | FLJ10292 | Hypothetical protein FLJ10292 |
| 311 | B7110 | AK124752 | PCDH21 | Protocadherin 21 |
| 312 | B8940 | BX641066 | KLF8 | Kruppel-like factor 8 |
| 313 | B9198 | AK123132 | MSRA | Methionine sulfoxide reductase A |
| 314 | A9475N | AF081195 | RASGRP1 | RAS guanyl releasing protein 1 (calcium and DAG-regulated) |
| 315 | B4930 | AL110157 | DUSP7 | Dual specificity phosphatase 7 |
| 316 | B6765N | AI346913 | SDCBP2 | Syndecan binding protein (syntenin) 2 |
| 317 | B6373 | BX423161 | LHPP | Phospholysine phosphohistidine inorganic pyrophosphate phosphatase |
| 318 | B8264 | NM_025261 | LY6G6C | Lymphocyte antigen 6 complex, locus G6C |
| 319 | B8308 | NM_001001936 | KIAA1914 | KIAA1914 |
| 320 | B8276 | BC009831 | RAB25 | RAB25, member RAS oncogene family |
| 321 | A3308N | NM_000889 | ITGB7 | Integrin, beta 7 |
| 322 | A8588 | BM683764 | PRKWNK4 | Protein kinase, lysine deficient 4 |
| 323 | B4591 | BM747025 | PERP | PERP, TP53 apoptosis effector |
| 324 | B6688 | NM_003042 | SLC6A1 | Solute carrier family 6 (neurotransmitter transporter, GABA), member 1 |
| 325 | B6103 | T89283 | | Clone IMAGE: 110436 mRNA sequence |
| 326 | B7741 | NM_177551 | GPR109A | G protein-coupled receptor 109A |
| 327 | B8954 | NM_032432 | ABLIM2 | Actin binding LIM protein family, member 2 |
| 328 | A0774N | BC012613 | CPA3 | Carboxypeptidase A3 (mast cell) |
| 329 | B1821N | AA886340 | CDH16 | Cadherin 16, KSP-cadherin |
| 330 | B0830N | BM473615 | ID4 | Inhibitor of DNA binding 4, dominant negative helix-loop-helix protein |
| 331 | B4592 | BC051895 | AMMECR1 | Hypothetical protein LOC286505 |
| 332 | B7105 | AK055782 | PDLIM2 | PDZ and LIM domain 2 (mystique) |
| 333 | B7281 | NM_058186 | FAM3B | Family with sequence similarity 3, member B |
| 334 | B8081 | BM981462 | FLJ13710 | Hypothetical protein FLJ13710 |
| 335 | B9611 | AB051541 | KIAA1754 | KIAA1754 |
| 336 | A0720N | L21998 | MUC2 | Mucin 2, intestinal/tracheal |
| 337 | A9346N | AY358379 | PP2135 | PP2135 protein |
| 338 | B3339 | AA728828 | TNNI2 | Troponin I, skeletal, fast |
| 339 | B4613 | H57105 | FLJ20273 | RNA-binding protein |
| 340 | B7353N | NM_176787 | PIGN | Phosphatidylinositol glycan, class N |
| 341 | A0955N | NM_006520 | TCTE1L | T-complex-associated-testis-expressed 1-like |
| 342 | B3349N | AK056590 | FLJ32028 | Hypothetical protein FLJ32028 |
| 343 | B3762 | BC035311 | ZD52F10 | Dermokine |
| 344 | B6524 | BM992839 | MGC39820 | Hypothetical protein MGC39820 |
| 345 | B7323N | AB104887 | APCDD1 | Adenomatosis polyposis coli down-regulated 1 |
| 346 | B9836 | R79561 | ARRDC3 | Arrestin domain containing 3 |
| 347 | A1779N | AF025534 | LILRB5 | Leukocyte immunoglobulin-like receptor, subfamily B (with TM and ITIM domains), member 5 |
| 348 | A6777 | BQ276959 | LGALS2 | Lectin, galactoside-binding, soluble, 2 (galectin 2) |
| 349 | B3330 | AA709236 | | Transcribed locus |
| 350 | B3655 | BC068277 | MGC42367 | Similar to 2010300C02Rik protein |
| 351 | B3929 | AK024356 | SOCS6 | Suppressor of cytokine signaling 6 |
| 352 | B6319 | BX414085 | ICSBP1 | Interferon consensus sequence binding protein 1 |

TABLE 1-continued down-regulated genes

| Assignment NO | LMMID | ACCESSION | SYMBOL | GENE NAME |
|---|---|---|---|---|
| 353 | B7526 | R40594 | CYP2U1 | Cytochrome P450, family 2, subfamily U, polypeptide 1 |
| 354 | B7360 | BU619898 | LTB4DH | Leukotriene B4 12-hydroxydehydrogenase |
| 355 | A0708N | NM_000092 | COL4A4 | Collagen, type IV, alpha 4 |
| 356 | B5126 | BX109845 | SH3BGRL2 | SH3 domain binding glutamic acid-rich protein like 2 |
| 357 | B5917N | BX648213 | PALMD | Palmdelphin |
| 358 | B5381N | D42047 | GPD1L | Glycerol-3-phosphate dehydrogenase 1-like |
| 359 | B6553 | AF506799 | KIBRA | KIBRA protein |
| 360 | A1807N | NM_000860 | HPGD | Hydroxyprostaglandin dehydrogenase 15-(NAD) |
| 361 | A9493N | BX094381 | | |
| 362 | B3930 | XM_290629 | C14orf78 | Chromosome 14 open reading frame 78 |
| 363 | B3965 | BX538289 | ELL2 | Elongation factor, RNA polymerase II, 2 |
| 364 | B9454 | AA033857 | RAB40A | RAB40A, member RAS oncogene family |
| 365 | B9462 | BC030115 | GAB1 | GRB2-associated binding protein 1 |
| 366 | B9652 | N47682 | CPEB4 | Cytoplasmic polyadenylation element binding protein 4 |
| 367 | A6574N | AJ314646 | RAB11FIP4 | RAB11 family interacting protein 4 (class II) |
| 368 | B4922N | AY358399 | LRP10 | Low density lipoprotein receptor-related protein 10 |
| 369 | B7465 | AL161983 | MGC39820 | Hypothetical protein MGC39820 |
| 370 | B8295 | NM_003884 | PCAF | P300/CBP-associated factor |
| 371 | B8485 | CA308403 | WIPI49 | WD40 repeat protein Interacting with phosphoInositides of 49 kDa |
| 372 | B9620 | AL050204 | | Transcribed locus, weakly similar to XP_375099.1 hypothetical protein LOC283585 [*Homo sapiens*] |
| 373 | A3079 | J04599 | BGN | Biglycan |
| 374 | A1981 | U58514 | CHI3L2 | Chitinase 3-like 2 |
| 375 | A6696 | NM_012072 | C1QR1 | Complement component 1, q subcomponent, receptor 1 |
| 376 | B3933 | AY358360 | ELTD1 | EGF, latrophilin and seven transmembrane domain containing 1 |
| 377 | B4392N | BC006428 | CXXC5 | CXXC finger 5 |
| 378 | B7167N | BC059408 | OVOL1 | Ovo-like 1(*Drosophila*) |
| 379 | B9455 | BQ447358 | | Similar to B230208J24Rik protein |
| 380 | B7425 | BC033858 | MGC45474 | Hypothetical protein MGC45474 |
| 381 | B9112 | AI096890 | RRAGD | Ras-related GTP binding D |
| 382 | A2547N | BM017946 | S100A10 | S100 calcium binding protein A10 (annexin II ligand, calpactin I, light polypeptide (p11)) |
| 383 | A4385N | BC039031 | IL1R2 | Interleukin 1 receptor, type II |
| 384 | B3586 | AA748009 | PPP2R5E | Protein phosphatase 2, regulatory subunit B (B56), epsilon isoform |
| 385 | B4083 | NM_003156 | STIM1 | Stromal interaction molecule 1 |
| 386 | A7666N | CA426441 | BZRP | Benzodiazapine receptor (peripheral) |
| 387 | B4291 | AK025198 | XIST | X (inactive)-specific transcript |
| 388 | B5776N | AF492675 | HOP | Homeodomain-only protein |
| 389 | B8377 | AA194913 | FLJ38725 | Hypothetical protein FLJ38725 |
| 390 | B7082 | AK055323 | | CDNA clone IMAGE: 5263177, partial cds |
| 391 | B8932 | AK127123 | TOLLIP | Toll interacting protein |
| 392 | B9135 | BC066977 | C1orf40 | Chromosome 1 open reading frame 40 |
| 393 | A0240N | NM_198974 | PTK9 | PTK9 protein tyrosine kinase 9 |
| 394 | B3108 | NM_015669 | PCDHB5 | Protocadherin beta 5 |
| 395 | B6482 | BC025724 | RDH12 | Retinol dehydrogenase 12 (all-trans and 9-cis) |

TABLE 1-continued down-regulated genes

| Assignment NO | LMMID | ACCESSION | SYMBOL | GENE NAME |
|---|---|---|---|---|
| 396 | B9470 | N29574 | RRAGD | Ras-related GTP binding D |
| 397 | A8259N | AA496108 | BNC2 | Basonuclin 2 |
| 398 | A8292N | AB037811 | FLJ11280 | Hypothetical protein FLJ11280 |
| 399 | B3851 | BC018984 | CDKN2B | Cyclin-dependent kinase inhibitor 2B (p15, inhibits CDK4) |
| 400 | B6267 | AB020715 | PCYOX1 | Prenylcysteine oxidase 1 |
| 401 | B6807N | AA921756 | NQO1 | NAD(P)H dehydrogenase, quinone 1 |
| 402 | A2019N | AA442410 | EMP1 | Epithelial membrane protein 1 |
| 403 | A8869N | BU737722 | HMGCR | 3-hydroxy-3-methylglutaryl-Coenzyme A reductase |
| 404 | B4042 | AW966019 | APG-1 | Heat shock protein (hsp110 family) |
| 405 | B8379 | XM_113763 | C14orf125 | Chromosome 14 open reading frame 125 |
| 406 | A2081N | BC012609 | SERPINB2 | Serine (or cysteine) proteinase inhibitor, clade B (ovalbumin), member 2 |
| 407 | B5059N | T88953 | | Transcribed locus |
| 408 | B6498 | CR613330 | PYM | PYM protein |
| 409 | B5992 | NM_003045 | SLC7A1 | Solute carrier family 7 (cationic amino acid transporter, y+ system), member 1 |
| 410 | B8234 | AF070632 | | Clone 24405 mRNA sequence |
| 411 | A4375N | NM_003617 | RGS5 | Regulator of G-protein signalling 5 |
| 412 | B5419 | AF287272 | KLF5 | Kruppel-like factor 5 (intestinal) |
| 413 | B6656 | BU624522 | | Transcribed locus |
| 414 | B7367 | CR616479 | AMACR | Alpha-methylacyl-CoA racemase |
| 415 | B7435 | AK093246 | RPL13 | Ribosomal protein L13 |
| 416 | B8627 | R39044 | RAB27B | RAB27B, member RAS oncogene family |
| 417 | B8909 | BM786734 | | CDNA: FLJ21274 fis, clone COL01781 |
| 418 | B6405 | AA045332 | ME1 | Malic enzyme 1, NADP(+)-dependent, cytosolic |
| 419 | B7221N | AW952452 | KNS2 | Kinesin 2 60/70 kDa |
| 420 | B8404 | AF173389 | EEA1 | Early endosome antigen 1, 162 kD |
| 421 | A4381N | U81523 | EBAF | Endometrial bleeding associated factor (left-right determination, factor A; transforming growth factor beta superfamily) |
| 422 | B3417 | AA719160 | | Transcribed locus |
| 423 | B3725 | AL832397 | C10orf57 | Chromosome 10 open reading frame 57 |
| 424 | B4062 | X14640 | KRT13 | Keratin 13 |
| 425 | B4848N | AY052784 | PRSS2 | Protease, serine, 2 (trypsin 2) |
| 426 | B7193N | BX109986 | | Transcribed locus |
| 427 | B4114 | NM_012137 | DDAH1 | Dimethylarginine dimethylaminohydrolase 1 |
| 428 | B4330 | AB020637 | KIAA0830 | KIAA0830 protein |
| 429 | B6510 | BX648949 | C9orf45 | Chromosome 9 open reading frame 45 |
| 430 | C0800 | AI037967 | TWIST2 | Twist homolog 2 (*Drosophila*) |
| 431 | C8469 | CR597039 | TIAM1 | T-cell lymphoma invasion and metastasis 1 |
| 432 | C4440 | AA807607 | PITPNC1 | Phosphatidylinositol transfer protein, cytoplasmic 1 |
| 433 | C6675 | AY358677 | FAM3D | Family with sequence similarity 3, member D |
| 434 | C8953 | AL136678 | DEPDC6 | DEP domain containing 6 |
| 435 | C6100 | BC071614 | DKFZp762A217 | Hypothetical protein DKFZp762A217 |
| 436 | C7625 | BU684240 | EHF | Ets homologous factor |
| 437 | C7512 | NM_000186 | CFH | Complement factor H |
| 438 | C9271 | AV728846 | RG9MTD3 | RNA (guanine-9-) methyltransferase domain containing 3 |
| 439 | C3769 | AK023223 | RAB10 | RAB10, member RAS oncogene family |

TABLE 1-continued down-regulated genes

| Assignment NO | LMMID | ACCESSION | SYMBOL | GENE NAME |
|---|---|---|---|---|
| 440 | C6082 | AB041036 | KLK11 | Kallikrein 11 |
| 441 | C7013 | AA058314 | LGALS3 | Lectin, galactoside-binding, soluble, 3 (galectin 3) |
| 442 | C7133 | NM_139205 | HDAC5 | Histone deacetylase 5 |
| 443 | C7172 | AF377960 | CTTNBP2 | Cortactin binding protein 2 |
| 444 | C8462 | NM_000104 | CYP1B1 | Cytochrome P450, family 1, subfamily B, polypeptide 1 |
| 445 | C8844 | BM916826 | C20orf104 | Chromosome 20 open reading frame 104 |
| 446 | C4549 | N64370 | TMOD2 | Tropomodulin 2 (neuronal) |
| 447 | C7157 | NM_017654 | SAMD9 | Sterile alpha motif domain containing 9 |
| 448 | C8471 | NM_006315 | RNF3 | Ring finger protein 3 |
| 449 | C1018 | BU615310 | | CDNA: FLJ22256 fis, clone HRC02860 |
| 450 | C6068 | AL831998 | ITGB6 | Integrin, beta 6 |
| 451 | C4936 | BX648303 | SLC9A3R1 | Solute carrier family 9 (sodium/hydrogen exchanger), isoform 3 regulator 1 |
| 452 | C8058 | BM701368 | UNQ1912 | HGS_RE408 |
| 453 | C9354 | NM_005555 | KRT6B | Keratin 6B |
| 454 | C1520 | BC014640 | COL14A1 | Collagen, type XIV, alpha 1 (undulin) |
| 455 | D1161 | BX537988 | ST7L | Suppression of tumorigenicity 7 like |
| 456 | C3647 | NM_006888 | CALM1 | Calmodulin 1 (phosphorylase kinase, delta) |
| 457 | C3690 | BC000140 | PCCA | Propionyl Coenzyme A carboxylase, alpha polypeptide |
| 458 | C6110 | W67193 | GFPT1 | Glutamine-fructose-6-phosphate transaminase 1 |
| 459 | C6130 | W68668 | | Transcribed locus |
| 460 | C6808 | AA040053 | ZDHHC21 | Zinc finger, DHHC domain containing 21 |
| 461 | C1466 | H03229 | GAB1 | GRB2-associated binding protein 1 |
| 462 | C6664 | AI142832 | MGC34923 | Hypothetical protein MGC34923 |
| 463 | C7461 | CR609766 | SNX24 | Sorting nexing 24 |
| 464 | C7847 | BM696919 | CRYAB | Crystallin, alpha B |
| 465 | C8786 | AA215586 | LOC389119 | Similar to RIKEN cDNA 6530418L21 |
| 466 | C8060 | AW293412 | HDAC11 | Histone deacetylase 11 |
| 467 | C7882 | NM_013261 | PPARGC1A | Peroxisome proliferative activated receptor, gamma, coactivator 1, alpha |
| 468 | C8848 | AF214736 | EHD3 | EH-domain containing 3 |
| 469 | C9764 | AY358433 | UNQ473 | DMC |
| 470 | C2154 | AF007144 | DIO2 | Deiodinase, iodothyronine, type II |
| 471 | C1030 | R87741 | | Transcribed locus |
| 472 | C4886 | AI336346 | | Transcribed locus |
| 473 | C6915 | AW016811 | | CDNA: FLJ22648 fis, clone HSI07329 |
| 474 | C7731 | AF245505 | DKFZp564I1922 | Adlican |
| 475 | C2086 | W61361 | SERPINB8 | Serine (or cysteine) proteinase inhibitor, clade B (ovalbumin), member 8 |
| 476 | C6882 | AF186022 | DAPP1 | Dual adaptor of phosphotyrosine and 3-phosphoinositides |
| 477 | C8161 | AI359788 | CEBPA | CCAAT/enhancer binding protein (C/EBP), alpha |
| 478 | C9877 | BQ001493 | EHD3 | EH-domain containing 3 |
| 479 | C0909 | U38276 | SEMA3F | Sema domain, immunoglobulin domain (Ig), short basic domain, secreted, (semaphorin) 3F |
| 480 | C4328 | AK023966 | | CDNA FLJ13904 fis, clone THYRO1001895 |
| 481 | C6559 | AW272352 | | Transcribed locus |
| 482 | C6871 | BC028377 | ZNF502 | Zinc finger protein 502 |
| 483 | C7403 | XM_166203 | CHASM | Likely ortholog of mouse calponin homology-associated smooth muscle protein |

TABLE 1-continued down-regulated genes

| Assignment NO | LMMID | ACCESSION | SYMBOL | GENE NAME |
|---|---|---|---|---|
| 484 | C8321 | CA435349 | ABLIM1 | Actin binding LIM protein 1 |
| 485 | C8174 | NM_016374 | ARID4B | AT rich interactive domain 4B (RBP1-like) |
| 486 | C8380 | AK026659 | | CDNA: FLJ23006 fis, clone LNG00414 |
| 487 | C9008 | D82786 | TA-PP2C | T-cell activation protein phosphatase 2C |
| 488 | C0716 | AI097310 | | Transcribed locus |
| 489 | C7721 | NM_000361 | THBD | Thrombomodulin |
| 490 | C9243 | AF218020 | DBNL | Drebrin-like |
| 491 | C0922 | AF378757 | PLXDC2 | Plexin domain containing 2 |
| 492 | C6572 | NM_005197 | CHES1 | Checkpoint suppressor 1 |
| 493 | C8146 | BF697545 | MGP | Matrix Gla protein |
| 494 | C4182 | BU681491 | | Transcribed locus |
| 495 | C7601 | AK129509 | GJB5 | Gap junction protein, beta 5 (connexin 31.1) |
| 496 | B9861 | AL137346 | | MRNA full length insert cDNA clone EUROIMAGE 1509279 |
| 497 | C4331 | CR749576 | FLJ37099 | FLJ37099 protein |
| 498 | C7353 | AK122903 | EPS8L2 | EPS8-like 2 |
| 499 | D1274 | BF435815 | | MRNA; cDNA DKFZp564O0862 (from clone DKFZp564O0862) |
| 500 | C7231 | XM_036115 | ZC3HDC5 | Zinc finger CCCH type domain containing 5 |
| 501 | D1135 | BX100753 | COBL | Cordon-bleu homolog (mouse) |
| 502 | D1258 | BC064848 | GAB1 | GRB2-associated binding protein 1 |
| 503 | C0357 | BC035779 | SLC9A9 | Solute carrier family 9 (sodium/hydrogen exchanger), isoform 9 |
| 504 | C1422 | AA095034 | GK001 | GK001 protein |
| 505 | C4970 | K03000 | ALDH1A1 | Aldehyde dehydrogenase 1 family, member A1 |
| 506 | C8182 | NM_024761 | MOBKL2B | MOB1, Mps One Binder kinase activator-like 2B (yeast) |
| 507 | C8897 | AA422013 | KRT24 | Keratin 24 |
| 508 | C0568 | BX648828 | ROBO2 | Roundabout, axon guidance receptor, homolog 2 (Drosophila) |
| 509 | C0903 | X80197 | KRTHB1 | Keratin, hair, basic, 1 |
| 510 | C4194 | XM_291315 | KIAA1815 | KIAA1815 |
| 511 | C4545 | N64339 | GJB6 | Gap junction protein, beta 6 (connexin 30) |
| 512 | C6719 | BC013892 | PVRL4 | Poliovirus receptor-related 4 |
| 513 | C8167 | BC008201 | C19orf32 | Chromosome 19 open reading frame 32 |
| 514 | C8880 | AA224978 | CAB39L | Calcium binding protein 39-like |
| 515 | D0410 | BX116168 | | Transcribed locus |
| 516 | C0358 | AA037425 | OGFRL1 | Opioid growth factor receptor-like 1 |
| 517 | C0578 | AA844234 | | Similar to RIKEN cDNA F730108M23 gene |
| 518 | C0706 | BX647199 | OIP106 | OGT(O-Glc-NAc transferase)-interacting protein 106 KDa |
| 519 | C2245 | AI346181 | MAX | MAX protein |
| 520 | C4281 | XM_087672 | KIAA1935 | KIAA1935 protein |
| 521 | C4981 | AK074480 | ANXA1 | Annexin A1 |
| 522 | C8388 | N92299 | AZI2 | 5-azacytidine induced 2 |
| 523 | C7956 | AK001763 | FLJ10901 | Hypothetical protein FLJ10901 |
| 524 | C8152 | D87463 | PHYHIP | Phytanoyl-CoA hydroxylase interacting protein |
| 525 | C9054 | AW629018 | | |
| 526 | C8580 | CR611223 | CLDN7 | Claudin 7 |
| 527 | D0385 | AK125106 | SYTL5 | Synaptotagmin-like 5 |
| 528 | D1418 | BC014006 | PGLS | 6-phosphogluconolactonase |
| 529 | C8023 | M81141 | HLA-DQB1 | Major histocompatibility complex, class II, DQ beta 1 |
| 530 | D2960 | NM_033281 | MRPS36 | Mitochondrial ribosomal protein S36 |
| 531 | D3738 | AA854756 | ZYX | Zyxin |
| 532 | D3747 | AA843607 | LOC120376 | Hypothetical protein LOC120376 |

TABLE 1-continued down-regulated genes

| Assignment NO | LMMID | ACCESSION | SYMBOL | GENE NAME |
|---|---|---|---|---|
| 533 | E0702 | BE045592 | SLC7A1 | Solute carrier family 7 (cationic amino acid transporter, y+ system), member 1 |
| 534 | D6549 | BC004888 | FLJ10052 | Hypothetical protein FLJ10052 |
| 535 | D7675 | AK127140 | RAB7B | RAB7B, member RAS oncogene family |
| 536 | E0203 | BC081542 | MAF | V-maf musculoaponeurotic fibrosarcoma oncogene homolog (avian) |
| 537 | E1379 | AK123877 | ALDH3A2 | Aldehyde dehydrogenase 3 family, member A2 |
| 538 | D3758 | H28090 | CYYR1 | Cysteine and tyrosine-rich 1 |
| 539 | D9508 | AA928325 | FLJ25124 | Hypothetical protein FLJ25124 |
| 540 | D3013 | AK096741 | SARG | Specifically androgen-regulated protein |
| 541 | E0942 | NM_173060 | CAST | Calpastatin |
| 542 | E0921 | AF309033 | TNKS2 | Tankyrase, TRF1-interacting ankyrin-related ADP-ribose polymerase 2 |
| 543 | D3229 | BC054488 | RICS | Rho GTPase-activating protein |
| 544 | D5318 | NM_004185 | WNT2B | Wingless-type MMTV integration site family, member 2B |
| 545 | D5082 | XM_374137 | | Hypothetical LOC389328 |
| 546 | E0523 | BC017483 | AHNAK | AHNAK nucleoprotein (desmoyokin) |
| 547 | E1815 | XM_041162 | NDFIP2 | Nedd4 family interacting protein 2 |
| 548 | E0542 | NM_152243 | CDC42EP1 | CDC42 effector protein (Rho GTPase binding) 1 |
| 549 | E0387 | AI242329 | ANKRD22 | Ankyrin repeat domain 22 |
| 550 | E0785 | BC039269 | NALP2 | NACHT, leucine rich repeat and PYD containing 2 |
| 551 | D3359 | AJ272268 | CACNA2D3 | Calcium channel, voltage-dependent, alpha 2/delta 3 subunit |
| 552 | D4215 | AB096175 | SP5 | Sp5 transcription factor |
| 553 | D4784 | AK026652 | PADI1 | Peptidyl arginine deiminase, type I |
| 554 | D5720 | AA970157 | FLJ10052 | Hypothetical protein FLJ10052 |
| 555 | D9210 | CA844321 | MGC3196 | Hypothetical protein MGC3196 |
| 556 | D8412 | BC071956 | ZBED2 | Zinc finger, BED domain containing 2 |
| 557 | E0009 | AA947873 | | |
| 558 | D5189 | BX101094 | FLJ21128 | Hypothetical protein FLJ21128 |
| 559 | D7736 | AI022908 | | Transcribed locus |
| 560 | D3893 | AK074037 | CAPN3 | Calpain 3, (p94) |
| 561 | D3442 | NM_145800 | 6-Sep | Septin 6 |
| 562 | D5553 | AA031882 | | Transcribed locus |
| 563 | D3309 | AA768426 | EVA1 | Epithelial V-like antigen 1 |
| 564 | D4861 | AA913741 | | Transcribed locus |
| 565 | D5799 | CA450336 | | Transcribed locus |
| 566 | D9407 | CR749484 | LOC152519 | Hypothetical protein LOC152519 |
| 567 | E0630 | CR591347 | KRT13 | Keratin 13 |
| 568 | D4231 | C05897 | ARL5 | ADP-ribosylation factor-like 5 |
| 569 | E0476 | AF000984 | DDX3Y | DEAD (Asp-Glu-Ala-Asp) box polypeptide 3, Y-linked |
| 570 | E0606 | AU159959 | ATP5A1 | ATP synthase, H+ transporting, mitochondrial F1 complex, alpha subunit, isoform 1, cardiac muscle |
| 571 | E0733 | NM_004684 | SPARCL1 | SPARC-like 1 (mast9, hevin) |
| 572 | E1304 | | | |
| 573 | D6657 | AA554045 | GALNT12 | UDP-N-acetyl-alpha-D-galactosamine:polypeptide N-acetylgalactosaminyltransferase 12 (GalNAc-T12) |
| 574 | D8524 | BX537500 | PDCD4 | Programmed cell death 4 (neoplastic transformation inhibitor) |
| 575 | D1811 | AK128814 | | CDNA FLJ25106 fis, clone CBR01467 |
| 576 | D4059 | BF512606 | | Transcribed locus |

TABLE 1-continued down-regulated genes

| Assignment NO | LMMID | ACCESSION | SYMBOL | GENE NAME |
|---|---|---|---|---|
| 577 | D4493 | BC040438 | MGC48915 | Hypothetical protein MGC48915 |
| 578 | D7516 | AI074524 | DKFZp434H2111 | Hypothetical protein DKFZp434H2111 |
| 579 | D4241 | CD356848 | SERPINB1 | Serine (or cysteine) proteinase inhibitor, clade B (ovalbumin), member 1 |
| 580 | D5210 | AA937197 | | Transcribed locus |
| 581 | D5265 | NM_015976 | SNX7 | Sorting nexin 7 |
| 582 | D8527 | CR613409 | CA2 | Carbonic anhydrase II |
| 583 | D8911 | NM_014912 | CPEB3 | Cytoplasmic polyadenylation element binding protein 3 |
| 584 | E1348 | BX640908 | EVI1 | Ecotropic viral integration site 1 |
| 585 | D3664 | BM726206 | | Hypothetical LOC387723 |
| 586 | D8494 | CR599578 | ACAA2 | Acetyl-Coenzyme A acyltransferase 2 (mitochondrial 3-oxoacyl-Coenzyme A thiolase) |
| 587 | E1775 | NM_002773 | PRSS8 | Protease, serine, 8 (prostasin) |
| 588 | D1767 | BC014357 | CCND2 | Cyclin D2 |
| 589 | D3483 | AI261804 | TRERF1 | Transcriptional regulating factor 1 |
| 590 | E0274 | AI094825 | | Transcribed locus |
| 591 | D4235 | BC068512 | FLJ20323 | Hypothetical protein FLJ20323 |
| 592 | D4858 | AA913711 | T2BP | TRAF2 binding protein |
| 593 | D9098 | BM971909 | HOXA3 | Homeo box A3 |
| 594 | D9339 | AI033474 | SNTB1 | Syntrophin, beta 1 (dystrophin-associated protein A1, 59 kDa, basic component 1) |
| 595 | D9939 | CA313473 | | Transcribed locus |
| 596 | A3096 | CR601701 | ANXA3 | Annexin A3 |
| 597 | F0352 | NM_018414 | SIAT7A | Sialyltransferase 7 ((alpha-N-acetylneuraminyl-2,3-beta-galactosyl-1,3)-N-acetyl galactosaminide alpha-2,6-sialyltransferase) A |
| 598 | B2819N | XM_209073 | LOC284207 | Hypothetical protein LOC284207 |
| 599 | F2306 | NM_015278 | SASH1 | SAM and SH3 domain containing 1 |
| 600 | F3391 | NM_005461 | MAFB | V-maf musculoaponeurotic fibrosarcoma oncogene homolog B (avian) |
| 601 | F7019 | AK001590 | C14orf132 | Chromosome 14 open reading frame 132 |
| 602 | F8408 | AJ007590 | RP2 | Retinitis pigmentosa 2 (X-linked recessive) |
| 603 | A3113 | M60445 | HDC | Histidine decarboxylase |
| 604 | B7331 | H45412 | EHD2 | EH-domain containing 2 |
| 605 | F1393 | CR623808 | CPB1 | Carboxypeptidase B1 (tissue) |
| 606 | F1134 | AL833218 | FMO2 | Flavin containing monooxygenase 2 |
| 607 | F2073 | NM_020990 | CKMT1 | Creatine kinase, mitochondrial 1 (ubiquitous) |
| 608 | F6601 | AL360204 | | MRNA full length insert cDNA clone EUROIMAGE 980547 |
| 609 | B6922 | AK075271 | | Transcribed locus, weakly similar to NP_035609.1 serine palmitoyltransferase, long chain base subunit 2 [*Mus musculus*] |
| 610 | F3501 | AK021708 | PDZRN3 | PDZ domain containing RING finger 3 |
| 611 | F8409 | BC041096 | CLCA2 | Chloride channel, calcium activated, family member 2 |
| 612 | A3116 | M38258 | RARG | Retinoic acid receptor, gamma |
| 613 | F3313 | AK025164 | FLJ21511 | Hypothetical protein FLJ21511 |
| 614 | F3839 | AF131754 | SH3BGRL2 | SH3 domain binding glutamic acid-rich protein like 2 |
| 615 | F5488 | AK075247 | GJB6 | Gap junction protein, beta 6 (connexin 30) |
| 616 | A4387N | AB006190 | AQP7 | Aquaporin 7 |
| 617 | F0482 | AK000008 | BHMT2 | Betaine-homocysteine methyltransferase 2 |

TABLE 1-continued down-regulated genes

| Assignment NO | LMMID | ACCESSION | SYMBOL | GENE NAME |
|---|---|---|---|---|
| 618 | F1478 | BC030816 | C9orf13 | Chromosome 9 open reading frame 13 |
| 619 | F5638 | NM_004669 | CLIC3 | Chloride intracellular channel 3 |
| 620 | F5279 | L76566 | HLA-DRB6 | Major histocompatibility complex, class II, DR beta 6 (pseudogene) |
| 621 | F6365 | AL080114 | C10orf72 | Chromosome 10 open reading frame 72 |
| 622 | F7620 | AI090141 | KSR | Kinase suppressor of ras |
| 623 | F8132 | AW975713 | | Hypothetical gene supported by AK125149 |
| 624 | F8153 | BF435861 | | Similar to EVI-5 homolog |
| 625 | F3457 | AB020630 | PPP1R16B | Protein phosphatase 1, regulatory (inhibitor) subunit 16B |
| 626 | F6060 | AK023814 | FLJ41603 | FLJ41603 protein |
| 627 | F6860 | BE464137 | | Similar to Envoplakin (210 kDa paraneoplastic pemphigus antigen) (p210) (210 kDa cornified envelope precursor) |
| 628 | F7748 | AW139719 | | Transcribed locus |
| 629 | B8706 | R52614 | CDK5R1 | Cyclin-dependent kinase 5, regulatory subunit 1 (p35) |
| 630 | G0364 | AF339767 | | Clone IMAGE: 116415, mRNA sequence |
| 631 | C8700 | AK125664 | | CDNA FLJ43676 fis, clone SYNOV4009129 |
| 632 | F0411 | AW898615 | | |
| 633 | C6003 | M20030 | SPRR2B | Small proline-rich protein 2B |
| 634 | D8310 | AA772401 | | |
| 635 | F3398 | AK027031 | ELOVL6 | ELOVL family member 6, elongation of long chain fatty acids (FEN1/Elo2, SUR4/Elo3-like, yeast) |
| 636 | F4079 | M60047 | FGFBP1 | Fibroblast growth factor binding protein 1 |
| 637 | F5885 | AK023050 | | |
| 638 | A0203N | NM_000043 | TNFRSF6 | Tumor necrosis factor receptor superfamily, member 6 |
| 639 | E2113 | BC005248 | EIF1AY | Eukaryotic translation initiation factor 1A, Y-linked |
| 640 | F3641 | AY099469 | SLAC2-B | SLAC2-B |
| 641 | B8192 | R53538 | BCL2L10 | BCL2-like 10 (apoptosis facilitator) |
| 642 | D8475 | AI242023 | | MRNA; cDNA DKFZp564F212 (from clone DKFZp564F212) |
| 643 | F0236 | AK021710 | KIAA1164 | Hypothetical protein KIAA1164 |
| 644 | F3279 | M61854 | CYP2C19 | Cytochrome P450, family 2, subfamily C, polypeptide 19 |
| 645 | F5888 | AK001044 | | Transcribed locus, weakly similar to XP_375099.1 hypothetical protein LOC283585 [Homo sapiens] |
| 646 | F7716 | BE178490 | | Hypothetical gene supported by AK093334; AL833330; BC020871; BC032492 |
| 647 | A0375N | BC057815 | RRAD | Ras-related associated with diabetes |
| 648 | F1451 | NM_000070 | CAPN3 | Calpain 3, (p94) |
| 649 | F7080 | AW973637 | GGTA1 | Glycoprotein, alpha-galactosyltransferase 1 |
| 650 | F7457 | BQ276976 | PIP | Prolactin-induced protein |
| 651 | F7477 | AW868740 | SYNPO2 | Synaptopodin 2 |
| 652 | F8116 | BF593260 | F8A | Coagulation factor VIII-associated (intronic transcript) |
| 653 | F0672 | AB007861 | MGC22014 | Hypothetical protein MGC22014 |
| 654 | A3263N | CR591371 | CSTB | Cystatin B (stefin B) |
| 655 | B3543 | AK092257 | | Similar to Calpain 9 (Digestive tract-specific calpain) (nCL-4) (CG36 protein) |

TABLE 1-continued down-regulated genes

| Assignment NO | LMMID | ACCESSION | SYMBOL | GENE NAME |
|---|---|---|---|---|
| 656 | B4617 | BG259776 | COBLL1 | COBL-like 1 |
| 657 | C6813 | BC025756 | MGC35558 | Hypothetical protein MGC35558 |
| 658 | F0243 | AL359055 | | Full length insert cDNA clone ZD75H06 |
| 659 | F0647 | AK001160 | MANSC1 | MANSC domain containing 1 |
| 660 | F2106 | AK000349 | CDKAL1 | CDK5 regulatory subunit associated protein 1-like 1 |
| 661 | F3287 | X56807 | DSC2 | Desmocollin 2 |
| 662 | A5977N | BX648892 | MLSTD2 | Male sterility domain containing 2 |
| 663 | F0035 | NM_000779 | CYP4B1 | Cytochrome P450, family 4, subfamily B, polypeptide 1 |
| 664 | F0461 | BC033897 | LOC51244 | Hypothetical protein LOC51244 |
| 665 | F0501 | NM_000389 | CDKN1A | Cyclin-dependent kinase inhibitor 1A (p21, Cip1) |
| 666 | F3565 | M61853 | CYP2C18 | Cytochrome P450, family 2, subfamily C, polypeptide 18 |
| 667 | B9118 | AK002158 | IAN4L1 | Immune associated nucleotide 4 like 1 (mouse) |
| 668 | C4829 | AK095022 | BOK | BCL2-related ovarian killer |
| 669 | D8392 | BC040326 | LOC338758 | Hypothetical protein LOC338758 |
| 670 | F0726 | AF217974 | TSRC1 | Thrombospondin repeat containing 1 |
| 671 | F0555 | BC004557 | FLJ22457 | Hypothetical protein FLJ22457 |
| 672 | F2445 | AK022644 | MGC3101 | Hypothetical protein MGC3101 |
| 673 | F3821 | AL117612 | MAL2 | Mal, T-cell differentiation protein 2 |
| 674 | F5702 | AK024358 | MPEG1 | Macrophage expressed gene 1 |
| 675 | F0471 | AK025015 | FLJ13955 | Hypothetical protein FLJ13955 |
| 676 | F1552 | AF163573 | CARKL | Carbohydrate kinase-like |
| 677 | E0382 | AF178930 | CARD15 | Caspase recruitment domain family, member 15 |
| 678 | F3433 | L13972 | SIAT4A | Sialyltransferase 4A (beta-galactoside alpha-2,3-sialyltransferase) |
| 679 | F0915 | M55284 | PRKCH | Protein kinase C, eta |
| 680 | F1655 | AL137343 | NSE1 | NSE1 |
| 681 | F3545 | AB016247 | SC5DL | Sterol-C5-desaturase (ERG3 delta-5-desaturase homolog, fungal)-like |
| 682 | F7934 | AI632692 | | Transcribed locus |
| 683 | A8350 | BG210119 | | Transcribed locus |
| 684 | C6412 | BX090035 | | Transcribed locus |
| 685 | D1066 | AI271468 | LOC146439 | Hypothetical LOC146439 |
| 686 | F4941 | U83115 | AIM1 | Absent in melanoma 1 |
| 687 | F5083 | CR596715 | FLJ11036 | Hypothetical protein FLJ11036 |
| 688 | F5815 | AK022162 | XRCC5 | X-ray repair complementing defective repair in Chinese hamster cells 5 (double-strand-break rejoining; Ku autoantigen, 80 kDa) |
| 689 | F5904 | XM_171054 | KIAA0527 | KIAA0527 protein |
| 690 | F0238 | AK001872 | PDCD1LG2 | Programmed cell death 1 ligand 2 |
| 691 | B1756 | NM_017520 | HSMPP8 | M-phase phosphoprotein, mpp8 |
| 692 | B3485 | AA725671 | | Hypothetical gene supported by BC039682 |
| 693 | G2700 | AK126982 | LHX6 | LIM homeobox 6 |
| 694 | G3894 | BC034423 | | Homo sapiens, clone IMAGE: 4821006, mRNA, partial cds |
| 695 | F1384 | AK024438 | FLJ38705 | Hypothetical protein FLJ38705 |
| 696 | G4040 | NM_176792 | MRPL43 | Mitochondrial ribosomal protein L43 |
| 697 | F0428 | AL442080 | | Transcribed locus, moderately similar to XP_371769.1 hypothetical LOC389321 [*Homo sapiens*] |
| 698 | F6366 | BE646407 | | PP12104 |
| 699 | F3811 | AK025142 | | |
| 700 | F9134 | NM_052931 | SLAMF6 | SLAM family member 6 |
| 701 | G2865 | BM973051 | NEBL | Nebulette |

TABLE 1-continued down-regulated genes

| Assignment NO | LMMID | ACCESSION | SYMBOL | GENE NAME |
|---|---|---|---|---|
| 702 | G0171 | BC014429 | KCNE4 | Potassium voltage-gated channel, Isk-related family, member 4 |
| 703 | G2920 | AK056882 | RASEF | RAS and EF hand domain containing |
| 704 | F1391 | AF131741 | | Hypothetical gene supported by AF131741 |
| 705 | G3995 | AL833666 | | MRNA; cDNA DKFZp667H1521 (from clone DKFZp667H1521) |
| 706 | G4008 | AL832268 | | MRNA; cDNA DKFZp667N1617 (from clone DKFZp667N1617) |
| 707 | F0475 | NM_000149 | FUT3 | Fucosyltransferase 3 (galactoside 3(4)-L-fucosyltransferase, Lewis blood group included) |
| 708 | B2314N | R41489 | DLGAP3 | Discs, large (*Drosophila*) homolog-associated protein 3 |
| 709 | G3565 | AK055411 | | Hypothetical gene supported by AK055411 |
| 710 | G6825 | AK093529 | | CDNA FLJ36210 fis, clone THYMU2000155 |
| 711 | G7829 | BM978663 | SERPINB3 | Serine (or cysteine) proteinase inhibitor, clade B (ovalbumin), member 3 |
| 712 | F0996 | NM_002034 | FUT5 | Fucosyltransferase 5 (alpha (1,3) fucosyltransferase) |
| 713 | F9178 | AF326350 | PRRG3 | Proline rich Gla (G-carboxyglutamic acid) 3 (transmembrane) |
| 714 | G3989 | AK091263 | | Hypothetical gene supported by AK091263 |
| 715 | F0078 | AK172792 | SCNN1A | Sodium channel, nonvoltage-gated 1 alpha |
| 716 | F0216 | NM_003954 | MAP3K14 | Mitogen-activated protein kinase kinase kinase 14 |
| 717 | F0595 | AK024035 | KIAA1160 | KIAA1160 protein |
| 718 | F9938 | XM_373433 | LOC90379 | Hypothetical protein BC002926 |
| 719 | F9254 | AK027740 | FLJ14834 | Hypothetical protein FLJ14834 |
| 720 | G2576 | BX537525 | ZNF185 | Zinc finger protein 185 (LIM domain) |
| 721 | G4004 | AL832797 | | Hypothetical gene supported by AL832797 |
| 722 | G5799 | AA946808 | DEFB1 | Defensin, beta 1 |
| 723 | G3001 | NM_003956 | CH25H | Cholesterol 25-hydroxylase |
| 724 | G3299 | AF193809 | RHCG | Rhesus blood group, C glycoprotein |
| 725 | G3825 | AK096000 | | CDNA FLJ38681 fis, clone KIDNE2000678 |
| 726 | F1071 | AL357535 | MESP1 | Mesoderm posterior 1 |
| 727 | F4167 | AK092850 | SVIL | Supervillin |

TABLE 2 up-regulated genes

| Assignment NO | LMMID | ACCESSION | SYMBOL | GENE NAME |
|---|---|---|---|---|
| 728 | A0816 | NM_004506 | HSF2 | Heat shock transcription factor 2 |
| 729 | A1571 | NM_003940 | USP13 | Ubiquitin specific protease 13 (isopeptidase T-3) |
| 730 | A1604 | X52186 | ITGB4 | Integrin, beta 4 |
| 731 | A1757 | M24486 | P4HA1 | Procollagen-proline, 2-oxoglutarate 4-dioxygenase (proline 4-hydroxylase), alpha polypeptide I |
| 732 | A2480 | NM_004484 | GPC3 | Glypican 3 |
| 733 | A3565 | L10678 | PFN2 | Profilin 2 |
| 734 | A4866 | NM_001631 | ALPI | Alkaline phosphatase, intestinal |
| 735 | A0378 | CR599617 | ADM | Adrenomedullin |

TABLE 2-continued up-regulated genes

| Assignment NO | LMMID | ACCESSION | SYMBOL | GENE NAME |
|---|---|---|---|---|
| 736 | A1054 | M13755 | G1P2 | Interferon, alpha-inducible protein (clone IFI-15K) |
| 737 | A0797 | J04162 | FCGR3A | Fc fragment of IgG, low affinity IIIb, receptor for (CD16) |
| 738 | A1589 | U97188 | IMP-3 | IGF-II mRNA-binding protein 3 |
| 739 | A1764 | NM_002526 | NT5E | 5'-nucleotidase, ecto (CD73) |
| 740 | A2466 | AJ223728 | CDC45L | CDC45 cell division cycle 45-like (*S. cerevisiae*) |
| 741 | A2237 | AB082525 | TGFB1I4 | Transforming growth factor beta 1 induced transcript 4 |
| 742 | A2355 | BC047350 | HSPD1 | Heat shock 60 kDa protein 1 (chaperonin) |
| 743 | A4630 | U89281 | RODH | 3-hydroxysteroid epimerase |
| 744 | A4873 | NM_002362 | MAGEA4 | Melanoma antigen, family A, 4 |
| 745 | A4963 | AB000449 | VRK1 | Vaccinia related kinase 1 |
| 746 | A5215 | H59101 | USP52 | Ubiquitin specific protease 52 |
| 747 | A6100 | BC014274 | STARD7 | START domain containing 7 |
| 748 | A1605 | NM_203401 | STMN1 | Stathmin 1/oncoprotein 18 |
| 749 | A1581 | NM_002318 | LOXL2 | Lysyl oxidase-like 2 |
| 750 | A3058 | NM_202002 | FOXM1 | Forkhead box M1 |
| 751 | A2735 | BC036811 | PTHR2 | Parathyroid hormone receptor 2 |
| 752 | A2978 | X04741 | UCHL1 | Ubiquitin carboxyl-terminal esterase L1 (ubiquitin thiolesterase) |
| 753 | A3981 | AJ000522 | DNAH17 | Dynein, axonemal, heavy polypeptide 17 |
| 754 | A4611 | S79851 | TXNRD1 | Thioredoxin reductase 1 |
| 755 | A4860 | NM_000057 | BLM | Bloom syndrome |
| 756 | A4750 | AL833398 | CTBP2 | C-terminal binding protein 2 |
| 757 | A5634 | XM_031561 | C15orf23 | Chromosome 15 open reading frame 23 |
| 758 | A1463 | BC002601 | NFKBIA | Nuclear factor of kappa light polypeptide gene enhancer in B-cells inhibitor, alpha |
| 759 | A3243 | CR624652 | TTK | TTK protein kinase |
| 760 | A5623 | AF044588 | PRC1 | Protein regulator of cytokinesis 1 |
| 761 | A0084 | BC075838 | LAMB3 | Laminin, beta 3 |
| 762 | A0812 | M16937 | HOXB7 | Homeo box B7 |
| 763 | A0782 | M26481 | TACSTD1 | Tumor-associated calcium signal transducer 1 |
| 764 | A1209 | NM_001071 | TYMS | Thymidylate synthetase |
| 765 | A2254 | NM_006845 | KIF2C | Kinesin family member 2C |
| 766 | A3097 | M65199 | EDN2 | Endothelin 2 |
| 767 | A4862 | NM_175743 | MAGEA2 | Melanoma antigen, family A, 2 |
| 768 | A5211 | R55332 | LRIG1 | Leucine-rich repeats and immunoglobulin-like domains 1 |
| 769 | A0094 | NM_002293 | LAMC1 | Laminin, gamma 1 (formerly LAMB2) |
| 770 | A0372 | BC039299 | STIP1 | Stress-induced-phosphoprotein 1 (Hsp70/Hsp90-organizing protein) |
| 771 | A0277 | NM_001406 | EFNB3 | Ephrin-B3 |
| 772 | A1774 | NM_001679 | ATP1B3 | ATPase, Na+/K+ transporting, beta 3 polypeptide |
| 773 | A2241 | BC015122 | LDHB | Lactate dehydrogenase B |
| 774 | A3587 | NM_003088 | FSCN1 | Fascin homolog 1, actin-bundling protein (Strongylocentrotus purpuratus) |
| 775 | A0947 | NM_006278 | SIAT4C | Sialyltransferase 4C (beta-galactoside alpha-2,3-sialyltransferase) |
| 776 | A1618 | X70683 | SOX4 | SRY (sex determining region Y)-box 4 |
| 777 | A4193 | BU737730 | RBP1 | Retinol binding protein 1, cellular |
| 778 | A4619 | U73727 | PTPRU | Protein tyrosine phosphatase, receptor type, U |
| 779 | A4959 | AF042282 | EXO1 | Exonuclease 1 |
| 780 | A0246 | U07620 | MAPK10 | Mitogen-activated protein kinase 10 |
| 781 | A0384 | NM_000582 | SPP1 | Secreted phosphoprotein 1 (osteopontin, bone sialoprotein I, early T-lymphocyte activation 1) |
| 782 | A0828 | M59911 | ITGA3 | Integrin, alpha 3 (antigen CD49C, alpha 3 subunit of VLA-3 receptor) |
| 783 | A1231 | X83957 | NEB | Nebulin |
| 784 | A2352 | NM_006907 | PYCR1 | Pyrroline-5-carboxylate reductase 1 |
| 785 | A4960 | AF043472 | KCNS3 | Potassium voltage-gated channel, delayed-rectifier, subfamily S, member 3 |
| 786 | A2143 | NM_001219 | CALU | Calumenin |
| 787 | A2490 | BC011674 | PLOD3 | Procollagen-lysine, 2-oxoglutarate 5-dioxygenase 3 |
| 788 | A3984 | AJ001381 | MYO1B | Myosin IB |
| 789 | A4585 | CR591649 | SMS | Spermine synthase |
| 790 | A4962 | S76474 | NTRK2 | Neurotrophic tyrosine kinase, receptor, type 2 |
| 791 | A5207 | CA422300 | MAC30 | Hypothetical protein MAC30 |
| 792 | A1907 | X53586 | ITGA6 | Integrin, alpha 6 |
| 793 | A2149 | U44772 | PPT1 | Palmitoyl-protein thioesterase 1 (ceroid-lipofuscinosis, neuronal 1, infantile) |

TABLE 2-continued up-regulated genes

| Assignment NO | LMMID | ACCESSION | SYMBOL | GENE NAME |
|---|---|---|---|---|
| 794 | A5229 | AA128437 | GNPTAG | N-acetylglucosamine-1-phosphotransferase, gamma subunit |
| 795 | A0905 | X14723 | CLU | Clusterin (complement lysis inhibitor, SP-40,40, sulfated glycoprotein 2, testosterone-repressed prostate message 2, apolipoprotein J) |
| 796 | A2027 | D83018 | NELL2 | NEL-like 2 (chicken) |
| 797 | A2576 | U20582 | LOC81569 | Actin like protein |
| 798 | A3730 | X02761 | FN1 | Fibronectin 1 |
| 799 | A0415 | M77349 | TGFBI | Transforming growth factor, beta-induced, 68 kDa |
| 800 | A0964 | L36818 | INPPL1 | Inositol polyphosphate phosphatase-like 1 |
| 801 | A3351 | NM_005544 | IRS1 | Insulin receptor substrate 1 |
| 802 | A5262 | NM_020182 | TMEPAI | Transmembrane, prostate androgen induced RNA |
| 803 | A5657 | BQ219156 | HSPC150 | HSPC150 protein similar to ubiquitin-conjugating enzyme |
| 804 | A5407 | AB002305 | ARNT2 | Aryl-hydrocarbon receptor nuclear translocator 2 |
| 805 | A0148 | M16038 | LYN | V-yes-1 Yamaguchi sarcoma viral related oncogene homolog |
| 806 | A0289 | U46838 | MCM6 | MCM6 minichromosome maintenance deficient 6 (MIS5 homolog, S. pombe) (S. cerevisiae) |
| 807 | A0692 | X57548 | CDH2 | Cadherin 2, type 1, N-cadherin (neuronal) |
| 808 | A1788 | D10704 | CHKA | Choline kinase alpha |
| 809 | A1687 | U29171 | CSNK1D | Casein kinase 1, delta |
| 810 | A3526 | BQ423966 | RQCD1 | RCD1 required for cell differentiation1 homolog (S. pombe) |
| 811 | A4376 | NM_173075 | APBB2 | Amyloid beta (A4) precursor protein-binding, family B, member 2 (Fe65-like) |
| 812 | A4513 | Z21488 | CNTN1 | Contactin 1 |
| 813 | A4685 | NM_001421 | ELF4 | E74-like factor 4 (ets domain transcription factor) |
| 814 | A2523 | D21238 | GLRX | Glutaredoxin (thioltransferase) |
| 815 | A2555 | AK056446 | HSPCA | Heat shock 90 kDa protein 1, alpha |
| 816 | A0161 | BC000013 | IGFBP3 | Insulin-like growth factor binding protein 3 |
| 817 | A1682 | D87119 | TRIB2 | Tribbles homolog 2 (Drosophila) |
| 818 | A2543 | NM_213674 | TPM2 | Tropomyosin 2 (beta) |
| 819 | A4141 | D84239 | FCGBP | Fc fragment of IgG binding protein |
| 820 | A5679 | BC037430 | | Transcribed locus, moderately similar to XP_375099.1 hypothetical protein LOC283585 [Homo sapiens] |
| 821 | A6307 | AA639599 | SLC12A2 | Solute carrier family 12 (sodium/potassium/chloride transporters), member 2 |
| 822 | A1153 | M61199 | SSFA2 | Sperm specific antigen 2 |
| 823 | A4672 | NM_022173 | TIA1 | TIA1 cytotoxic granule-associated RNA binding protein |
| 824 | A4700 | U51336 | ITPK1 | Inositol 1,3,4-triphosphate 5/6 kinase |
| 825 | A0333 | NM_002466 | MYBL2 | V-myb myeloblastosis viral oncogene homolog (avian)-like 2 |
| 826 | A1783 | AK055379 | MCM7 | MCM7 minichromosome maintenance deficient 7 (S. cerevisiae) |
| 827 | A1824 | NM_002224 | ITPR3 | Inositol 1,4,5-triphosphate receptor, type 3 |
| 828 | A3889 | NM_002226 | JAG2 | Jagged 2 |
| 829 | A5576 | BC008141 | TREX2 | Three prime repair exonuclease 2 |
| 830 | A0018 | NM_198433 | STK6 | Serine/threonine kinase 6 |
| 831 | A4559 | AK055599 | CTSL | Cathepsin L |
| 832 | A5290 | AK126848 | DKFZP564K0822 | Hypothetical protein DKFZp564K0822 |
| 833 | A1510 | NM_004385 | CSPG2 | Chondroitin sulfate proteoglycan 2 (versican) |
| 834 | A2898 | AB030905 | CBX3 | Chromobox homolog 3 (HP1 gamma homolog, Drosophila) |
| 835 | A3156 | L02870 | COL7A1 | Collagen, type VII, alpha 1 (epidermolysis bullosa, dystrophic, dominant and recessive) |
| 836 | A3890 | AF020774 | ALOX12P2 | Arachidonate 12-lipoxygenase pseudogene 2 |
| 837 | A5422 | W91908 | GALNAC4S-6ST | B cell RAG associated protein |
| 838 | A0215 | NM_021874 | CDC25B | Cell division cycle 25B |
| 839 | A1797 | D00244 | PLAU | Plasminogen activator, urokinase |
| 840 | A3298 | M91670 | UBE2S | Ubiquitin-conjugating enzyme E2S |
| 841 | A3555 | K02581 | TK1 | Thymidine kinase 1, soluble |
| 842 | A4954 | AB024402 | ING1 | Inhibitor of growth family, member 1 |
| 843 | A5556 | BC071586 | TIMP2 | Tissue inhibitor of metalloproteinase 2 |
| 844 | A0429 | BM554470 | UBE2C | Ubiquitin-conjugating enzyme E2C |
| 845 | A3015 | NM_201442 | C1S | Complement component 1, s subcomponent |

TABLE 2-continued up-regulated genes

| Assignment NO | LMMID | ACCESSION | SYMBOL | GENE NAME |
|---|---|---|---|---|
| 846 | A1835 | U18018 | ETV4 | Ets variant gene 4 (E1A enhancer binding protein, E1AF) |
| 847 | A2647 | NM_004350 | RUNX3 | Runt-related transcription factor 3 |
| 848 | A6089 | CR749654 | PHLDB2 | Pleckstrin homology-like domain, family B, member 2 |
| 849 | A1956 | NM_004010 | DMD | Dystrophin (muscular dystrophy, Duchenne and Becker types) |
| 850 | A4895 | BC007290 | TSPAN-1 | Tetraspan 1 |
| 851 | A0611 | BC037236 | DUSP6 | Dual specificity phosphatase 6 |
| 852 | A2324 | M16650 | ODC1 | Ornithine decarboxylase 1 |
| 853 | A3181 | NM_002193 | INHBB | Inhibin, beta B (activin AB beta polypeptide) |
| 854 | A6389 | AB005754 | POLS | Polymerase (DNA directed) sigma |
| 855 | A8210 | BM682097 | KIAA0934 | KIAA0934 |
| 856 | A9464 | NM_181746 | LASS2 | LAG1 longevity assurance homolog 2 (*S. cerevisiae*) |
| 857 | B0593 | Z98457 | TNIK | TRAF2 and NCK interacting kinase |
| 858 | B2439 | U04735 | STCH | Stress 70 protein chaperone, microsome-associated, 60 kDa |
| 859 | B8086 | AK027560 | CYP26A1 | Cytochrome P450, family 26, subfamily A, polypeptide 1 |
| 860 | C2112 | AI022193 | A1BG | Alpha-1-B glycoprotein |
| 861 | C0649 | AK095608 | CASBL | Carbonic anhydrase VB-like |
| 862 | A7341 | N68321 | | Transcribed locus |
| 863 | B3449 | AF269150 | SMBP | SM-11044 binding protein |
| 864 | B4367 | BC020553 | PYCR2 | Pyrroline-5-carboxylate reductase family, member 2 |
| 865 | B4849 | NM_005964 | MYH10 | Myosin, heavy polypeptide 10, non-muscle |
| 866 | B6782 | NM_025076 | UXS1 | UDP-glucuronate decarboxylase 1 |
| 867 | A6532 | AY358336 | LOC255743 | Hypothetical protein LOC255743 |
| 868 | A6923 | AA677283 | KIRREL | Kin of IRRE like (*Drosophila*) |
| 869 | A7793 | AI376713 | NEDD4L | Neural precursor cell expressed, developmentally down-regulated 4-like |
| 870 | A9286 | AA453356 | TNRC6 | Trinucleotide repeat containing 6 |
| 871 | A9174 | AB011089 | TRIM2 | Tripartite motif-containing 2 |
| 872 | B2466 | BX537724 | ITPKB | Inositol 1,4,5-trisphosphate 3-kinase B |
| 873 | B4033 | CR624122 | TUSC3 | Tumor suppressor candidate 3 |
| 874 | C4869 | AA621719 | SMC4L1 | SMC4 structural maintenance of chromosomes 4-like 1 (yeast) |
| 875 | A9531 | BM680495 | TOP1MT | Topoisomerase (DNA) I, mitochondrial |
| 876 | A9014 | AK023320 | FTS | Fused toes homolog (mouse) |
| 877 | A9357 | R98981 | ANKRD10 | Ankyrin repeat domain 10 |
| 878 | B0727 | AA631782 | | Transcribed locus |
| 879 | B4084 | NM_000484 | APP | Amyloid beta (A4) precursor protein (protease nexin-II, Alzheimer disease) |
| 880 | B8220 | AF074264 | LRP6 | Low density lipoprotein receptor-related protein 6 |
| 881 | C3692 | AI816254 | USP11 | Ubiquitin specific protease 11 |
| 882 | A6670 | AB018279 | SV2A | Synaptic vesicle glycoprotein 2A |
| 883 | A8106 | AA868635 | | |
| 884 | A8521 | AI253195 | KIAA1126 | KIAA1126 protein |
| 885 | B0604 | AK128046 | | MRNA; cDNA DKFZp686C24246 (from clone DKFZp686C24246) |
| 886 | B4227 | CR625671 | FLJ10439 | Hypothetical protein FLJ10439 |
| 887 | C4982 | BX647555 | SLC20A1 | Solute carrier family 20 (phosphate transporter), member 1 |
| 888 | A6518 | AJ005580 | ADAM23 | A disintegrin and metalloproteinase domain 23 |
| 889 | A6656 | AK096350 | C9orf25 | Chromosome 9 open reading frame 25 |
| 890 | A7144 | X51441 | SAA2 | Serum amyloid A2 |
| 891 | A7856 | AA237013 | HNRPL | Heterogeneous nuclear ribonucleoprotein L |
| 892 | A6681 | AK023594 | SMYD3 | SET and MYND domain containing 3 |
| 893 | A7277 | N34387 | GRK7 | G protein-coupled receptor kinase 7 |
| 894 | A8204 | BX648041 | NEDD9 | Neural precursor cell expressed, developmentally down-regulated 9 |
| 895 | B4078 | AK093049 | SERPINA3 | Serine (or cysteine) proteinase inhibitor, clade A (alpha-1 antiproteinase, antitrypsin), member 3 |
| 896 | A6657 | BX451670 | FLJ30525 | Hypothetical protein FLJ30525 |
| 897 | A6786 | CR594469 | RHOQ | Ras homolog gene family, member Q |
| 898 | A7296 | N47009 | FLJ00012 | Hypothetical protein FLJ00012 |
| 899 | A8544 | NM_014519 | ZNF232 | Zinc finger protein 232 |
| 900 | B0930 | AI671885 | SLC20A1 | Solute carrier family 20 (phosphate transporter), member 1 |
| 901 | B1423 | AA151771 | ATP1B3 | ATPase, Na+/K+ transporting, beta 3 polypeptide |
| 902 | A6387 | NM_016548 | GOLPH2 | Golgi phosphoprotein 2 |

TABLE 2-continued up-regulated genes

| Assignment NO | LMMID | ACCESSION | SYMBOL | GENE NAME |
|---|---|---|---|---|
| 903 | A6508 | R15881 | CHRM3 | Cholinergic receptor, muscarinic 3 |
| 904 | A8883 | AY358553 | DHRS8 | Dehydrogenase/reductase (SDR family) member 8 |
| 905 | A9459 | CR607674 | MESDC1 | Mesoderm development candidate 1 |
| 906 | B0741 | BM991954 | | Transcribed locus |
| 907 | B5994 | T81301 | AFURS1 | ATPase family homolog up-regulated in senescence cells |
| 908 | B6773 | BC077077 | DPYSL3 | Dihydropyrimidinase-like 3 |
| 909 | A6410 | XM_496907 | PEG10 | Paternally expressed 10 |
| 910 | B1742 | BX648888 | SSFA2 | Sperm specific antigen 2 |
| 911 | B2451 | BM994359 | FGFR1 | Fibroblast growth factor receptor 1 (fms-related tyrosine kinase 2, Pfeiffer syndrome) |
| 912 | B4097 | CR596974 | MLP | MARCKS-like protein |
| 913 | A7280 | NM_152740 | HIBADH | 3-hydroxyisobutyrate dehydrogenase |
| 914 | A9825 | AF052120 | FLJ43806 | Hypothetical protein FLJ43806 |
| 915 | A6979 | AI357616 | LOC90133 | Hypothetical protein LOC90133 |
| 916 | A7190 | BX537966 | TFRC | Transferrin receptor (p90, CD71) |
| 917 | B4847 | AA490011 | LTBP1 | Latent transforming growth factor beta binding protein 1 |
| 918 | A7608 | BG354579 | CBX2 | Chromobox homolog 2 (Pc class homolog, *Drosophila*) |
| 919 | A7863 | NM_003388 | CYLN2 | Cytoplasmic linker 2 |
| 920 | A8172 | XM_371891 | KIAA0877 | KIAA0877 protein |
| 921 | A8287 | R87657 | DKFZp762E1312 | Hypothetical protein DKFZp762E1312 |
| 922 | B6662 | AK128043 | OSBPL9 | Oxysterol binding protein-like 9 |
| 923 | A6625 | BX538010 | NRCAM | Neuronal cell adhesion molecule |
| 924 | A6724 | BC033453 | DHX35 | DEAH (Asp-Glu-Ala-His) box polypeptide 35 |
| 925 | B4210 | NM_004444 | EPHB4 | EphB4 |
| 926 | B9283 | NM_015213 | RAB6IP1 | RAB6 interacting protein 1 |
| 927 | A8787 | AF281255 | BCL2L14 | BCL2-like 14 (apoptosis facilitator) |
| 928 | B0811 | AW183154 | KIF14 | Kinesin family member 14 |
| 929 | A6363 | CR621577 | | *Homo sapiens*, clone IMAGE: 5301514, mRNA |
| 930 | A6725 | AK096250 | LHX4 | LIM homeobox 4 |
| 931 | A7710 | AK125609 | CKIP-1 | CK2 interacting protein 1; HQ0024c protein |
| 932 | A8335 | BC028421 | MGC33630 | Hypothetical protein MGC33630 |
| 933 | A7426 | BG617617 | SAA2 | Serum amyloid A2 |
| 934 | A7908 | AA490691 | HOXD11 | Homeo box D11 |
| 935 | A8487 | AA523105 | TRIAD3 | TRIAD3 protein |
| 936 | B0232 | BC060858 | SOCS3 | Suppressor of cytokine signaling 3 |
| 937 | A9723 | BC067131 | RDH10 | Retinol dehydrogenase 10 (all-trans) |
| 938 | B2375 | BQ025233 | BCAS3 | Breast carcinoma amplified sequence 3 |
| 939 | A6585 | R46164 | | |
| 940 | A8648 | X54101 | GNLY | Granulysin |
| 941 | A9371 | AB098597 | FAD104 | FAD104 |
| 942 | B9250 | AB027289 | HERC5 | Hect domain and RLD 5 |
| 943 | A6598 | BM677885 | RASL11B | RAS-like, family 11, member B |
| 944 | A7024 | BU734286 | RBP1 | Retinol binding protein 1, cellular |
| 945 | A6869 | BC011665 | TCF3 | Transcription factor 3 (E2A immunoglobulin enhancer binding factors E12/E47) |
| 946 | A8156 | BQ010373 | HEG | HEG homolog |
| 947 | B3019 | CR627386 | HEXA | Hexosaminidase A (alpha polypeptide) |
| 948 | B4536 | AK091608 | FADS3 | Fatty acid desaturase 3 |
| 949 | B4008 | XM_167709 | C10orf38 | Chromosome 10 open reading frame 38 |
| 950 | C4166 | BQ230791 | TNNI3 | Troponin I, cardiac |
| 951 | A7230 | NM_001845 | COL4A1 | Collagen, type IV, alpha 1 |
| 952 | A9381 | AL117605 | | CDNA: FLJ21418 fis, clone COL04072 |
| 953 | B0338 | AL136942 | LAPTM4B | Lysosomal associated protein transmembrane 4 beta |
| 954 | B1799 | NM_013437 | LRP12 | Low density lipoprotein-related protein 12 |
| 955 | B1677 | CN415212 | | Similar to uroplakin 3B isoform b; uroplakin IIIb |
| 956 | B4220 | AA459632 | SMARCA3 | SWI/SNF related, matrix associated, actin dependent regulator of chromatin, subfamily a, member 3 |
| 957 | B3753 | AK000437 | WDR8 | WD repeat domain 8 |
| 958 | B4692 | AA525966 | DKFZP586L0724 | DKFZP586L0724 protein |
| 959 | B4556 | NM_020531 | C20orf3 | Chromosome 20 open reading frame 3 |
| 960 | B7330N | BM726315 | GALNT6 | UDP-N-acetyl-alpha-D-galactosamine:polypeptide N-acetylgalactosaminyltransferase 6 (GalNAc-T6) |
| 961 | B8953 | R50344 | | Transcribed locus |
| 962 | B9826 | AA055976 | SLIT2 | Slit homolog 2 (*Drosophila*) |
| 963 | A7605 | R15801 | NRN1 | Neuritin 1 |

TABLE 2-continued up-regulated genes

| Assignment NO | LMMID | ACCESSION | SYMBOL | GENE NAME |
|---|---|---|---|---|
| 964 | B4394 | N46424 | RAI14 | Retinoic acid induced 14 |
| 965 | B3827 | N20989 | ANTXR1 | Anthrax toxin receptor 1 |
| 966 | B5904 | BC008947 | C10orf3 | Chromosome 10 open reading frame 3 |
| 967 | B7534 | AI298501 | SDK1 | Sidekick homolog 1 (chicken) |
| 968 | B9633 | XM_085049 | | |
| 969 | A9236N | BX117945 | | Transcribed locus |
| 970 | B5489 | NM_003916 | AP1S2 | Adaptor-related protein complex 1, sigma 2 subunit |
| 971 | B6359 | AA608839 | KIAA1212 | KIAA1212 |
| 972 | B6905 | BU675191 | CGI-72 | CGI-72 protein |
| 973 | B4721N | BE795997 | NCOR2 | Nuclear receptor co-repressor 2 |
| 974 | B6779 | D86961 | LHFPL2 | Lipoma HMGIC fusion partner-like 2 |
| 975 | B7749 | BC023152 | GYG2 | Glycogenin 2 |
| 976 | B7968 | R46597 | LRCH3 | Leucine-rich repeats and calponin homology (CH) domain containing 3 |
| 977 | B9223 | AK023319 | KIAA0643 | KIAA0643 protein |
| 978 | A4739N | AJ306929 | AFURS1 | ATPase family homolog up-regulated in senescence cells |
| 979 | A8317N | BQ013695 | FLJ10420 | Hypothetical protein FLJ10420 |
| 980 | B4161 | BX538214 | C6orf167 | Chromosome 6 open reading frame 167 |
| 981 | B4558N | AK027019 | MGC45731 | Hypothetical protein MGC45731 |
| 982 | B5373N | D86962 | GRB10 | Growth factor receptor-bound protein 10 |
| 983 | B7887 | BU580616 | FLJ10159 | Hypothetical protein FLJ10159 |
| 984 | B9579 | AK055994 | FLJ25084 | Hypothetical protein FLJ25084 |
| 985 | A6448N | AK127801 | FLJ46603 | FLJ46603 protein |
| 986 | A8508N | BX647338 | TM4SF13 | Transmembrane 4 superfamily member 13 |
| 987 | A9518N | AA570186 | | Hypothetical gene supported by AK096951; BC066547 |
| 988 | B8814 | BC007754 | SUV39H2 | Suppressor of variegation 3-9 homolog 2 (*Drosophila*) |
| 989 | A3200N | AK122763 | COL5A1 | Collagen, type V, alpha 1 |
| 990 | A5073 | L09235 | ATP6V1A | ATPase, H+ transporting, lysosomal 70 kDa, V1 subunit A |
| 991 | B5175N | BC038183 | CAMTA1 | Calmodulin binding transcription activator 1 |
| 992 | B8480 | N62352 | KIAA1573 | KIAA1573 protein |
| 993 | B9615 | CA314364 | | MRNA; cDNA DKEZp434L201 (from clone DKFZp434L201) |
| 994 | A8542N | AF542548 | AHSA2 | AHA1, activator of heat shock 90 kDa protein ATPase homolog 2 (yeast) |
| 995 | A9534N | AK000993 | C7orf28B | Chromosome 7 open reading frame 28B |
| 996 | A5065 | BC036661 | CMKOR1 | Chemokine orphan receptor 1 |
| 997 | B3358 | AA731746 | CPSF6 | Cleavage and polyadenylation specific factor 6, 68 kDa |
| 998 | B3958 | AF145713 | SCHIP1 | Schwannomin interacting protein 1 |
| 999 | B4587 | AB096683 | MGC57827 | Similar to RIKEN cDNA 2700049P18 gene |
| 1000 | B4217 | BU608626 | WFDC2 | WAP four-disulfide core domain 2 |
| 1001 | B6125N | T57349 | DRE1 | DRE1 protein |
| 1002 | B6968 | BC016950 | MGC22679 | Hypothetical protein MGC22679 |
| 1003 | B7480 | AF407165 | PPP1R14C | Protein phosphatase 1, regulatory (inhibitor) subunit 14C |
| 1004 | B7554 | CA503163 | ADNP | Activity-dependent neuroprotector |
| 1005 | B8521 | AK001617 | SNCAIP | Synuclein, alpha interacting protein (synphilin) |
| 1006 | B9234 | AK090777 | PGM2L1 | Phosphoglucomutase 2-like 1 |
| 1007 | B3160N | AA778238 | LOC374654 | Similar to kinesin family member 21A; N-5 kinesin |
| 1008 | B4915N | NM_175864 | CBFA2T2 | Core-binding factor, runt domain, alpha subunit 2; translocated to, 2 |
| 1009 | B5382N | AK125194 | MAP1B | Microtubule-associated protein 1B |
| 1010 | B7109 | AA872071 | C11orf23 | Chromosome 11 open reading frame 23 |
| 1011 | B9838 | AA018510 | MGC33382 | Hypothetical protein MGC33382 |
| 1012 | B7484 | CR617865 | ANKRD10 | Ankyrin repeat domain 10 |
| 1013 | B8716 | AY376439 | ECT2 | Epithelial cell transforming sequence 2 oncogene |
| 1014 | A5678N | BC037346 | TMPO | Thymopoietin |
| 1015 | B4818N | NM_033641 | COL4A6 | Collagen, type IV, alpha 6 |
| 1016 | B5451 | CR627457 | 11-Sep | Septin 11 |
| 1017 | B5461 | R56840 | MCM8 | MCM8 minichromosome maintenance deficient 8 (*S. cerevisiae*) |
| 1018 | B7370 | AA001074 | CNNM4 | Cyclin M4 |
| 1019 | B8211 | AF382034 | NY-REN-41 | Hypothetical protein AF301222 |
| 1020 | A9044 | BC003186 | Pfs2 | DNA replication complex GINS protein PSF2 |
| 1021 | B6813 | BX092653 | | Transcribed locus |
| 1022 | A5346N | AA747005 | PRKWNK2 | Protein kinase, lysine deficient 2 |

TABLE 2-continued up-regulated genes

| Assignment NO | LMMID | ACCESSION | SYMBOL | GENE NAME |
|---|---|---|---|---|
| 1023 | A3822 | BC067289 | CTSL2 | Cathepsin L2 |
| 1024 | A0327N | NM_002421 | MMP1 | Matrix metalloproteinase 1 (interstitial collagenase) |
| 1025 | A0584N | NM_003236 | TGFA | Transforming growth factor, alpha |
| 1026 | B8016 | AA528243 | RTN4RL1 | Reticulon 4 receptor-like 1 |
| 1027 | A3538 | J03464 | COL1A2 | Collagen, type I, alpha 2 |
| 1028 | A0061 | AF053306 | BUB1B | BUB1 budding uninhibited by benzimidazoles 1 homolog beta (yeast) |
| 1029 | A9617N | BX109949 | FAM24A | Family with sequence similarity 24, member A |
| 1030 | B4456 | BX537652 | FLJ12892 | Hypothetical protein FLJ12892 |
| 1031 | B9482 | NM_020919 | ALS2 | Amyotrophic lateral sclerosis 2 (juvenile) |
| 1032 | A2065N | AK124656 | ENO2 | Enolase 2 (gamma, neuronal) |
| 1033 | B6283 | AY257469 | CIT | Citron (rho-interacting, serine/threonine kinase 21) |
| 1034 | B2587 | BC038986 | REV3L | REV3-like, catalytic subunit of DNA polymerase zeta (yeast) |
| 1035 | B5279 | BC004107 | FST | Follistatin |
| 1036 | B6262 | NM_001259 | CDK6 | Cyclin-dependent kinase 6 |
| 1037 | B7198N | AA193472 | USP13 | Ubiquitin specific protease 13 (isopeptidase T-3) |
| 1038 | B8547 | BC033746 | PNCK | Pregnancy upregulated non-ubiquitously expressed CaM kinase |
| 1039 | A8900N | AL512760 | FADS1 | Fatty acid desaturase 1 |
| 1040 | B3732 | XM_499250 | LFNG | Lunatic fringe homolog (*Drosophila*) |
| 1041 | B8059 | BC011000 | CDCA5 | Cell division cycle associated 5 |
| 1042 | A2515 | X16396 | MTHFD2 | Methylene tetrahydrofolate dehydrogenase (NAD+ dependent), methenyltetrahydrofolate cyclohydrolase |
| 1043 | B2404N | AF200348 | D2S448 | Melanoma associated gene |
| 1044 | B4250 | CA420794 | LOC339924 | Hypothetical protein LOC339924 |
| 1045 | B8048 | BQ448718 | CDK11 | Cyclin-dependent kinase (CDC2-like) 11 |
| 1046 | B9094 | AF084481 | WFS1 | Wolfram syndrome 1 (wolframin) |
| 1047 | B5081N | AL832416 | C9orf13 | Chromosome 9 open reading frame 13 |
| 1048 | B4812N | NM_004900 | APOBEC3B | Apolipoprotein B mRNA editing enzyme, catalytic polypeptide-like 3B |
| 1049 | B8930 | AA513445 | RBM21 | RNA binding motif protein 21 |
| 1050 | C1730 | BU682808 | GNAS | GNAS complex locus |
| 1051 | C3653 | BC066956 | VIM | Vimentin |
| 1052 | C4599 | AF189011 | RNASE3L | Nuclear RNase III Drosha |
| 1053 | C6048 | AK075509 | NRM | Nurim (nuclear envelope membrane protein) |
| 1054 | C6771 | NM_002610 | PDK1 | Pyruvate dehydrogenase kinase, isoenzyme 1 |
| 1055 | C6425 | W94690 | | Full length insert cDNA clone ZE04G11 |
| 1056 | C7835 | NM_000356 | TCOF1 | Treacher Collins-Franceschetti syndrome 1 |
| 1057 | C8621 | AW195492 | TYRP1 | Tyrosinase-related protein 1 |
| 1058 | C9718 | W94051 | DTNA | Dystrobrevin, alpha |
| 1059 | B9997 | AI184562 | SR140 | U2-associated SR140 protein |
| 1060 | C2050 | BF060678 | C14orf118 | Chromosome 14 open reading frame 118 |
| 1061 | C3797 | BC025729 | CD99L2 | CD99 antigen-like 2 |
| 1062 | C4763 | AB103330 | KIAA1199 | KIAA1199 |
| 1063 | C8947 | AL833303 | | Full length insert cDNA clone YZ04E02 |
| 1064 | C8802 | AA436403 | FZD3 | Frizzled homolog 3 (*Drosophila*) |
| 1065 | D1199 | NM_001426 | EN1 | Engrailed homolog 1 |
| 1066 | D1348 | BC064663 | NLK | Nemo like kinase |
| 1067 | B9974 | AK126766 | LEPREL2 | Leprecan-like 2 |
| 1068 | C8075 | X07290 | ZNF3 | Zinc finger protein 3 (A8-51) |
| 1069 | C8479 | BI768625 | UNC84B | Unc-84 homolog B (*C. elegans*) |
| 1070 | B9998 | H99016 | USP11 | Ubiquitin specific protease 11 |
| 1071 | C0236 | BC021252 | SCMH1 | Sex comb on midleg homolog 1 (*Drosophila*) |
| 1072 | C3636 | XM_056455 | D2S448 | Melanoma associated gene |
| 1073 | C2208 | AL049246 | FLJ10618 | Hypothetical protein FLJ10618 |
| 1074 | C4385 | AB032427 | TRPV4 | Transient receptor potential cation channel, subfamily V, member 4 |
| 1075 | C4622 | N66741 | ABCC1 | ATP-binding cassette, sub-family C (CFTR/MRP), member 1 |
| 1076 | C6454 | BC060820 | ZNF281 | Zinc finger protein 281 |
| 1077 | C8632 | BM682754 | IREB2 | Iron-responsive element binding protein 2 |
| 1078 | C0658 | W60844 | FLJ31340 | Hypothetical protein FLJ31340 |
| 1079 | C0777 | BC047362 | | Transcribed locus, moderately similar to XP_375099.1 hypothetical protein LOC283585 [*Homo sapiens*] |
| 1080 | C2020 | CA420307 | SF3B1 | Splicing factor 3b, subunit 1, 155 kDa |
| 1081 | C1538 | BM683254 | DLG1 | DKFZP586B0319 protein |
| 1082 | C7256 | NM_021963 | NAP1L2 | Nucleosome assembly protein 1-like 2 |
| 1083 | C8051 | BM685415 | C10orf16 | Chromosome 10 open reading frame 116 |

TABLE 2-continued up-regulated genes

| Assignment NO | LMMID | ACCESSION | SYMBOL | GENE NAME |
|---|---|---|---|---|
| 1084 | C8088 | D87465 | SPOCK2 | Sparc/osteonectin, cwcv and kazal-like domains proteoglycan (testican) 2 |
| 1085 | C8624 | NM_005858 | AKAP8 | A kinase (PRKA) anchor protein 8 |
| 1086 | C9490 | N26092 | SNAI2 | Snail homolog 2 (Drosophila) |
| 1087 | C0488 | AA781195 | PRAME | Preferentially expressed antigen in melanoma |
| 1088 | C0186 | CR749813 | SLC39A10 | Solute carrier family 39 (zinc transporter), member 10 |
| 1089 | C4883 | N79601 | | |
| 1090 | C5287 | N91945 | KIAA0746 | KIAA0746 protein |
| 1091 | C7529 | AF311339 | C6orf162 | Chromosome 6 open reading frame 162 |
| 1092 | C9527 | R27734 | | |
| 1093 | C0772 | AF326917 | AUTS2 | Autism susceptibility candidate 2 |
| 1094 | C2021 | AL118812 | UGT8 | UDP glycosyltransferase 8 (UDP-galactose ceramide galactosyltransferase) |
| 1095 | C8611 | NM_017870 | HSPA5BP1 | Heat shock 70 kDa protein 5 (glucose-regulated protein, 78 kDa) binding protein 1 |
| 1096 | C0787 | AL832207 | PLEKHH2 | Pleckstrin homology domain containing, family H (with MyTH4 domain) member 2 |
| 1097 | D0587 | AA872040 | INHBB | Inhibin, beta B (activin AB beta polypeptide) |
| 1098 | C1849 | BC049171 | FJX1 | Four jointed box 1 (Drosophila) |
| 1099 | C0458 | H05777 | | Transcribed locus |
| 1100 | C3803 | NM_004265 | FADS2 | Fatty acid desaturase 2 |
| 1101 | C3648 | AK023450 | ANTXR2 | Anthrax toxin receptor 2 |
| 1102 | C7674 | AA148213 | TAZ | Transcriptional co-activator with PDZ-binding motif (TAZ) |
| 1103 | C9517 | H73947 | POLR2J | Polymerase (RNA) II (DNA directed) polypeptide J, 13.3 kDa |
| 1104 | C6826 | X52203 | LOC91316 | Similar to bK246H3.1 (immunoglobulin lambda-like polypeptide 1, pre-B-cell specific) |
| 1105 | C8487 | T56982 | PDE7A | Phosphodiesterase 7A |
| 1106 | D0748 | H03747 | | CDNA: FLJ21652 fis, clone COL08582 |
| 1107 | C4973 | BC013575 | PLAU | Plasminogen activator, urokinase |
| 1108 | C8121 | BC040492 | SCRN1 | Secernin 1 |
| 1109 | C9016 | AA255900 | STK38L | Serine/threonine kinase 38 like |
| 1110 | C9976 | CA431254 | SH3MD1 | SH3 multiple domains 1 |
| 1111 | C9189 | BC065544 | C14orf106 | Chromosome 14 open reading frame 106 |
| 1112 | C9608 | AI762244 | GSTA2 | Glutathione S-transferase A2 |
| 1113 | D0491 | AA815427 | FLJ43855 | Similar to sodium- and chloride-dependent creatine transporter |
| 1114 | D0058 | BC041882 | ATF7IP2 | Activating transcription factor 7 interacting protein 2 |
| 1115 | B9930 | AK024493 | SLC12A7 | Solute carrier family 12 (potassium/chloride transporters), member 7 |
| 1116 | C8557 | AA536113 | TMEPAI | Transmembrane, prostate androgen induced RNA |
| 1117 | C9858 | NM_006892 | DNMT3B | DNA (cytosine-5-)-methyltransferase 3 beta |
| 1118 | C6209 | AF130988 | EDAR | Ectodysplasin A receptor |
| 1119 | C7607 | AL832674 | ANP32E | Acidic (leucine-rich) nuclear phosphoprotein 32 family, member E |
| 1120 | D0006 | NM_145697 | CDCA1 | Cell division cycle associated 1 |
| 1121 | D0062 | CR593221 | OSR2 | Odd-skipped-related 2A protein |
| 1122 | C0400 | BC021290 | IMP-2 | IGF-II mRNA-binding protein 2 |
| 1123 | C0764 | AA045020 | RDH10 | Retinol dehydrogenase 10 (all-trans) |
| 1124 | C9231 | AB011124 | ProSAPiP1 | ProSAPiP1 protein |
| 1125 | C0318 | M16451 | CKB | Creatine kinase, brain |
| 1126 | C5950 | CF146489 | NKX3-1 | NK3 transcription factor related, locus 1 (Drosophila) |
| 1127 | C5013 | CR602284 | FUS | Fusion (involved in t(12; 16) in malignant liposarcoma) |
| 1128 | C6875 | AA043381 | HOXD10 | Homeo box D10 |
| 1129 | C3905 | AK091130 | LOC152485 | Hypothetical protein LOC152485 |
| 1130 | C7105 | R50993 | | yg63f02.s1 Soares infant brain 1NIB Homo sapiens cDNA clone IMAGE: 37373 3', mRNA sequence. |
| 1131 | C9041 | AJ580093 | ATP11C | ATPase, Class VI, type 11C |
| 1132 | C1093 | AW976357 | CDCA1 | Cell division cycle associated 1 |
| 1133 | C1948 | CR594190 NM_012242 | DKK1 | Dickkopf homolog 1 (Xenopus laevis) |
| 1134 | C5005 | BX648571 | FLJ38736 | Hypothetical protein FLJ38736 |
| 1135 | C8384 | X98834 | SALL2 | Sal-like 2 (Drosophila) |
| 1136 | C1442 | AA807192 | FLJ20522 | Hypothetical protein FLJ20522 |
| 1137 | C7756 | H03641 | FAM13A1 | Family with sequence similarity 13, member A1 |
| 1138 | C8926 | BU569535 | CHODL | Chondrolectin |

TABLE 2-continued up-regulated genes

| Assignment NO | LMMID | ACCESSION | SYMBOL | GENE NAME |
|---|---|---|---|---|
| 1139 | C6880 | AK027224 | DKFZp434B227 | Hypothetical protein DKFZp434B227 |
| 1140 | D0648 | AA416843 | MGC42105 | Hypothetical protein MGC42105 |
| 1141 | C6217 | NM_001448 | GPC4 | Glypican 4 |
| 1142 | C6906 | AK122672 | RAI3 | Retinoic acid induced 3 |
| 1143 | C9046 | BC034999 | MGC33211 | Similar to RIKEN cDNA 4933439B08 gene |
| 1144 | D3549 | BU620736 | MAGI-3 | Membrane-associated guanylate kinase-related (MAGI-3) |
| 1145 | D6450 | BQ001345 | GTF2IRD2B | GTF2I repeat domain containing 2 |
| 1146 | E0002 | BF195994 | PIAS2 | Protein inhibitor of activated STAT, 2 |
| 1147 | E0537 | BX647115 | DPYSL2 | Dihydropyrimidinase-like 2 |
| 1148 | D4376 | AA883952 | | Transcribed locus |
| 1149 | D7468 | BC010943 | OSMR | Oncostatin M receptor |
| 1150 | E0838 | BC030133 | SDC2 | Syndecan 2 (heparan sulfate proteoglycan 1, cell surface-associated, fibroglycan) |
| 1151 | E1278 | BF353850 | ATP11B | ATPase, Class VI, type 11B |
| 1152 | D9484 | NM_021809 | TGIF2 | TGFB-induced factor 2 (TALE family homeobox) |
| 1153 | E1173 | CB250397 | P4HA1 | Procollagen-proline, 2-oxoglutarate 4-dioxygenase (proline 4-hydroxylase), alpha polypeptide I |
| 1154 | E1497 | BU625507 | SLC16A3 | Solute carrier family 16 (monocarboxylic acid transporters), member 3 |
| 1155 | D6136 | AF448439 | CLIC6 | Chloride intracellular channel 6 |
| 1156 | D6767 | BM312795 | | Transcribed locus |
| 1157 | D8920 | AI038231 | USP13 | Ubiquitin specific protease 13 (isopeptidase T-3) |
| 1158 | D8587 | AI223250 | | Transcribed locus |
| 1159 | E1387 | D87448 | TOPBP1 | Topoisomerase (DNA) II binding protein 1 |
| 1160 | D3218 | AL122043 | C20orf112 | Chromosome 20 open reading frame 112 |
| 1161 | D9500 | AI361654 | | |
| 1162 | D8150 | BF965334 | PRKRA | Protein kinase, interferon-inducible double stranded RNA dependent activator |
| 1163 | D9437 | W67209 | SESN3 | Sestrin 3 |
| 1164 | E0167 | AI090289 | DRE1 | DRE1 protein |
| 1165 | E0694 | BX641036 | CSPG2 | Chondroitin sulfate proteoglycan 2 (versican) |
| 1166 | D5491 | AA947258 | | Transcribed locus |
| 1167 | D6311 | BI771102 | PHYHIPL | Family with sequence similarity 13, member C1 |
| 1168 | E0663 | CR600961 | TM4SF13 | Transmembrane 4 superfamily member 13 |
| 1169 | E0556 | BM997546 | ECE1 | Endothelin converting enzyme 1 |
| 1170 | E0686 | BC036067 | FLJ14146 | Hypothetical protein FLJ14146 |
| 1171 | E0787 | BM697477 | ShrmL | Shroom-related protein |
| 1172 | D4351 | BX102008 | MECP2 | Methyl CpG binding protein 2 (Rett syndrome) |
| 1173 | D9504 | BC010918 | NTS | Neurotensin |
| 1174 | E0664 | AY299090 | SPRED2 | Sprouty-related, EVH1 domain containing 2 |
| 1175 | E0552 | AL832438 | FLJ20152 | Hypothetical protein FLJ20152 |
| 1176 | D6314 | NM_018243 | 11-Sep | Septin 11 |
| 1177 | D8837 | NM_012189 | CABYR | Calcium-binding tyrosine-(Y)-phosphorylation regulated (fibrousheathin 2) |
| 1178 | E0837 | AB040875 | SLC7A11 | Solute carrier family 7, (cationic amino acid transporter, y+ system) member 11 |
| 1179 | D8001 | AW976634 | | Transcribed locus |
| 1180 | D9027 | CN480522 | WTIP | WT1-interacting protein |
| 1181 | E0451 | BC005963 | MAGEA3 | Melanoma antigen, family A, 3 |
| 1182 | E0139 | AL390147 | FAM20C | Family with sequence similarity 20, member C |
| 1183 | E1423 | NM_152624 | DCP2 | Decapping enzyme hDcp2 |
| 1184 | D8457 | AA830551 | FLJ13848 | Hypothetical protein FLJ13848 |
| 1185 | D9933 | BX648297 | LPP | LIM domain containing preferred translocation partner in lipoma |
| 1186 | D6668 | AA744607 | MFHAS1 | Malignant fibrous histiocytoma amplified sequence 1 |
| 1187 | D4093 | CK299098 | | Hypothetical gene supported by BC044741 |
| 1188 | D8458 | AA830668 | | |
| 1189 | D9544 | H05758 | | Transcribed locus |
| 1190 | E0598 | NM_005504 | BCAT1 | Branched chain aminotransferase 1, cytosolic |
| 1191 | E1001 | NM_018212 | ENAH | Enabled homolog (*Drosophila*) |
| 1192 | D6398 | AI792205 | | Transcribed locus |
| 1193 | E0455 | CR614398 | ODC1 | Ornithine decarboxylase 1 |
| 1194 | D8515 | CR591759 | LUM | Lumican |
| 1195 | D5583 | AK125904 | DDHD2 | DDHD domain containing 2 |
| 1196 | D5596 | BM991753 | | CDNA clone IMAGE: 4862812, partial cds |
| 1197 | E0133 | AW451133 | FLJ10719 | Hypothetical protein FLJ10719 |
| 1198 | D8466 | AI619500 | | Transcribed locus |

TABLE 2-continued up-regulated genes

| Assignment NO | LMMID | ACCESSION | SYMBOL | GENE NAME |
|---|---|---|---|---|
| 1199 | D8905 | AI021894 | MAP4K3 | Mitogen-activated protein kinase kinase kinase kinase 3 |
| 1200 | B0869N | AF274048 | UHRF1 | Ubiquitin-like, containing PHD and RING finger domains, 1 |
| 1201 | F1457 | M16006 | SERPINE1 | Serine (or cysteine) proteinase inhibitor, clade E (nexin, plasminogen activator inhibitor type 1), member 1 |
| 1202 | F5449 | AK026753 | | |
| 1203 | F8140 | AW976457 | MBNL1 | Muscleblind-like (*Drosophila*) |
| 1204 | F9101 | BC010527 | | CDNA FLJ31059 fis, clone HSYRA2000832 |
| 1205 | F8575 | BF433322 | ELK4 | ELK4, ETS-domain protein (SRF accessory protein 1) |
| 1206 | A7714 | AB002351 | DMN | Desmuslin |
| 1207 | B4412N | BC016815 | DCBLD2 | Discoidin, CUB and LCCL domain containing 2 |
| 1208 | E1732 | NM_014916 | LMTK2 | Lemur tyrosine kinase 2 |
| 1209 | E1395 | AU1473221 | EDD | E3 identified by differential display |
| 1210 | F2724 | AK024275 | FLJ14213 | Hypothetical protein FLJ14213 |
| 1211 | F3387 | AK126185 | PPFIA4 | Protein tyrosine phosphatase, receptor type, f polypeptide (PTPRF), interacting protein (liprin), alpha 4 |
| 1212 | F5148 | AL831813 | RUNDC1 | RUN domain containing 1 |
| 1213 | F3888 | U22816 | PPFIA1 | Protein tyrosine phosphatase, receptor type, f polypeptide (PTPRF), interacting protein (liprin), alpha 1 |
| 1214 | F0969 | AK026201 | RAB3IP | RAB3A interacting protein (rabin3) |
| 1215 | F0931 | AF026941 | cig5 | Viperin |
| 1216 | F2986 | AK027232 | LBH | Likely ortholog of mouse limb-bud and heart gene |
| 1217 | F3496 | AB023148 | KIAA0931 | KIAA0931 protein |
| 1218 | F6350 | AL389956 | FBXO32 | F-box protein 32 |
| 1219 | F3184 | NM_033380 | COL4A5 | Collagen, type IV, alpha 5 (Alport syndrome) |
| 1220 | B4350N | AF037364 | PNMA1 | Paraneoplastic antigen MA1 |
| 1221 | F1277 | AF151020 | TMEM9 | Transmembrane protein 9 |
| 1222 | A0576N | NM_138555 | KIF23 | Kinesin family member 23 |
| 1223 | B0068 | R15836 | LAPTM4B | Lysosomal associated protein transmembrane 4 beta |
| 1224 | F0119 | AL049354 | LOC221362 | Hypothetical protein LOC221362 |
| 1225 | F0938 | AK160383 | CENTD2 | Centaurin, delta 2 |
| 1226 | F2217 | AF288571 | LEF1 | Lymphoid enhancer-binding factor 1 |
| 1227 | F4281 | AF199023 | PLSCR4 | Phospholipid scramblase 4 |
| 1228 | F7951 | N66690 | ATP6V1E2 | ATPase, H+ transporting, lysosomal 31 kDa, V1 subunit E isoform 2 |
| 1229 | F9119 | BC015512 | | *Homo sapiens*, clone IMAGE: 3887266, mRNA |
| 1230 | F0896 | AF131790 | SHANK2 | SH3 and multiple ankyrin repeat domains 2 |
| 1231 | A1375 | D43968 | RUNX1 | Runt-related transcription factor 1 (acute myeloid leukemia 1; aml1 oncogene) |
| 1232 | A7732 | BC017984 | ARG99 | ARG99 protein |
| 1233 | A3802 | NM_005245 | FAT | FAT tumor suppressor homolog 1 (*Drosophila*) |
| 1234 | F0299 | NM_145693 | LPIN1 | Lipin 1 |
| 1235 | F3374 | AF195765 | RAMP | RA-regulated nuclear matrix-associated protein |
| 1236 | F4635 | AK021519 | FLJ11457 | Hypothetical protein FLJ11457 |
| 1237 | A6660 | CA418643 | GPR153 | G protein-coupled receptor 153 |
| 1238 | F5376 | AK025105 | ITGB1BP1 | Integrin beta 1 binding protein 1 |
| 1239 | F7497 | AW973864 | SYNJ2BP | Synaptojanin 2 binding protein |
| 1240 | F0924 | NM_012309 | SHANK2 | SH3 and multiple ankyrin repeat domains 2 |
| 1241 | A2921 | NM_002391 | MDK | Midkine (neurite growth-promoting factor 2) |
| 1242 | B4390N | AB006624 | KIAA0286 | KIAA0286 protein |
| 1243 | B4479 | AF258572 | GSDML | Gasdermin-like |
| 1244 | F1415 | NM_002759 | PRKR | Protein kinase, interferon-inducible double stranded RNA dependent |
| 1245 | F2746 | AJ251506 | SLCO1B3 | Solute carrier organic anion transporter family, member 1B3 |
| 1246 | F2092 | BC001873 | HEY1 | Hairy/enhancer-of-split related with YRPW motif 1 |
| 1247 | F7332 | AI936859 | RTKN | Rhotekin |
| 1248 | D8010 | AI734110 | FMNL2 | Formin-like 2 |
| 1249 | F0920 | AF098269 | PCOLCE2 | Procollagen C-endopeptidase enhancer 2 |
| 1250 | F2294 | AK024900 | AP2B1 | Adaptor-related protein complex 2, beta 1 subunit |
| 1251 | F2929 | AF022109 | CDC6 | CDC6 cell division cycle 6 homolog (*S. cerevisiae*) |
| 1252 | F2095 | NM_006449 | CDC42EP3 | CDC42 effector protein (Rho GTPase binding) 3 |

TABLE 2-continued up-regulated genes

| Assignment NO | LMMID | ACCESSION | SYMBOL | GENE NAME |
|---|---|---|---|---|
| 1253 | F3395 | AB032953 | ODZ2 | Odz, odd Oz/ten-m homolog 2 (*Drosophila*) |
| 1254 | A0636 | Z29066 | NEK2 | NIMA (never in mitosis gene a)-related kinase 2 |
| 1255 | F0410 | AW369770 | PACS1 | Phosphofurin acidic cluster sorting protein 1 |
| 1256 | F1732 | AK023642 | | CDNA FLJ13580 fis, clone PLACE1008851 |
| 1257 | F3598 | AK001332 | LRRC5 | Leucine rich repeat containing 5 |
| 1258 | F6994 | BM920112 | PSMB9 | Proteasome (prosome, macropain) subunit, beta type, 9 (large multifunctional protease 2) |
| 1259 | F7579 | AW629129 | SVH | SVH protein |
| 1260 | F8888 | AK027091 | | Transcribed locus, weakly similar to XP_375099.1 hypothetical protein LOC283585 [*Homo sapiens*] |
| 1261 | B5040N | AA126782 | CHST2 | Carbohydrate (N-acetylglucosamine-6-O) sulfotransferase 2 |
| 1262 | F5946 | AL137529 | FLJ23751 | Hypothetical protein FLJ23751 |
| 1263 | F4158 | BC047767 | APOBEC2 | Apolipoprotein B mRNA editing enzyme, catalytic polypeptide-like 2 |
| 1264 | A3896 | BC015050 | OIP5 | Opa-interacting protein 5 |
| 1265 | E2104 | CN280172 | | CDNA clone IMAGE: 4734740, partial cds |
| 1266 | F1646 | AB011109 | ARK5 | AMP-activated protein kinase family member 5 |
| 1267 | F1446 | AJ277587 | SPIRE1 | Spire homolog 1 (*Drosophila*) |
| 1268 | B9057 | AF361494 | SOSTDC1 | Sclerostin domain containing 1 |
| 1269 | F2462 | NM_182734 | PLCB1 | Phospholipase C, beta 1 (phosphoinositide-specific) |
| 1270 | A0359N | BC015753 | CXCL2 | Chemokine (C—X—C motif) ligand 2 |
| 1271 | F8483 | BG003072 | TFCP2L3 | Transcription factor CP2-like 3 |
| 1272 | A2439 | AF053305 | BUB1 | BUB1 budding uninhibited by benzimidazoles 1 homolog (yeast) |
| 1273 | A9111 | NM_016607 | ARMCX3 | Armadillo repeat containing, X-linked 3 |
| 1274 | F1916 | AF119418 | SIAT9 | Sialyltransferase 9 (CMP-NeuAc:lactosylceramide alpha-2,3-sialyltransferase; GM3 synthase) |
| 1275 | F4063 | AL109779 | HDGFRP3 | Hepatoma-derived growth factor, related protein 3 |
| 1276 | E2082 | BX537667 | FARP1 | FERM, RhoGEF (ARHGEF) and pleckstrin domain protein 1 (chondrocyte-derived) |
| 1277 | F9079 | AF339769 | | Clone IMAGE: 123704, mRNA sequence |
| 1278 | A3453 | BC064689 | TNFAIP3 | Tumor necrosis factor, alpha-induced protein 3 |
| 1279 | E0341 | AK093143 | SSFA2 | Sperm specific antigen 2 |
| 1280 | F0283 | AK123311 | GAP43 | Growth associated protein 43 |
| 1281 | F3997 | AL049987 | FLJ40092 | FLJ40092 protein |
| 1282 | F4952 | AL080082 | | MRNA; cDNA DKFZp564G1162 (from clone DKFZp564G1162) |
| 1283 | F3618 | AK172810 | SLC39A14 | Solute carrier family 39 (zinc transporter), member 14 |
| 1284 | F2037 | AK024124 | LOC80298 | Transcription termination factor-like protein |
| 1285 | F4451 | AK022204 | EDD | E3 identified by differential display |
| 1286 | F3878 | NM_020800 | KIAA1374 | KIAA1374 protein |
| 1287 | F8184 | AK022856 | | CDNA FLJ12794 fis, clone NT2RP2002041 |
| 1288 | F9909 | BC009431 | MGC15606 | Hypothetical protein MGC15606 |
| 1289 | G2245 | AW450464 | ZNF181 | Zinc finger protein 181 (HHZ181) |
| 1290 | G2660 | AK094334 | MRPS25 | Mitochondrial ribosomal protein S25 |
| 1291 | G2984 | AA778186 | KBTBD9 | Kelch repeat and BTB (POZ) domain containing 9 |
| 1292 | G3257 | BQ020994 | KIAA0146 | KIAA0146 protein |
| 1293 | G4110 | AA128462 | | Transcribed locus |
| 1294 | G4171 | BX106478 | | Transcribed locus |
| 1295 | G4302 | AI733332 | | Transcribed locus, weakly similar to XP_375099.1 hypothetical protein LOC283585 [*Homo sapiens*] |
| 1296 | G4661 | AK057918 | | Hypothetical gene supported by AK057918 |
| 1297 | G4356 | BX094336 | | Similar to AE2 protein |
| 1298 | G4650 | AK057706 | CHD7 | Chromodomain helicase DNA binding protein 7 |
| 1299 | G4705 | AK090872 | | Transcribed locus, weakly similar to XP_375099.1 hypothetical protein LOC283585 [*Homo sapiens*] |
| 1300 | G5030 | BX091458 | MTSS1 | Metastasis suppressor 1 |
| 1301 | G5296 | AW975990 | | HepG2 partial cDNA, clone hmd1a08m5. |
| 1302 | G6837 | AA703048 | TOP1 | Topoisomerase (DNA) I |
| 1303 | G6924 | CA503069 | EEF1G | Eukaryotic translation elongation factor 1 gamma |
| 1304 | G7153 | BM991930 | | Transcribed locus |
| 1305 | G7142 | BQ184075 | | Transcribed locus |
| 1306 | G7476 | BF591074 | | |
| 1307 | G7204 | BX537577 | | HepG2 3' region cDNA, clone hmd1c07. |
| 1308 | G7867 | BQ004940 | | |

TABLE 2-continued up-regulated genes

| Assignment NO | LMMID | ACCESSION | SYMBOL | GENE NAME |
|---|---|---|---|---|
| 1309 | G7894 | BX648286 | RAB22A | RAB22A, member RAS oncogene family |
| 1310 | G7821 | BM974197 | STXBP6 | Syntaxin binding protein 6 (amisyn) |
| 1311 | G7860 | BM996527 | OPHN1 | Oligophrenin 1 |
| 1312 | G7888 | BQ025514 | ADK | Adenosine kinase |
| 1313 | F5967 | NM_003519 CR988892 | | CR988892 RZPD no. 9017 Homo sapiens cDNA clone RZPDp9017D0310 5', mRNA sequence. |
| 1314 | G1119 | AK025202 | LARGE | Like-glycosyltransferase |
| 1315 | F9145 | BC001316 | MGC5528 | Defective in sister chromatid cohesion homolog 1 (S. cerevisiae) |
| 1316 | G1899 | BI490961 | ETV6 | Ets variant gene 6 (TEL oncogene) |
| 1317 | G2801 | U55853 | GOLPH4 | Golgi phosphoprotein 4 |
| 1318 | G3085 | BM992422 | FHOD3 | Formin homology 2 domain containing 3 |
| 1319 | G2825 | BQ773653 | JAG2 | Jagged 2 |
| 1320 | G3673 | BM677658 | PHIP | Pleckstrin homology domain interacting protein |
| 1321 | G3374 | AI740551 | SMARCA2 | SWI/SNF related, matrix associated, actin dependent regulator of chromatin, subfamily a, member 2 |
| 1322 | G4230 | AA460431 | HSPC150 | HSPC150 protein similar to ubiquitin-conjugating enzyme |
| 1323 | G5380 | BC012776 | KUB3 | Ku70-binding protein 3 |
| 1324 | G5190 | NM_006544 | SEC10L1 | SEC10-like 1 (S. cerevisiae) |
| 1325 | G7017 | AL832577 | PHACTR3 | Phosphatase and actin regulator 3 |
| 1326 | G7052 | AW376957 | | FP6778 |
| 1327 | G7074 | AW057520 | TCF12 | Transcription factor 12 (HTF4, helix-loop-helix transcription factors 4) |
| 1328 | G7311 | AW273713 | | Immunoglobulin heavy chain, V-region (SPH1.17) |
| 1329 | G7334 | AW444577 | PRKDC | Protein kinase, DNA-activated, catalytic polypeptide |
| 1330 | G7392 | AI700994 | KIAA1287 | KIAA1287 protein |
| 1331 | G7756 | BM673560 | CUL1 | Cullin 1 |
| 1332 | G7409 | AV661871 | ALDOB | Aldolase B, fructose-bisphosphate |
| 1333 | G7433 | AK022426 | | |
| 1334 | G7944 | AL833181 | BCL11A | B-cell CLL/lymphoma 11A (zinc finger protein) |
| 1335 | G8118 | BC041347 | FLNB | Filamin B, beta (actin binding protein 278) |
| 1336 | F3260 | AK022675 | FLJ20542 | Hypothetical protein FLJ20542 |
| 1337 | G1502 | BG219755 | JMY | Junction-mediating and regulatory protein |
| 1338 | G2206 | AB044088 | BHLHB3 | Basic helix-loop-helix domain containing, class B, 3 |
| 1339 | G2234 | BI496248 | VEZATIN | Transmembrane protein vezatin |
| 1340 | G2919 | BF114768 | FLJ10808 | Hypothetical protein FLJ10808 |
| 1341 | G2629 | AK091973 | IGF1R | Insulin-like growth factor 1 receptor |
| 1342 | G2620 | N39603 | MAP3K5 | Mitogen-activated protein kinase kinase kinase 5 |
| 1343 | G3228 | AW450394 | PLAG1 | Pleiomorphic adenoma gene 1 |
| 1344 | G4095 | AA022935 | FMNL2 | Formin-like 2 |
| 1345 | G4140 | BI918168 | | CDNA clone IMAGE: 4811759, partial cds |
| 1346 | G4068 | BU078631 | PKD2 | Polycystic kidney disease 2 (autosomal dominant) |
| 1347 | G4120 | AA151666 | | Transcribed locus, highly similar to XP_343158.1 similar to RIKEN cDNA 0910001B06 [Rattus norvegicus] |
| 1348 | G4165 | BM470637 | KLF3 | Kruppel-like factor 3 (basic) |
| 1349 | G4451 | AU122725 | | Transcribed locus, weakly similar to XP_214982.2 similar to junction-mediating and regulatory protein; p300 transcriptional cofactor JMY [Rattus norvegicus] |
| 1350 | G4999 | BC043409 | KCNH5 | Potassium voltage-gated channel, subfamily H (eag-related), member 5 |
| 1351 | G5013 | H16790 | | Homo sapiens, clone IMAGE: 4821290, mRNA |
| 1352 | G6627 | BC043583 | DNAJC13 | DnaJ (Hsp40) homolog, subfamily C, member 13 |
| 1353 | G6831 | BQ447463 | SAMD4 | Sterile alpha motif domain containing 4 |
| 1354 | G7491 | AI088195 | | CDNA FLJ41461 fis, clone BRSTN2016335 |
| 1355 | G7220 | AI373767 | | Transcribed locus |
| 1356 | G7267 | AW081263 | | Transcribed locus |
| 1357 | G8169 | AL832210 | WWOX | WW domain containing oxidoreductase |
| 1358 | G7895 | BQ027862 | GNB5 | Guanine nucleotide binding protein (G protein), beta 5 |
| 1359 | G7889 | BQ025551 | SLC7A8 | Solute carrier family 7 (cationic amino acid transporter, y+ system), member 8 |

TABLE 2-continued up-regulated genes

| Assignment NO | LMMID | ACCESSION | SYMBOL | GENE NAME |
|---|---|---|---|---|
| 1360 | F1800 | AK021742 | | DKFZp781G05150_r1 781 (synonym: hlcc4) |
| | | BX951495 | | Homo sapiens cDNA clone DKFZp781G05150 5', mRNA sequence. |
| 1361 | G4204 | BX100147 | | Hypothetical LOC402485 |
| 1362 | G5381 | XM_373575 | | Similar to hypothetical protein |
| 1363 | G5148 | N59381 | FLJ12476 | Hypothetical protein FLJ12476 |
| 1364 | G6967 | AK093278 | | CDNA FLJ35959 fis, clone TESTI2012444 |
| 1365 | G5819 | AL832755 | SLC30A6 | Solute carrier family 30 (zinc transporter), member 6 |
| 1366 | G5976 | H57111 | ZNF518 | Zinc finger protein 518 |
| 1367 | G7727 | BM666927 | PROX1 | Prospero-related homeobox 1 |
| 1368 | G7320 | AK096522 | LOC283514 | Similar to seven in absentia 2 |
| 1369 | G7410 | BQ025216 | PHIP | Pleckstrin homology domain interacting protein |
| 1370 | G7434 | AK023377 | HEXA | Hexosaminidase A (alpha polypeptide) |
| 1371 | G7945 | AK097655 | | CDNA FLJ40336 fis, clone TESTI2031986 |
| 1372 | G8773 | AV699579 | DKFZP564K0822 | Hypothetical protein DKFZp564K0822 |
| 1373 | G7236 | AK130576 | | Transcribed locus, moderately similar to NP_083546.1 Rho GTPase activating protein 24 [*Mus musculus*] |
| 1374 | F6729 | BE965780 | | 601659547R1 NIH_MGC_70 Homo sapiens cDNA clone IMAGE: 3896243 3', mRNA sequence. |
| 1375 | G0226 | BC006512 | MGC4308 | Hypothetical protein MGC4308 |
| 1376 | G2260 | NM_182920 | ADAMTS9 | A disintegrin-like and metalloprotease (reprolysin type) with thrombospondin type 1 motif, 9 |
| 1377 | G2686 | AK056824 | PWWP1 | PWWP domain containing 1 |
| 1378 | G4082 | AA004878 | STARD13 | START domain containing 13 |
| 1379 | G4173 | AK091238 | FLJ10211 | Hypothetical protein FLJ10211 |
| 1380 | G5034 | CB959761 | DAB2 | Disabled homolog 2, mitogen-responsive phosphoprotein (*Drosophila*) |
| 1381 | G5053 | H66650 | CD58 | CD58 antigen, (lymphocyte function-associated antigen 3) |
| 1382 | G5300 | AW007021 | TFDP1 | Transcription factor Dp-1 |
| 1383 | G5085 | AL833602 | SLC2A12 | Solute carrier family 2 (facilitated glucose transporter), member 12 |
| 1384 | G6746 | BQ027724 | PDE4DIP | Phosphodiesterase 4D interacting protein (myomegalin) |
| 1385 | G7446 | BC029450 | SLC33A1 | Solute carrier family 33 (acetyl-CoA transporter), member 1 |
| 1386 | G7163 | AI968300 | LOC91137 | Hypothetical protein BC017169 |
| 1387 | G7188 | BX093022 | A2M | Alpha-2-macroglobulin |
| 1388 | G8170 | AL832099 | ATXN7L4 | Ataxin 7-like 1 |
| 1389 | G7824 | BM975524 | B4GALT5 | UDP-Gal:betaGlcNAc beta 1,4-galactosyltransferase, polypeptide 5 |
| 1390 | G8216 | BI494395 | ADD3 | Adducin 3 (gamma) |
| 1391 | F8600 | AW977584 | HDLBP | High density lipoprotein binding protein (vigilin) |
| 1392 | G2452 | AA525021 | MACF1 | Microtubule-actin crosslinking factor 1 |
| 1393 | G2580 | AW975290 | | Transcribed locus |
| 1394 | G2876 | BX099865 | NRXN1 | Neurexin 1 |
| 1395 | G2853 | BQ026279 | THOC2 | THO complex 2 |
| 1396 | G2869 | BM674818 | CENTG2 | Trinucleotide repeat containing 17 |
| 1397 | G3659 | BM718282 | | FP6778 |
| 1398 | G3755 | BQ025315 | FLJ32810 | Hypothetical protein FLJ32810 |
| 1399 | G4205 | AA448989 | PTPN3 | Protein tyrosine phosphatase, non-receptor type 3 |
| 1400 | G4233 | AK127860 | PIK3CG | Phosphoinositide-3-kinase, catalytic, gamma polypeptide |
| 1401 | G4245 | AA703239 | FAD104 | FAD104 |
| 1402 | G4271 | AL599933 | PRKG1 | Protein kinase, cGMP-dependent, type I |
| 1403 | G4594 | AK056722 | | DKFZp686B17119_r1 686 (synonym: hlcc3) |
| | | AL700484 | | Homo sapiens cDNA clone DKFZp686B17119 5', mRNA sequence. |
| 1404 | G6993 | BM968300 | | Transcribed locus |
| 1405 | G7010 | AW149839 | NPAS3 | Neuronal PAS domain protein 3 |
| 1406 | G7115 | BF508564 | RBBP7 | Retinoblastoma binding protein 7 |
| 1407 | G7021 | BG190202 | FBXO15 | F-box protein 15 |
| 1408 | G6144 | R41724 | FMNL2 | Formin-like 2 |
| 1409 | G7315 | AW277126 | | Transcribed locus |
| 1410 | G7728 | BM669438 | BFSP2 | Beaded filament structural protein 2, phakinin |
| 1411 | G7695 | AK122626 | GPR82 | G protein-coupled receptor 82 |
| 1412 | G7948 | AW593931 | CENTB2 | Centaurin, beta 2 |

TABLE 2-continued up-regulated genes

| Assignment NO | LMMID | ACCESSION | SYMBOL | GENE NAME |
|---|---|---|---|---|
| 1413 | G8010 | BQ447982 | | *Homo sapiens*, clone IMAGE: 4827253, mRNA |
| 1414 | G8055 | AK096377 | FLJ39058 | Hypothetical protein FLJ39058 |
| 1415 | G7929 | AI827546 | APP | Amyloid beta (A4) precursor protein (protease nexin-II, Alzheimer disease) |
| 1416 | G2316 | AJ412030 | | B-cell neoplasia associated transcript, (BCMS gene), splice variant B, non coding transcript |
| 1417 | G2990 | AW973337 | SPRED2 | Sprouty-related, EVH1 domain containing 2 |
| 1418 | G3606 | BM680332 | | UI-E-EO1-aiy-h-05-0-UI.s1 UI-E-EO1 *Homo sapiens* cDNA clone UI-E-EO1-aiy-h-05-0-UI 3', mRNA sequence. |
| 1419 | G4372 | CK816153 | DLG1 | DKFZP586B0319 protein |
| 1420 | G5585 | BE729311 | XYLT1 | Xylosyltransferase I |
| 1421 | G6788 | X67334 | MCM2 | MCM2 minichromosome maintenance deficient 2, mitotin (*S. cerevisiae*) |
| 1422 | G6876 | AK055712 | | *Homo sapiens*, clone IMAGE: 4821804, mRNA, partial cds |
| 1423 | G5694 | AA102634 | TRAF5 | TNF receptor-associated factor 5 |
| 1424 | G5547 | BF997835 | DOCK5 | Dedicator of cytokinesis 5 |
| 1425 | G6851 | AK056005 | ZNF232 | Zinc finger protein 232 |
| 1426 | G6893 | AI056903 | | Transcribed locus |
| 1427 | G7199 | BF431313 | SLC13A3 | Solute carrier family 13 (sodium-dependent dicarboxylate transporter), member 3 |
| 1428 | G7216 | AI953227 | | Transcribed locus |
| 1429 | G7145 | AF150329 | VAV3 | Vav 3 oncogene |
| 1430 | G7189 | AW977068 | AFTIPHILIN | Aftiphilin protein |
| 1431 | G7518 | AK097137 | | Transcribed locus, weakly similar to NP_078841.2 hypothetical protein FLJ14166 [*Homo sapiens*] |
| 1432 | G7222 | BX110631 | NT5C2 | 5'-nucleotidase, cytosolic II |
| 1433 | G7870 | BQ007450 | F2RL2 | Coagulation factor II (thrombin) receptor-like 2 |
| 1434 | G7877 | BQ015552 | | UI-H-EI1-azf-m-15-0-UI.s1 NCI_CGAP_EI1 *Homo sapiens* cDNA clone IMAGE: 5848118 3', mRNA sequence. |
| 1435 | F8619 | AI632567 | TFCP2L1 | Transcription factor CP2-like 1 |
| 1436 | G0874 | BC023611 | EFHD2 | EF hand domain containing 2 |
| 1437 | G2535 | AI700987 | C11orf23 | Chromosome 11 open reading frame 23 |
| 1438 | G3171 | AW188318 | | Transcribed locus |
| 1439 | G2892 | AI024536 | | Transcribed locus |
| 1440 | G3123 | AL552527 | | Full-length cDNA clone CS0DI067YL24 of Placenta Cot 25-normalized of *Homo sapiens* (human) |
| 1441 | G3676 | BM669634 | | UI-E-DX1-agw-g-08-0-UI.s1 UI-E-DX1 *Homo sapiens* cDNA clone UI-E-DX1-agw-g-08-0-UI 3', mRNA sequence. |
| 1442 | G3386 | BC069024 | CENTG1 | Centaurin, gamma 1 |
| 1443 | G3756 | BQ025740 | DSTN | Destrin (actin depolymerizing factor) |
| 1444 | G3996 | AL833566 | ALCAM | Activated leukocyte cell adhesion molecule |
| 1445 | G4272 | AA669226 | | Similar to RIKEN cDNA 3110050N22 |
| 1446 | G4286 | AA873056 | RAD51 | RAD51 homolog (RecA homolog, *E. coli*) (*S. cerevisiae*) |
| 1447 | G4495 | AK054746 | CACNA1A | Calcium channel, voltage-dependent, P/Q type, alpha 1A subunit |
| 1448 | G5129 | N51068 | KCNMA1 | Potassium large conductance calcium-activated channel, subfamily M, alpha member 1 |
| 1449 | G5187 | BU626581 | NQO2 | NAD(P)H dehydrogenase, quinone 2 |
| 1450 | G5193 | AF113687 | RGS6 | Regulator of G-protein signalling 6 |
| 1451 | G6969 | AI798727 | | Transcribed locus |
| 1452 | G5950 | H17455 | | ym36a08.s1 Soares infant brain 1NIB *Homo sapiens* cDNA clone IMAGE: 50060 3', mRNA sequence. |
| 1453 | G6034 | N51961 | THRAP1 | Thyroid hormone receptor associated protein 1 |
| 1454 | G7101 | AI630821 | | tx53f04.x1 NCI_CGAP_Lu24 *Homo sapiens* cDNA clone IMAGE: 2273311 3', mRNA sequence. |
| 1455 | G7316 | AK097857 | | Hypothetical LOC157813 |
| 1456 | G7353 | AF085854 | | Full length insert cDNA clone YI54D04 |
| 1457 | G7713 | BM678413 | PPM1H | Protein phosphatase 1H (PP2C domain containing) |
| 1458 | G7772 | BM677476 | TOX | Thymus high mobility group box protein TOX |
| 1459 | G7699 | BC020838 | CLDN20 | Claudin 20 |
| 1460 | G7364 | AW978315 | PHGDHL1 | Phosphoglycerate dehydrogenase like 1 |
| 1461 | G8584 | BQ310416 | THRAP2 | Thyroid hormone receptor associated protein 2 |
| 1462 | G8030 | AK098270 | | FP6778 |

TABLE 2-continued up-regulated genes

| Assignment NO | LMMID | ACCESSION | SYMBOL | GENE NAME |
|---|---|---|---|---|
| 1463 | G7967 | BQ181903 | | UI-H-EU0-azv-1-14-0-UI.s1 NCI_CGAP_Car1 *Homo sapiens* cDNA clone IMAGE: 5854237 3', mRNA sequence. |
| 1464 | G8082 | AK094332 | | Hypothetical gene supported by AK094332 |
| 1465 | F8283 | AI133478 | UBE3A | Ubiquitin protein ligase E3A (human papilloma virus E6-associated protein, Angelman syndrome) |
| 1466 | G2616 | BX470806 | PRKWNK1 | Protein kinase, lysine deficient 1 |
| 1467 | G2943 | BQ448624 | C7orf6 | Chromosome 7 open reading frame 6 |
| 1468 | G2981 | AA573217 | CHD1L | Chromodomain helicase DNA binding protein 1-like |
| 1469 | G3016 | XM_499110 | | LOC441345 |
| 1470 | G2992 | AI807658 | SNX27 | Sorting nexin family member 27 |
| 1471 | G3600 | AK074226 | SUV420H1 | Suppressor of variegation 4-20 homolog 1 (*Drosophila*) |
| 1472 | G4136 | AI800735 | | CDNA FLJ11397 fis, clone HEMBA1000622 |
| 1473 | G3870 | BQ446672 | | UI-H-EU1-bac-c-08-0-UI.s1 NCI_CGAP_Ct1 *Homo sapiens* cDNA clone UI-H-EU1-bac-c-08-0-UI 3', mRNA sequence. |
| 1474 | G4645 | AK057639 | UBE2B | Ubiquitin-conjugating enzyme E2B (RAD6 homolog) |
| 1475 | G4332 | AI668557 | | yj83d08.x5 Soares breast 2NbHBst *Homo sapiens* cDNA clone IMAGE: 155343 3', mRNA sequence. |
| 1476 | G5235 | R40058 | NRCAM | Neuronal cell adhesion molecule |
| 1477 | G5028 | R11869 | ATF6 | Activating transcription factor 6 |
| 1478 | G5270 | T59016 | | yb49c12.s1 Stratagene fetal spleen (#937205) *Homo sapiens* cDNA clone IMAGE: 74518 3', mRNA sequence. |
| 1479 | G5043 | AW973785 | NIPBL | Nipped-B homolog (*Drosophila*) |
| 1480 | G5587 | BG281555 | | Hypothetical gene supported by BC019009 |
| 1481 | G6767 | AB036693 | RAB9B | RAB9B, member RAS oncogene family |
| 1482 | G7916 | BF921173 | | MR2-NT0135-161100-006-a08 NT0135 *Homo sapiens* cDNA, mRNA sequence. |
| 1483 | B5869N | NM_015259 | ICOSL | Inducible T-cell co-stimulator ligand |
| 1484 | G2037 | BG462138 | | Transcribed locus |
| 1485 | G2819 | AK095968 | | CDNA FLJ38649 fis, clone HHDPC2007302 |
| 1486 | G3342 | BE156543 | | QV0-HT0368-310100-091-h06 HT0368 *Homo sapiens* cDNA, mRNA sequence. |
| 1487 | G4254 | BU739793 | PDE4B | Phosphodiesterase 4B, cAMP-specific (phosphodiesterase E4 dunce homolog, *Drosophila*) |
| 1488 | G4287 | BX537672 | KIAA0934 | KIAA0934 |
| 1489 | G4511 | AK054893 | | Hypothetical protein LOC146713 |
| 1490 | G4531 | AK055134 | STAG1 | Stromal antigen 1 |
| 1491 | G4894 | AK096262 | | CDNA FLJ38943 fis, clone NT2NE2017480 |
| 1492 | G4925 | AK097171 | | CDNA FLJ39852 fis, clone SPLEN2014865 |
| 1493 | G5095 | H98216 | C14orf24 | Chromosome 14 open reading frame 24 |
| 1494 | G5160 | N63395 | MLSTD2 | Male sterility domain containing 2 |
| 1495 | G5123 | N48593 | | CDNA FLJ36725 fis, clone UTERU2012230 |
| 1496 | G6039 | BC036620 | C9orf99 | Chromosome 9 open reading frame 99 |
| 1497 | G7046 | AK074042 | PARVG | Parvin, gamma |
| 1498 | G7119 | BM977618 | PLEKHA5 | Pleckstrin homology domain containing, family A member 5 |
| 1499 | G6983 | CN479411 | IREM2 | Immune receptor expressed on myeloid cells 2 |
| 1500 | G6059 | N67553 | PLEKHA5 | Pleckstrin homology domain containing, family A member 5 |
| 1501 | G7317 | AW292370 | | Transcribed locus |
| 1502 | G7733 | BM676496 | PPEF2 | Protein phosphatase, EF hand calcium-binding domain 2 |
| 1503 | G7651 | AK055059 | SEMA6A | Sema domain, transmembrane domain (TM), and cytoplasmic domain, (semaphorin) 6A |
| 1504 | G7346 | AW470328 | PPFIA1 | Protein tyrosine phosphatase, receptor type, f polypeptide (PTPRF), interacting protein (liprin), alpha 1 |
| 1505 | G7960 | BI430555 | | Transcribed locus |
| 1506 | G7979 | AA535272 | | nf93d02.s1 NCI_CGAP_Co3 *Homo sapiens* cDNA clone IMAGE: 927459 3', mRNA sequence. |
| 1507 | G0130 | AB058773 | COL27A1 | Collagen, type XXVII, alpha 1 |
| 1508 | F8082 | BF058212 | FLJ40125 | Hypothetical protein FLJ40125 |
| 1509 | G2925 | AK093779 | | Hypothetical gene supported by AK093779 |
| 1510 | G3578 | AK057616 | MTVR1 | Mouse Mammary Turrmor Virus Receptor homolog 1 |

TABLE 2-continued up-regulated genes

| Assignment NO | LMMID | ACCESSION | SYMBOL | GENE NAME |
|---|---|---|---|---|
| 1511 | G3255 | AK002088 | UBE2E3 | Ubiquitin-conjugating enzyme E2E 3 (UBC4/5 homolog, yeast) |
| 1512 | G4118 | AA149783 | | Transcribed locus |
| 1513 | G4145 | W25631 | MGC34646 | Hypothetical protein MGC34646 |
| 1514 | G4124 | AA169173 | RGL1 | Ral guanine nucleotide dissociation stimulator-like 1 |
| 1515 | G4333 | AI668582 | ZNF609 | Zinc finger protein 609 |
| 1516 | G5221 | NM_005867 | DSCR4 | Down syndrome critical region gene 4 |
| 1517 | G5037 | H56731 | | Transcribed locus |
| 1518 | G5542 | XM_209824 | | Similar to matrilin 2 precursor |
| 1519 | G5642 | XM_212106 BG004461 | | MR3-GN0186-211100-009-f09 GN0186 *Homo sapiens* cDNA, mRNA sequence. |
| 1520 | G7141 | BQ001753 | DISC1 | Disrupted in schizophrenia 1 |
| 1521 | G7202 | AI825890 | | Transcribed locus |
| 1522 | G7241 | AW003728 | | Transcribed locus |
| 1523 | G7264 | AW069500 | | Transcribed locus |
| 1524 | G7462 | BF055457 | | Transcribed locus |
| 1525 | G7224 | AI951426 | DUSP10 | Dual specificity phosphatase 10 |
| 1526 | G7257 | AK023296 | XRCC5 | X-ray repair complementing defective repair in Chinese hamster cells 5 (double-strand-break rejoining; Ku autoantigen, 80 kDa) |
| 1527 | G8180 | AW292980 | | UI-H-BW0-aih-c-01-0-UI.s1 NCI_CGAP_Sub6 *Homo sapiens* cDNA clone IMAGE: 2729089 3', mRNA sequence. |
| 1528 | G8234 | BU076203 | MAPK10 | Mitogen-activated protein kinase 10 |
| 1529 | G2403 | CR591879 | TncRNA | Trophoblast-derived noncoding RNA |
| 1530 | G3135 | AL109783 | | MRNA full length insert cDNA clone EUROIMAGE 163507 |
| 1531 | G3399 | AF295378 | MAGEF1 | Melanoma antigen, family F, 1 |
| 1532 | G4514 | AK054930 | | |
| 1533 | G4608 | AK057035 | | CDNA FLJ32473 fis, clone SKNMC2000374 |
| 1534 | G5177 | N72313 | | yv31b09.r1 Soares fetal liver spleen 1NFLS *Homo sapiens* cDNA clone IMAGE: 244313 5', mRNA sequence. |
| 1535 | G6269 | BG755974 | C14orf125 | Chromosome 14 open reading frame 125 |
| 1536 | G6250 | W86987 | IGF1R | Insulin-like growth factor 1 receptor |
| 1537 | G7318 | BF196963 | ZMYND11 | Zinc finger, MYND domain containing 11 |
| 1538 | G7668 | BQ712480 | SLC27A1 | Solute carrier family 27 (fatty acid transporter), member 1 |
| 1539 | G7717 | BM681618 | | Transcribed locus |
| 1540 | G7432 | AK022190 | LDB2 | LIM domain binding 2 |
| 1541 | G7398 | BE501478 | | Transcribed locus |
| 1542 | G8512 | BC028198 | FLJ25200 | Hypothetical protein FLJ25200 |
| 1543 | G8117 | AK091697 | | Transcribed locus, weakly similar to NP_872601.1 ubiquitously transcribed tetratricopeptide repeat gene, Y-linked [*Homo sapiens*] |

TABLE 3

RT-PCR primer set

| LMMID | F-primer | SEQ ID NO | R-primer | SEQ ID NO |
|---|---|---|---|---|
| A2466 | CACAACCATTTTG ACCTCTCAGT | 34 | GCTTCTACATCTC AAATCATGTCC | 4 |
| A2735 | CCTCAGGTCTTCA CTCTTTCTTCT | 35 | TGCCATGTACAAT GTAGTAACAGC | 36 |
| A3802 | TAGAGAACCCCA TGCCCCTTA | 37 | TCAGTAAGAAAG ACTGGCTAATGGT | 38 |
| A4513 | AGCCATTTGATGG AGAAGAATG | 39 | TGGATGAAGGGG TTCCCGAAT | 40 |
| A5065 | CCAGTCTTGGCTG AAATGTTTT | 41 | CTCTCTGAAATGC AACTGTTCGT | 42 |
| A6598 | GAGGAAGAATTG CTTTTCTCTTACC | 43 | TTTTAAAGTGCAT CTGTGGAGG | 44 |
| A7296 | GTGGTAACGTTCA GCAAAAGC | 45 | ATGGCTCCTTACC TGAGAGAAAC | 46 |
| A7608 | GACAGCAAAGTC TTGACTCCTTC | 47 | AAAGTGGCTGGG AGTAAGGTATC | 48 |
| A7856 | AGACAAAGAGAG AAAGAGACGCA | 49 | AGAGGATCCTATT GTCTTGGAGG | 50 |
| A7908 | CAGAATCGCAGG ATGAAAGATA | 51 | GTGACTCATGCCT TGATATGACA | 52 |
| A8172 | TATCTGTGATTGT TGCTCACCTG | 53 | GCCCATCCTTACT TTCCTCATAC | 54 |

TABLE 3-continued

RT-PCR primer set

| LMMID | F-primer | SEQ ID NO | R-primer | SEQ ID NO |
|---|---|---|---|---|
| A8335 | CTTGAAGAAGAACTTCCAGACGA | 55 | AATGTTCTAAAGATGAGAGGGGG | 56 |
| A8487 | GCCTTAAAACTGGAGAGAGGAAT | 57 | TAGCAGAGCGCACAAACATTTA | 58 |
| A9371 | GTGCACCAAAACACTGACATTT | 59 | GGCTTTGCAACTTTGTCCATT | 60 |
| A9723 | TCTGAAGCCTGATTACTGTGTGA | 61 | ATGTGCACTGGACTGAAACATCT | 62 |
| B3827 | TGTGTGAGCATTTGACAAGACT | 63 | AATTTTAACAGCAAGTGGTGGG | 64 |
| B4161 | ACTGCAAATGGGAGTGCTTAGTA | 65 | GGAGAGGGTATGAGTCCTTTGAT | 66 |
| B6125N | CAGCTGTATCCCCTAAACAACC | 67 | GGTGAGGTATCCTGTCTTCAGAG | 68 |
| B7534 | TCCAGAATTGCTTGTTACGTAGG | 69 | GGTTCTCAGAGCTGTTTTGCTT | 70 |
| B8814 | GTATTACCGATGCCTCTGAAAAG | 71 | TGAGGTGTATGCAAGTTGAATC | 72 |
| C1948 | TAGAGTCTAGAACGCAAGGATCTC | 73 | CAAAAACTATCACAGCCTAAAGGG | 74 |
| C6209 | ATTAGAATTCTGGGGCTGTAAGG | 75 | CTACCCTGGGGTGTTTTCTAAAT | 76 |
| C8926 | GGTGCATAAACACTAATGCAGTC | 77 | GTTAAAGGAGCACAGGGACATA | 78 |
| C9016 | CACCCATAACCAAGAGAACTCAG | 79 | GGGATGTCTGTTCCTTTTATTCC | 80 |
| C9046 | GTGGCCACTGAATGTAAAACAAC | 81 | AGTAACTCTGTCTTCATCCGCAG | 82 |
| C9098 | CAATTTTCCCATGGTCTTATCC | 1 | GCGTTTTCAAGATCTAGCATGTG | 2 |
| C9490 | GTTTTGGCCCAATTAACCAGTA | 83 | GCACTTGGAAGGGGTATTGTATT | 84 |
| C9517 | ATTCATTCTGGACCAAAGATCC | 85 | TCTACTGTGGACAAGAAGCCTGT | 86 |
| C9858 | AGCAGTCAGGACAGACATACAT | 87 | AAGGTAAACTCTAGGCATCCGTC | 88 |
| D8457 | AAAGAGGAACACACTGGGTGTAA | 89 | AGGAGCCTAGAGAAGCAATCATC | 90 |
| D9504 | TCTTCAGCATGATGTGTTGTGT | 91 | TGAGAGATTCATGAGGAAGTCTTG | 92 |
| E0133 | AGGTGTACTGAGTGGGGAAGAAT | 93 | CTGGCATAACAGTGGCTTAAGTT | 94 |
| E0341 | GCTCCTTCTCTCATGGATTACCT | 95 | CAAGTGGGTAAAATGCTGTCTTC | 96 |
| E0556 | ACAAGTGCGAAGTCTGGTAAG | 97 | ACAGTGGTATTTGTGGCGTATC | 98 |
| E2191 | CCAAAAGCTAAGCAGTGGTGAAC | 99 | CTGTGCAACAGTTCCCAAAATG | 100 |
| F5946 | TTGACAAGCTGTAGAACTGGATT | 101 | AAAGTTGGAATGCCGATGACA | 102 |
| G3996 | CAGCCTCAATGGATACTGGC | 103 | GCTAGAAAGCAAACTCATGCTCTG | 104 |
| A3097 | TATGGTCTCCGTGCCTACCAC | 107 | ATACAGACAGGAAAAGCAGAGCA | 108 |
| ACTB | GAGGTGATAGCATTGCTTTCG | 105 | CAAGTCAGTGTACAGGTAAGC | 106 |

TABLE 4 down-regulated genes in lymph-node-positive casees

| Assignment NO | LMMID | ACCESSION | SYMBOL | GENENAME |
|---|---|---|---|---|
| 1544 | C8947 | AL833303 | | Full length insert cDNA clone YZ04E02 |
| 1545 | B2112 | S74221 | IK | IK cytokine, down-regulator of HLA II |
| 1546 | A2720 | AJ002231 | GNPDA1 | Glucosamine-6-phosphate deaminase 1 |
| 1547 | B4433 | AJ420556 | SEC5L1 | SEC5-like 1 (*S. cerevisiae*) |
| 1548 | B8117 | AA994071 | | Zinc finger protein 192 |
| 1549 | C1063 | AK096960 | RAD1 | RAD1 homolog (*S. pombe*) |
| 1550 | A5355 | NM_201222 | MAGED2 | Melanoma antigen family D, 2 |
| 1551 | B6373 | BX423161 | LHPP | Phospholysine phosphohistidine inorganic pyrophosphate phosphatase |
| 1552 | A9475N | AF081195 | RASGRP1 | RAS guanyl releasing protein 1 (calcium and DAG-regulated) |
| 1553 | B7525 | NM_015266 | SLC9A8 | Solute carrier family 9 (sodium/hydrogen exchanger), isoform 8 |
| 1554 | B4394 | N46424 | RAI14 | Retinoic acid induced 14 |
| 1555 | A2301N | BC028600 | SLC2A2 | Solute carrier family 20 (phosphate transporter), member 2 |
| 1556 | A1219 | NM_001905 | CTPS | CTP synthase |
| 1557 | A6309 | BM701413 | SEC61B | Sec61 beta subunit |
| 1558 | D3350 | R45979 | | EST |
| 1559 | D6495 | AA993602 | HSPC63 | HSPC063 protein |
| 1560 | A1084 | BM905965 | HSPE1 | Heat shock 10 kDa protein 1 (chaperonin 10) |
| 1561 | F3819 | AK000471 | | EST |

TABLE 4-continued down-regulated genes in lymph-node-positive casees

| Assignment NO | LMMID | ACCESSION | SYMBOL | GENENAME |
|---|---|---|---|---|
| 1562 | D4231 | C05897 | ARL5 | ADP-ribosylation factor-like 5 |
| 1563 | B5126 | BX109845 | SH3BGRL2 | SH3 domain binding glutamic acid-rich protein like 2 |
| 1564 | B6528 | AF159447 | SUFU | Suppressor of fused homolog (*Drosophila*) |
| 1565 | A1859N | NM_001002295 | GATA3 | GATA binding protein 3 |
| 1566 | F6308 | XM_375105 | KIAA329 | KIAA0329 |
| 1567 | B3960 | AF234532 | MYO1 | Myosin X |
| 1568 | B6051 | R32860 | MOBKL2B | Transcribed locus |
| 1569 | C7642 | AK001431 | FLJ1569 | Hypothetical protein FLJ10569 |
| 1570 | C6830 | R49122 | FLJ148 | Hypothetical protein FLJ14800 |
| 1571 | C4865 | AK095215 | C21orf18 | Chromosome 21 open reading frame 18 |
| 1572 | B4932 | AA909294 | MUM1 | Melanoma associated antigen (mutated) 1 |
| 1573 | B4159 | BU634102 | C9orf116 | Chromosome 9 open reading frame 116 |
| 1574 | B6560 | BC011728 | ARMC7 | Armadillo repeat containing 7 |
| 1575 | B9577 | N48793 | KIAA1546 | KIAA1546 protein |
| 1576 | B4930 | AL110157 | DUSP7 | Dual specificity phosphatase 7 |
| 1577 | A2759N | X16260 | ITIH1 | Inter-alpha (globulin) inhibitor H1 |
| 1578 | B9454 | AA033857 | RAB4A | RAB40A, member RAS oncogene family |
| 1579 | B7123 | CA418716 | STXBP5 | Syntaxin binding protein 5 (tomosyn) |
| 1580 | B8754 | AL833264 | FEM1B | Fem-1 homolog b (*C. elegans*) |
| 1581 | B0830N | BM473615 | ID4 | Inhibitor of DNA binding 4, dominant negative helix-loop-helix protein |
| 1582 | C3772 | U70063 | ASAH1 | N-acylsphingosine amidohydrolase (acid ceramidase) 1 |
| 1583 | B9198 | AK123132 | MSRA | Methionine sulfoxide reductase A |
| 1584 | A6996 | AL832899 | RAPGEF6 | KIAA1961 gene |
| 1585 | A5364 | BC004309 | RAB4A | RAB4A, member RAS oncogene family |
| 1586 | B3769 | N91145 | CARF | Collaborates/cooperates with ARF (alternate reading frame) protein |
| 1587 | B8469 | CR598871 | GFPT1 | Clone 114 tumor rejection antigen mRNA, complete cds |
| 1588 | B1465N | AK074306 | FLJ23518 | Hypothetical protein FLJ23518 |
| 1589 | B8098 | R42864 | PAPOLA | Poly(A) polymerase alpha |
| 1590 | B8277 | H05711 | FLJ3536 | Hypothetical protein FLJ35036 |
| 1591 | A6649N | AK026613 | GOLGA7 | Golgi autoantigen, golgin subfamily a, 7 |
| 1592 | A4647N | NM_004169 | SHMT1 | Serine hydroxymethyltransferase 1 (soluble) |
| 1593 | B4176 | AF037629 | | Transcribed locus |
| 1594 | A6342N | AI057185 | SIPA1 | Signal-induced proliferation-associated gene 1 |
| 1595 | B8141 | BC042478 | DKFZP434F318 | Hypothetical protein DKFZp434F0318 |
| 1596 | B9157 | R44292 | FLJ3778 | Hypothetical protein FLJ37078 |
| 1597 | A3384N | NM_002024 | FMR1 | Fragile X mental retardation 1 |
| 1598 | B5168 | AL834437 | FLJ31818 | Hypothetical protein FLJ31818 |
| 1599 | A6777 | BQ276959 | LGALS2 | Lectin, galactoside-binding, soluble, 2 (galectin 2) |
| 1600 | C6087 | BU676496 | MTAC2D1 | Membrane targeting (tandem) C2 domain containing 1 |
| 1601 | A1878N | U88666 | SRPK2 | SFRS protein kinase 2 |
| 1602 | B6103 | T89283 | | Clone IMAGE: 110436 mRNA sequence |

TABLE 5 up-regulated genes in lymph-node-positive casees

| Assignment NO | LMMID | ACCESSION | SYMBOL | GENENAME |
|---|---|---|---|---|
| 1603 | A3166N | BX953609 | GFPT1 | Glutamine-fructose-6-phosphate transaminase 1 |
| 1604 | A1750 | D31716 | BTEB1 | Kruppel-like factor 9 |
| 1605 | B3701 | AY249859 | DUSP22 | Dual specificity phosphatase 22 |
| 1606 | C3692 | AI816254 | USP11 | Ubiquitin specific protease 11 |
| 1607 | A1026 | M60091 | GALT | Galactose-1-phosphate uridylyltransferase |
| 1608 | B3777 | AW574563 | CERK | Ceramide kinase |
| 1609 | A3923 | AF038440 | PLD2 | Phospholipase D2 |
| 1610 | B9111 | NM_014811 | KIAA649 | KIAA0649 |
| 1611 | B8069 | NM_013366 | ANAPC2 | Anaphase promoting complex subunit 2 |
| 1612 | B6768N | AA919178 | STK24 | Serine/threonine kinase 24 (STE20 homolog, yeast) |
| 1613 | B3543 | AK092257 | | Calpain 14 |
| 1614 | A1350 | NM_013314 | BLNK | B-cell linker |

TABLE 5-continued up-regulated genes in lymph-node-positive casees

| Assignment NO | LMMID | ACCESSION | SYMBOL | GENENAME |
|---|---|---|---|---|
| 1615 | B8715 | NM_080836 | STK35 | Serine/threonine kinase 35 |
| 1616 | B9038 | AY304473 | WDR26 | WD repeat domain 26 |
| 1617 | B4721N | BE795997 | NCOR2 | Nuclear receptor co-repressor 2 |
| 1618 | B9158 | CR622145 | SCDR1 | Short-chain dehydrogenase/reductase 10 |
| 1619 | B3350 | AK056402 | TDRKH | Tudor and KH domain containing |
| 1620 | A4791 | AF065482 | SNX2 | Sorting nexin 2 |
| 1621 | F3895 | AF100742 | ZFR | Zinc finger RNA binding protein |
| 1622 | A2321 | NM_005831 | NDP52 | Nuclear domain 10 protein |
| 1623 | B0122 | BC009534 | PINK1 | PTEN induced putative kinase 1 |
| 1624 | A2374 | X97999 | TAF7 | TAF7 RNA polymerase II, TATA box binding protein (TBP)-associated factor, 55 kDa |
| 1625 | A1619 | BC013873 | CETN2 | Centrin, EF-hand protein, 2 |
| 1626 | A3953 | NM_004661 | CDC23 | CDC23 (cell division cycle 23, yeast, homolog) |
| 1627 | A5419 | BU630296 | ARRDC4 | Arrestin domain containing 4 |
| 1628 | B3737 | NM_014647 | LKAP | Limkain b1 |
| 1629 | B4095 | BC014070 | MAGED1 | Melanoma antigen family D, 1 |
| 1630 | A2079 | NM_001183 | ATP6AP1 | ATPase, H+ transporting, lysosomal accessory protein 1 |
| 1631 | A6411 | AL137764 | LOC64744 | Hypothetical protein AL133206 |
| 1632 | A2490 | BC011674 | PLOD3 | Procollagen-lysine, 2-oxoglutarate 5-dioxygenase 3 |
| 1633 | A5269 | U80743 | EP4 | E1A binding protein p400 |
| 1634 | A3130 | L36529 | THOC1 | THO complex 1 |
| 1635 | A4415 | U17838 | PRDM2 | PR domain containing 2, with ZNF domain |
| 1636 | B0132 | AK056512 | C5orf14 | Chromosome 5 open reading frame 14 |
| 1637 | A8596 | AA632025 | | Transcribed locus |
| 1638 | C4735 | AL136805 | ZNF537 | Zinc finger protein 537 |
| 1639 | A4325 | AK123352 | HRMT1L1 | HMT1 hnRNP methyltransferase-like 1 (*S. cerevisiae*) |
| 1640 | B3943 | XM_377060 | LOC23547 | Hypothetical protein LOC203547 |
| 1641 | A6891 | BU616541 | PIAS2 | Protein inhibitor of activated STAT, 2 |
| 1642 | A5825 | BX640683 | C18orf25 | Chromosome 18 open reading frame 25 |
| 1643 | A2228 | AK023953 | GNPAT | Glyceronephosphate O-acyltransferase |
| 1644 | A9256 | BC051850 | TMPIT | Transmembrane protein induced by tumor necrosis factor alpha |
| 1645 | A0582 | BC034409 | ICAM3 | Intercellular adhesion molecule 3 |
| 1646 | B4362 | BX648218 | ASXL2 | Additional sex combs like 2 (*Drosophila*) |
| 1647 | B7278 | BC005125 | FLJ1475 | Hypothetical LOC79954 |
| 1648 | B3770 | BQ650605 | Dlc2 | Dynein light chain 2 |
| 1649 | B8113 | BC020848 | RNASE6 | Ribonuclease, RNase A family, k6 |
| 1650 | A5767 | AI096898 | NKAP | NF-kappaB activating protein |
| 1651 | A0232 | NM_006219 | PIK3CB | Phosphoinositide-3-kinase, catalytic, beta polypeptide |
| 1652 | C4884 | AA036952 | Gup1 | GRINL1A complex upstream protein |
| 1653 | B6529 | CA314443 | PLXNA3 | Plexin A3 |
| 1654 | C3645 | AK000403 | CKLFSF6 | Chemokine-like factor super family 6 |
| 1655 | C0258 | NM_000484 | APP | Amyloid beta (A4) precursor protein (protease nexin-II, Alzheimer disease) |
| 1656 | B5104 | CR613027 | C21orf4 | Chromosome 21 open reading frame 4 |
| 1657 | B4556 | NM_020531 | C2orf3 | Chromosome 20 open reading frame 3 |
| 1658 | A4719N | BC048259 | PICALM | Phosphatidylinositol binding clathrin assembly protein |
| 1659 | D9475 | AW089912 | OAZ1 | Ornithine decarboxylase antizyme 1 |
| 1660 | E0215 | AI091879 | | Transcribed locus |
| 1661 | E1229 | NM_003470 | USP7 | Ubiquitin specific protease 7 (herpes virus-associated) |
| 1662 | E1378 | AK025645 | SLA2 | Src-like-adaptor 2 |
| 1663 | A0183N | NM_004431 | EPHA2 | EPH receptor A2 |
| 1664 | D7869 | NM_007175 | C8orf2 | SPFH domain family, member 2 |
| 1665 | E0052 | AI081459 | PSMA6 | Proteasome (prosome, macropain) subunit, alpha type, 6 |
| 1666 | E1522 | BM550980 | MGC521 | Hypothetical protein MGC52010 |
| 1667 | C0328 | CR592555 | | Full-length cDNA clone CS0DE011YI04 of Placenta of Homo sapiens (human) |

TABLE 5-continued up-regulated genes in lymph-node-positive casees

| Assignment NO | LMMID | ACCESSION | SYMBOL | GENENAME |
|---|---|---|---|---|
| 1668 | E0523 | BC017483 | AHNAK | AHNAK nucleoprotein (desmoyokin) |
| 1669 | E1379 | AK123877 | ALDH3A2 | Aldehyde dehydrogenase 3 family, member A2 |
| 1670 | D6549 | BC004888 | FLJ152 | Hypothetical protein FLJ10052 |
| 1671 | D3747 | AA843607 | LOC12376 | Hypothetical protein LOC120376 |
| 1672 | C7731 | AF245505 | DKFZp564I1922 | Adlican |
| 1673 | A0954 | NM_000252 | MTM1 | Myotubularin 1 |
| 1674 | B2801 | AK130734 | FLJ1371 | Hypothetical protein FLJ13710 |
| 1675 | A8688 | CR597998 | NPDC1 | Neural proliferation, differentiation and control, 1 |
| 1676 | B0629 | AK126877 | FLJ1521 | Hypothetical protein FLJ10521 |
| 1677 | A7145 | X52005 |  | EST |
| 1678 | A6751 | NM_002258 | KLRB1 | Killer cell lectin-like receptor subfamily B, member 1 |
| 1679 | A9307 | BC053677 | FLJ37562 | Hypothetical protein FLJ37562 |

TABLE 6

Down-regulated genes in recurrence-positive casees

| Assignment NO | LMMID | ACCESSION | GENENAME |
|---|---|---|---|
| 1680 | A1989 | M86737 | Structure specific recognition protein 1 |
| 1681 | A2156 | L15189 | Heat shock 70 kDa protein 9B (mortalin-2) |
| 1682 | A6411 | AL137764 | Hypothetical protein AL 133206 |
| 1683 | A2457 | NM_003680 | Tyrosyl-tRNA synthetase |
| 1684 | B0201 | X71490 | EST |
| 1685 | B4964 | CR622891 | Basic leucine zipper and W2 domains 2 |
| 1686 | A5713 | AK074119 | Zinc finger, ZZ domain containing 3 |
| 1687 | A8122 | AA625409 | Mediator of RNA polymerase II transcription, subunit 9 homolog (yeast) |
| 1688 | B8113 | BC020848 | Ribonuclease, RNase A family, k6 |

TABLE 7

Up-regulated genes in recurrence-positive casees

| Assignment NO | LMMID | ACCESSION | GENENAME |
|---|---|---|---|
| 1689 | F7415 | BE964060 | EST |
| 1690 | A1701 | AK130450 | Ribosomal protein L3 |
| 1691 | A1701 | AK130450 | Ribosomal protein L3 |
| 1692 | D5019 | AA921313 | EST |
| 1693 | D1723 | BG251399 | Ribosomal protein L36a |
| 1694 | A0774N | BC012613 | Carboxypeptidase A3 (mast cell) |
| 1695 | A3317 | NM_033500 | Hexokinase 1 |
| 1696 | A3317 | NM_033500 | Hexokinase 1 |
| 1697 | F1956 | NM_024554 | PiggyBac transposable element derived 5 |
| 1698 | E0569 | BU608360 | Hypothetical protein LOC51255 |
| 1699 | D2335 | BQ018544 | Hypothetical LOC389908 |
| 1700 | F0429 | AK022634 | Proto-oncogene 8 |
| 1701 | D4861 | AA913741 | Transcribed locus |
| 1702 | F2429 | AF097366 | Solute carrier family 24 (sodium/potassium/calcium exchanger), member 2 |
| 1703 | C4978 | NM_170707 | Lamin A/C |
| 1704 | A0463 | BM923584 | Ribosomal protein S15 |
| 1705 | A8729 | AI337816 | Ribosomal protein L35 |
| 1706 | E0577 | NM_170707 | Lamin A/C |
| 1707 | C3870 | NM_002804 | Proteasome (prosome, macropain) 26S subunit, ATPase, 3 |
| 1708 | G2545 | NM_001202 | Bone morphogenetic protein 4 |
| 1709 | D5183 | AA936173 | Ribosomal protein S11 |
| 1710 | D8489 | AA961412 | Ubiquitin A-52 residue ribosomal protein fusion product 1 |
| 1711 | F3279 | M61854 | Cytochrome P450, family 2, subfamily C, polypeptide 19 |
| 1712 | B6765N | AI346913 | Syndecan binding protein (syntenin) 2 |
| 1713 | G4019 | AI207670 | Hypothetical protein FLJ12078 |
| 1714 | D1736 | BG425369 | Ribosomal protein S17 |
| 1715 | A2085 | CD555959 | Ribosomal protein L31 |
| 1716 | A0449 | BG110168 | Transmembrane 4 superfamily member tetraspan NET-5 |

TABLE 8

Sequence of specific double-stranded oligonucleotide inserted into siRNA expression vector and target sequences of each siRNAs.

| SEQ ID NO: | Nucleotide Sequence | genes | | Positions |
|---|---|---|---|---|
| 6 | GAAGCAGCACGACTTCTTC | EGFP | target | siRNA |
| 7 | GCGCGCTTTGTAGGATTCG | SCR | target | siRNA |

TABLE 8-continued

Sequence of specific double-stranded oligonucleotide inserted into siRNA expression vector and target sequences of each siRNAs.

| SEQ ID NO: | Nucleotide Sequence | genes | | | Positions |
|---|---|---|---|---|---|
| 8 | GATGCACTCACCTTGTAGT | ECT2 | target | siRNA | 1268-1286 |
| 9 | GGCAAATACTCCTGAGCTC | ECT2 | target | siRNA | 1416-1434 |
| 10 | GAGACATCCTCTTTGACTA | CDC45L | target | siRNA | 575-593 |
| 11 | CAGACCAGTGGGTGCAAGA | CDC45L | target | siRNA | 704-722 |
| 12 | TCCCGAAGCAGCACGACTTCTTCT TCAAGAGAGAAGAAGTCGTGCTG CTTC | EGFP | insert | siRNA | |
| 13 | AAAAGAAGCAGCACGACTTCTTCT CTCTTGAAGAAGAAGTCGTGCTGC TTC | EGFP | insert | siRNA | |
| 14 | GAAGCAGCACGACTTCTTCTTCAA GAGAGAAGAAGTCGTGCTGCTTC | EGFP | hairpin | siRNA | |
| 15 | TCCCGCGCGCTTTGTAGGATTCGT TCAAGAGACGAATCCTACAAAGC GCGC | SCR | insert | siRNA | |
| 16 | AAAAGCGCGCTTTGTAGGATTCGT CTCTTGAACGAATCCTACAAAGCG CGC | SCR | insert | siRNA | |
| 17 | GCGCGCTTTGTAGGATTCGTTCAA GAGACGAATCCTACAAAGCGCGC | SCR | hairpin | siRNA | |
| 18 | TCCCGATGCACTCACCTTGTAGTT TCAAGAGAACTACAAGGTGAGTG CATC | ECT2 | insert | siRNA | |
| 19 | AAAAGATGCACTCACCTTGTAGTT CTCTTGAAACTACAAGGTGAGTGC ATC | ECT2 | insert | siRNA | |
| 20 | GATGCACTCACCTTGTAGTTTCAA GAGAACTACAAGGTGAGTGCATC | ECT2 | hairpin | siRNA | |
| 21 | TCCCGGCAAATACTCCTGAGCTCT TCAAGAGAGAGCTCAGGAGTATT TGCC | ECT2 | insert | siRNA | |
| 22 | AAAAGGCAAATACTCCTGAGCTCT CTCTTGAAGAGCTCAGGAGTATTT GCC | ECT2 | insert | siRNA | |
| 23 | GGCAAATACTCCTGAGCTCTTCAA GAGAGAGCTCAGGAGTATTTGCC | ECT2 | hairpin | siRNA | |
| 24 | TCCCGAGACATCCTCTTTGACTAT TCAAGAGATAGTCAAAGAGGATG TCTC | CDC45L | insert | siRNA | |
| 25 | AAAAGAGACATCCTCTTTGACTAT CTCTTGAATAGTCAAAGAGGATGT CTC | CDC45L | insert | siRNA | |

TABLE 8-continued

Sequence of specific double-stranded oligonucleotide inserted into siRNA expression vector and target sequences of each siRNAs.

| SEQ ID NO: | Nucleotide Sequence | genes | Positions |
|---|---|---|---|
| 26 | GAGACATCCTCTTTGACTATTCAA GAGATAGTCAAAGAGGATGTCTC | CDC45L hairpin siRNA | |
| 27 | TCCCCAGACCAGTGGGTGCAAGA TTCAAGAGATCTTGCACCCACTGG TCTG | CDC45L insert siRNA | |
| 28 | AAAACAGACCAGTGGGTGCAAGA TCTCTTGAATCTTGCACCCACTGG TCTG | CDC45L insert siRNA | |
| 29 | CAGACCAGTGGGTGCAAGATTCA AGAGATCTTGCACCCACTGGTCTG | CDC45L hairpin siRNA | |

TABLE 9A

Association between DKK1-positivity in ESCC tissues and patients' characteristics (n = 220)

| | Total n = 220 | DKK1 strong positive n = 60 | DKK1 weak positive n = 75 | DKK1 absent n = 85 | P-value strong/weak vs absent |
|---|---|---|---|---|---|
| Gender | | | | | |
| Male | 202 | 53 | 69 | 80 | NS |
| Female | 18 | 7 | 6 | 5 | |
| Age (years) | | | | | |
| <65 | 138 | 40 | 52 | 46 | NS |
| ≧65 | 82 | 20 | 23 | 39 | |
| pT factor | | | | | |
| T1 + T2 | 98 | 20 | 37 | 41 | 0.0479* |
| T3 + T4 | 122 | 40 | 38 | 44 | |
| pN factor | | | | | |
| N0 | 80 | 15 | 30 | 35 | 0.0404* |
| N1 + N2 | 140 | 45 | 45 | 50 | |

ADC, adenocarcinoma;
SCC, squamous-cell carcinoma
*P < 0.05 (Fisher's exact test)
NS, no significance

TABLE 9B

Cox's proportional hazards model analysis of prognostic factors in patients with ESCCs

| Variables | Hazards ratio | 95% CI | Unfavorable/Favorable | P-value |
|---|---|---|---|---|
| Univariate analysis | | | | |
| DKK1 | 1.477 | 1.012-2.157 | Strong(+)/Weak(+) or (−) | 0.0433* |
| Age (years) | 0.911 | 0.629-1.319 | 65≧/<65 | NS |
| Gender | 2.120 | 0.932-4.819 | Male/Female | NS |
| pT factor | 1.889 | 1.411-2.528 | T3 + T4/T1 + T2 | <0.0001* |
| pN factor | 2.76 | 1.626-4.571 | N1 + N2/N0 | 0.0001* |
| Multivariate analysis | | | | |
| DKK1 | 1.181 | 0.804-1.734 | Strong(+)/Weak(+) or (−) | NS |
| pT factor | 2.054 | 1.223-3.447 | T3 + T4/T1 + T2 | 0.0065* |
| pN factor | 2.256 | 1.454-3.502 | N1 + N2/N0 | 0.0003* |

*P < 0.05
NS, no significance

TABLE 10A

Association between DKK1-positivity in NSCLC tissues and patients' characteristics (n = 279)

| | Total n = 279 | DKK1 strong positive n = 125 | DKK1 weak positive n = 102 | DKK1 absent n = 52 | P-value strong vs weak/absent |
|---|---|---|---|---|---|
| Gender | | | | | |
| Male | 183 | 94 | 62 | 27 | 0.0024* |
| Female | 96 | 31 | 40 | 25 | |
| Age (years) | | | | | |
| <65 | 134 | 51 | 59 | 24 | 0.0309* |
| ≧65 | 145 | 74 | 43 | 28 | |
| Histological type | | | | | |
| ADC | 161 | 48 | 70 | 43 | <0.001* |
| non-ADC | 118 | 77 | 32 | 9 | |
| pT factor | | | | | |
| T1 + T2 | 241 | 111 | 84 | 46 | NS |
| T3 + T4 | 38 | 14 | 18 | 6 | |
| pN factor | | | | | |
| N0 | 210 | 88 | 85 | 37 | NS |
| N1 + N2 | 69 | 37 | 17 | 15 | |

ADC, adenocarcinoma; SCC, squamous-cell carcinoma
non-ADC, SCC, large-cell carcinoma (LCC), and adenosquamous-cell carcinoma (ASC)
*P < 0.05 (Fisher's exact test)
NS, no significance

TABLE 10B

Cox's proportional hazards model analysis of prognostic factors in patients with NSCLCs

| Variables | Hazards ratio | 95% CI | Unfavorable/Favorable | P-value |
|---|---|---|---|---|
| Univariate analysis | | | | |
| DKK1 | 1.977 | 1.234-3.169 | Strong(+)/Weak(+) or (−) | 0.0046* |
| Age (years) | 2.214 | 1.365-3.592 | 65≧/<65 | 0.0013* |
| Gender | 1.958 | 1.147-3.345 | Male/Female | 0.0138* |
| Histological type | 2.279 | 1.418-3.661 | non-ADC/ADC1 | 0.0007* |
| pT factor | 2.431 | 1.374-4.303 | T3 + T4/T1 + T2 | 0.0023* |
| pN factor | 3.811 | 2.387-6.084 | N1 + N2/N0 | <0.0001* |
| Multivariate analysis | | | | |
| DKK1 | 1.798 | 1.114-2.903 | Strong(+)/Weak(+) or (−) | 0.0163* |
| pT factor | 2.407 | 1.349-4.294 | T3 + T4/T1 + T2 | 0.0029* |
| pN factor | 3.418 | 2.124-5.500 | N1 + N2/N0 | <0.0001* |

1ADC, adenocarcinoma
*P < 0.05

The invention claimed is:

1. A method of diagnosing esophageal cancer or a predisposition for developing esophageal cancer in a subject, comprising determining a gene expression level of an esophageal cancer-associated gene in an esophageal tissue or cell sample from the subject, wherein an increase in the gene expression level in the sample from said subject as compared to the gene expression level in a normal control sample indicates that said subject suffers from or is at risk of developing esophageal cancer, wherein said esophageal cancer-associated gene is cell division cycle 45-like (CDC45L).

2. The method of claim 1, wherein said gene expression level in the sample from said subject is at least 10% greater than said gene expression level in the normal control sample.

3. The method of claim 1, wherein said esophageal cancer is esophageal squamous-cell carcinoma.

4. The method of claim 1, wherein said esophageal tissue or cell sample comprises an epithelial cell.

5. The method of claim 1, wherein said gene expression level is determined by a method selected from the group consisting of:
(a) detecting mRNA of the esophageal cancer-associated gene,
(b) detecting a protein encoded by the esophageal cancer-associated gene, and
(c) detecting a biological activity of a protein encoded by the esophageal cancer-associated gene.

* * * * *